(12) United States Patent
Hatakeyama et al.

(10) Patent No.: US 11,139,438 B2
(45) Date of Patent: Oct. 5, 2021

(54) ORGANIC ELECTROLUMINESCENT ELEMENT

(71) Applicants: Kwansei Gakuin Educational Foundation, Nishinomiya (JP); SK Materials JNC Co., Ltd., Gyeonggi-do (KR)

(72) Inventors: Takuji Hatakeyama, Hyogo (JP); Yuko Yamaga, Tokyo (JP); Daisuke Baba, Chiba (JP); Kazushi Shiren, Chiba (JP)

(73) Assignees: Kwansei Gakuin Educational Foundation, Hyogo (JP); SK Materials JNC Co., Ltd., Gyeonggi-do (KR)

( * ) Notice: Subject to any disclaimer, the term of this patent is extended or adjusted under 35 U.S.C. 154(b) by 151 days.

(21) Appl. No.: 16/244,454

(22) Filed: Jan. 10, 2019

(65) Prior Publication Data
US 2019/0229277 A1    Jul. 25, 2019

(30) Foreign Application Priority Data

Jan. 24, 2018  (JP) .............................. JP2018-009620
Oct. 15, 2018  (JP) .............................. JP2018-194216

(51) Int. Cl.
*H01L 51/00* (2006.01)
*H01L 51/52* (2006.01)
(Continued)

(52) U.S. Cl.
CPC ........ *H01L 51/0074* (2013.01); *H01L 51/008* (2013.01); *H01L 51/0054* (2013.01);
(Continued)

(58) Field of Classification Search
None
See application file for complete search history.

(56) References Cited

U.S. PATENT DOCUMENTS

2007/0106103 A1    5/2007  Ikeda et al.

FOREIGN PATENT DOCUMENTS

CN    106883203    *  6/2017   ........... C07D 307/77
EP    3109253 A1    12/2016
(Continued)

OTHER PUBLICATIONS

Kaafarani et al. "Bis (carbazolyl) derivatives of pyrene and tetrahydropyrene: synthesis, structures, optical properties, electrochemistry, and electroluminescence." Journal of Materials Chemistry C 1, No. 8 (2013): 1638-165 (Year: 2013).*
(Continued)

*Primary Examiner* — Robert S Loewe
(74) *Attorney, Agent, or Firm* — Foley & Lardner LLP

(57) ABSTRACT

By manufacturing an organic EL element using a material for a light emitting layer including a pyrene-based compound represented by the following formula (2) as a host material and a polycyclic aromatic compound in which a plurality of aromatic rings is linked with a boron atom and a nitrogen atom or an oxygen atom as a dopant material, an organic EL element having, for example, excellent light emission efficiency is provided.

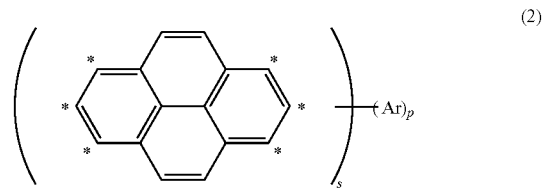

In the above formula (2), at least one hydrogen atom in a pyrene moiety may be substituted by an aryl having 6 to 10
(Continued)

carbon atoms or the like. Ar represents an aryl having 14 to 40 carbon atoms or a heteroaryl having 12 to 40 carbon atoms. These groups may be substituted by an aryl having 6 to 10 carbon atoms or the like. s and p each independently represent an integer of 1 or 2. s and p do not simultaneously represent 2. One or more hydrogen atoms in a compound represented by formula (2) may be each independently substituted by a halogen atom, cyano, or a deuterium atom.

10 Claims, 1 Drawing Sheet

(51) Int. Cl.
*H01L 51/50* (2006.01)
*C07D 209/82* (2006.01)
*C07D 333/52* (2006.01)
*C07D 307/78* (2006.01)

(52) U.S. Cl.
CPC ...... *H01L 51/0058* (2013.01); *H01L 51/0059* (2013.01); *H01L 51/0072* (2013.01); *H01L 51/0073* (2013.01); *H01L 51/0077* (2013.01); *H01L 51/5092* (2013.01); *H01L 51/5206* (2013.01); *H01L 51/5221* (2013.01); *C07D 209/82* (2013.01); *C07D 307/78* (2013.01); *C07D 333/52* (2013.01); *H01L 51/5012* (2013.01); *H01L 51/5056* (2013.01); *H01L 51/5072* (2013.01)

(56) References Cited

FOREIGN PATENT DOCUMENTS

| | | |
|---|---|---|
| JP | 2001-172232 A | 6/2001 |
| JP | 2005-170911 A | 6/2005 |
| WO | WO 2004/061047 A2 | 7/2004 |
| WO | WO 2015/102118 A1 | 7/2015 |
| WO | WO-2017104767 A1 * | 6/2017 ............. H01L 51/50 |

OTHER PUBLICATIONS

Machine translation of CN-106883203, translation generated Oct. 2020, 12 pages. (Year: 2020).*

* cited by examiner

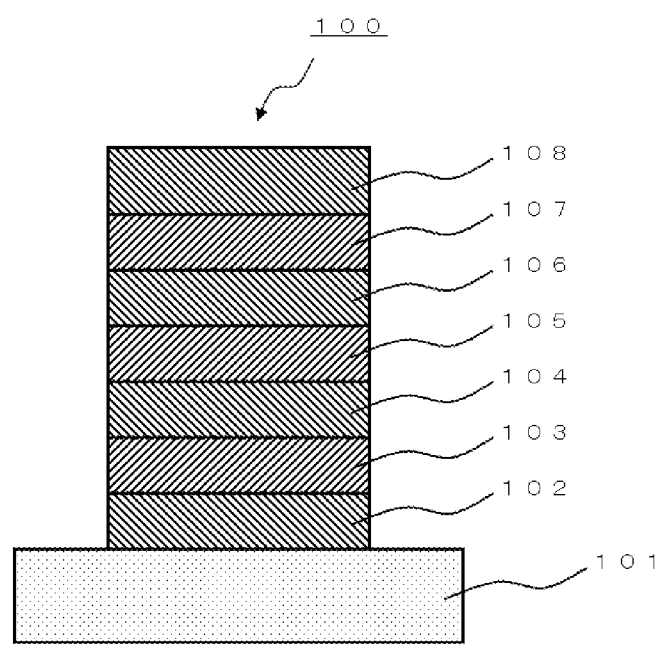

ORGANIC ELECTROLUMINESCENT ELEMENT

BACKGROUND

Technical Field

The present invention relates to an organic electroluminescent element having a light emitting layer containing a polycyclic aromatic compound as a dopant material and a specific pyrene compound as a host material, and a display apparatus and a lighting apparatus using the same.

Related Art

Conventionally, a display apparatus employing a luminescent element that is electroluminescent can be subjected to reduction of power consumption and thickness reduction, and therefore various studies have been conducted thereon. Furthermore, an organic electroluminescent element (hereinafter, referred to as an organic EL element) formed from an organic material has been studied actively because weight reduction or size expansion can be easily achieved. Particularly, active studies have been hitherto conducted on development of an organic material having light emitting characteristics for blue light which is one of the primary colors of light, or the like, and a combination of a plurality of materials having optimum light emitting characteristics, irrespective of whether the organic material is a high molecular weight compound or a low molecular weight compound.

An organic EL element has a structure having a pair of electrodes composed of a positive electrode and a negative electrode, and a single layer or a plurality of layers disposed between the pair of electrodes and containing an organic compound. The layer containing an organic compound includes a light emitting layer and a charge transport/injection layer for transporting or injecting charges such as holes or electrons. Various organic materials suitable for these layers have been developed.

As a material for a light emitting layer, for example, a benzofluorene-based compound has been developed (WO 2004/061047 A). Furthermore, as a hole transport material, for example, a triphenylamine-based compound has been developed (JP 2001-172232 A). Furthermore, as an electron transport material, for example, an anthracene-based compound has been developed (JP 2005-170911 A).

Furthermore, in recent years, a compound having a plurality of aromatic rings fused with a boron atom or the like as a central atom has also been reported (WO 2015/102118 A). This literature has evaluated an organic EL element in a case where the compound having a plurality of aromatic rings fused is selected as a dopant material of a light emitting layer, and particularly an anthracene-based compound (BH1 on page 442) or the like is selected among a very large number of materials described as a host material. However, a combination other than the above combination has not been specifically verified. Furthermore, if a combination constituting the light emitting layer is different, light emitting characteristics are also different. Therefore, characteristics obtained from another combination have not been found.

PRIOR ART REFERENCES

WO 2004/061047 A
JP 2001-172232 A
JP 2005-170911 A
WO 2015/102118 A

SUMMARY

As described above, various materials used in an organic EL element have been developed. However, in order to further enhance light emitting characteristics or to increase options of a material for a light emitting layer, it is desired to develop a combination of materials different from a conventional combination. Particularly, organic EL characteristics (particularly optimal light emitting characteristics) obtained from a combination other than the specific combination of host and dopant reported in Examples of WO 2015/102118 A have not been found.

As a result of intensive studies to solve the above problems, the present inventors have found that an excellent organic EL element can be obtained by disposing a light emitting layer containing a polycyclic aromatic compound having a plurality of aromatic rings linked with a boron atom and a nitrogen atom or an oxygen atom and a specific pyrene-based compound between a pair of electrodes to constitute an organic EL element, and have completed the present invention.

According to a preferable embodiment of the present invention, it is possible to provide a compound represented by formula (1) and a compound represented by formula (2), capable of obtaining optimum light emitting characteristics in combination with the compound represented by formula (1) By manufacturing an organic EL element using a material for a light emitting layer obtained by combining these compounds, it is possible to provide an organic EL element that is excellent in at least one of chromaticity, driving voltage, and quantum efficiency.

Item 1.

An organic electroluminescent element including a pair of electrodes composed of a positive electrode and a negative electrode and a light emitting layer disposed between the pair of electrodes, in which the light emitting layer includes at least one of a compound represented by the following general formula (1) and a multimer having a plurality of structures each represented by the following general formula (1), and at least one pyrene-based compound represented by the following general formula (2)

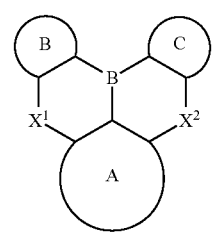

(1)

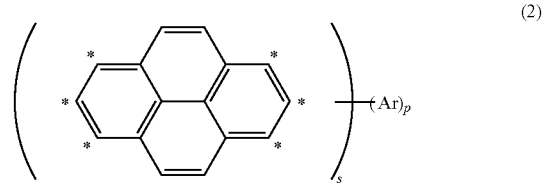

(2)

In the above formula (1), the ring A, ring B, and ring C each independently represent an aryl ring or a heteroaryl ring, and at least one hydrogen atom in these rings may be substituted, $X^1$ and $X^2$ each independently represent >O or >N—R, R in the >N—R represents an optionally substituted aryl, an optionally substituted heteroaryl, an optionally substituted alkyl, or an optionally substituted cycloalkyl, and R in the >N—R may be bonded to the ring A, ring B, and/or ring C with a linking group or a single bond, and at least one hydrogen atom in the compound or the structure represented by formula (1) may be each independently substituted by a halogen atom, cyano, or a deuterium atom, in the above formula (2), s pyrene moieties are bonded to p Ar moieties at any position of * in each of the pyrene moieties and any position in each of the Ar moieties, at least one hydrogen atom of the pyrene moieties may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, and at least one hydrogen atom in these substituents may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, Ar's each independently represent an aryl having 14 to 40 carbon atoms or a heteroaryl having 12 to 40 carbon atoms, and at least one hydrogen atom in these groups may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, s and p each independently represent an integer of 1 or 2, s and p do not simultaneously represent 2, when s represents 2, the two pyrene moieties including a substituent may be structurally the same or different, and when p represents 2, the two Ar moieties including a substituent may be structurally the same or different, and at least one hydrogen atom in the compound represented by formula (2) may be each independently substituted by a halogen atom, cyano, or a deuterium atom.

Item 2.

The organic electroluminescent element according to item 1, in which the Ar's each independently represent a group represented by the following general formula (Ar-1) or (Ar-2)

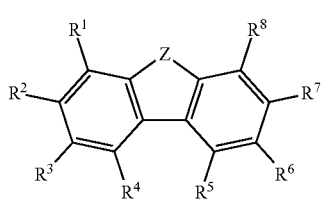

(Ar-1)

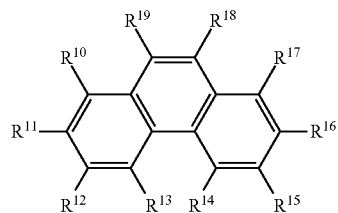

(Ar-2)

In each of the above formulas,

Z represents $>CR_2$, >N—R, >O, or >S,

R's in $>CR_2$ each independently represent an alkyl having 1 to 6 carbon atoms, a cycloalkyl having 3 to 14 carbon atoms, an aryl having 6 to 12 carbon atoms, or a heteroaryl having 2 to 12 carbon atoms, at least one hydrogen atom in the aryl and the heteroaryl may be substituted by an alkyl having 1 to 4 carbon atoms or a cycloalkyl having 5 to 10 carbon atoms, and R's may be bonded to each other to form a ring, R in >N—R represents an alkyl having 1 to 4 carbon atoms, a cycloalkyl having 5 to 10 carbon atoms, an aryl having 6 to 12 carbon atoms, or a heteroaryl having 2 to 12 carbon atoms, and at least one hydrogen atom in the aryl and the heteroaryl may be substituted by an alkyl having 1 to 4 carbon atoms or a cycloalkyl having 5 to 10 carbon atoms, $R^1$ to $R^8$ and $R^{10}$ to $R^{19}$ each independently represent a hydrogen atom, an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, at least one hydrogen atom in these groups may be substituted by an alkyl having 1 to 6 carbon atoms or a cycloalkyl having 3 to 14 carbon atoms, adjacent groups among $R^1$ to $R^8$ or adjacent groups among $R^{10}$ to $R^{19}$ may be bonded to each other to form a fused ring, the fused rings thus formed may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, and at least one hydrogen atom in these substituents may be substituted by an alkyl having 1 to 6 carbon atoms or a cycloalkyl having 3 to 14 carbon atoms, at least one hydrogen atom in the group represented by the above formula (Ar-1) or (Ar-2) may be each independently substituted by a halogen atom, cyano, or a deuterium atom, and the pyrene moiety in formula (2) is bonded to any position in the group represented by the above formula (Ar-1) or (Ar-2).

Item 3.

The organic electroluminescent element according to item 1 or 2, in which the compound represented by the above general formula (1) is a compound represented by the following general formula (1')

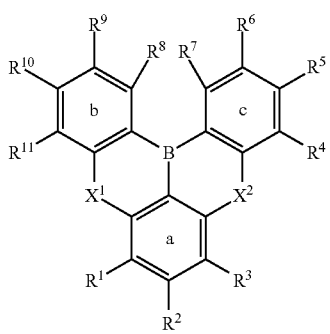

(1')

(In the above formula (1'), $R^1$ to $R^{11}$ each independently represent a hydrogen atom, an aryl, a heteroaryl, a diarylamino, a diheteroarylamino, an arylheteroarylamino, an alkyl, a cycloalkyl, an alkoxy, or an aryloxy, at least one hydrogen atom in these groups may be each independently substituted by an aryl, a heteroaryl, an alkyl, or a cycloalkyl, adjacent groups among $R^1$ to $R^{11}$ may be bonded to each other to form an aryl ring or a heteroaryl ring together with ring a, ring b, or ring c, at least one hydrogen atom in the ring thus formed may be each independently substituted by an aryl, a heteroaryl, a diarylamino, a diheteroarylamino, an arylheteroarylamino, an alkyl, a cycloalkyl, an alkoxy, or an aryloxy, and at least one hydrogen atom in these substituents may be each independently substituted by an aryl, a heteroaryl, an alkyl, or a cycloalkyl, $X^1$ and $X^2$ each independently represent >O or >N—R, R in the >N—R represents an aryl having 6 to 12 carbon atoms, a heteroaryl having 2 to 15 carbon atoms, an alkyl having 1 to 6 carbon atoms, or a cycloalkyl having 3 to 14 carbon atoms, at least one hydrogen atom in the aryl or the heteroaryl may be substituted by an alkyl having 1 to 4 carbon atoms or a cycloalkyl having 5 to 10 carbon atoms, R in the >N—R may be bonded to the ring a, ring b, and/or ring c via —O—, —S—, —C(—R)$_2$—, or a single bond, R in the —C(—R)$_2$— represents an alkyl having 1 to 6 carbon atoms or a cycloalkyl having 3 to 14 carbon atoms, and at least one hydrogen atom in the compound represented by formula (1') may be each independently substituted by a halogen atom, cyano, or a deuterium atom.

Item 4.

The organic electroluminescent element according to any one of items 1 to 3, in which the Ar's each independently represent a group represented by any one of the following general formulas (Ar-1-1) to (Ar-1-12) and (Ar-2-1) to (Ar-2-4).

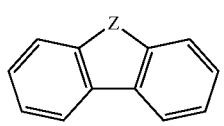

(Ar-1-1)

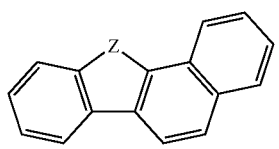

(Ar-1-2)

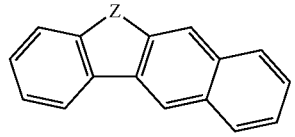

(Ar-1-3)

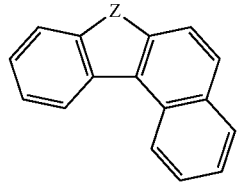

(Ar-1-4)

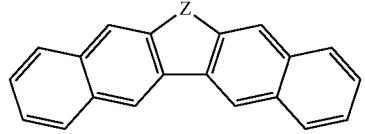

(Ar-1-5)

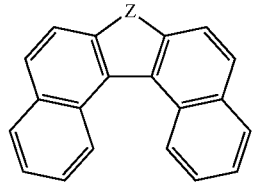

(Ar-1-6)

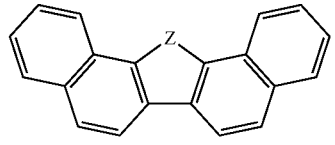

(Ar-1-7)

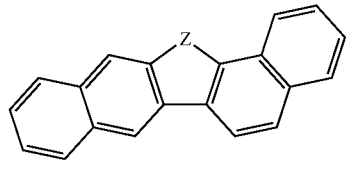

(Ar-1-8)

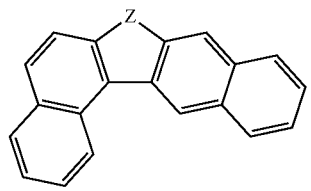

(Ar-1-9)

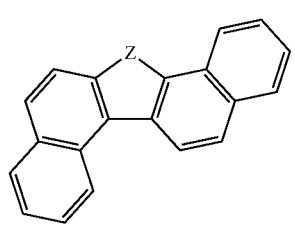

(Ar-1-10)

-continued (Ar-1-11)
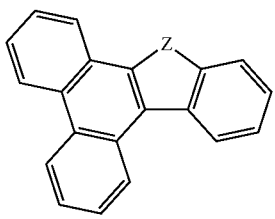

(Ar-1-12)
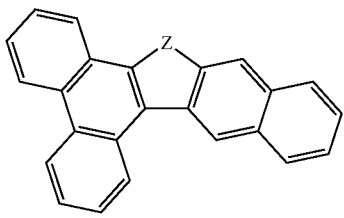

(Ar-2-1)
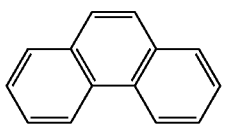

(Ar-2-2)
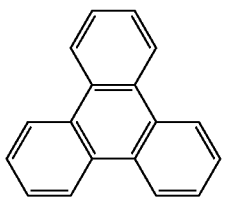

(Ar-2-3)
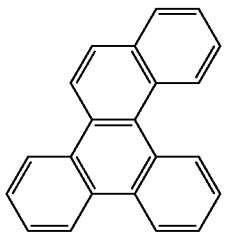

(Ar-2-4)
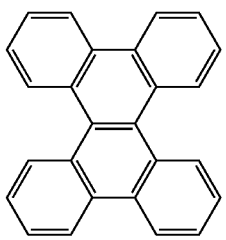

In each of the above formulas,

Z represents >CR$_2$, >N—R, >O, or >S,

R's in >CR$_2$ each independently represent an alkyl having 1 to 6 carbon atoms, a cycloalkyl having 3 to 14 carbon atoms, or an aryl having 6 to 12 carbon atoms, and R's may be bonded to each other to form a ring, R in >N—R represents an alkyl having 1 to 4 carbon atoms, a cycloalkyl having 5 to 10 carbon atoms, or an aryl having 6 to 12 carbon atoms, at least one hydrogen atom in each of groups represented by the above formulas may be each independently substituted by an aryl having 6 to 10 carbon atoms, a heteroaryl having 2 to 11 carbon atoms, an alkyl having 1 to 30 carbon atoms, or a cycloalkyl having 3 to 24 carbon atoms, at least one hydrogen atom in each of the groups represented by the above formulas may be each independently substituted by a halogen atom, cyano, or a deuterium atom, and the pyrene moiety in formula (2) is bonded to any position in a group represented by any one of the above formulas (Ar-1-1) to (Ar-1-12) and (Ar-2-1) to (Ar-2-4).

Item 5.

The organic electroluminescent element according to any one of items 1 to 4, in which the pyrene-based compound represented by the above general formula (2) is a compound represented by any one of the following structural formulas.

(2-1)
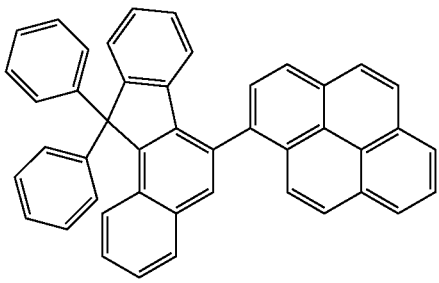

(2-46)
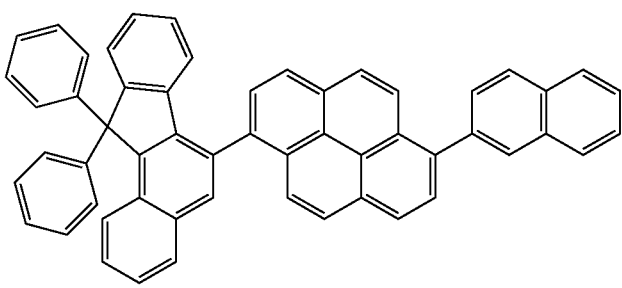

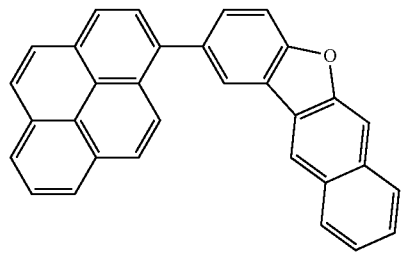
(2-174)
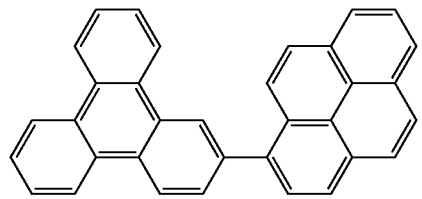
(2-350)
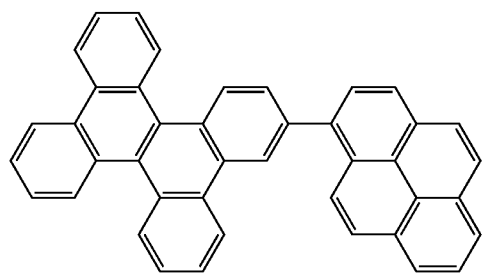
(2-356)
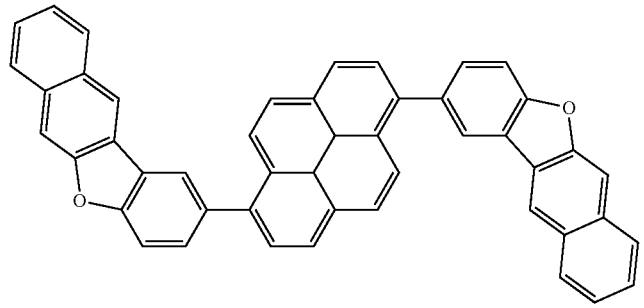
(2-359)
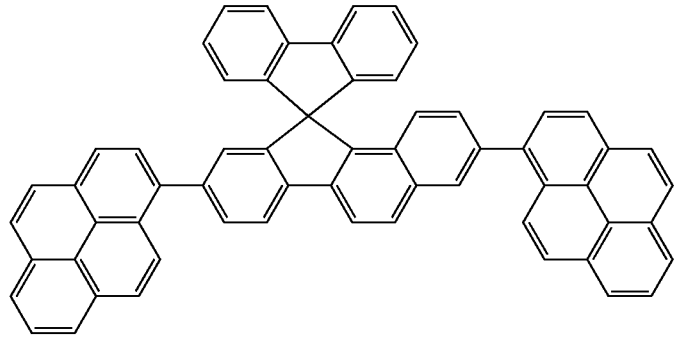
(2-1001)

-continued

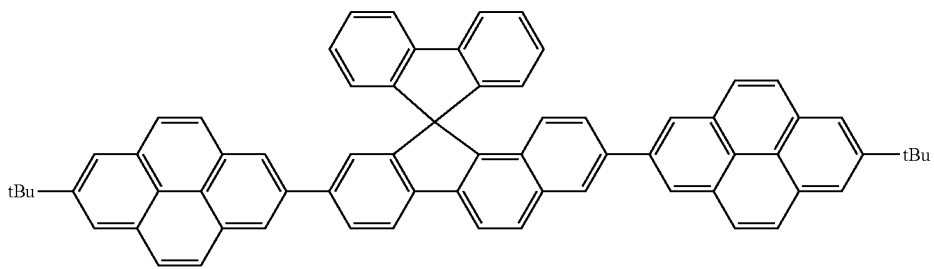
(2-1080)

Item 6.

The organic electroluminescent element according to any one of items 1 to 5, further including an electron transport layer and/or an electron injection layer disposed between the negative electrode and the light emitting layer, in which at least one of the electron transport layer and the electron injection layer includes at least one selected from the group consisting of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, and a quinolinol-based metal complex.

Item 7.

The organic electroluminescent element according to item 6, in which the electron transport layer and/or the electron injection layer further include/includes at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

Item 8.

A display apparatus including the organic electroluminescent element according to any one of items 1 to 7.

Item 9.

A lighting apparatus including the organic electroluminescent element according to any one of items 1 to 7.

Item 10.

A pyrene-based compound represented by the following general formula (2).

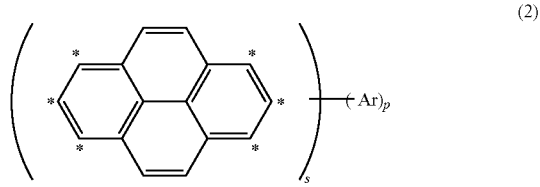
(2)

In the above formula, s pyrene moieties are bonded to p Ar moieties at any position of * in each of the pyrene moieties and any position in each of the Ar moieties, at least one hydrogen atom of the pyrene moieties may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 1 to 30 carbon atoms, an alkoxy having 1 to 30 carbon atoms, or an aryloxy having 1 to 30 carbon atoms, and at least one hydrogen atom in these substituents may be substituted by an alkyl having 1 to 6 carbon atoms or a cycloalkyl having 3 to 14 carbon atoms, Ar represents a group represented by the following general formula (Ar-1) or (Ar-3),

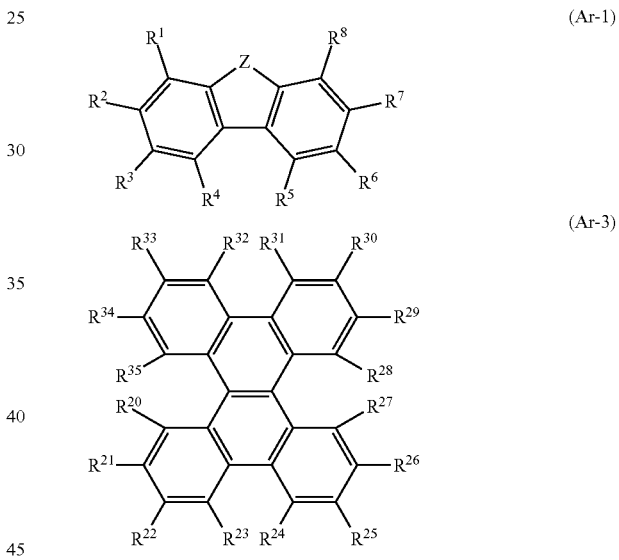

in each of the above formulas,

Z represents $>CR_2$,

R's in $>CR_2$ each independently represent an alkyl having 1 to 6 carbon atoms, a cycloalkyl having 3 to 14 carbon atoms, an aryl having 6 to 12 carbon atoms, or a heteroaryl having 2 to 12 carbon atoms, at least one hydrogen atom in the aryl and the heteroaryl may be substituted by an alkyl having 1 to 4 carbon atoms or a cycloalkyl having 5 to 10 carbon atoms, and R's may be bonded to each other to form a ring, $R^1$ to $R^8$ and $R^{20}$ to $R^{35}$ each independently represent a hydrogen atom, an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 1 to 30 carbon atoms, an alkoxy having 1 to 30 carbon atoms, or an aryloxy having 1 to 30 carbon atoms, at least one hydrogen atom in these groups may be substituted by an alkyl having 1 to 6 carbon atoms or a cycloalkyl having 3 to 14 carbon atoms, adjacent groups among $R^1$ to $R^8$ are bonded to each other to form a fused ring, adjacent groups among $R^{20}$ to $R^{35}$ may be bonded to each other to form a fused ring, the rings thus formed may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl group having 1 to 30 carbon atoms, an alkoxy having 1 to 30 carbon atoms, or an aryloxy having 1 to 30 carbon atoms, and at least one hydrogen atom in these substituents may be substituted by an alkyl having 1 to 6 carbon atoms or a cycloalkyl having 3 to 14 carbon atoms, s and p each independently represent an integer of 1 or 2, s and p do not simultaneously represent 2, when s represents 2, the two pyrene moieties including a substituent may be structurally the same or different, and when p represents 2, the two Ar moieties including a substituent may be structurally the same or different, and at least one hydrogen atom in the compound represented by formula (2) may be each independently substituted by a halogen atom, cyano, or a deuterium atom.

Item 11.

The pyrene-based compound according to item 10, represented by any one of the following structural formulas.

material for a light emitting layer obtained by combining these compounds, it is possible to provide an organic EL element particularly having excellent light emission efficiency and exhibiting well-balanced performance.

Furthermore, by introducing a cycloalkyl group into the compound of the above general formula (1) and a multimer thereof, reduction in melting point and sublimation temperature thereof can be expected. This means that thermal decomposition of a material and the like can be avoided because purification can be performed at a relatively low temperature in sublimation purification that is almost indispensable as a method for purifying a material for an organic device requiring high purity, such as an organic EL element. This also applies to a vacuum vapor deposition process which is a powerful means for manufacturing an organic device such as an organic EL element, and the process can be performed at a relatively low temperature. Therefore, thermal decomposition of a material can be avoided. As a result, a high performance organic device can be obtained. Furthermore, many of the above multimers have high sublimation temperatures due to high molecular weight, high planarity, and the like. Therefore, reduction in sublimation (2-1)

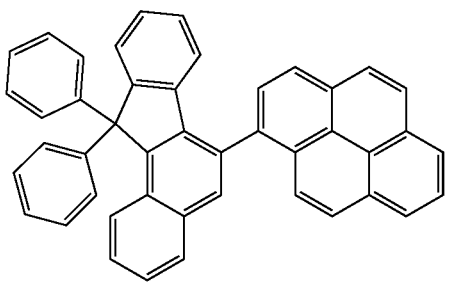

(2-46)

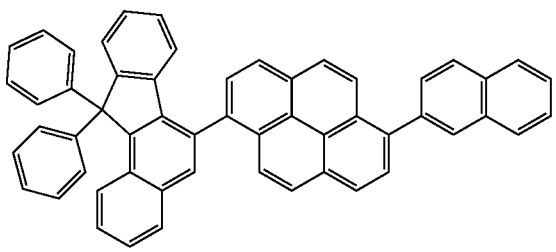

(2-356)

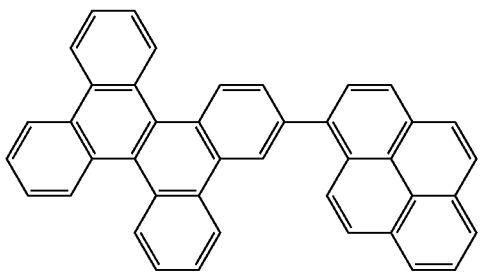

(2-1001)

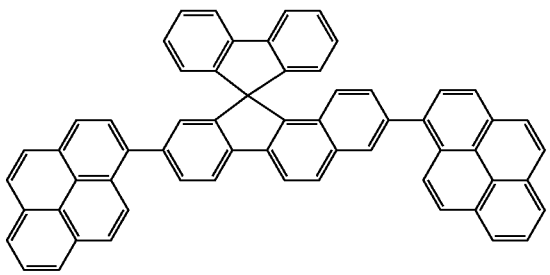

(2-1080)

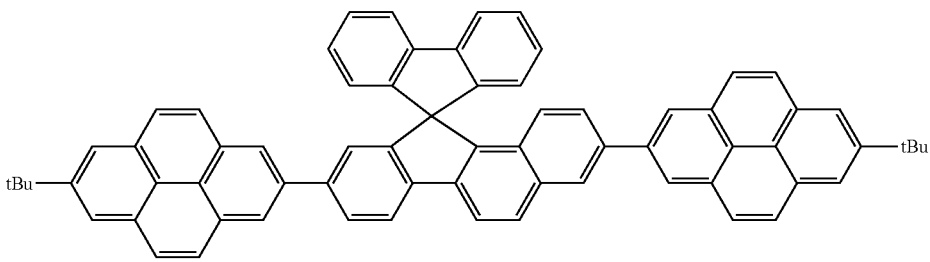

According to a preferable embodiment of the present invention, it is possible to provide a polycyclic aromatic compound represented by formula (1) and a pyrene-based compound represented by formula (2), capable of obtaining optimum light emitting characteristics in combination with the polycyclic aromatic compound represented by formula (1). By manufacturing an organic EL element using a temperature by introduction of a cycloalkyl group is more effective. Furthermore, solubility in an organic solvent is improved by the introduction of a cycloalkyl group. Therefore, application to manufacturing an element using a coating process is also possible. In addition, concentration quenching can be suppressed by introducing a substituent having a large size, such as a cycloalkyl. However, the present invention is not particularly limited to these principles.

BRIEF DESCRIPTION OF DRAWINGS

FIG. 1 is a schematic cross-sectional view illustrating an organic EL element according to the present embodiment.

DETAILED DESCRIPTION

1. Organic Electroluminescent Element According to an Embodiment of the Present Invention The present invention relates to an organic electroluminescent element including a pair of electrodes composed of a positive electrode and a negative electrode and a light emitting layer disposed between the pair of electrodes, in which the light emitting layer includes at least one polycyclic aromatic compound represented by the following general formula (1) and a multimer thereof having a plurality of structures each represented by the following general formula (1), and at least one pyrene-based compound represented by the following general formula (2).

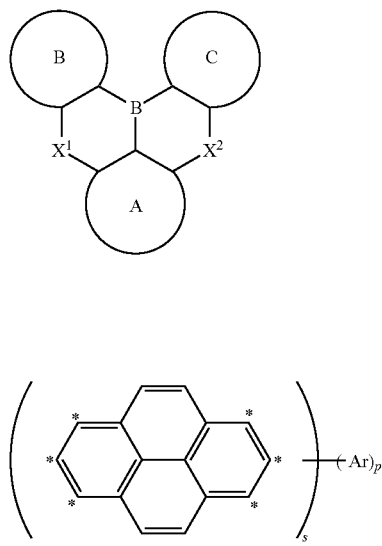

Note that the definitions of the reference signs in formulas (1) and (2) are the same as the definitions described above. Hereinafter, the definitions of the reference signs in the other formulas are the same as the definitions of the reference signs in the corresponding formulas described above unless otherwise particularly specified.

2. Polycyclic Aromatic Compound and Multimer Thereof

The polycyclic aromatic compound and a multimer thereof used in the present invention are a compound represented by the following general formula (1) or a multimer thereof having a plurality of structures each represented by the following general formula (1), and preferably, a compound represented by the following general formula (1') or a multimer having a plurality of structures each represented by the following general formula (1'). These compounds basically function as dopants.

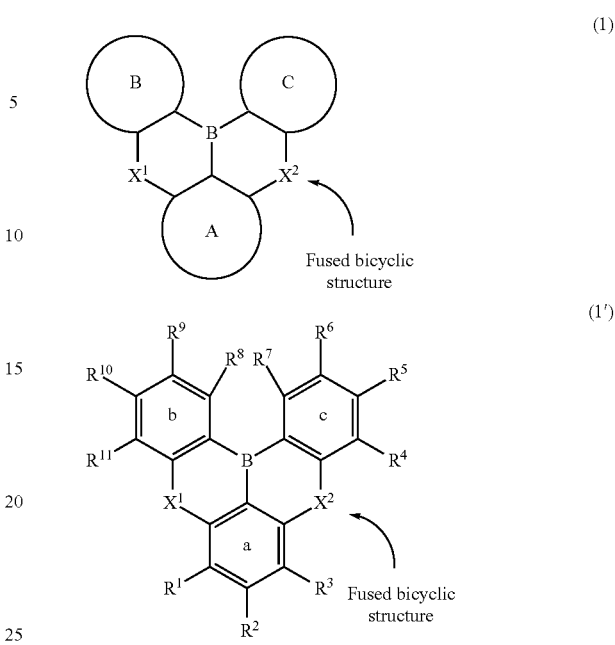

The ring A, ring B, and ring C in general formula (1) each independently represent an aryl ring or a heteroaryl ring, and at least one hydrogen atom in these rings may be substituted by a substituent. This substituent is preferably a substituted or unsubstituted aryl, a substituted or unsubstituted heteroaryl, a substituted or unsubstituted diarylamino, a substituted or unsubstituted diheteroarylamino, a substituted or unsubstituted arylheteroarylamino (an amino group having an aryl and a heteroaryl), a substituted or unsubstituted alkyl, a substituted or unsubstituted cycloalkyl, a substituted or unsubstituted alkoxy, or a substituted or unsubstituted aryloxy. In a case where these groups have substituents, examples of the substituents include an aryl, a heteroaryl, an alkyl, and a cycloalkyl. Furthermore, the aryl ring or the heteroaryl ring preferably has a 5-membered ring or 6-membered ring sharing a bond with a fused bicyclic structure at the center of general formula (1) constituted by a central element B (boron), $X^1$, and $X^2$.

Here, the "fused bicyclic structure" means a structure in which two saturated hydrocarbon rings including a central element B (boron), $X^1$, and $X^2$, indicated at the center of general formula (1), are fused. Furthermore, the "6-membered ring sharing a bond with the fused bicyclic structure" means, for example, ring a (benzene ring (6-membered ring)) fused to the fused bicyclic structure as represented by the above general formula (1'). Furthermore, the phrase "aryl ring or heteroaryl ring (which is ring A) has this 6-membered ring" means that the ring A is formed only with this 6-membered ring, or the ring A is formed by further fusing another ring or the like to this 6-membered ring so as to include this 6-membered ring. In other words, the "aryl ring or heteroaryl ring (which is ring A) having a 6-membered ring" referred to herein means that the 6-membered ring constituting the entirety or a part of the ring A is fused to the fused bicyclic structure. Similar description applies to the "ring B (ring b)", "ring C (ring c)", and the "5-membered ring".

The ring A (or ring B or ring C) in general formula (1) corresponds to ring a and its substituents $R^1$ to $R^3$ (or ring b and its substituents $R^8$ to $R^{11}$, or ring c and its substituents $R^4$ to $R^7$) in general formula (1'). That is, general formula (1') corresponds to a structure in which "rings A to C each having a 6-membered ring" have been selected as the rings A to C of general formula (1). For this meaning, the rings of general formula (1') are represented by small letters a to c.

In general formula (1'), adjacent groups among the substituents $R^1$ to $R^{11}$ of the ring a, ring b, and ring c may be bonded to each other to form an aryl ring or a heteroaryl ring together with the ring a, ring b, or ring c, at least one hydrogen atom in the ring thus formed may be substituted by an aryl, a heteroaryl, a diarylamino, a diheteroarylamino, an arylheteroarylamino, an alkyl, a cycloalkyl, an alkoxy, or an aryloxy, and at least one hydrogen atom in these substituents may be substituted by an aryl, a heteroaryl, an alkyl, or a cycloalkyl. Therefore, in a polycyclic aromatic compound represented by general formula (1'), a ring structure constituting a compound changes as represented by the following formulas (1'-1) and (1'-2) according to a mutual bonding form of substituents in the ring a, ring b, and ring c. Ring A', ring B', and ring C' in each formula correspond to the ring A, ring B, and ring C in general formula (1), respectively.

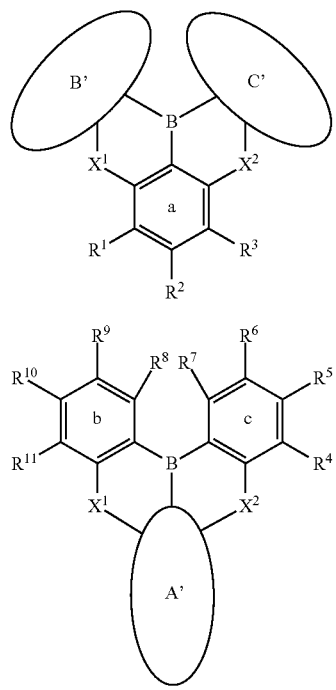

(1'-1)

(1'-2)

The ring A', ring B', and ring C' in the above formulas (1'-1) and (1'-2) each represent, to be described in connection with general formula (1'), an aryl ring or a heteroaryl ring formed by bonding adjacent groups among the substituents $R^1$ to $R^{11}$ together with the ring a, ring b, and ring c, respectively (may also be referred to as a fused ring obtained by fusing another ring structure to the ring a, ring b, or ring c). Incidentally, although not indicated in the formula, there is also a compound in which all of the ring a, ring b, and ring c have been changed to the ring A', ring B' and ring C'. Furthermore, as apparent from the above formulas (1'-1) and (1'-2), for example, $R^8$ of the ring b and $R^7$ of the ring c, $R^{11}$ of the ring b and $R^1$ of the ring a, $R^4$ of the ring c and $R^3$ of the ring a, and the like do not correspond to "adjacent groups", and these groups are not bonded to each other. That is, the term "adjacent groups" means adjacent groups on the same ring.

For example, the compound represented by formula (1'-1) or (1'-2) is a compound having ring A' (or ring B' or ring C') which is formed by fusing a benzene ring, an indole ring, a pyrrole ring, a benzofuran ring, or a benzothiophene ring to the benzene ring which is the ring a (or ring b or ring c), and the fused ring A' (or fused ring B' or fused ring C') that has been formed is a naphthalene ring, a carbazole ring, an indole ring, a dibenzofuran ring, or a dibenzothiophene ring.

$X^1$ and $X^2$ in general formula (1) each independently represent >O or >N—R, while R in the >N—R represents an optionally substituted aryl, an optionally substituted heteroaryl, an optionally substituted alkyl, or an optionally substituted cycloalkyl, and R in the >N—R may be bonded to the ring B and/or ring C with a linking group or a single bond. The linking group is preferably —O—, —S— or —C(—R)$_2$—. Incidentally, R in the "—C(—R)$_2$—" represents a hydrogen atom, an alkyl, or a cycloalkyl. This description also applies to $X^1$ and $X^2$ in general formula (1')

Here, the provision that "R in the >N—R is bonded to the ring A, ring B, and/or ring C with a linking group or a single bond" for general formula (1) corresponds to the provision that "R in the >N—R is bonded to the ring a, ring b, and/or ring c with —O—, —S—, —C(—R)$_2$— or a single bond" for general formula (1').

This provision can be expressed by a compound having a ring structure in which $X^1$ or $X^2$ is incorporated into the fused ring B' or fused ring C', represented by the following formula (1'-3-1). That is, for example, the compound is a compound having the ring B' (or ring C') formed by fusing another ring to a benzene ring which is the ring b (or ring c) in general formula (1') so as to incorporate $X^1$ (or $X^2$). The fused ring B' (or fused ring C') thus formed is, for example, a phenoxazine ring, a phenothiazine ring, or an acridine ring.

Furthermore, the above provision can be expressed by a compound having a ring structure in which $X^1$ and/or $X^2$ are/is incorporated into the fused ring A', represented by the following formula (1'-3-2) or (1'-3-3). That is, for example, the compound is a compound having ring A' formed by fusing another ring to a benzene ring which is the ring a in general formula (1') so as to incorporate $X^1$ (and/or $X^2$). The fused ring A' thus formed is, for example, a phenoxazine ring, a phenothiazine ring, or an acridine ring.

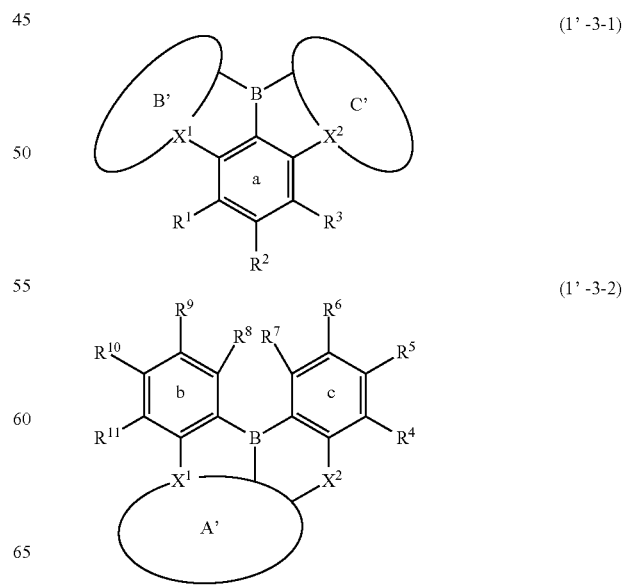

(1'-3-1)

(1'-3-2)

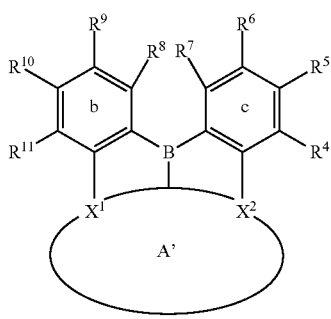

(1'-3-3)

The "aryl ring" as the ring A, ring B, or ring C of general formula (1) is, for example, an aryl ring having 6 to 30 carbon atoms, and the aryl ring is preferably an aryl ring having 6 to 16 carbon atoms, more preferably an aryl ring having 6 to 12 carbon atoms, and particularly preferably an aryl ring having 6 to 10 carbon atoms. Incidentally, this "aryl ring" corresponds to the "aryl ring formed by bonding adjacent groups among $R^1$ to $R^{11}$ together with the ring a, ring b, or ring c" defined by general formula (1'). The ring a (or ring b or ring c) is already constituted by a benzene ring having 6 carbon atoms, and therefore the carbon number of 9 in total of a fused ring obtained by fusing a 5-membered ring to this benzene ring becomes a lower limit of the carbon number.

Specific examples of the "aryl ring" include a benzene ring which is a monocyclic system; a biphenyl ring which is a bicyclic system; a naphthalene ring which is a fused bicyclic system; a terphenyl ring (m-terphenyl, o-terphenyl, or p-terphenyl) which is a tricyclic system; an acenaphthylene ring, a fluorene ring, a phenalene ring and a phenanthrene ring which are fused tricyclic systems; a triphenylene ring, a pyrene ring and a naphthacene ring which are fused tetracyclic systems; and a perylene ring and a pentacene ring which are fused pentacyclic systems.

The "heteroaryl ring" as the ring A, ring B, or ring C of general formula (1) is, for example, a heteroaryl ring having 2 to 30 carbon atoms, and the heteroaryl ring is preferably a heteroaryl ring having 2 to 25 carbon atoms, more preferably a heteroaryl ring having 2 to 20 carbon atoms, still more preferably a heteroaryl ring having 2 to 15 carbon atoms, and particularly preferably a heteroaryl ring having 2 to 10 carbon atoms. In addition, examples of the "heteroaryl ring" include a heterocyclic ring containing 1 to 5 heteroatoms selected from an oxygen atom, a sulfur atom, and a nitrogen atom in addition to a carbon atom as a ring-constituting atom. Incidentally, this "heteroaryl ring" corresponds to the "heteroaryl ring formed by bonding adjacent groups among the $R^1$ to $R^{11}$ together with the ring a, ring b, or ring c" defined by general formula (1'). The ring a (or ring b or ring c) is already constituted by a benzene ring having 6 carbon atoms, and therefore the carbon number of 6 in total of a fused ring obtained by fusing a 5-membered ring to this benzene ring becomes a lower limit of the carbon number.

Specific examples of the "heteroaryl ring" include a pyrrole ring, an oxazole ring, an isoxazole ring, a thiazole ring, an isothiazole ring, an imidazole ring, an oxadiazole ring, a thiadiazole ring, a triazole ring, a tetrazole ring, a pyrazole ring, a pyridine ring, a pyrimidine ring, a pyridazine ring, a pyrazine ring, a triazine ring, an indole ring, an isoindole ring, a 1H-indazole ring, a benzimidazole ring, a benzoxazole ring, a benzothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an acridine ring, a phenoxathiin ring, a phenoxazine ring, a phenothiazine ring, a phenazine ring, an indolizine ring, a furan ring, a benzofuran ring, an isobenzofuran ring, a dibenzofuran ring, a thiophene ring, a benzothiophene ring, a dibenzothiophene ring, a furazane ring, and a thianthrene ring.

At least one hydrogen atom in the above "aryl ring" or "heteroaryl ring" may be substituted by a substituted or unsubstituted "aryl", a substituted or unsubstituted "heteroaryl", a substituted or unsubstituted "diarylamino", a substituted or unsubstituted "diheteroarylamino", a substituted or unsubstituted "arylheteroarylamino", a substituted or unsubstituted "alkyl", a substituted or unsubstituted "cycloalkyl", a substituted or unsubstituted "alkoxy", or a substituted or unsubstituted "aryloxy", which is a primary substituent. Examples of the aryl of the "aryl", "heteroaryl", and "diarylamino", the heteroaryl of the "diheteroarylamino", the aryl and the heteroaryl of the "arylheteroarylamino", and the aryl of the "aryloxy" as these primary substituents include a monovalent group of the "aryl ring" or "heteroaryl ring" described above.

Furthermore, the "alkyl" as the primary substituent may be either linear or branched, and examples thereof include a linear alkyl having 1 to 24 carbon atoms and a branched alkyl having 3 to 24 carbon atoms. The alkyl is preferably an alkyl having 1 to 18 carbon atoms (branched alkyl having 3 to 18 carbon atoms), more preferably an alkyl having 1 to 12 carbon atoms (branched alkyl having 3 to 12 carbon atoms), still more preferably an alkyl having 1 to 6 carbon atoms (branched alkyl having 3 to 6 carbon atoms), and particularly preferably an alkyl having 1 to 4 carbon atoms (branched alkyl having 3 or 4 carbon atoms).

Specific examples of the alkyl include a methyl, an ethyl, an n-propyl, an isopropyl, an n-butyl, an isobutyl, an s-butyl, a t-butyl, an n-pentyl, an isopentyl, a neopentyl, a t-pentyl, an n-hexyl, a 1-methylpentyl, a 4-methyl-2-pentyl, a 3,3-dimethylbutyl, a 2-ethylbutyl, an n-heptyl, a 1-methylhexyl, an n-octyl, a t-octyl, a 1-methylheptyl, a 2-ethylhexyl, a 2-propylpentyl, an n-nonyl, a 2,2-dimethylheptyl, a 2,6-dimethyl-4-heptyl, a 3,5,5-trimethylhexyl, an n-decyl, an n-undecyl, a 1-methyldecyl, an n-dodecyl, an n-tridecyl, a 1-hexylheptyl, an n-tetradecyl, an n-pentadecyl, an n-hexadecyl, an n-heptadecyl, an n-octadecyl, and an n-eicosyl.

Examples of the "cycloalkyl" as the first substituent include a cycloalkyl having 3 to 24 carbon atoms, a cycloalkyl having 3 to 20 carbon atoms, a cycloalkyl having 3 to 16 carbon atoms, a cycloalkyl having 3 to 14 carbon atoms, a cycloalkyl having 5 to 10 carbon atoms, a cycloalkyl having 5 to 8 carbon atoms, a cycloalkyl having 5 or 6 carbon atoms, and a cycloalkyl having 5 carbon atoms.

Specific examples of the cycloalkyl include cyclopropyl, methylcyclopropyl, cyclobutyl, methylcyclobutyl, cyclopentyl, methylcyclopentyl, cyclohexyl, methylcyclohexyl, cycloheptyl, methylcycloheptyl, cyclooctyl, methylcyclooctyl, cyclononyl, methylcyclononyl, cyclodecyl, methylcyclodecyl, bicyclo[1.0.1]butyl, bicyclo[1.1.1]pentyl, bicyclo[2.0.1]pentyl, bicyclo[1.2.1]hexyl, bicyclo[3.0.1]hexyl, bicyclo[2.1.2]heptyl, bicyclo[2.2.2]octyl, adamantyl, diamantyl, decahydronaphthalenyl, and decahydroazulenyl.

Furthermore, examples of the "alkoxy" as the primary substituent include a linear alkoxy having 1 to 24 carbon atoms and a branched alkoxy having 3 to 24 carbon atoms. The alkoxy is preferably an alkoxy having 1 to 18 carbon atoms (branched alkoxy having 3 to 18 carbon atoms), more preferably an alkoxy having 1 to 12 carbon atoms (branched alkoxy having 3 to 12 carbon atoms), still more preferably an alkoxy having 1 to 6 carbon atoms (branched alkoxy having 3 to 6 carbon atoms), and particularly preferably an alkoxy having 1 to 4 carbon atoms (branched alkoxy having 3 or 4 carbon atoms).

Specific examples of the alkoxy include methoxy, ethoxy, propoxy, isopropoxy, butoxy, isobutoxy, s-butoxy, t-butoxy, pentyloxy, hexyloxy, heptyloxy, and octyloxy.

In the substituted or unsubstituted "aryl", substituted or unsubstituted "heteroaryl", substituted or unsubstituted "diarylamino", substituted or unsubstituted "diheteroarylamino", substituted or unsubstituted "arylheteroarylamino", substituted or unsubstituted "alkyl", substituted or unsubstituted "cycloalkyl", substituted or unsubstituted "alkoxy", or substituted or unsubstituted "aryloxy", which is the primary substituent, at least one hydrogen atom may be substituted by a secondary substituent, as described to be substituted or unsubstituted. Examples of this secondary substituent include an aryl, a heteroaryl, an alkyl, and a cycloalkyl, and for specific examples thereof, the above description on the monovalent group of the "aryl ring" or "heteroaryl ring" and the "alkyl" or "cycloalkyl" as the primary substituent can be referred to. Furthermore, the aryl or heteroaryl as the secondary substituent includes a group in which at least one hydrogen atom in the aryl or heteroaryl is substituted by an aryl such as phenyl (specific examples are the groups described above), an alkyl such as methyl (specific examples are the groups described above), or a cycloalkyl such as cyclohexyl (specific examples are the groups described above). For example, when the secondary substituent is a carbazolyl group, a carbazolyl group in which at least one hydrogen atom at the 9-position is substituted by an aryl such as phenyl, an alkyl such as methyl, or a cycloalkyl such as cyclohexyl is also included in the heteroaryl as the secondary substituent.

Examples of the aryl, the heteroaryl, the aryl of the diarylamino, the heteroaryl of the diheteroarylamino, the aryl and heteroaryl of the arylheteroarylamino, or the aryl of the aryloxy in $R^1$ to $R^{11}$ of general formula (1') include the monovalent groups of the "aryl ring" or "heteroaryl ring" described in general formula (1). Furthermore, for the alkyl, cycloalkyl, or alkoxy in $R^1$ to $R^{11}$, the above description on the "alkyl", "cycloalkyl", or "alkoxy" as the primary substituent in the above description of general formula (1) can be referred to. In addition, similar description applies to the aryl, the heteroaryl, the alkyl, or the cycloalkyl as a substituent on these groups. Furthermore, similar description applies to the heteroaryl, the diarylamino, the diheteroarylamino, the arylheteroarylamino, the alkyl, the cycloalkyl, the alkoxy, or the aryloxy in a case of forming an aryl ring or a heteroaryl ring by bonding adjacent groups among $R^1$ to $R^{11}$ together with the ring a, ring b, or ring c, as a substituent on these rings, and the aryl, the heteroaryl, the alkyl, or the cycloalkyl as a further substituent.

R in >N—R in $X^1$ and $X^2$ of general formula (1) represents an aryl, a heteroaryl, an alkyl, or a cycloalkyl which may be substituted by the secondary substituent described above, and at least one hydrogen atom in the aryl, heteroaryl, alky, or cycloalkyl may be substituted by, for example, an alkyl or a cycloalkyl. Examples of this aryl, heteroaryl, alkyl, and cycloalkyl include the groups described above. Particularly, an aryl having 6 to 10 carbon atoms (for example, phenyl or naphthyl), a heteroaryl having 2 to 15 carbon atoms (for example, carbazolyl), an alkyl having 1 to 4 carbon atoms (for example, methyl or ethyl), and a cycloalkyl having 3 to 16 carbon atoms (for example, bicyclooctyl or adamantyl) are preferable. This description also applies to $X^1$ and $X^2$ in general formula (1').

R in "—C(—R)$_2$—" which is a linking group in general formula (1) represents a hydrogen atom, an alkyl, or a cycloalkyl, and examples of the alkyl and cycloalkyl include the groups described above. Particularly, an alkyl having 1 to 4 carbon atoms (for example, methyl or ethyl) is preferable. This description also applies to "—C(—R)$_2$—" as a linking group for general formula (1').

Furthermore, the invention of the present application relates to a multimer of a polycyclic aromatic compound having a plurality of unit structures each represented by general formula (1), and preferably to a multimer of a polycyclic aromatic compound having a plurality of unit structures each represented by general formula (1'). The multimer is preferably a dimer to a hexamer, more preferably a dimer or a trimer, and a particularly preferably a dimer. The multimer only needs to be in a form having a plurality of unit structures described above in one compound, and for example, the multimer may be in a form in which a plurality of unit structures is bonded with a linking group such as a single bond, an alkylene group having 1 to 3 carbon atoms, a phenylene group, or a naphthylene group. In addition, the multimer may be in a form in which a plurality of unit structures is bonded such that any ring contained in the unit structure (ring A, ring B or ring C, or ring a, ring b or ring c) is shared by the plurality of unit structures, or may be in a form in which the unit structures are bonded such that any rings contained in the unit structures (ring A, ring B or ring C, or ring a, ring b or ring c) are fused.

Examples of such a multimer include multimer compounds represented by the following formulas (1'-4), (1'-4-1), (1'-4-2), (1'-5-1) to (1'-5-4), and (1'-6). To be described in connection with general formula (1'), the multimer compound represented by the following formula (1'-4) includes a plurality of unit structures each represented by general formula (1') in one compound so as to share a benzene ring as the ring a. Furthermore, to be described in connection with general formula (1'), the multimer compound represented by the following formula (1'-4-1) includes two unit structures each represented by general formula (1') in one compound so as to share a benzene ring as the ring a. Furthermore, to be described in connection with general formula (1'), the multimer compound represented by the following formula (1'-4-2) includes three unit structures each represented by general formula (1') in one compound so as to share a benzene ring as the ring a. Furthermore, to be described in connection with general formula (1'), each of the multimer compounds represented by the following formulas (1'-5-1) to (1'-5-4) includes a plurality of unit structures each represented by general formula (1') in one compound so as to share a benzene ring as ring b (or ring c). Furthermore, to be described in connection with general formula (1'), for example, the multimer compound represented by the following formula (1'-6) includes a plurality of unit structures each represented by general formula (1') in one compound such that a benzene ring as ring b (or ring a or ring c) of a certain unit structure and a benzene ring as ring b (or ring a or ring c) of a certain unit structure are fused.

(1'-4)
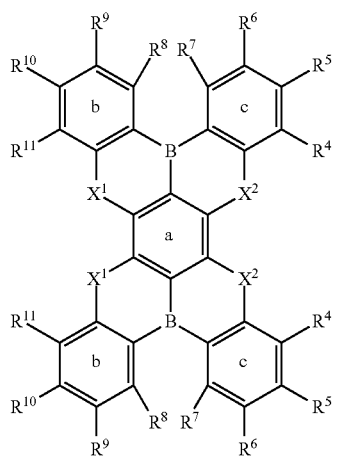
(1'-4-1)
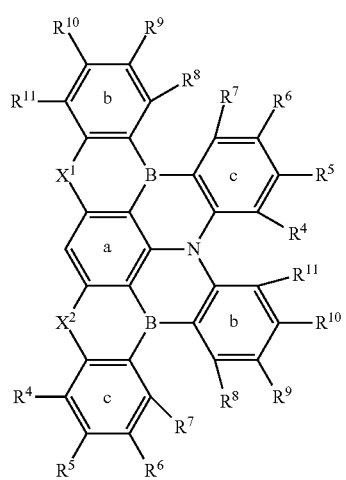
(1'-4-2)
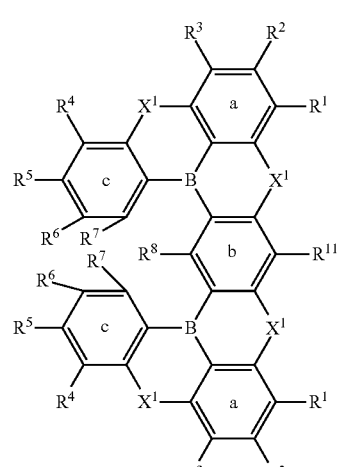
(1'-5-1)
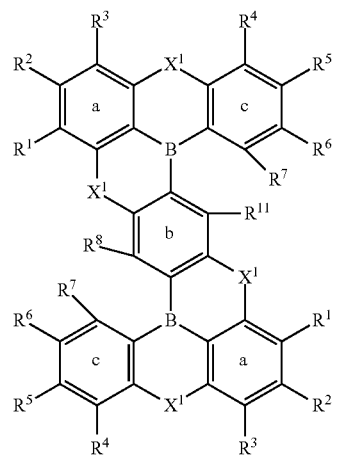
(1'-5-2)
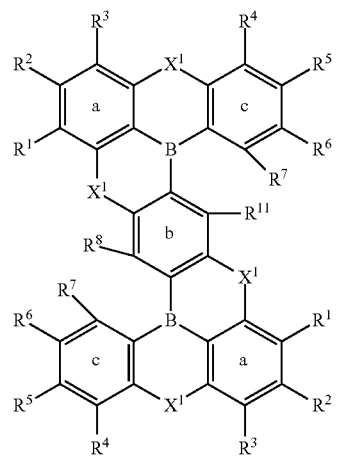
(1'-5-3)
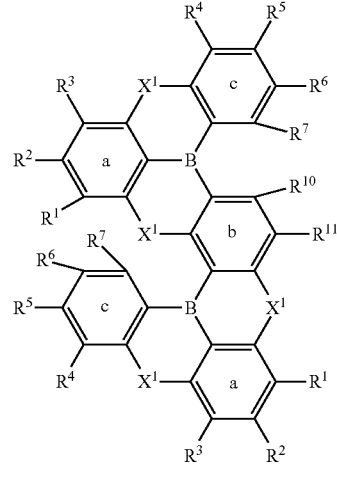

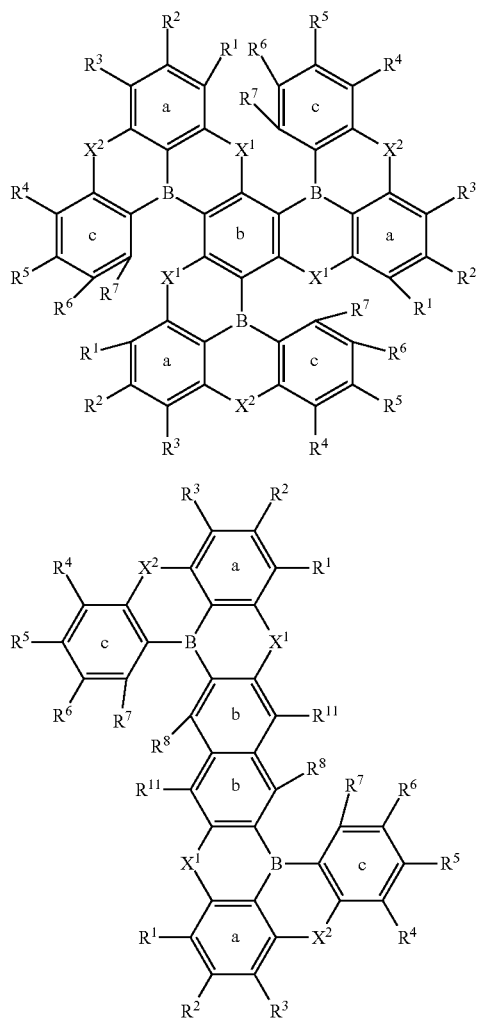

(1'-5-4)

(1'-6)

The multimer compound may be a multimer in which a multimer form represented by formula (1'-4), (1'-4-1), or (1'-4-2) and a multimer form represented by any one of formulas (1'-5-1) to (1'-5-4) or (1'-6) are combined, may be a multimer in which a multimer form represented by any one of formula (1'-5-1) to (1'-5-4) and a multimer form represented by formula (1'-6) are combined, or may be a multimer in which a multimer form represented by formula (1'-4), (1'-4-1), or (1'-4-2), a multimer form represented by any one of formulas (1'-5-1) to (1'-5-4), and a multimer form represented by formula (1'-6) are combined.

Furthermore, all or some of the hydrogen atoms in a chemical structure of the polycyclic aromatic compound represented by general formula (1) or (1') or a multimer thereof may be substituted by halogen atoms, cyanos, or deuterium atoms. For example, in formula (1), a hydrogen atom in the ring A, ring B, ring C (ring A to ring C are aryl rings or heteroaryl rings), substituents on the ring A to ring C, and R (=aryl, heteroaryl, alkyl, or cycloalkyl) when $X^1$ and $X^2$ each represent >N—R may be substituted by a halogen atom, cyano, or a deuterium atom. Among these forms, a form in which all or some of the hydrogen atoms in the aryl or heteroaryl are substituted by halogen atoms, cyanos, or deuterium atoms may be mentioned. The halogen is fluorine, chlorine, bromine, or iodine, preferably fluorine, chlorine, or bromine, and more preferably fluorine or chlorine.

Specific examples of the polycyclic aromatic compound according to an embodiment of the present invention include compounds represented by the following structural formulas. Incidentally, in the following structural formulas, "Me" represents a methyl group, "tBu" represents a tertiary butyl group, "iPr" represents an isopropyl group, "Ph" represents a phenyl group, and "D" a represents deuterium atom.

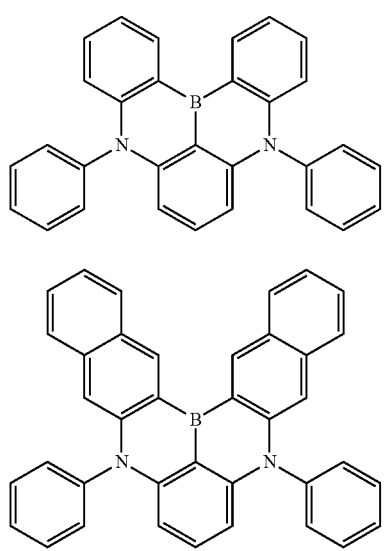

-continued
(1-5)
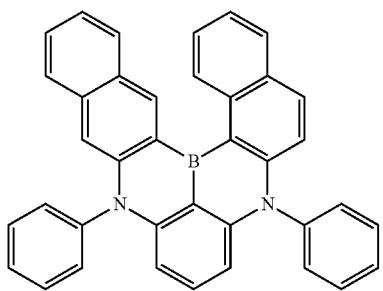
(1-6)
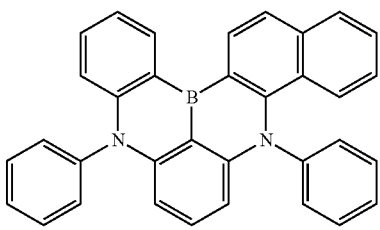
(1-7)
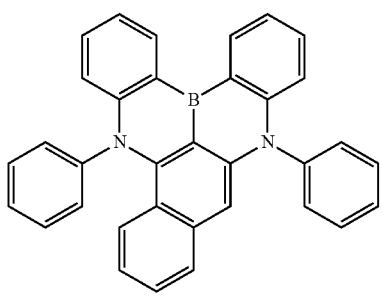
(1-8)
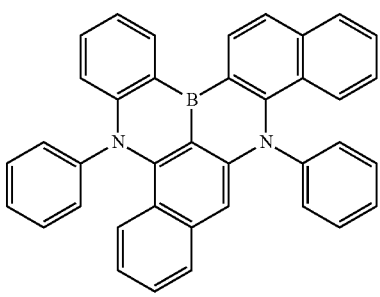
(1-9)
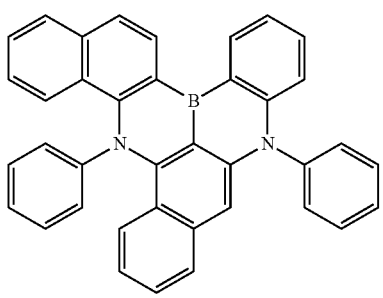
(1-10)
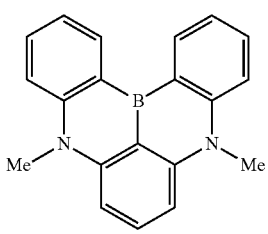
(1-11)
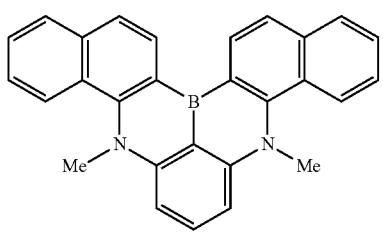
(1-12)
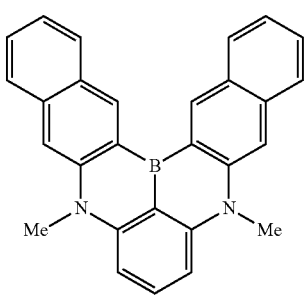
(1-13)
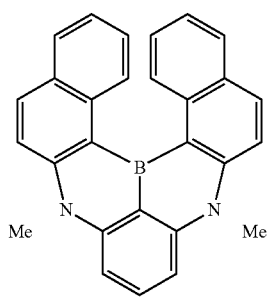
(1-14)
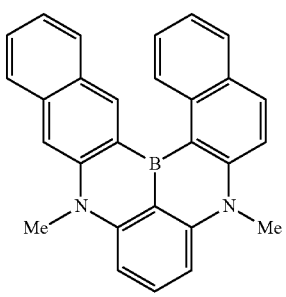

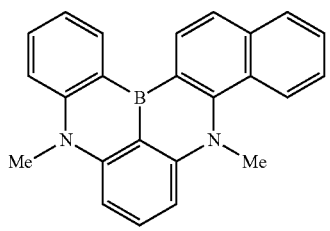
(1-15)
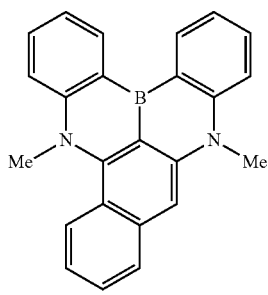
(1-16)
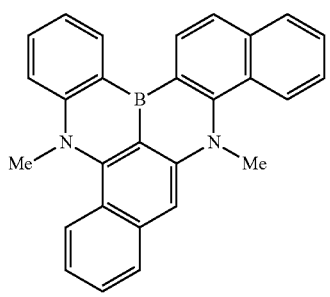
(1-17)
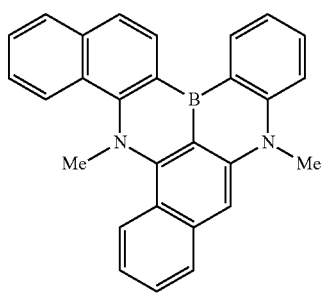
(1-18)
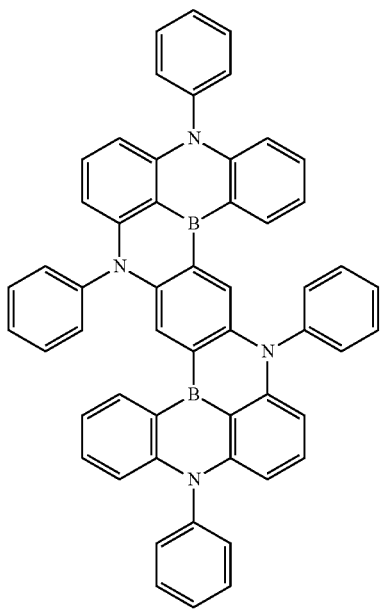
(1-19)
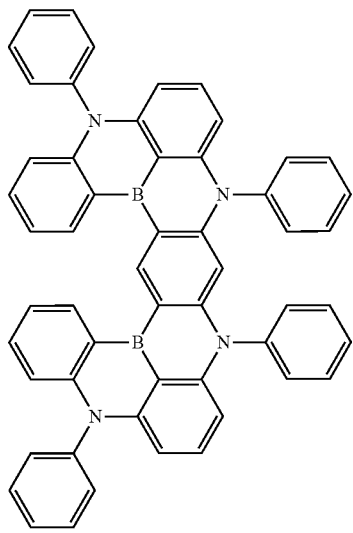
(1-20)
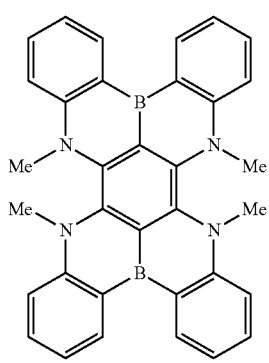
(1-21)
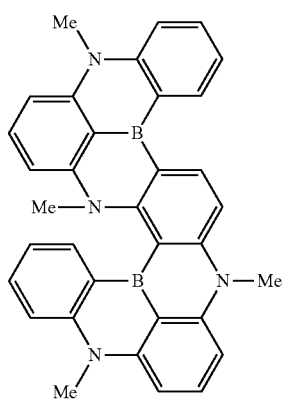
(1-22)

-continued
(1-23)
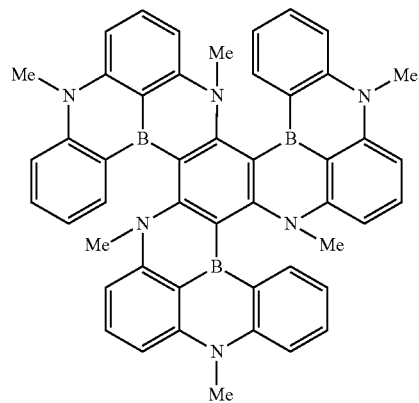
(1-24)
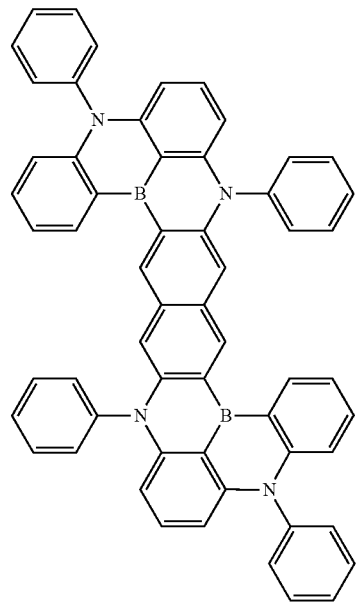
(1-25)
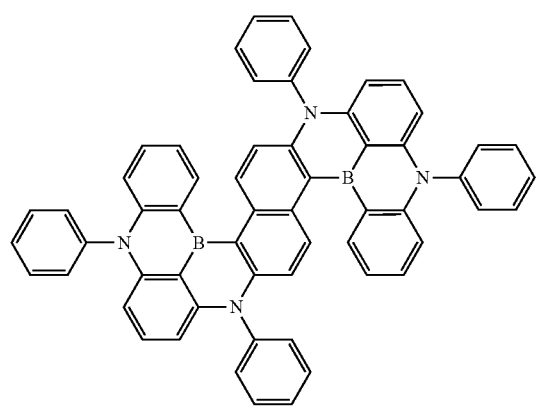
(1-26)
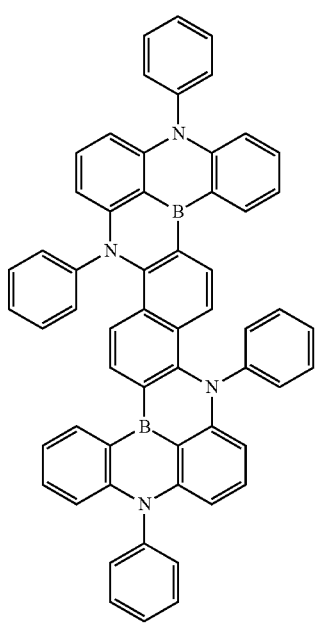

-continued
(1-27)
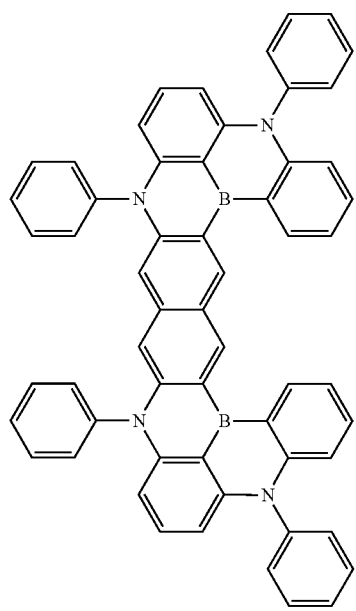
(1-28)
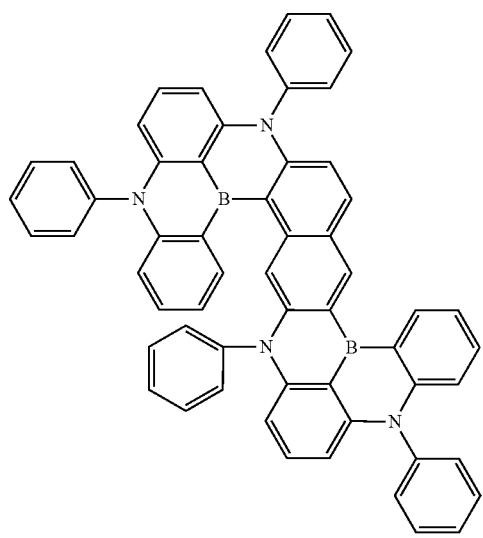
(1-30)
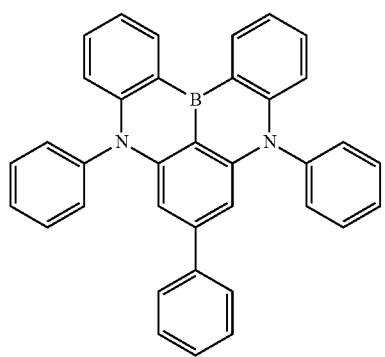
(1-31)
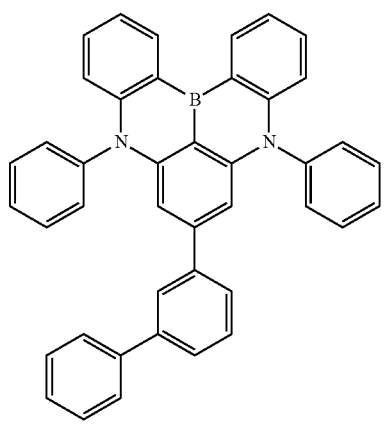
(1-32)
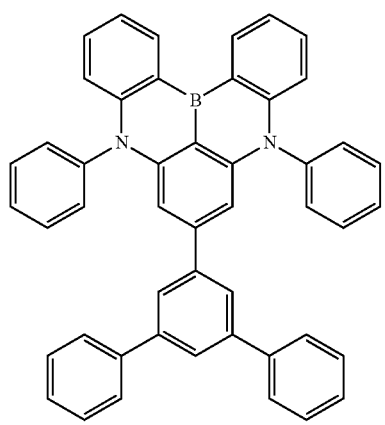
(1-33)
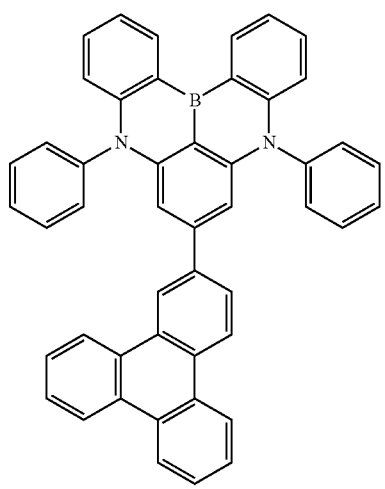

(1-34)
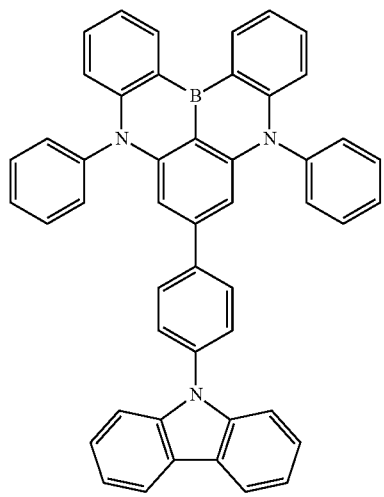
(1-35)
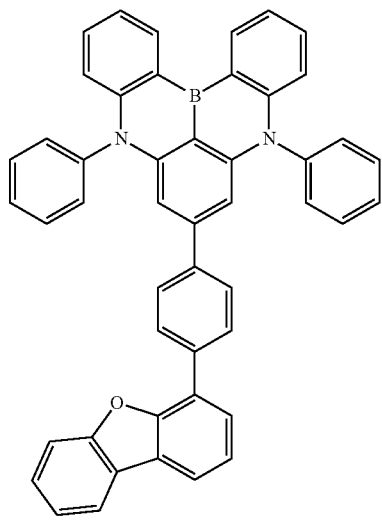
(1-36)
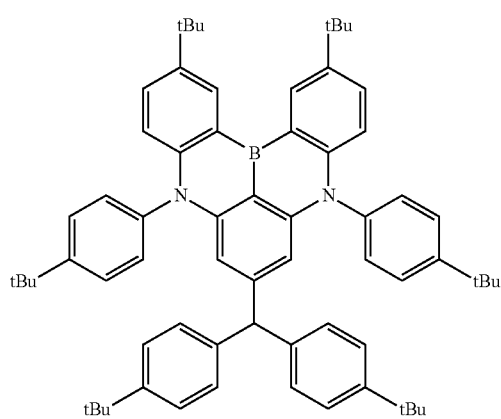
(1-37)
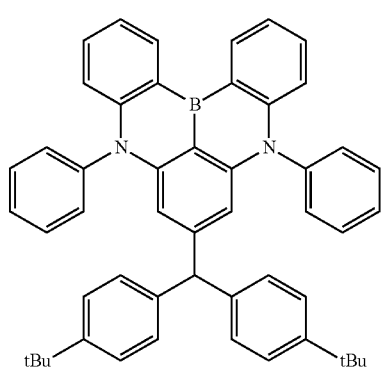
(1-38)
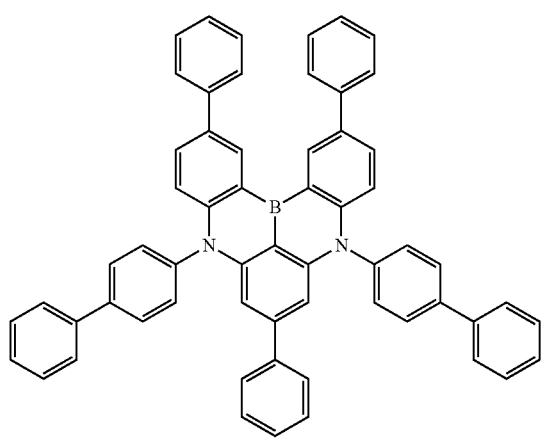
(1-39)
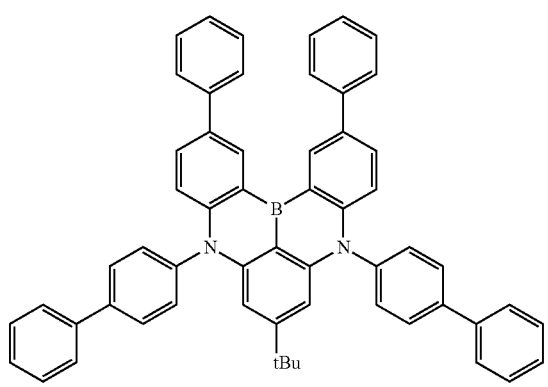
(1-40)
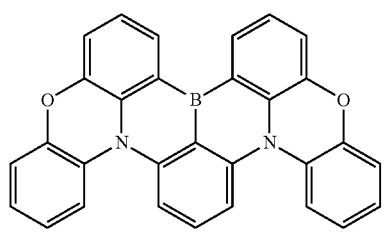
(1-41)
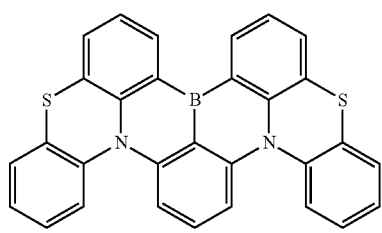

(1-42)
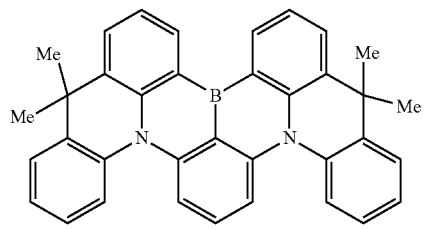
(1-43)
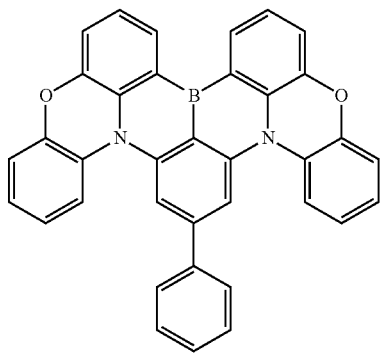
(1-44)
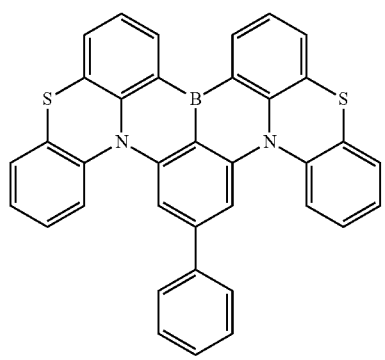
(1-45)
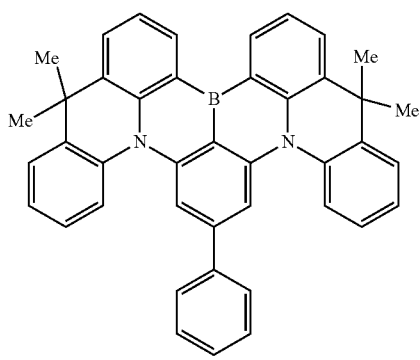
(1-46)
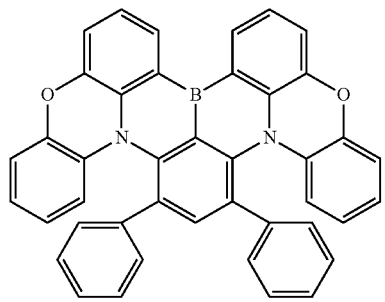
(1-47)
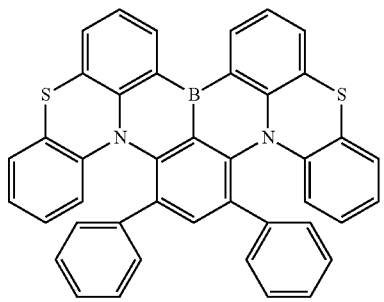
(1-48)
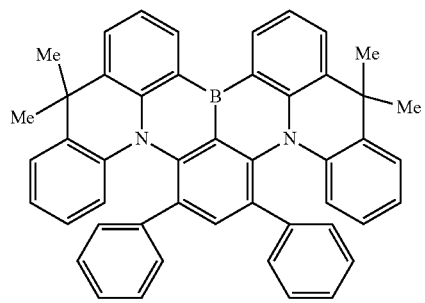
(1-49)
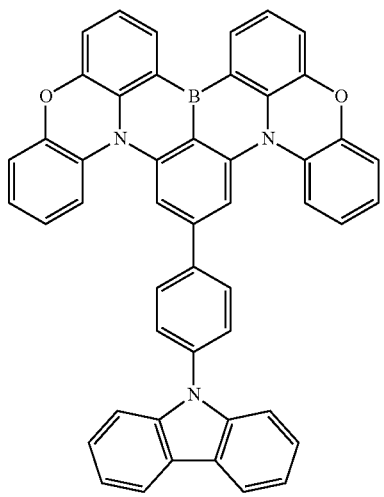

(1-50)
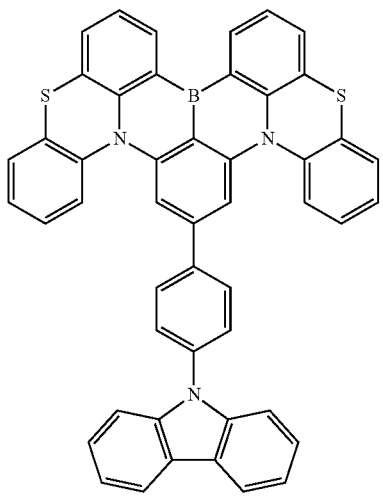
(1-51)
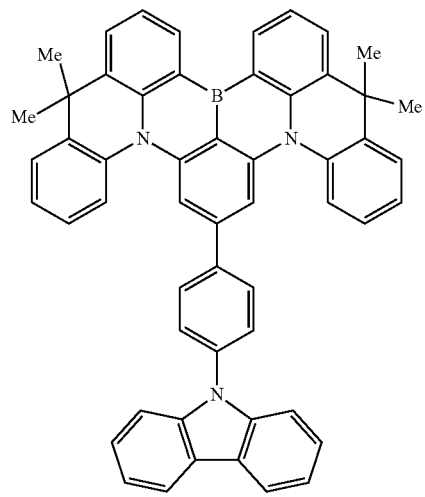
(1-60)
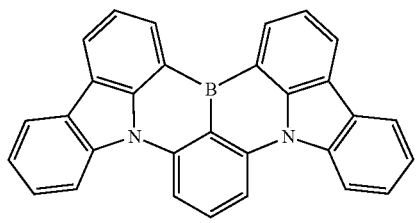
(1-61)
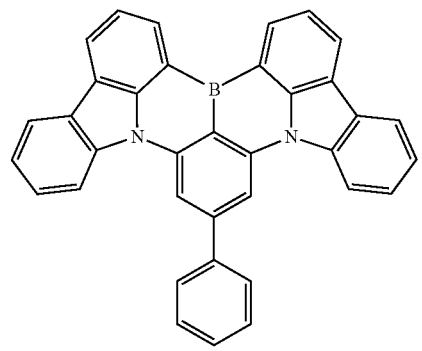
(1-62)
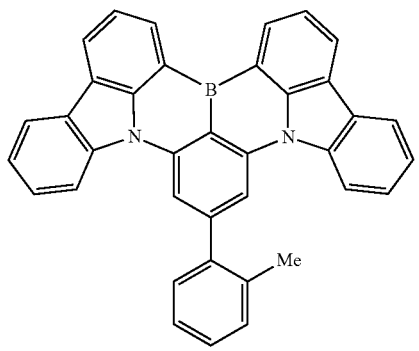
(1-63)
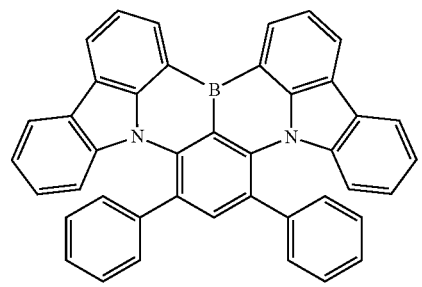
(1-64)
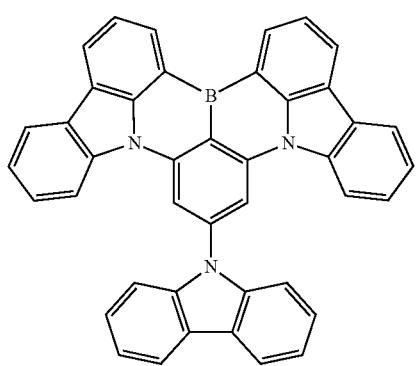
(1-65)
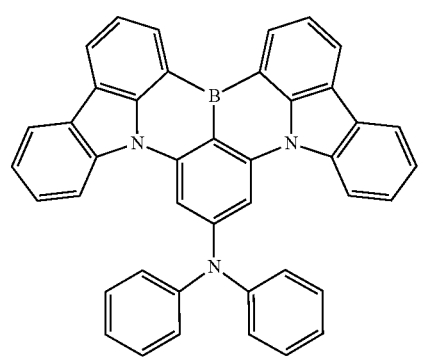

-continued
(1-66)
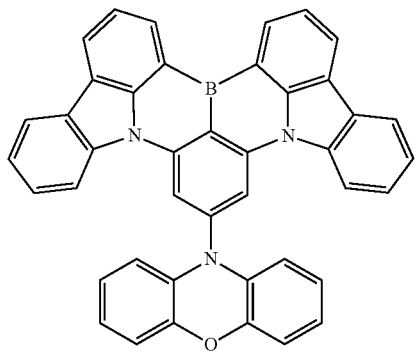
(1-67)
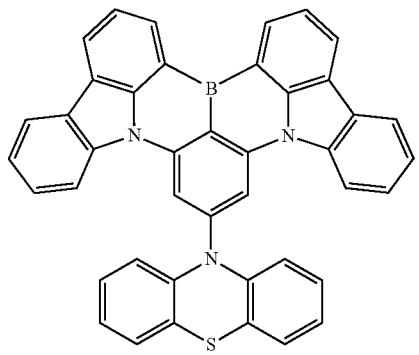
(1-68)
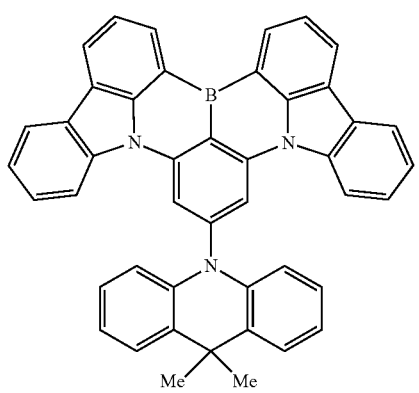
(1-69)
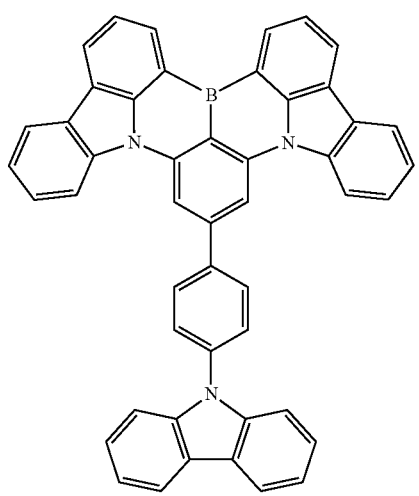
(1-70)
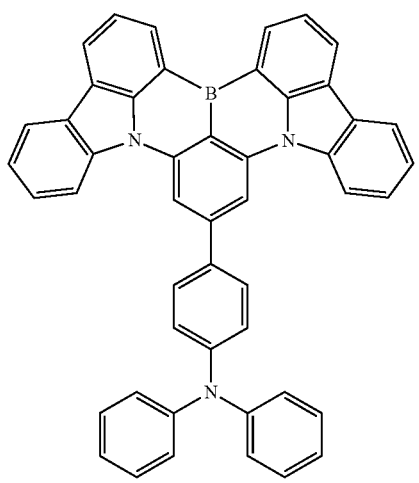
(1-71)
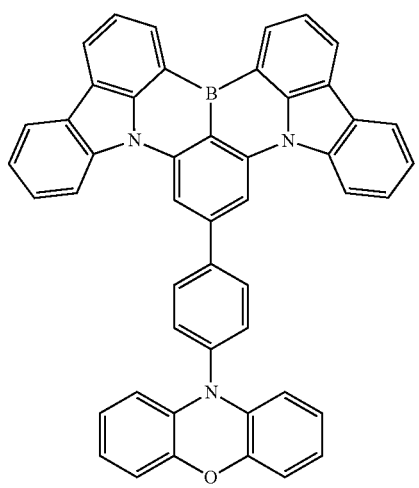

-continued
(1-72)
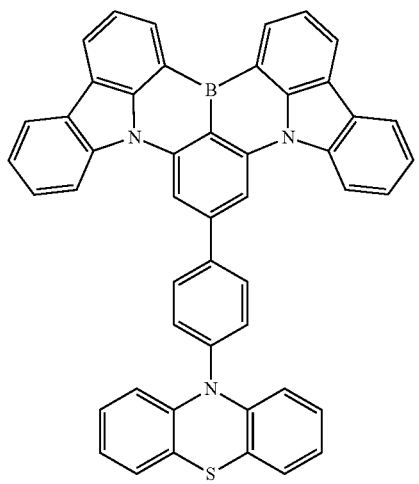
(1-73)
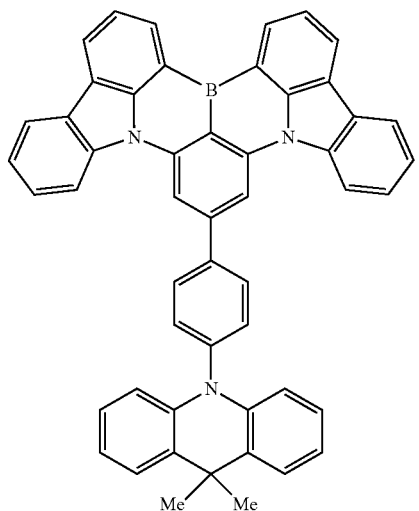
(1-74)
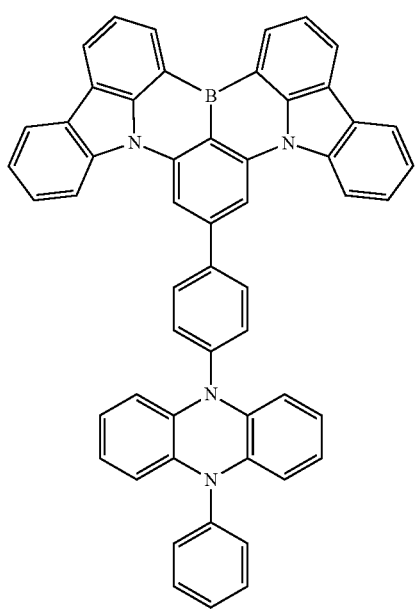
(1-80)
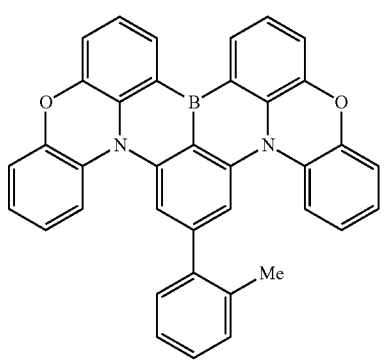
(1-81)
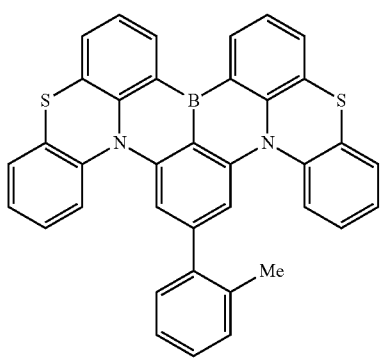
(1-82)
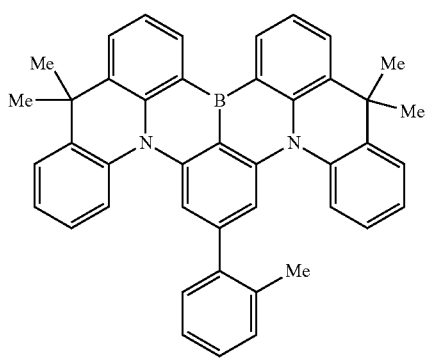

-continued
(1-83)
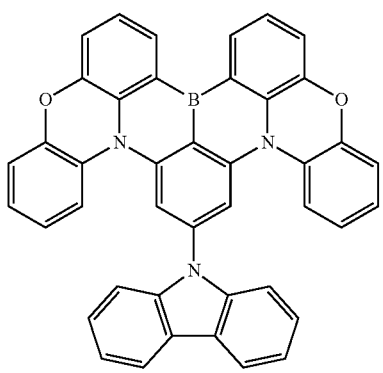
(1-84)
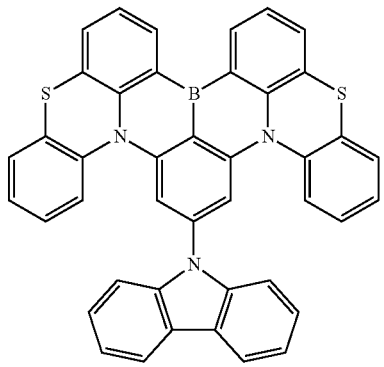
(1-85)
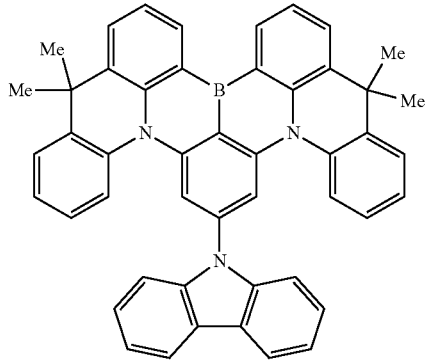
(1-86)
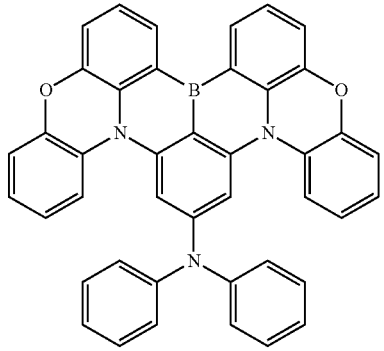
(1-87)
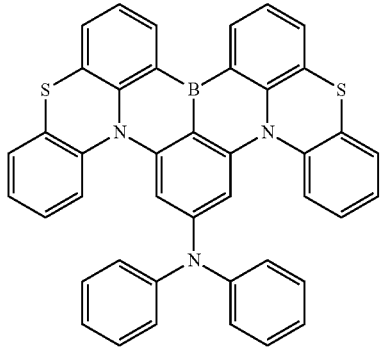
(1-88)
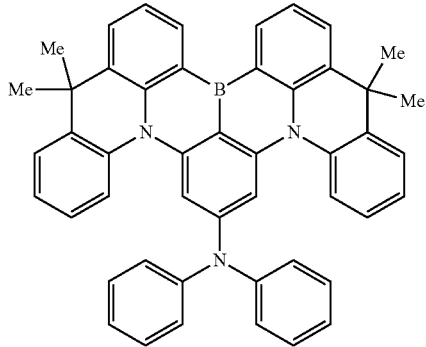
(1-89)
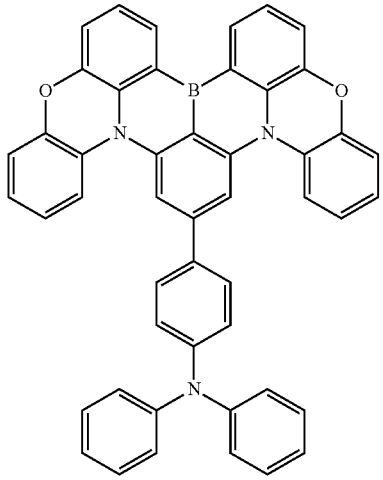
(1-90)
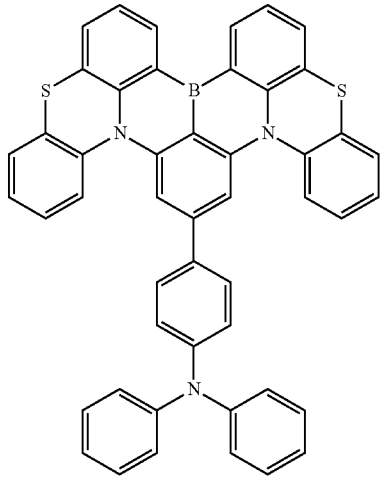

-continued
(1-91)
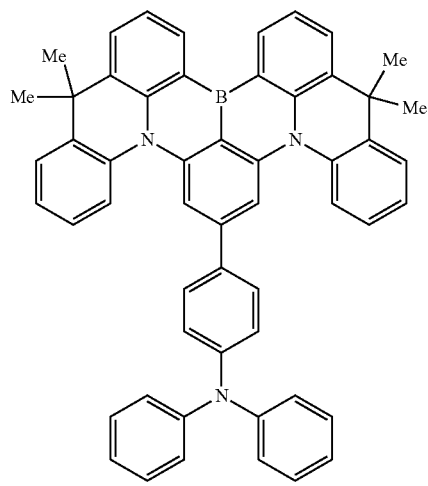
(1-92)
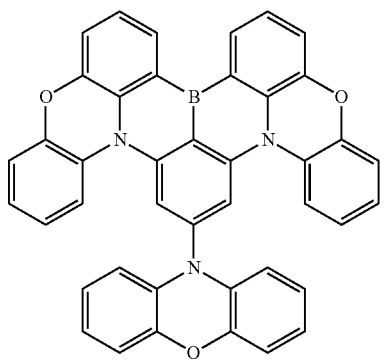
(1-93)
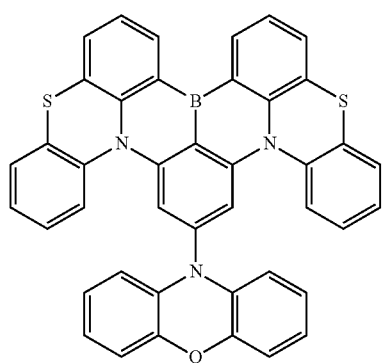
(1-94)
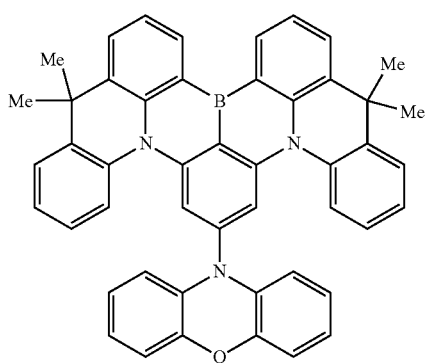
(1-100)
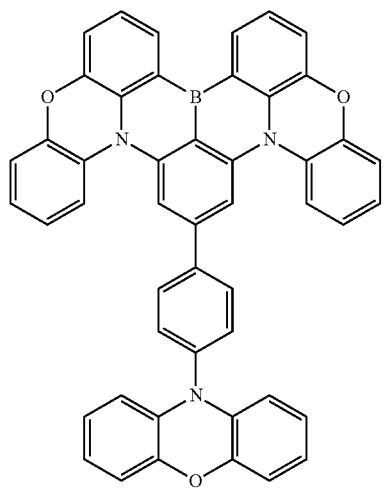
(1-101)
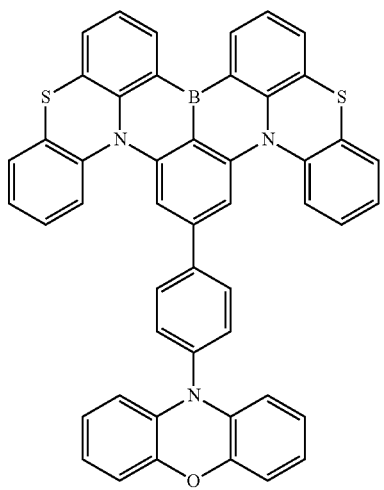

-continued
(1-102)
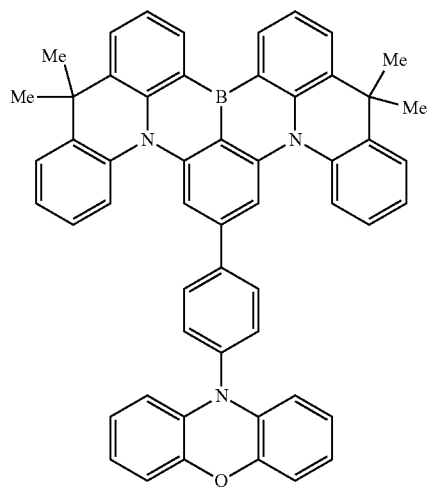
(1-103)
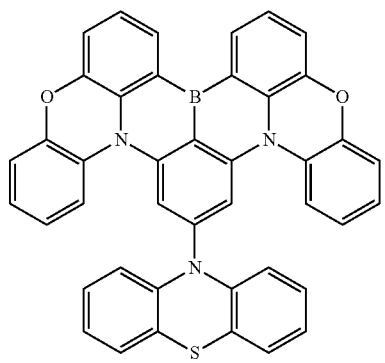
(1-104)
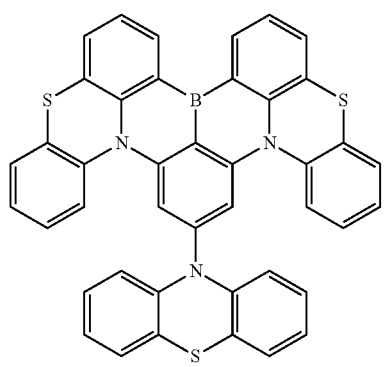
(1-105)
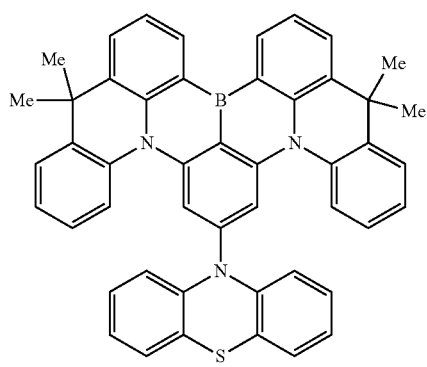
(1-106)
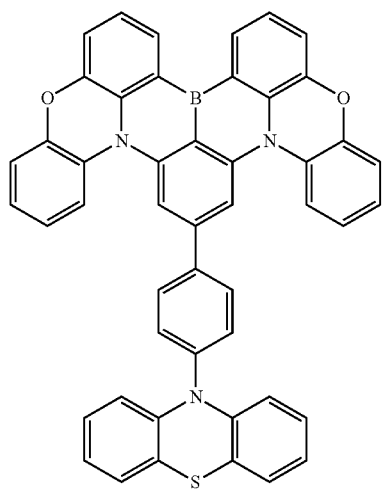
(1-107)
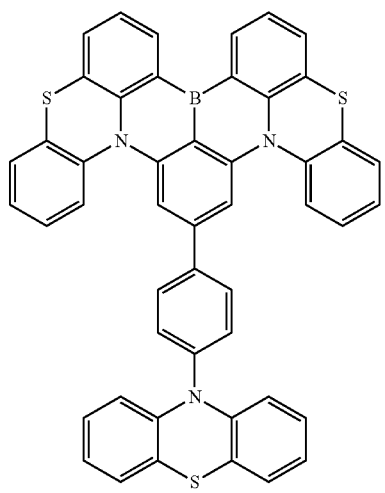

-continued
(1-108)
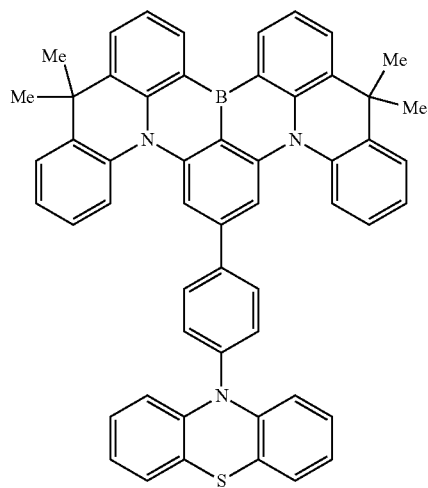
(1-109)
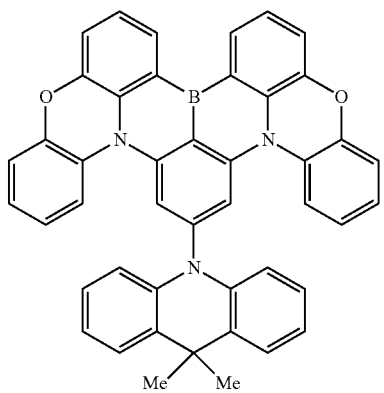
(1-110)
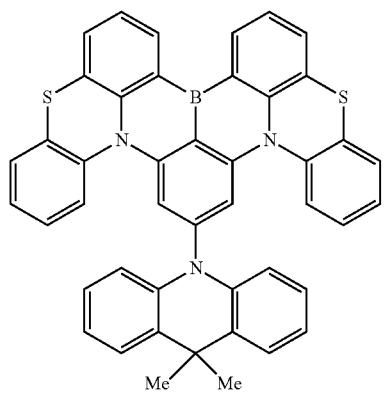
(1-111)
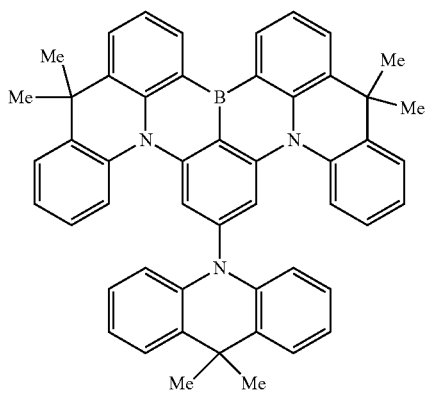
(1-112)
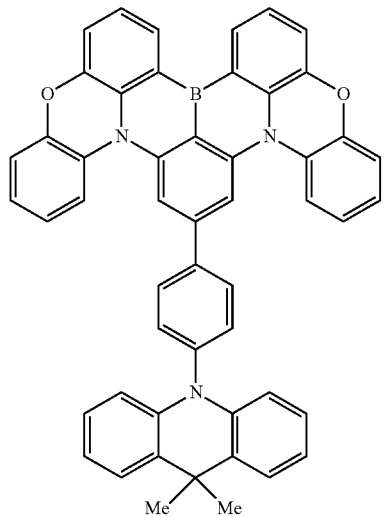
(1-113)
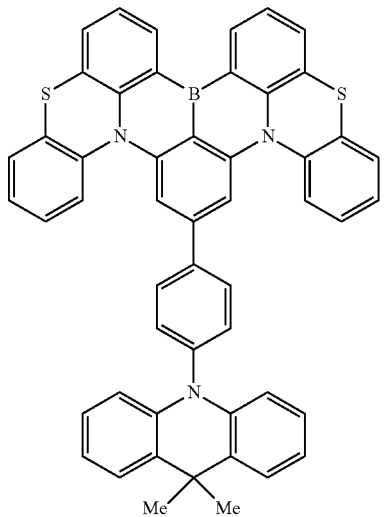

-continued
(1-114)
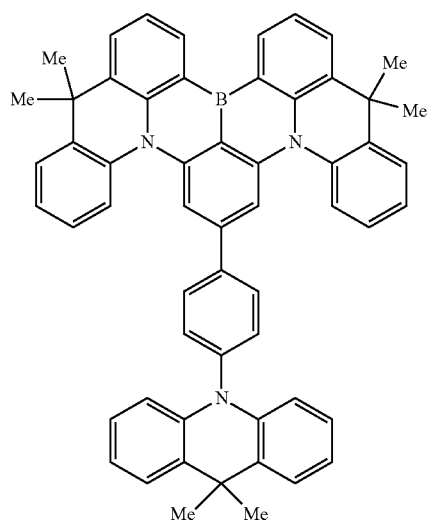
(1-115)
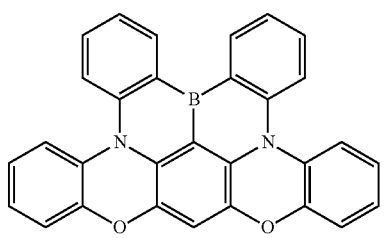
(1-116)
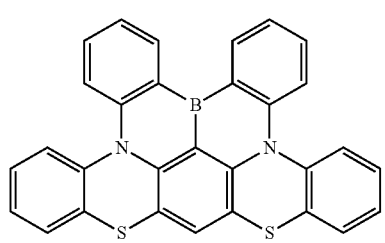
(1-117)
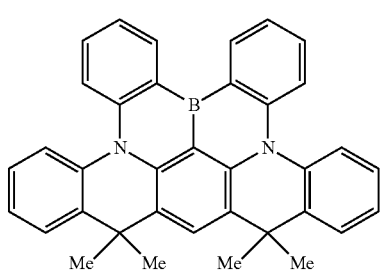
(1-118)
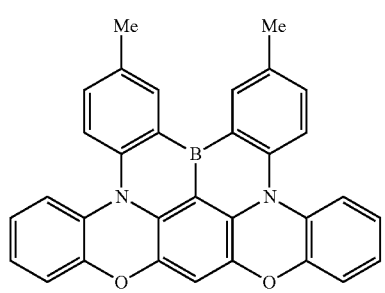
(1-119)
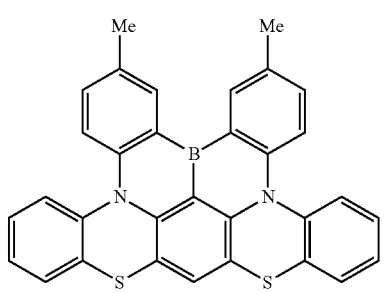
(1-120)
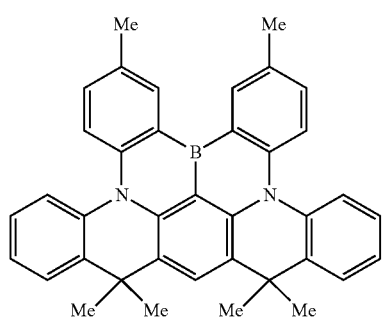
(1-121)
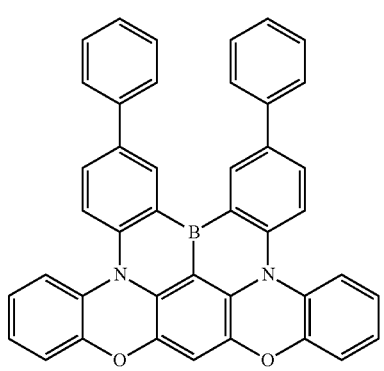

-continued
(1-122)
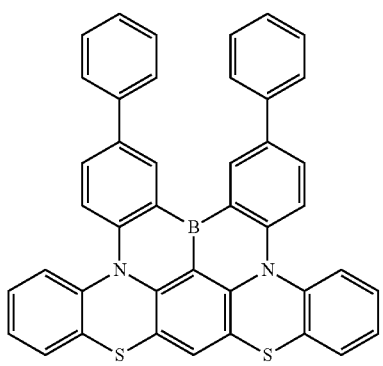
(1-123)
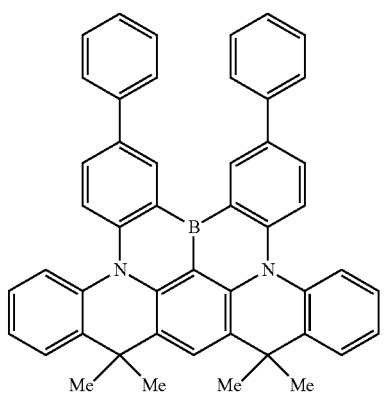
(1-124)
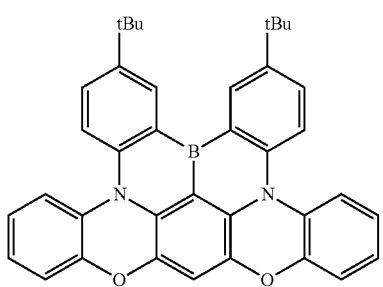
(1-125)
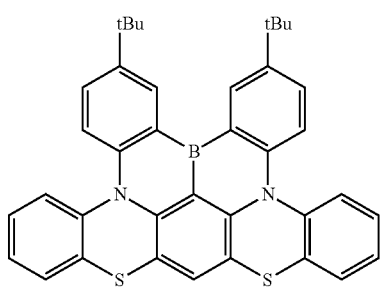
(1-126)
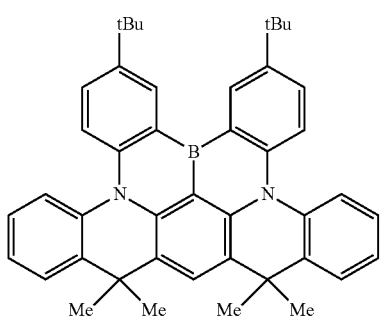
(1-130)
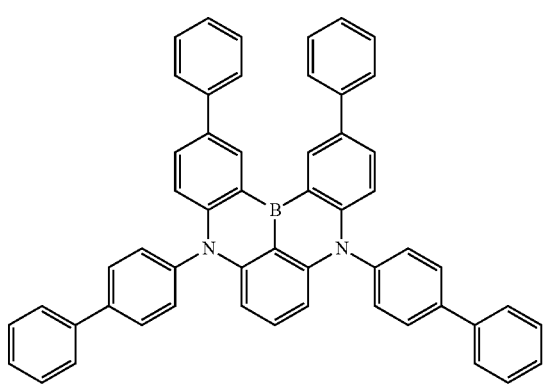
(1-131)
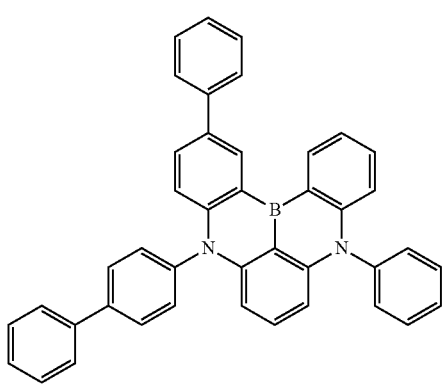
(1-132)
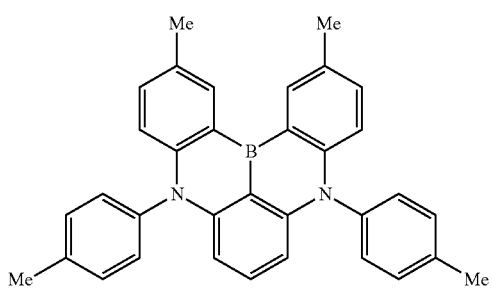

-continued
(1-133)
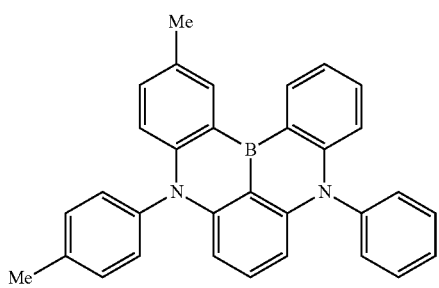
(1-134)
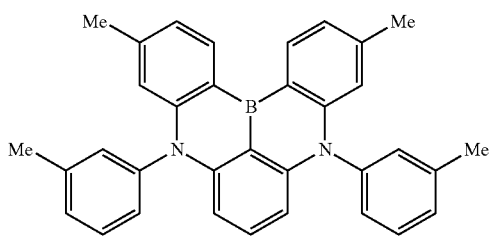
(1-135)
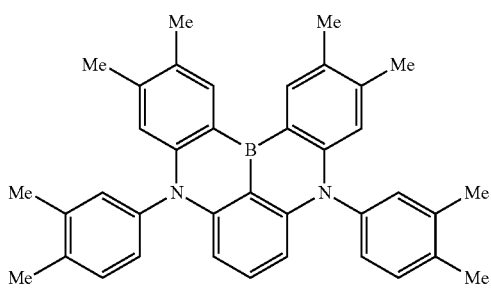
(1-136)
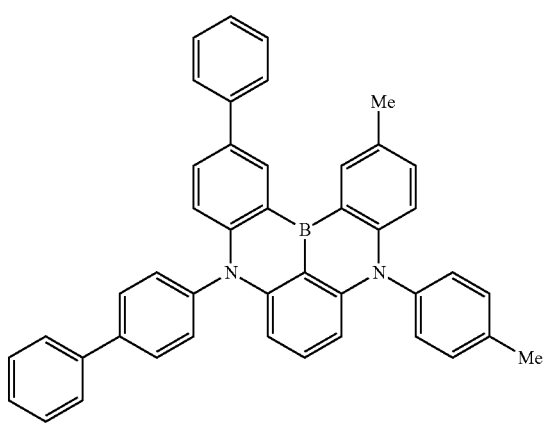
(1-137)
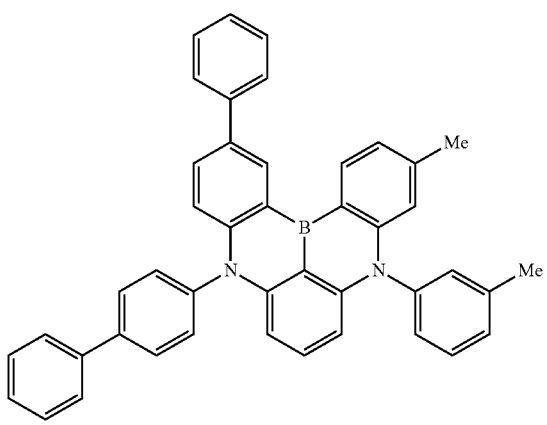
(1-138)
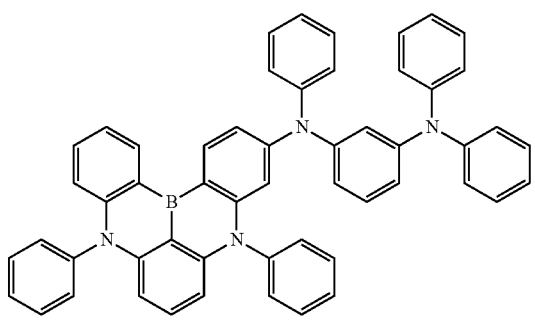
(1-139)
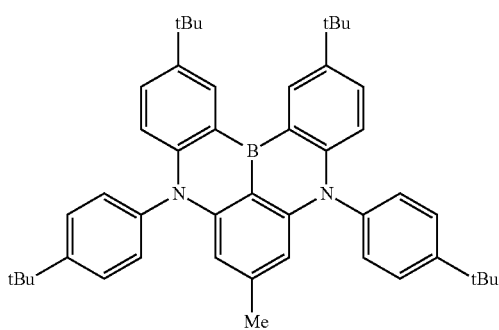
(1-150)
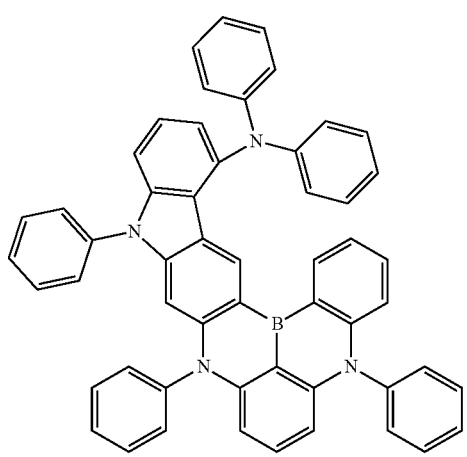

-continued
(1-151)
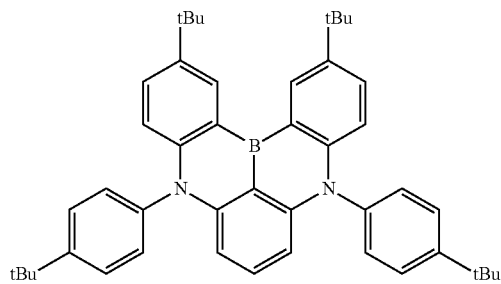
(1-152)
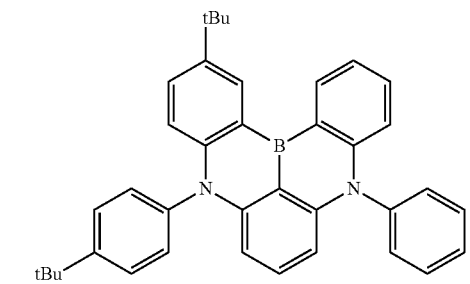
(1-153)
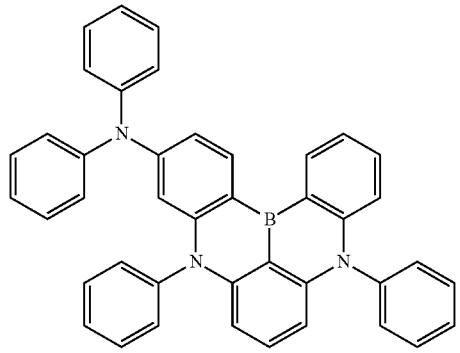
(1-154)
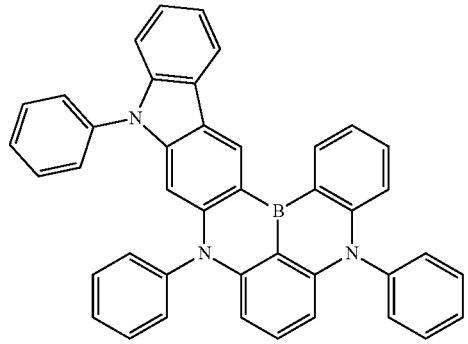
(1-155)
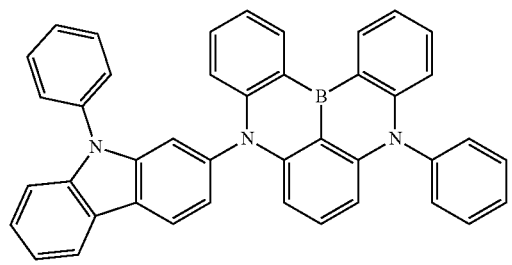
(1-156)
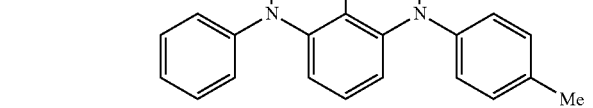
(1-157)
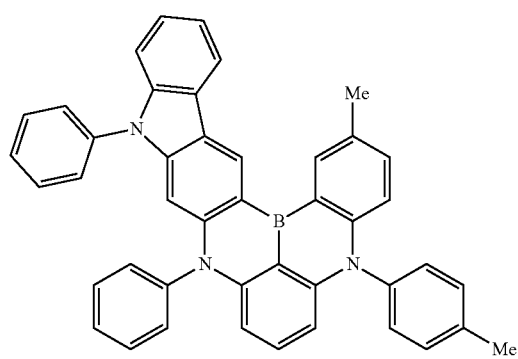
(1-158)
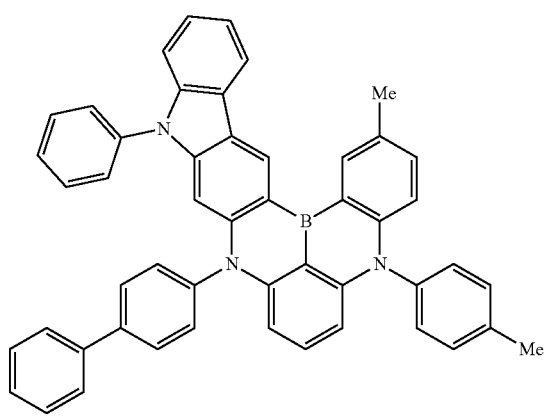

-continued
(1-159)
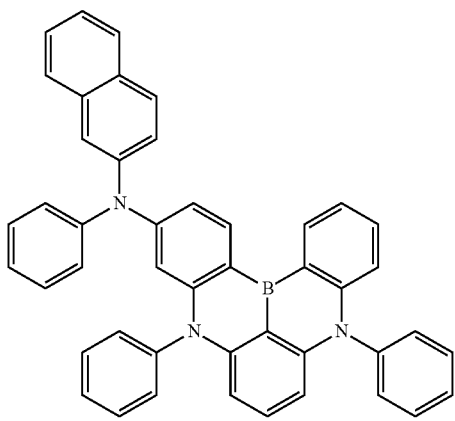
(1-160)
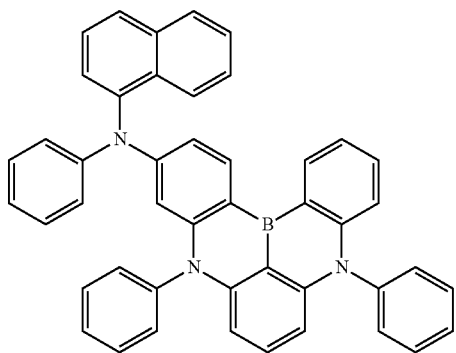
(1-161)
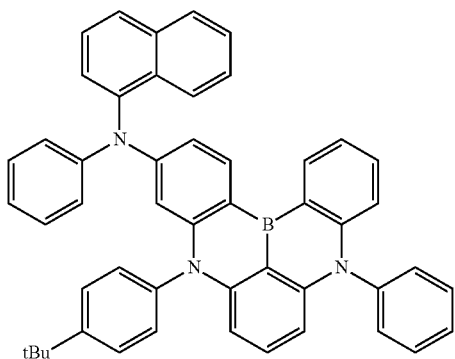
(1-162)
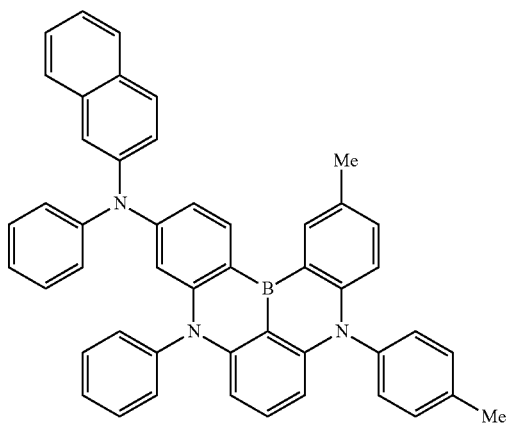
(1-163)
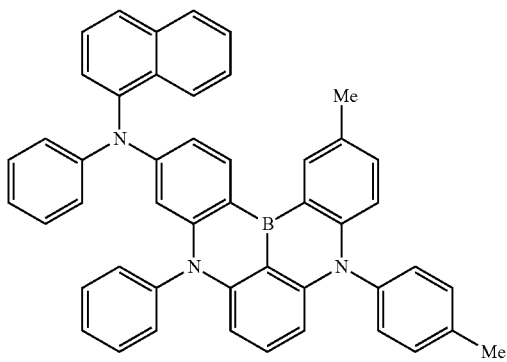
(1-164)
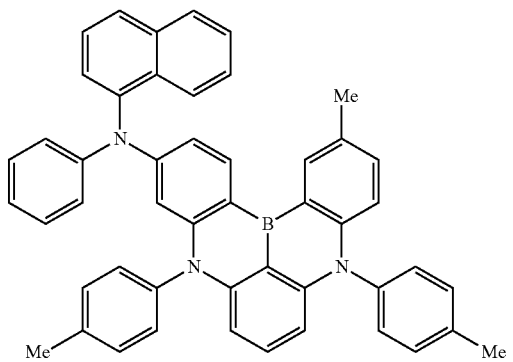

-continued
(1-170)
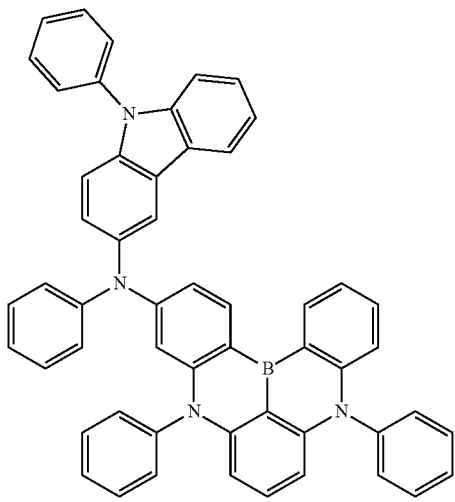
(1-171)
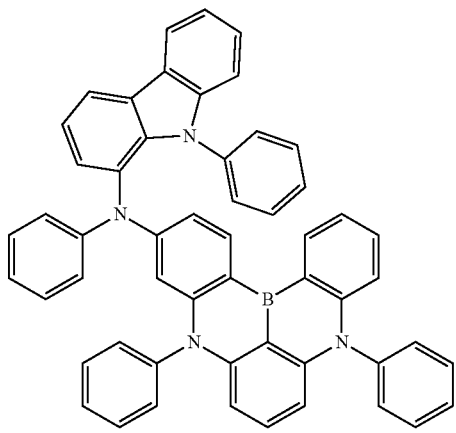
(1-172)
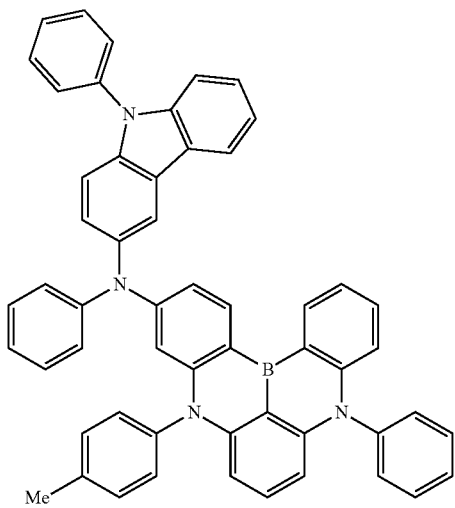
(1-173)
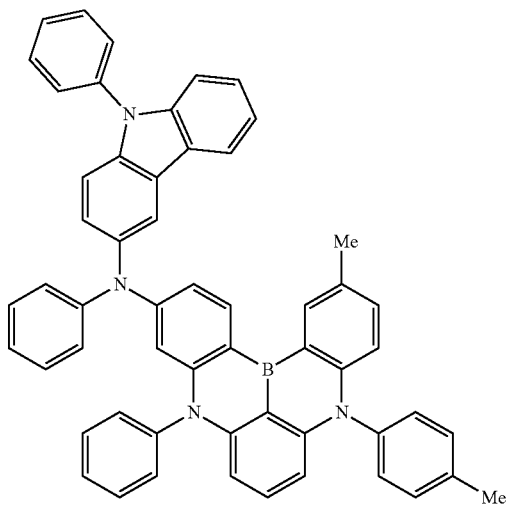
(1-174)
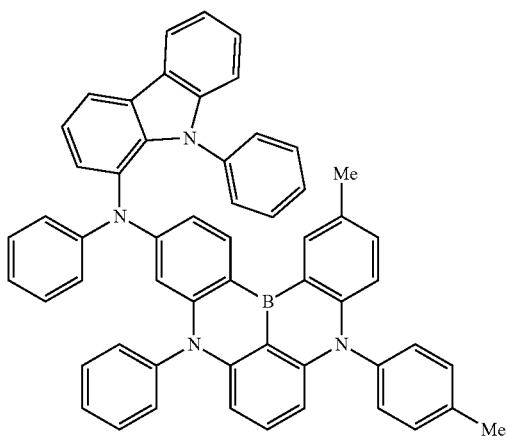
(1-175)
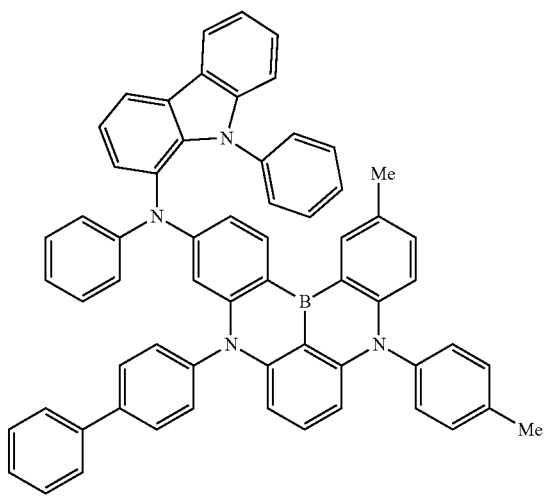

-continued
(1-176)
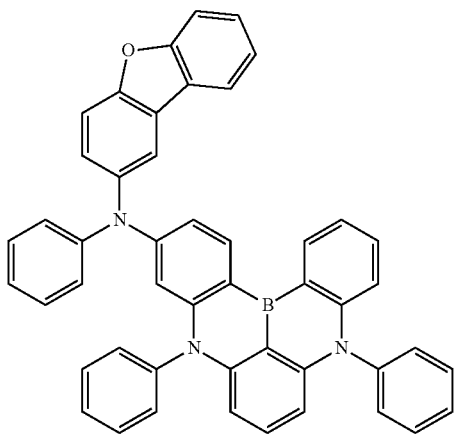
(1-177)
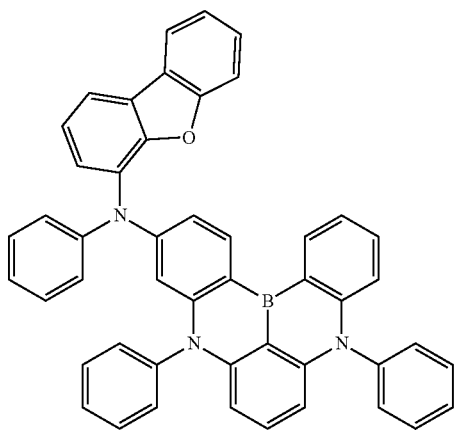
(1-178)
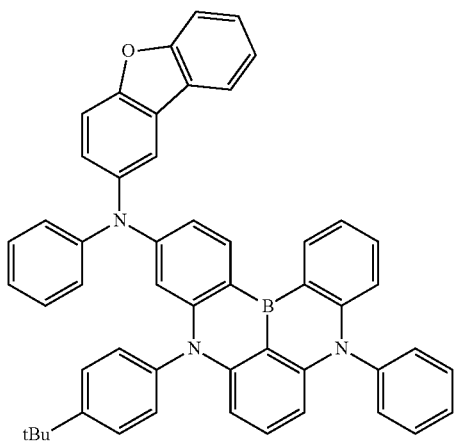
(1-179)
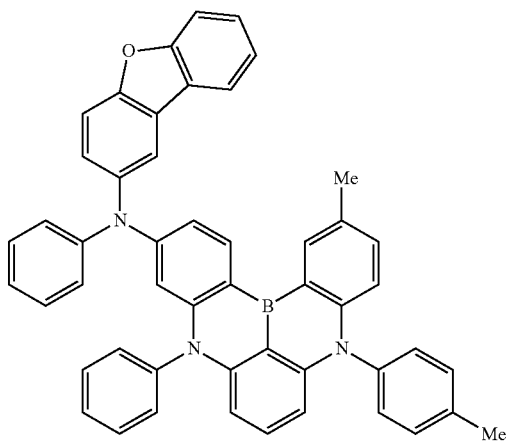
(1-180)
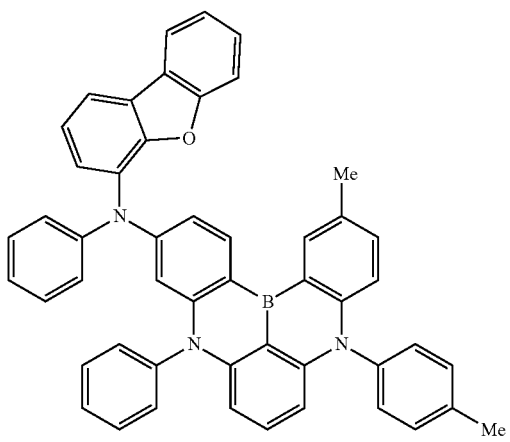
(1-181)
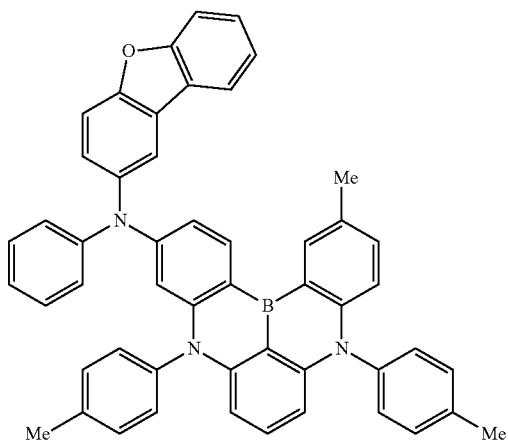

-continued
(1-190)
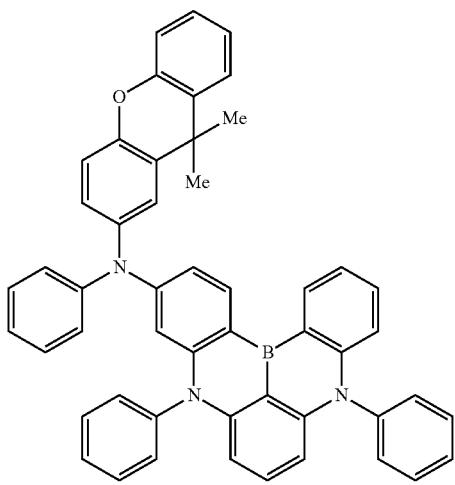
(1-191)
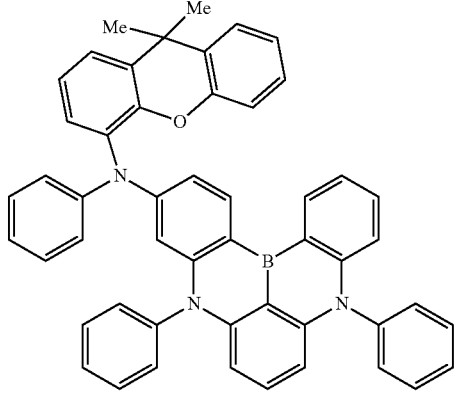
(1-192)
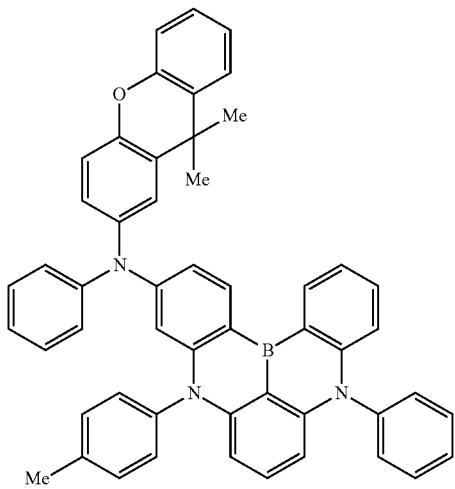
(1-193)
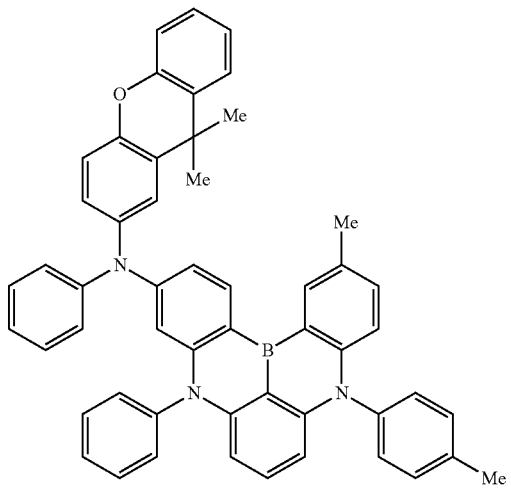
(1-194)
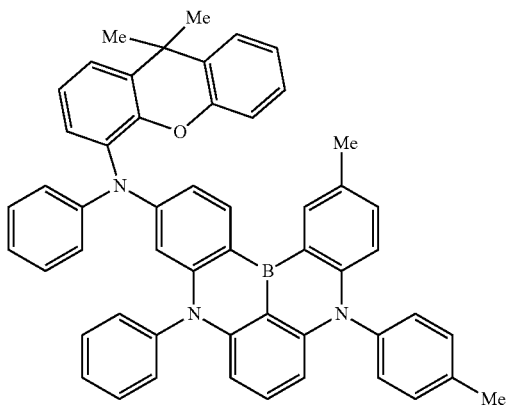
(1-195)
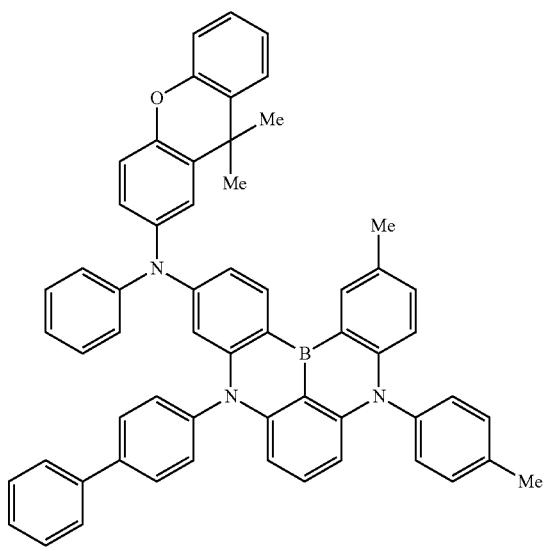

-continued
(1-196)
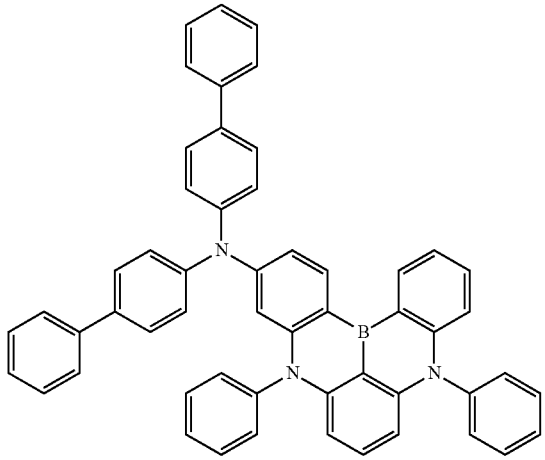
(1-197)
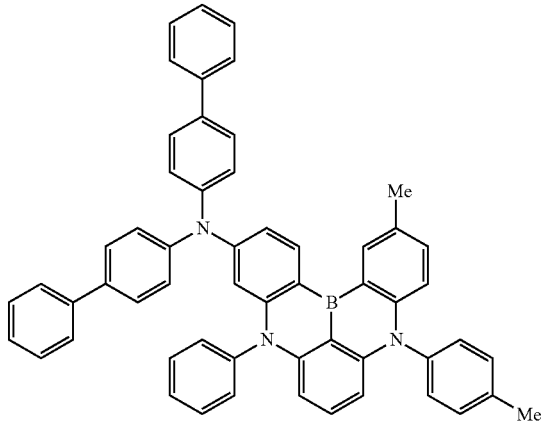
(1-198)
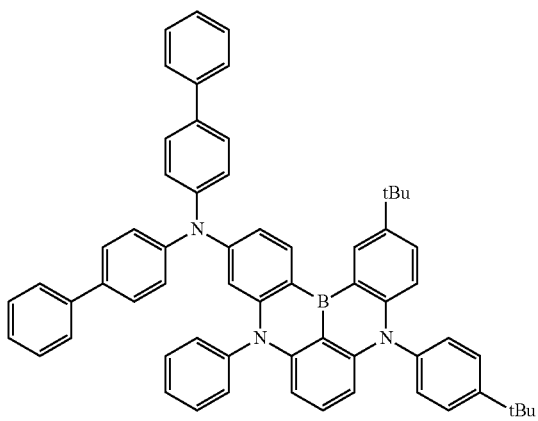
(1-199)
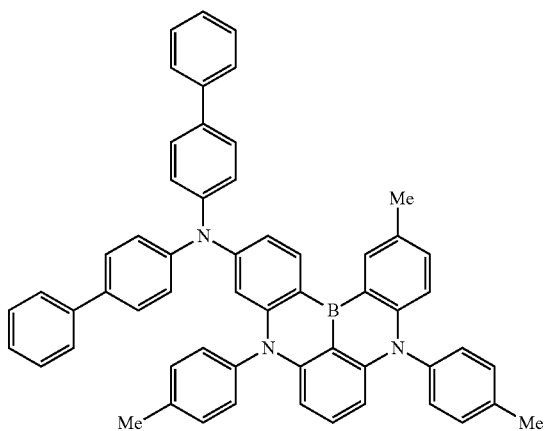
(1-210)
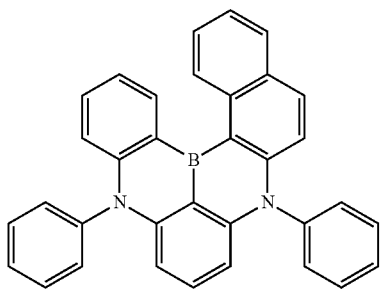
(1-211)
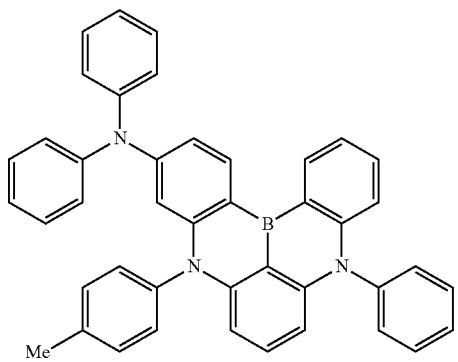

-continued
(1-212)
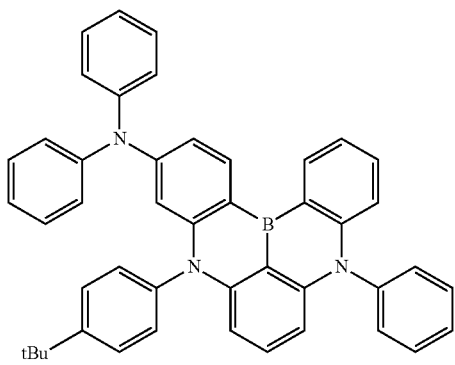
(1-213)
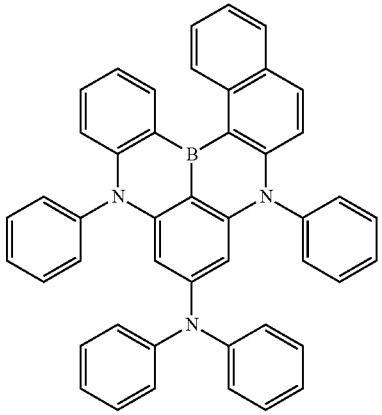
(1-214)
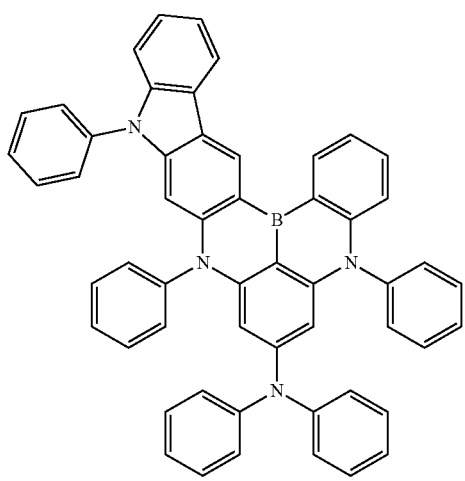
(1-215)
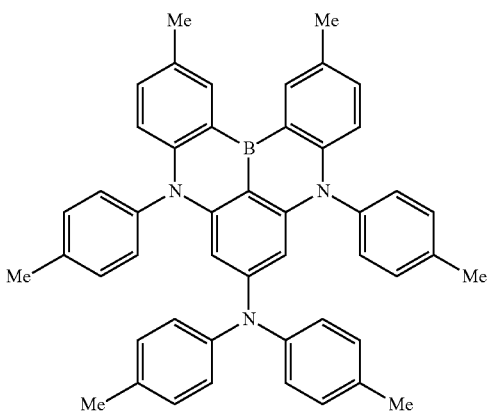
(1-216)
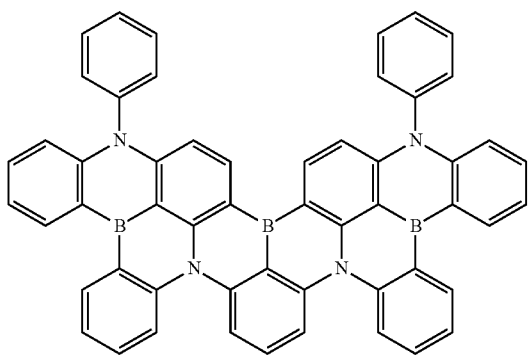
(1-217)
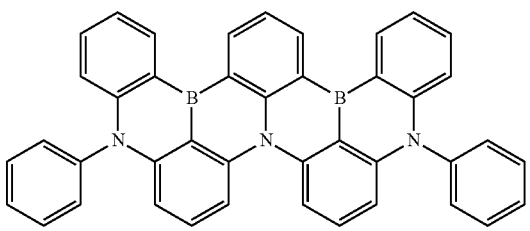
(1-218)
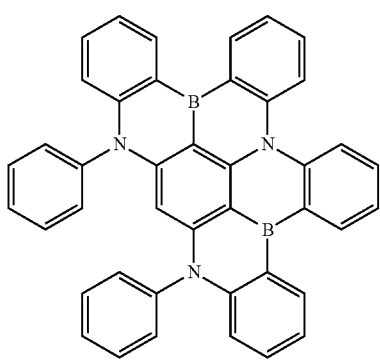
(1-219)
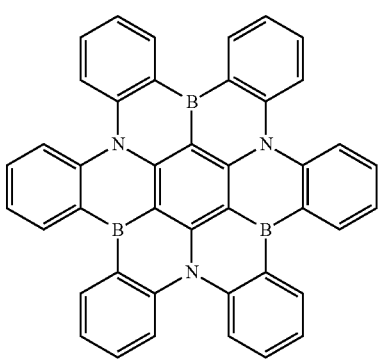

-continued
(1-220)
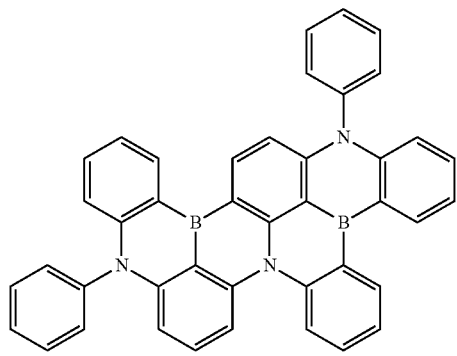
(1-230)
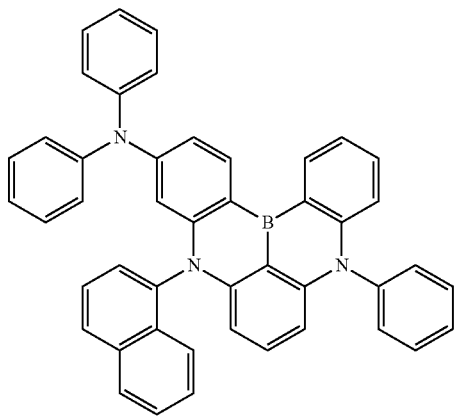
(1-231)
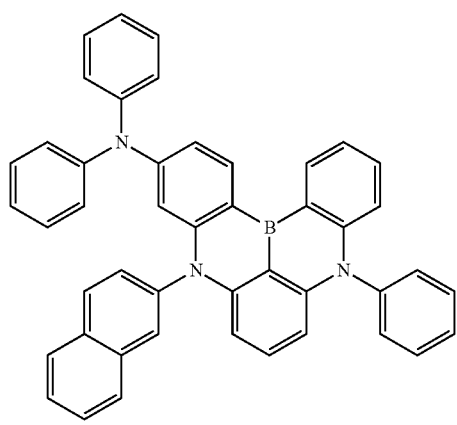
(1-232)
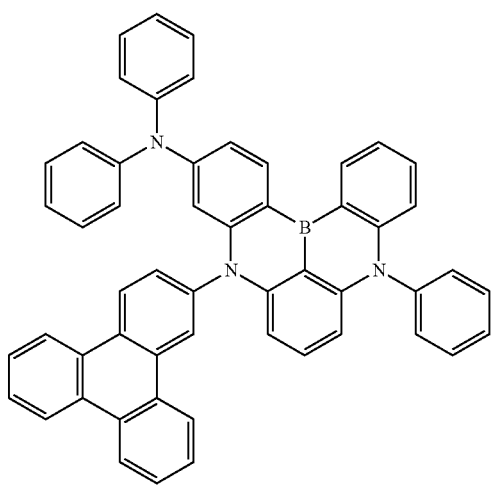
(1-233)
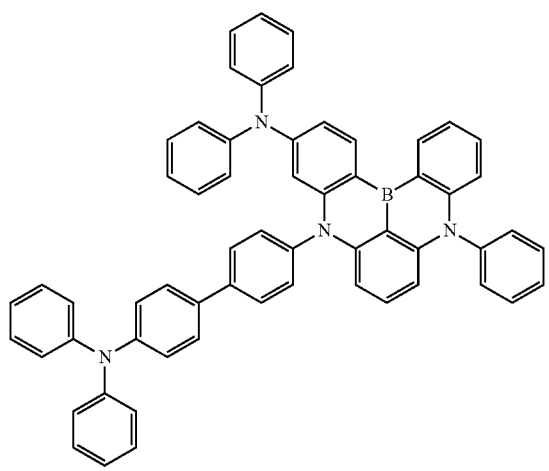
(1-234)
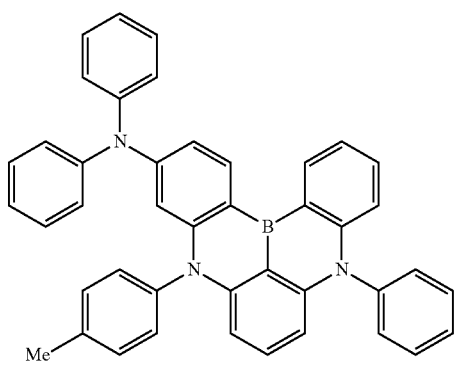

-continued
(1-235)
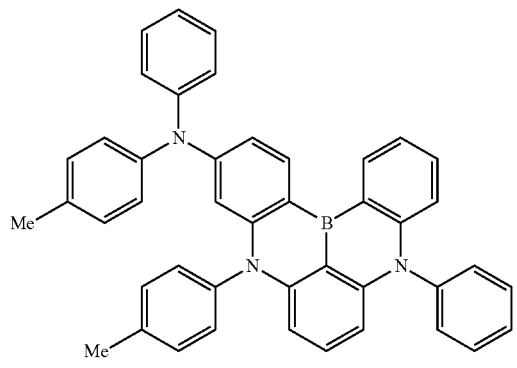
(1-236)
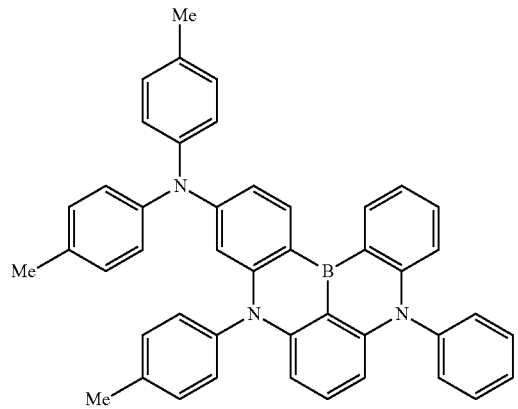
(1-237)
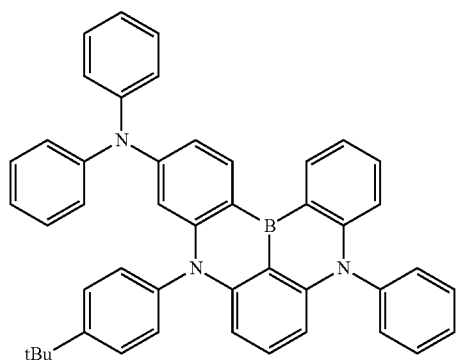
(1-238)
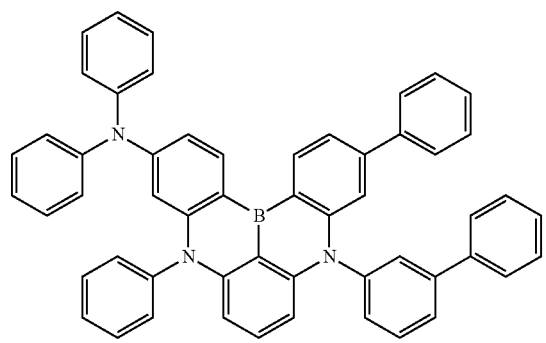
(1-239)
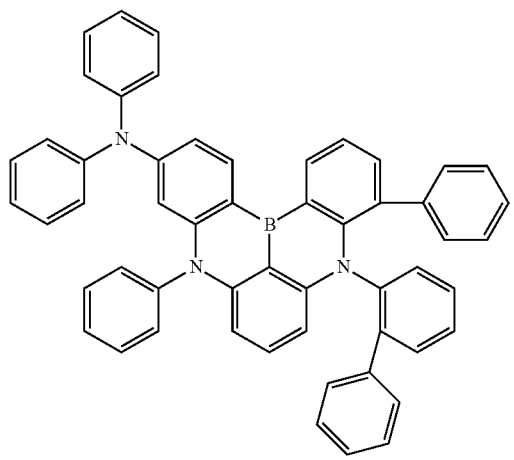
(1-240)
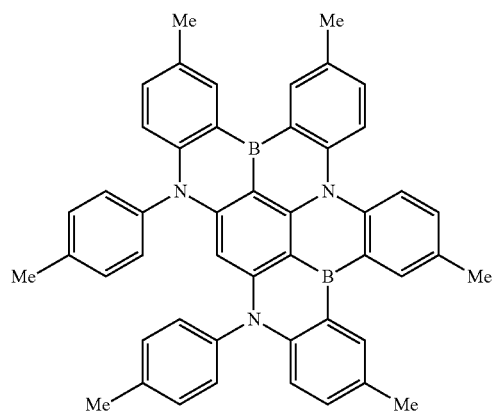

(1-250)
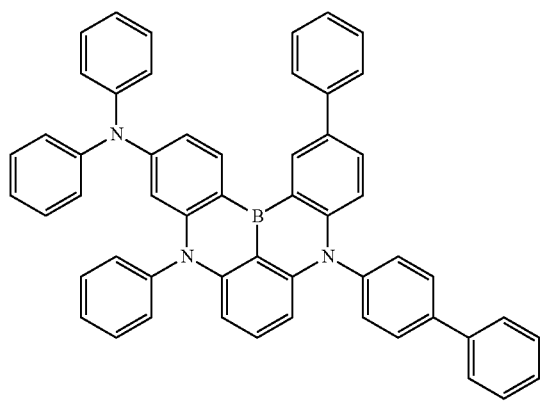
(1-251)
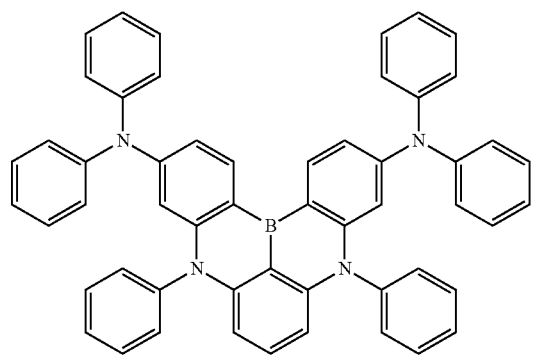
(1-252)
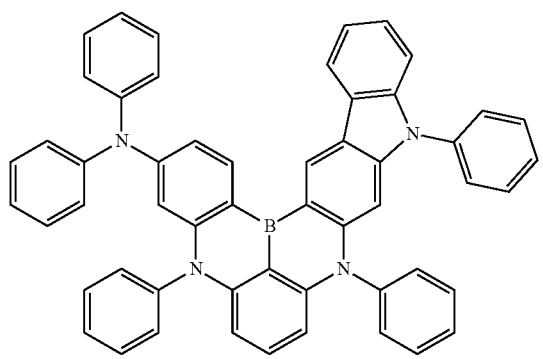
(1-253)
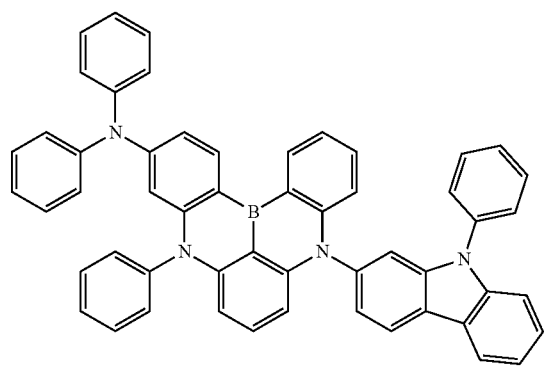
(1-254)
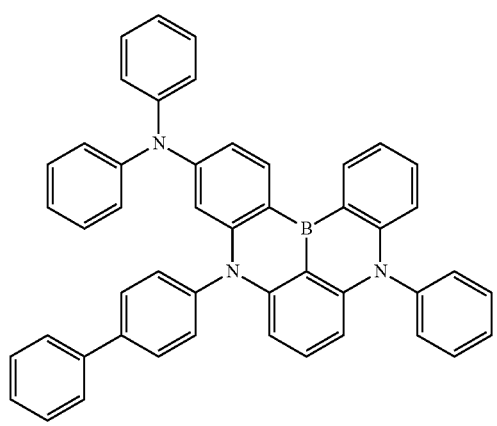
(1-255)
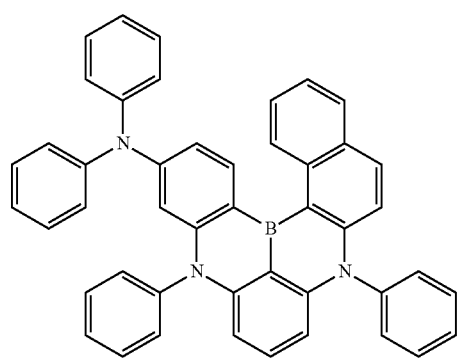

-continued
(1-256)
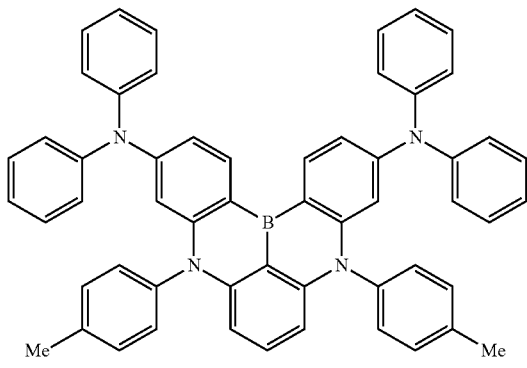
(1-257)
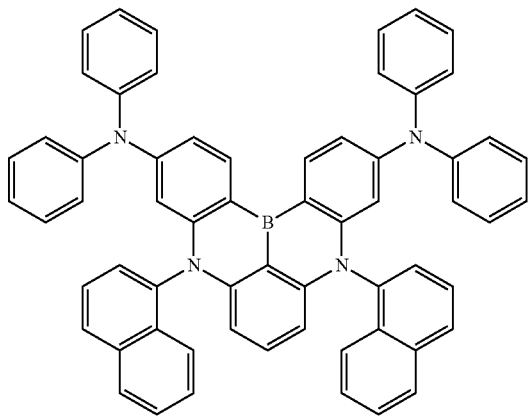
(1-260)
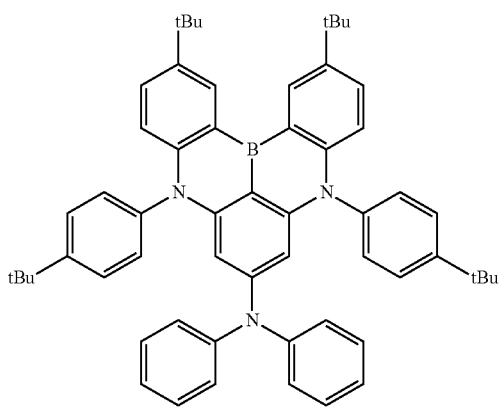
(1-261)
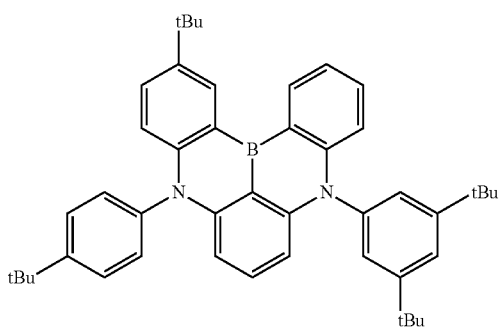
(1-262)
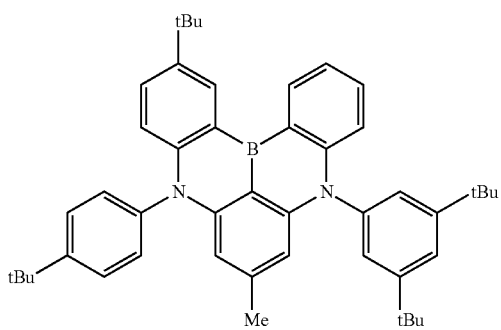
(1-263)
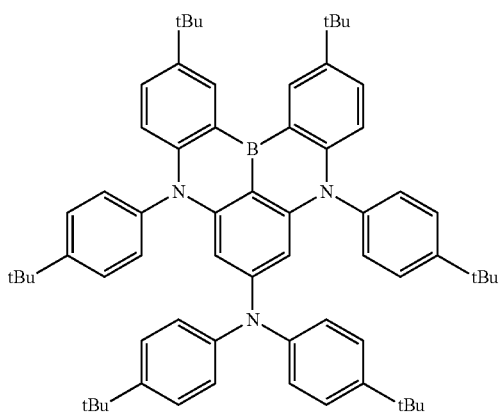

-continued
(1-264)
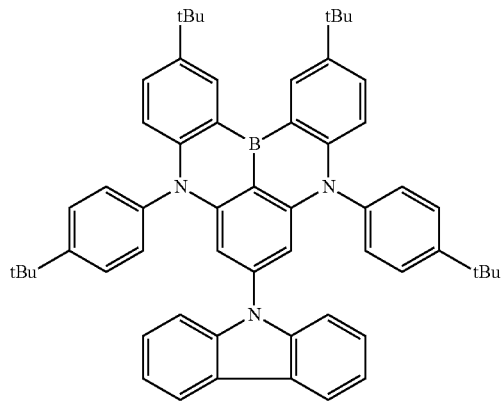
(1-265)
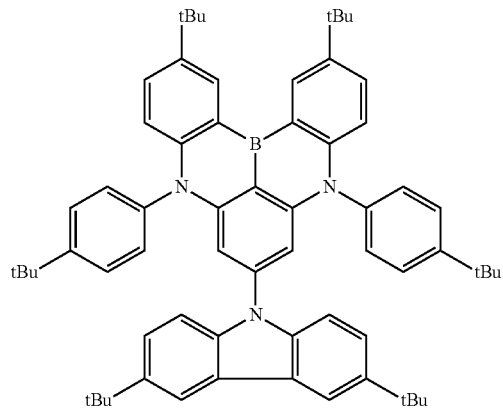
(1-266)
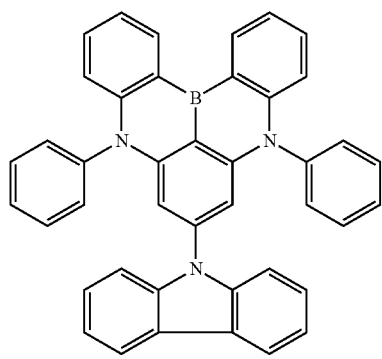
(1-267)
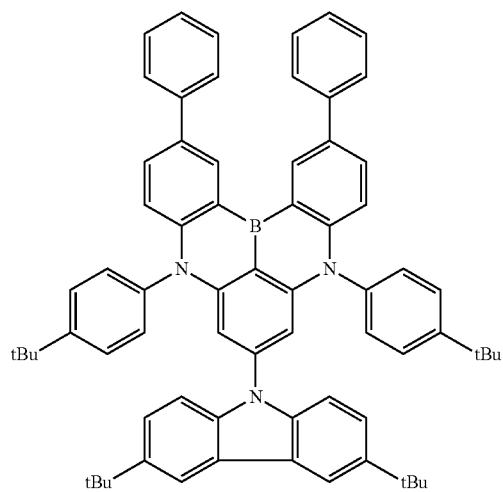
(1-270)
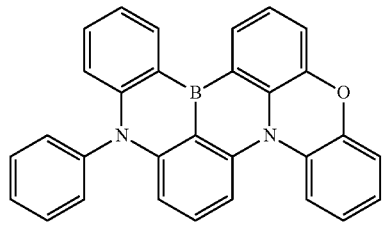
(1-271)
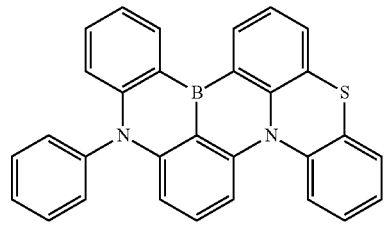
(1-272)
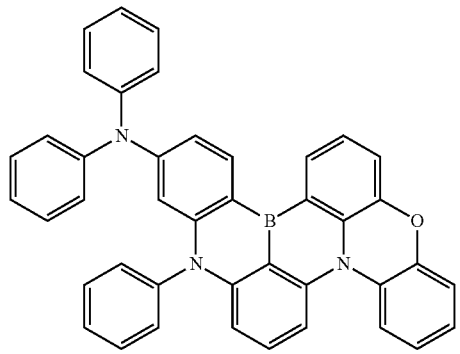
(1-273)
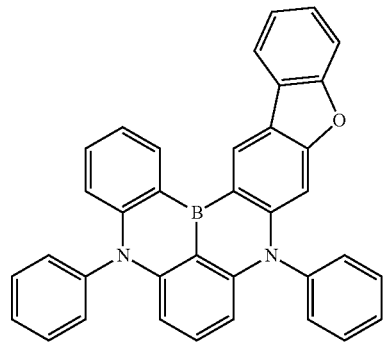

-continued
(1-274) 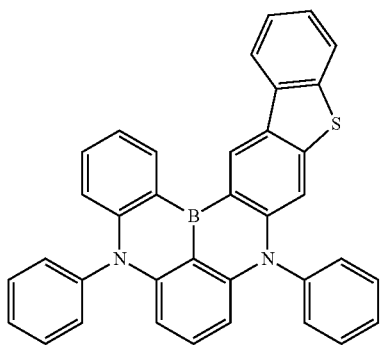
(1-275) 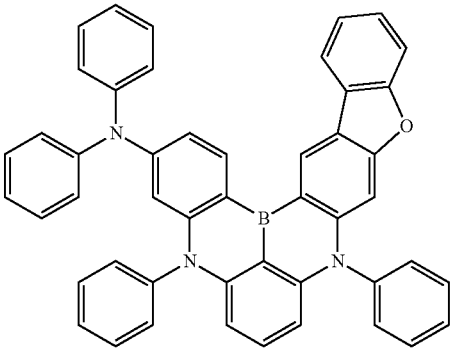
(1-276) 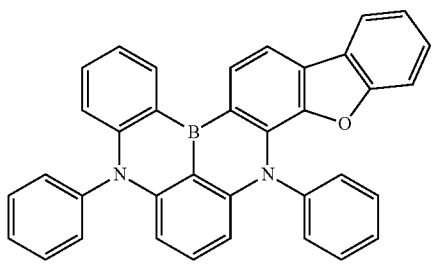
(1-277) 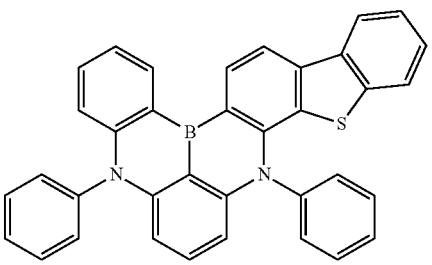
(1-278) 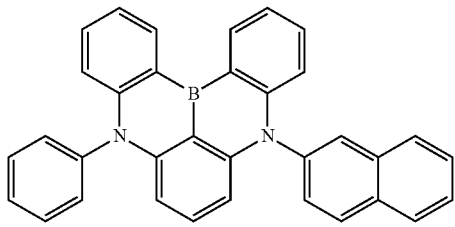
(1-279) 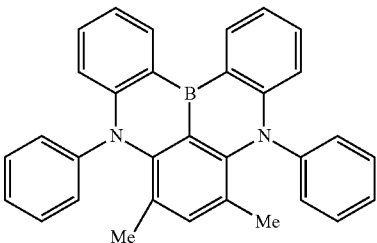
(1-280) 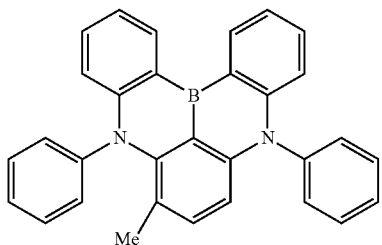
(1-281) 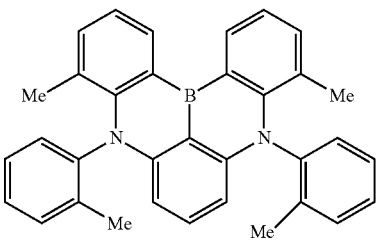
(1-282) 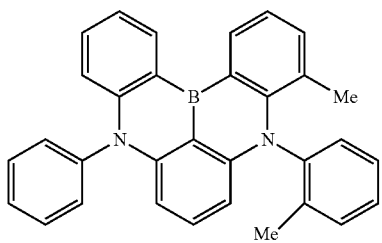
(1-283) 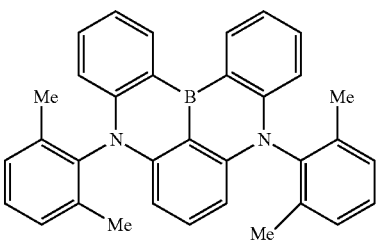

-continued
(1-284)
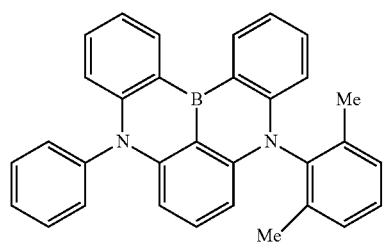
(1-290)
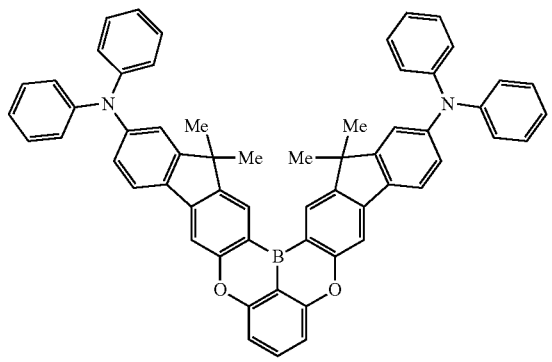
(1-291)
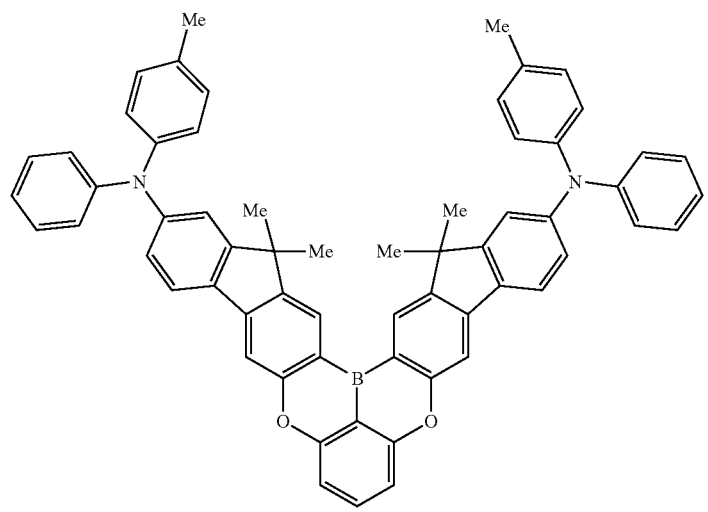
(1-292)
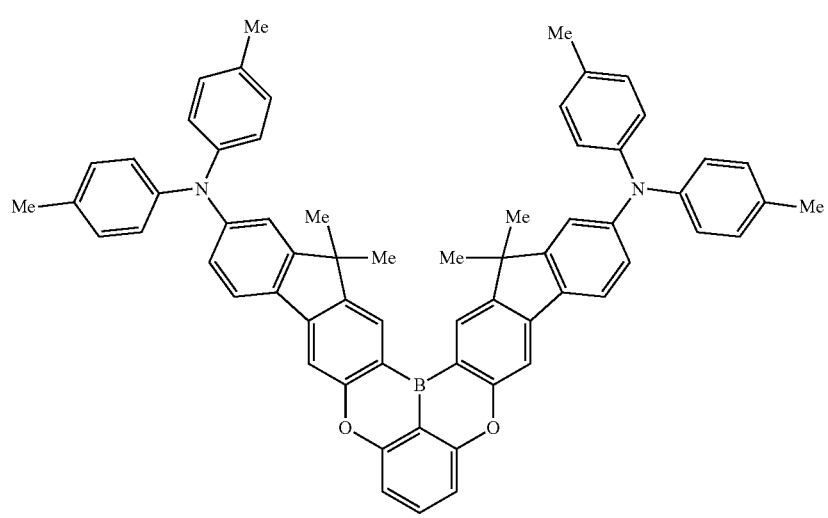

(1-293)
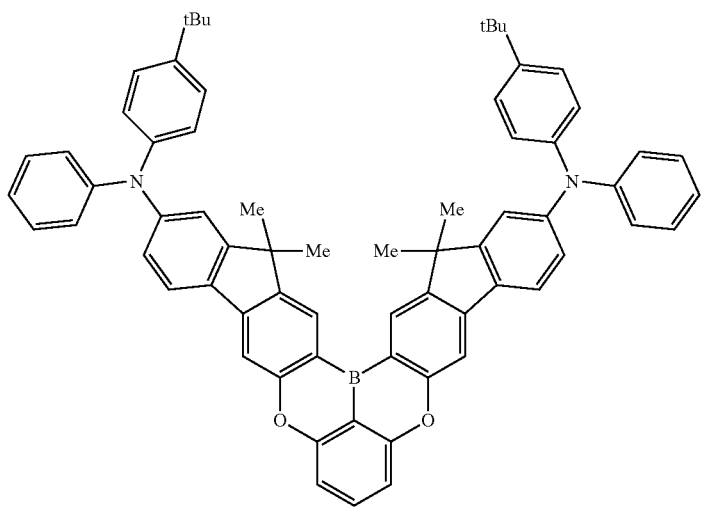
(1-294)
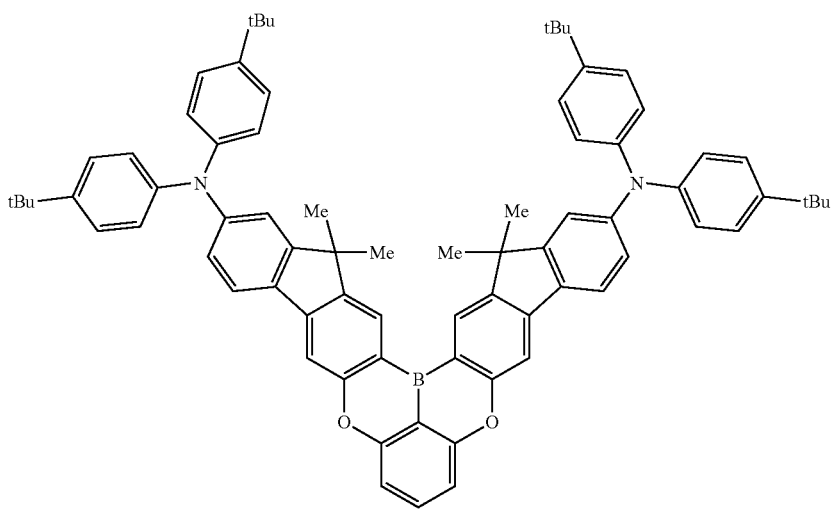
(1-295) (1-300)
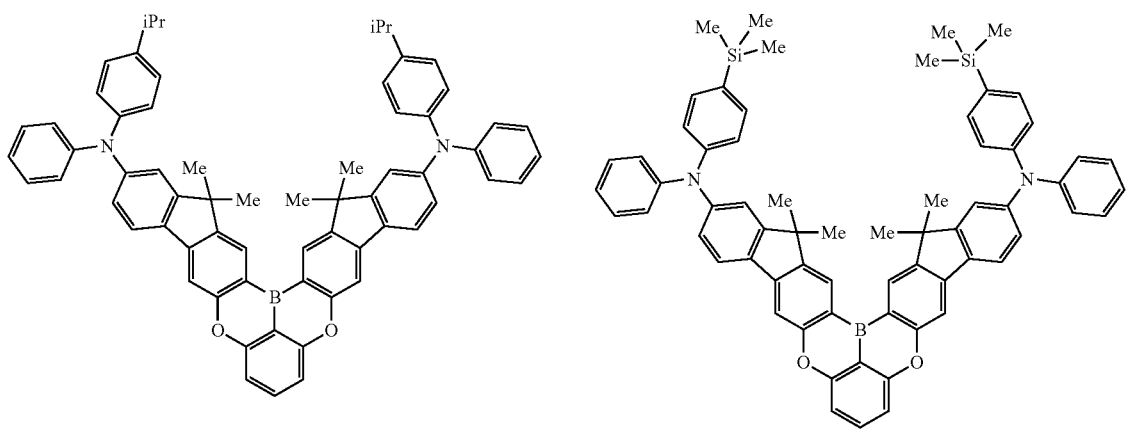

-continued
(1-301)
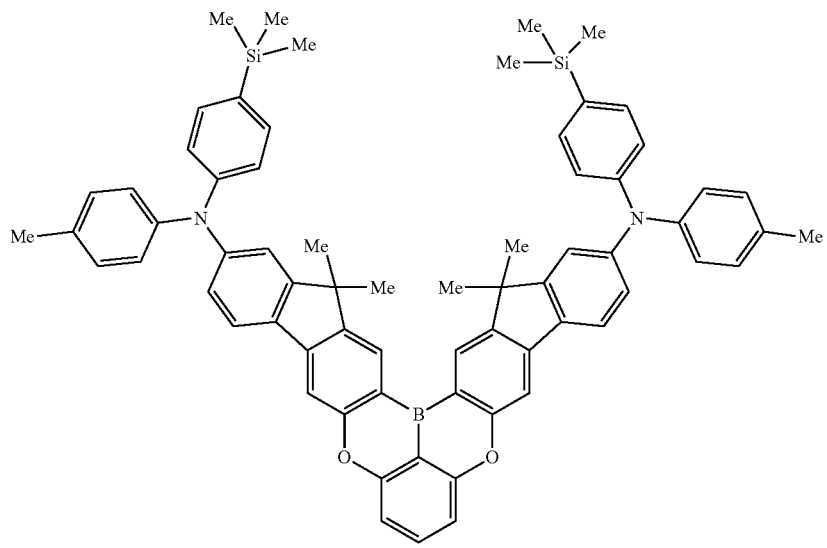
(1-302)
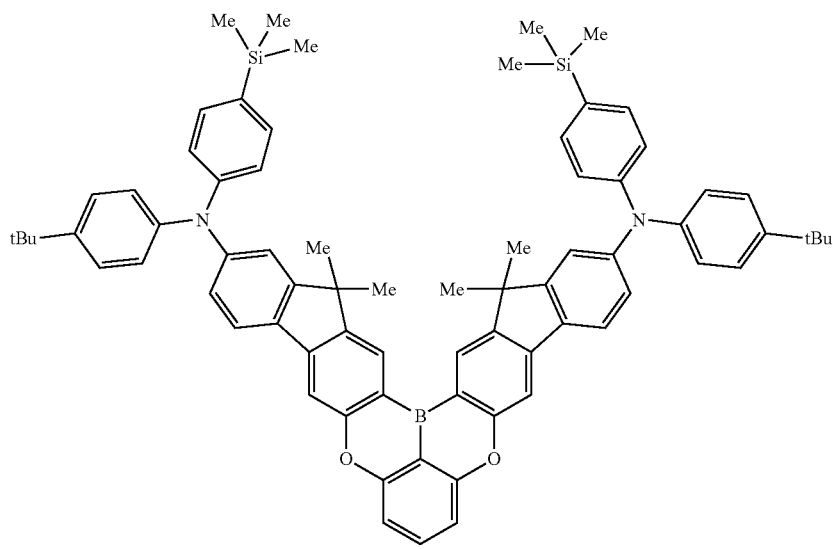
(1-303)
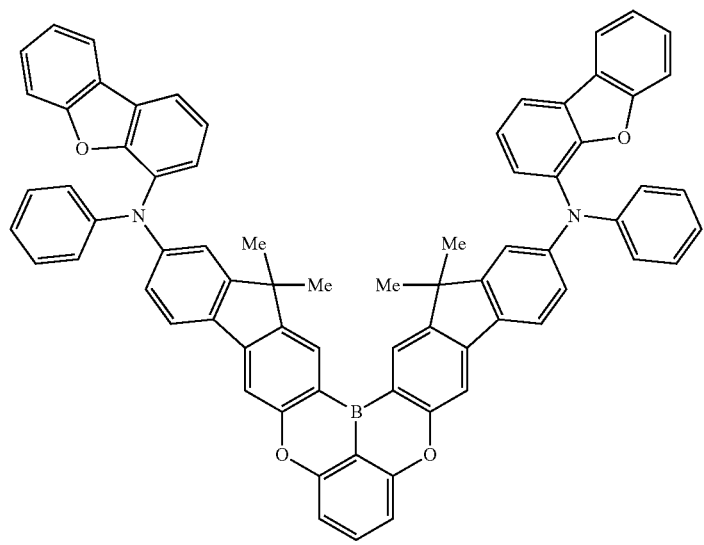

(1-304)
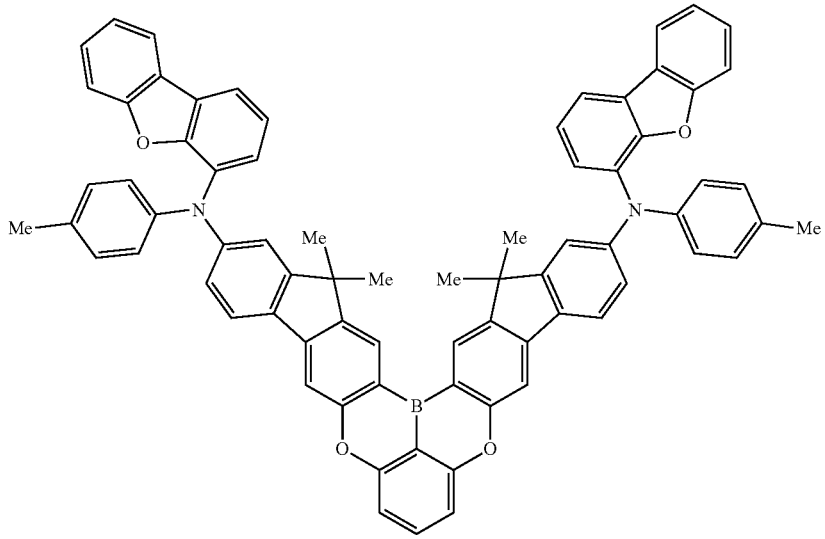
(1-305)
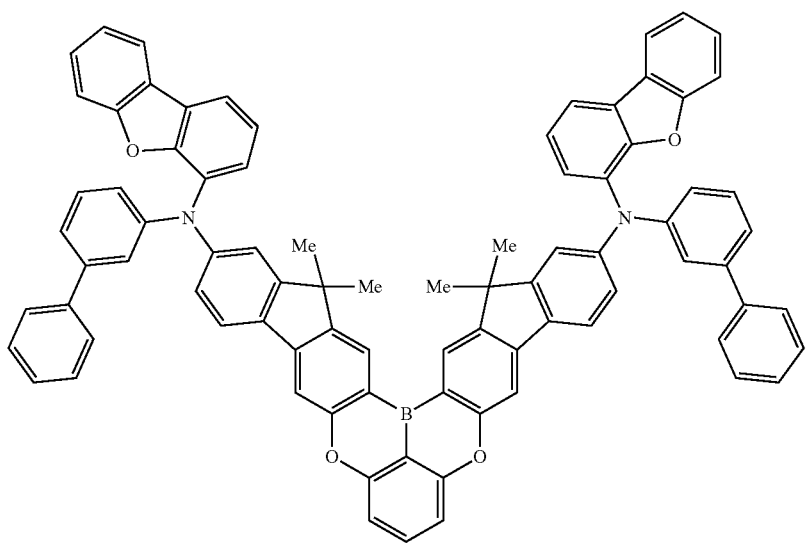
(1-310)
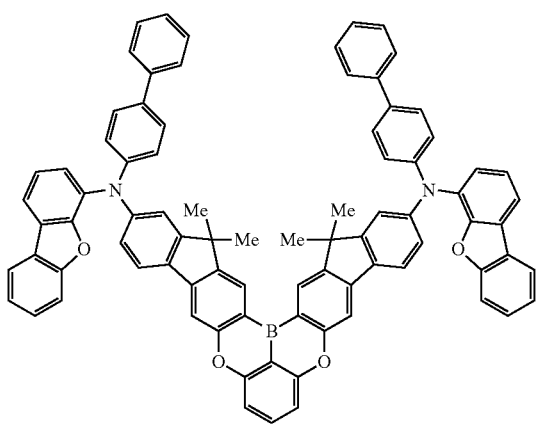
(1-311)
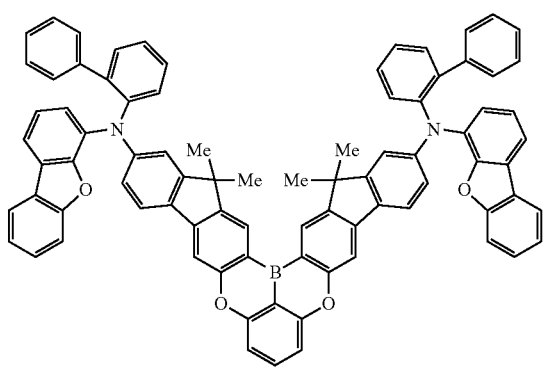

-continued
(1-312)
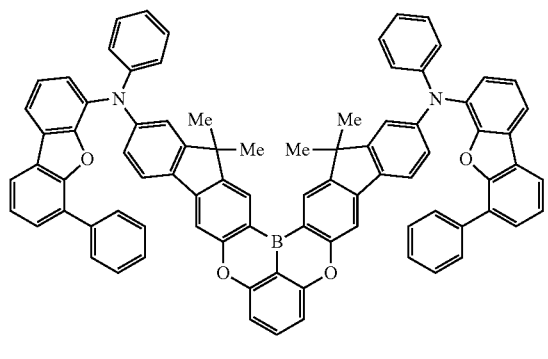
(1-313)
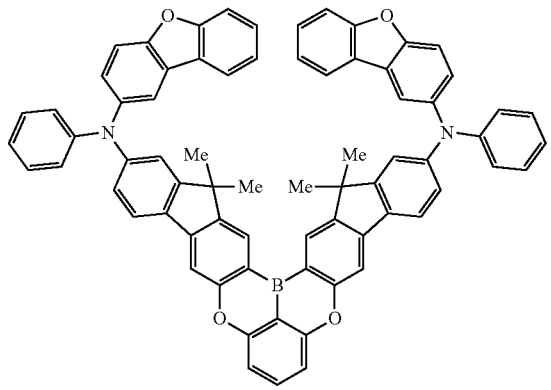
(1-314)
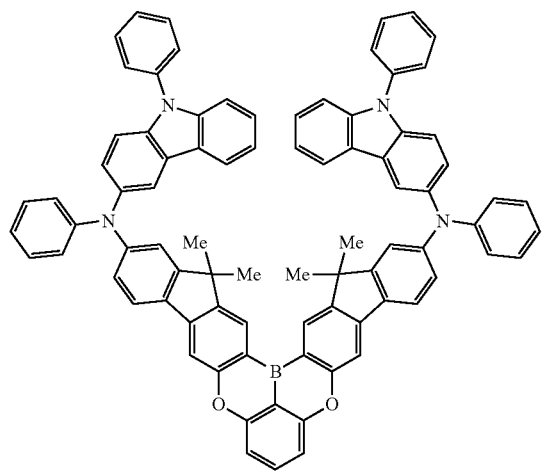
(1-315)
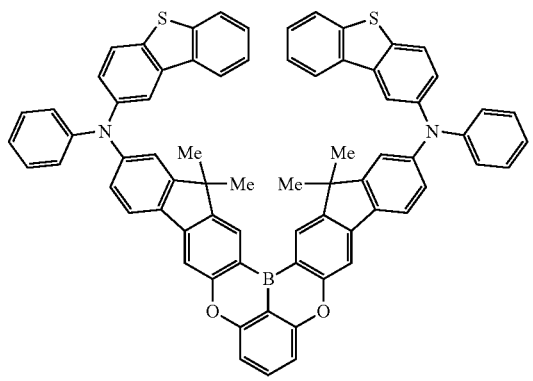
(1-320)
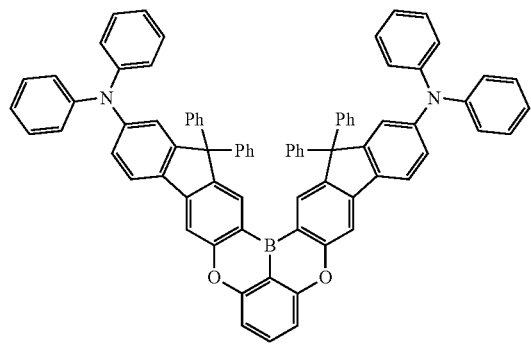
(1-321)
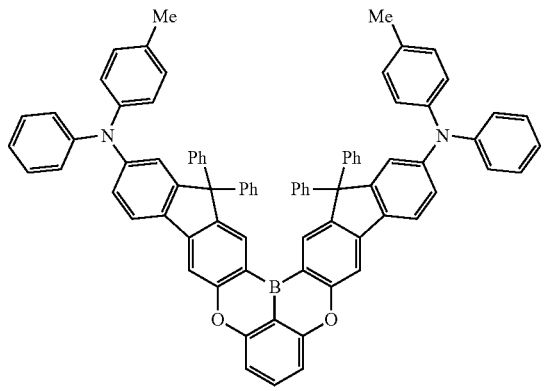

-continued
(1-322)
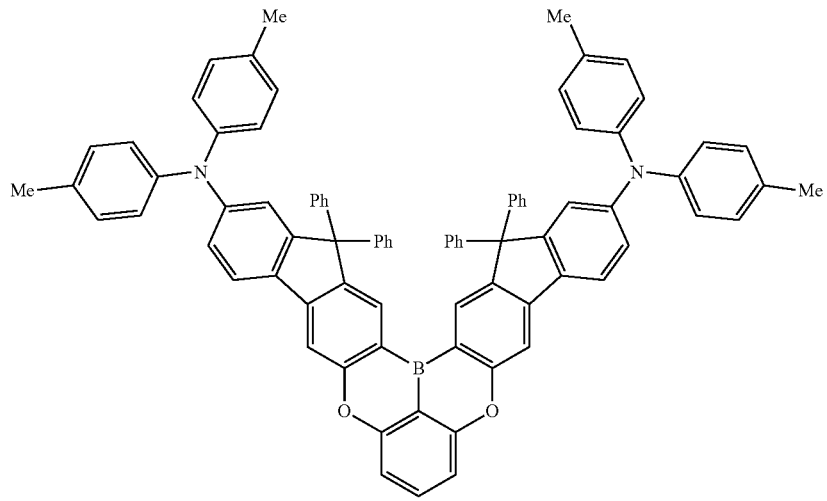
(1-323)
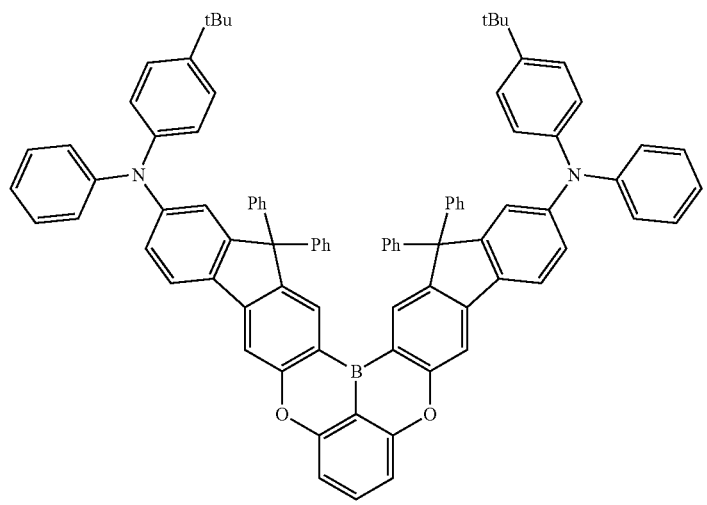
(1-324)
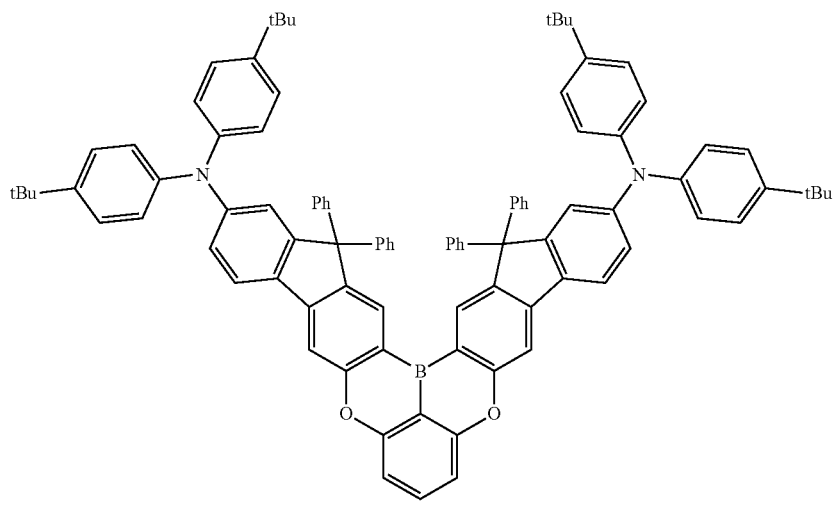

(1-325)
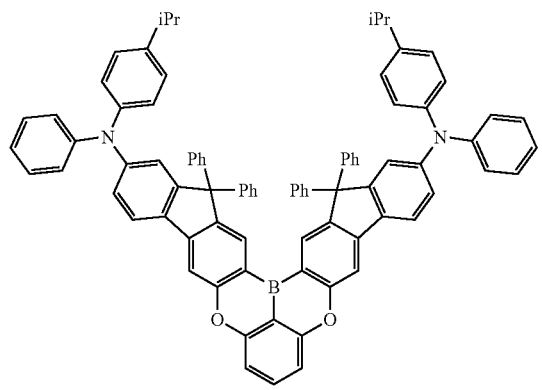
(1-330)
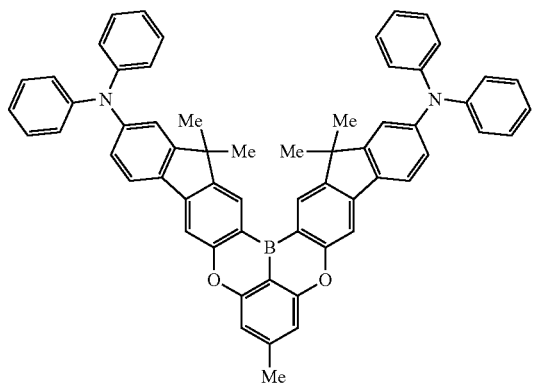
(1-331)
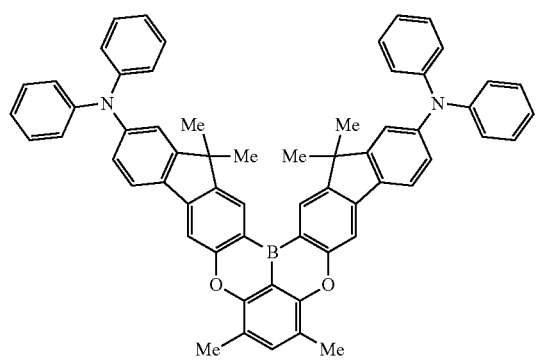
(1-332)
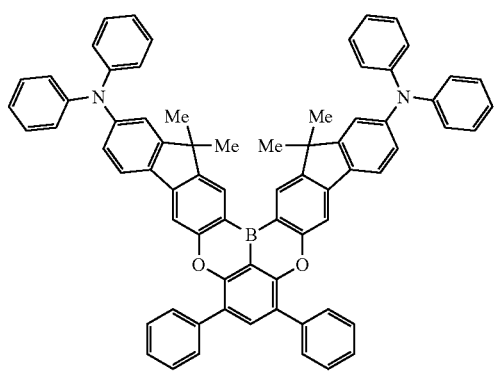
(1-333)
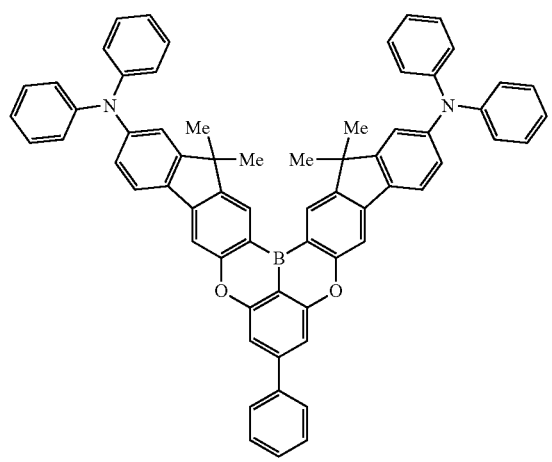
(1-334)
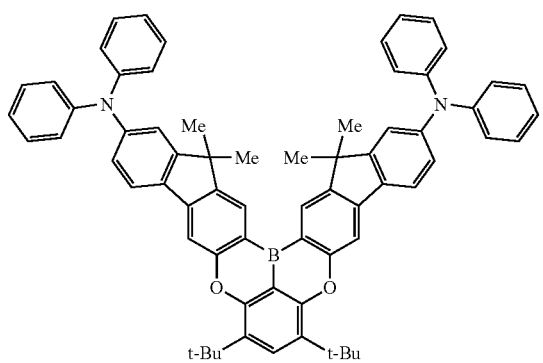

-continued
(1-335)
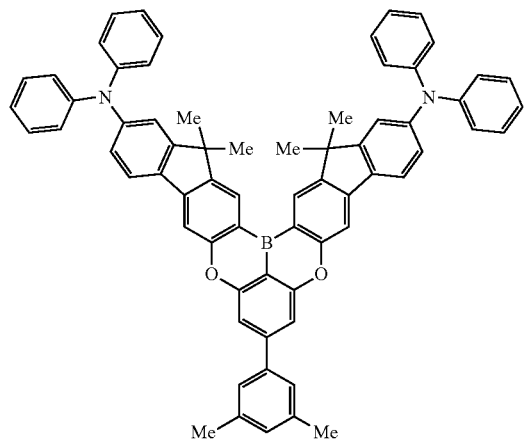
(1-340)
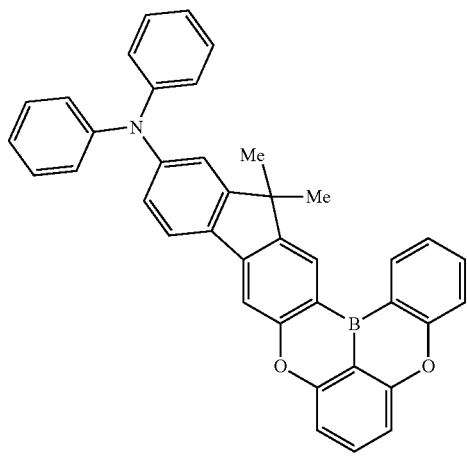
(1-341)
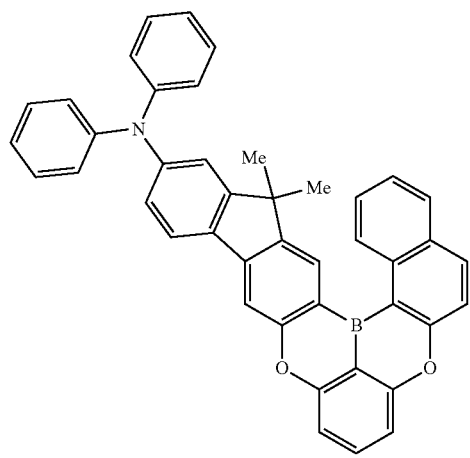
(1-342)
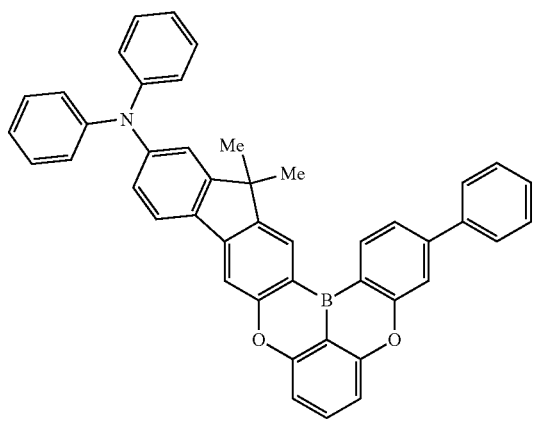
(1-343)
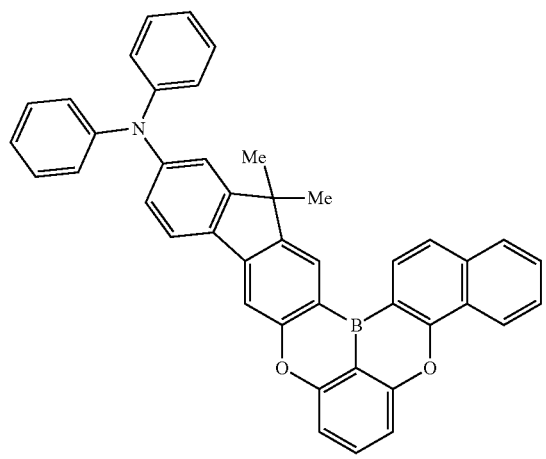
(1-344)
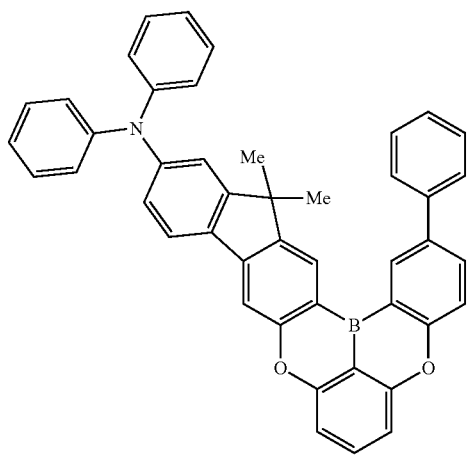

-continued
(1-345)
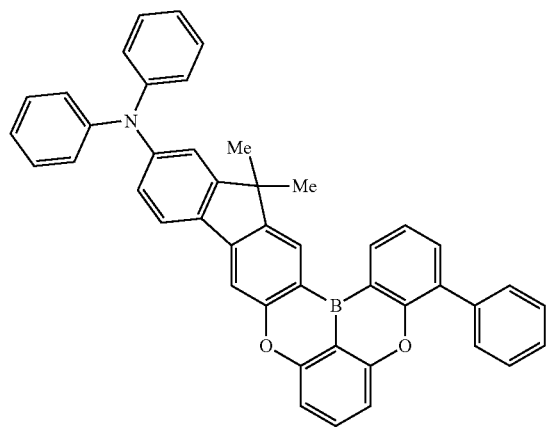
(1-346)
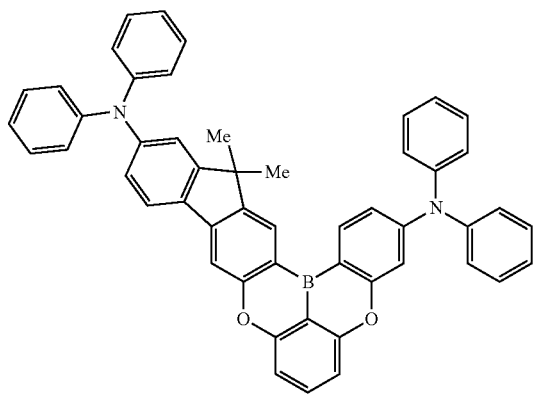
(1-347)
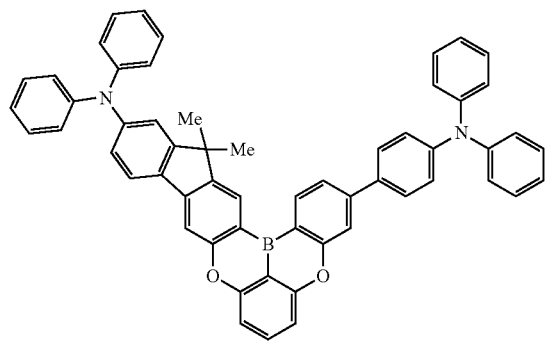
(1-350)
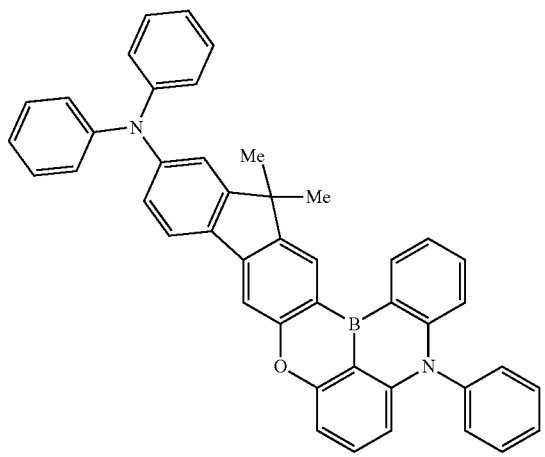
(1-351)
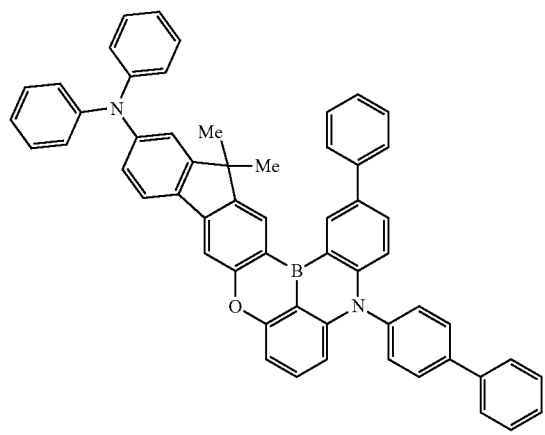
(1-352)
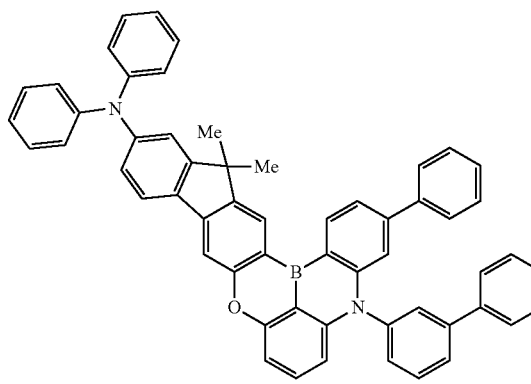

-continued
(1-353)
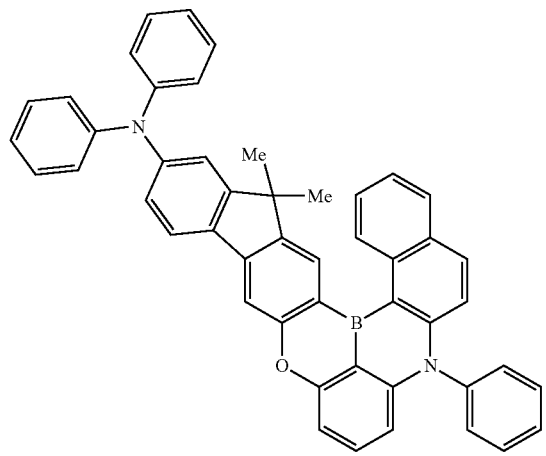
(1-354)
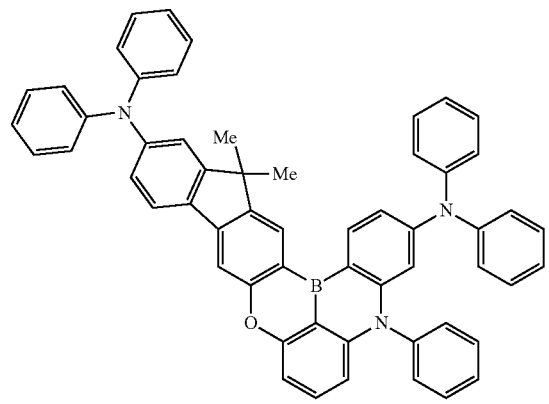
(1-355)
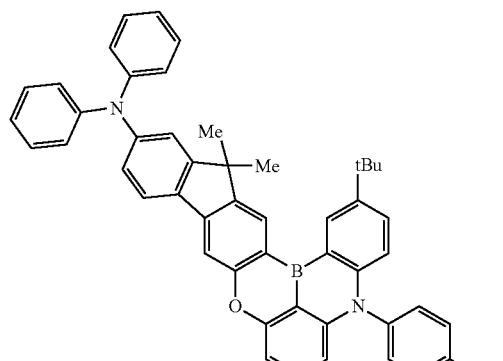
(1-360)
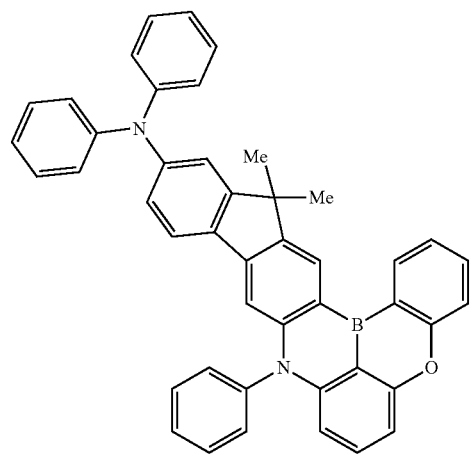
(1-361)
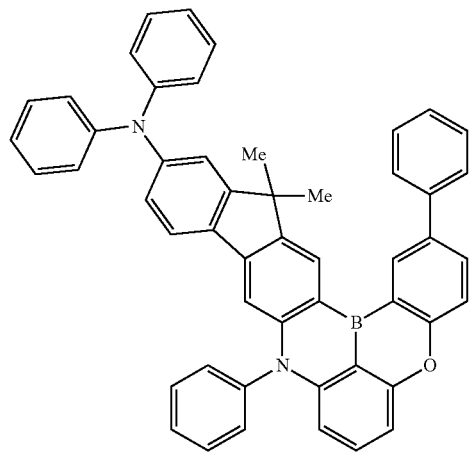
(1-362)
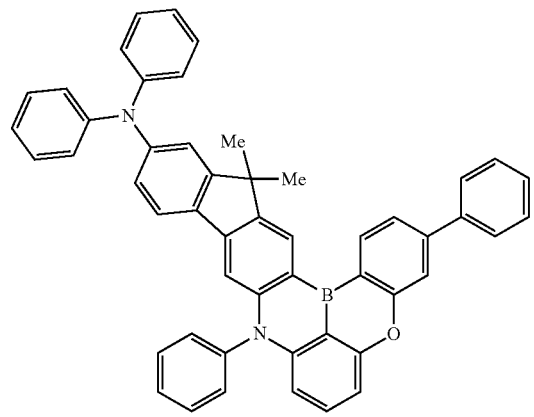

(1-363)
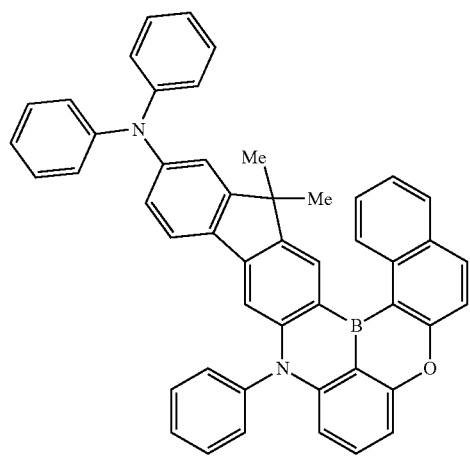
(1-364)
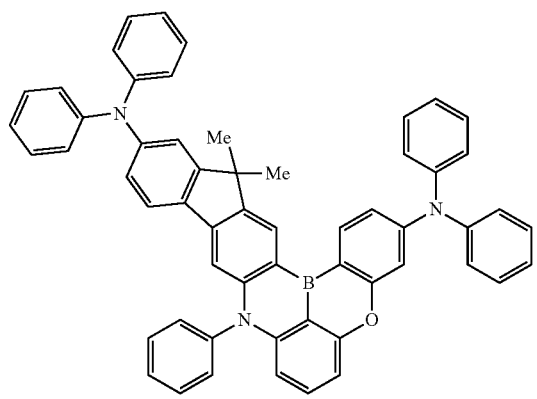
(1-365)
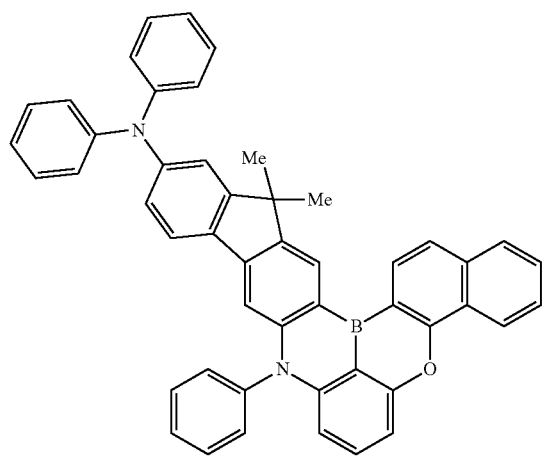
(1-370)
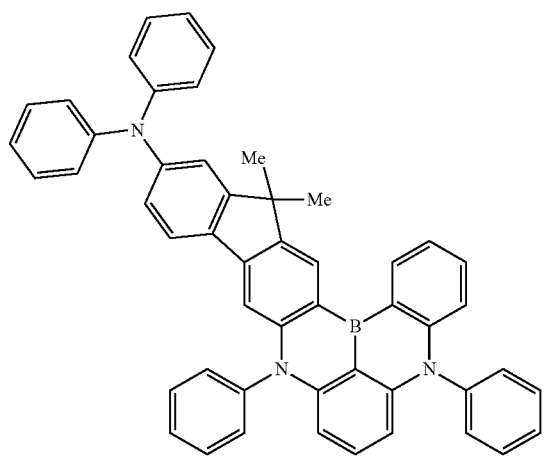
(1-371)
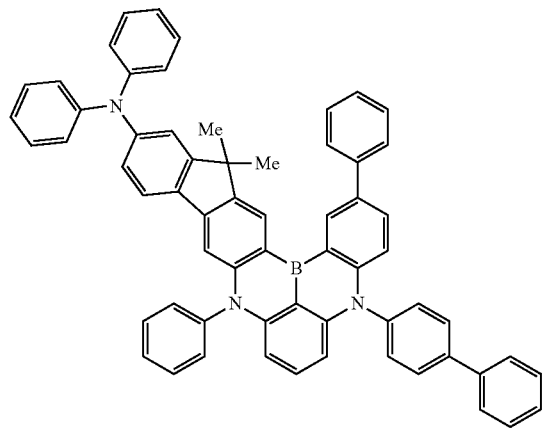
(1-372)
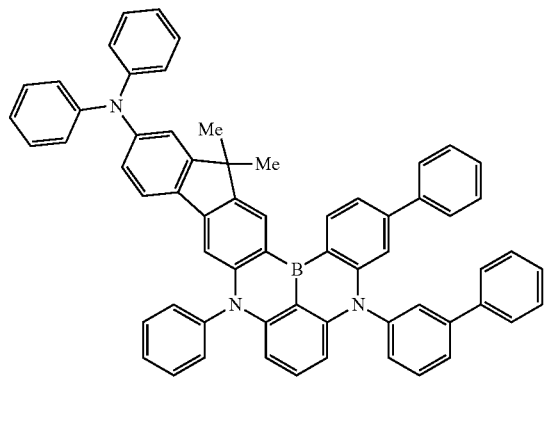

-continued
(1-373)
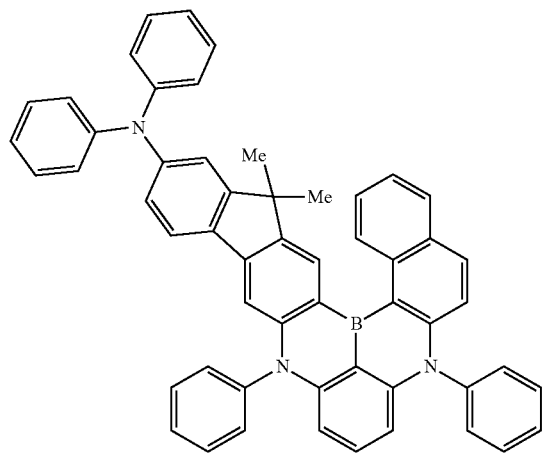
(1-374)
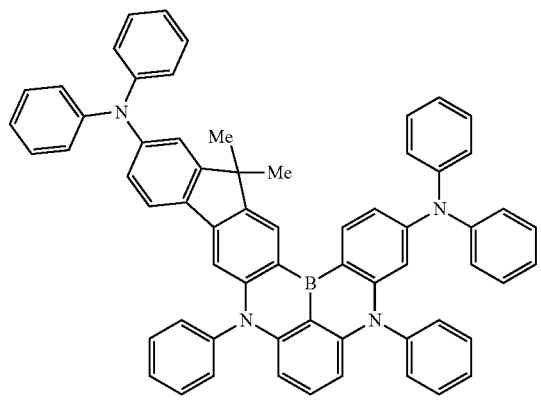
(1-375)
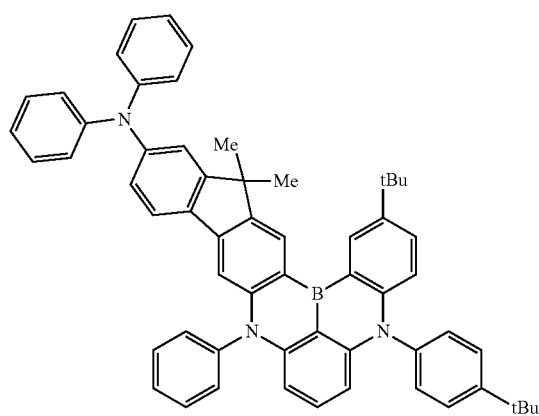
(1-376)
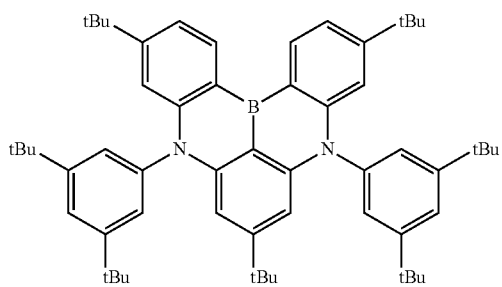
(1-377)
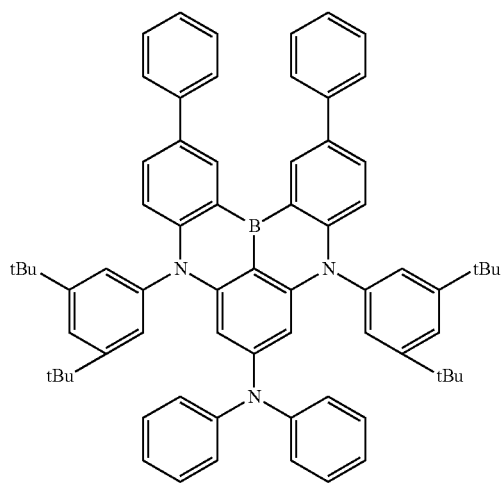
(1-380)
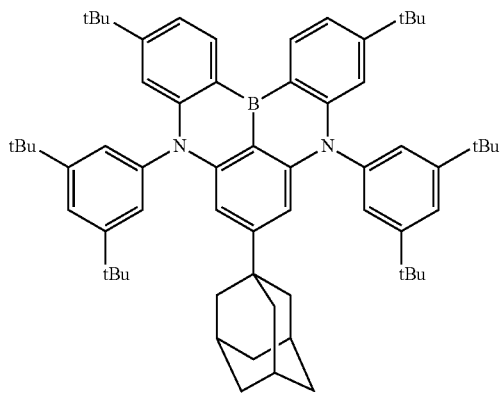

-continued
(1-380)
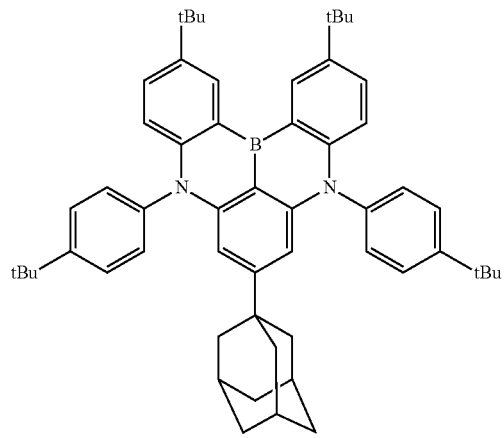
(1-380)
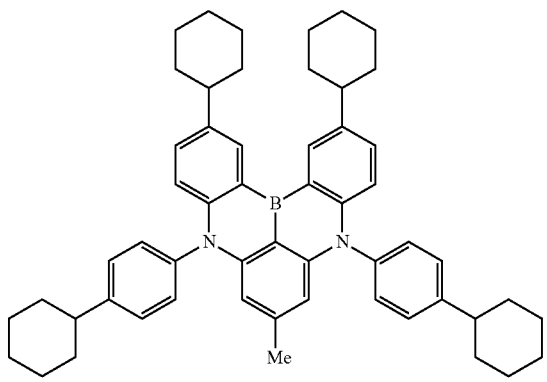
(1-380)
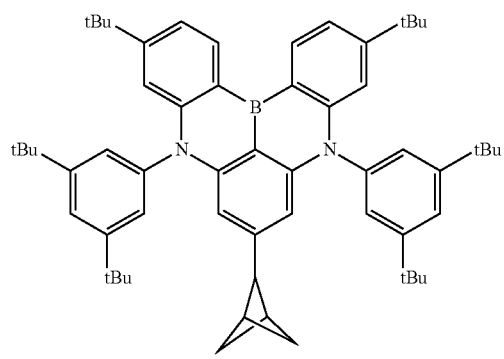
(1-381)
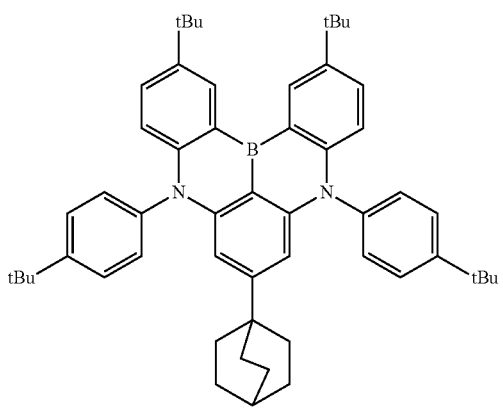
(1-382)
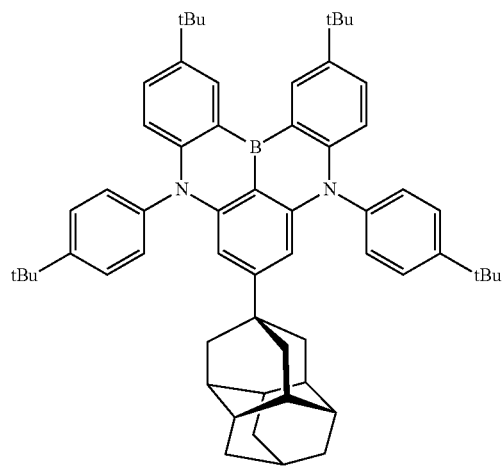
(1-383)
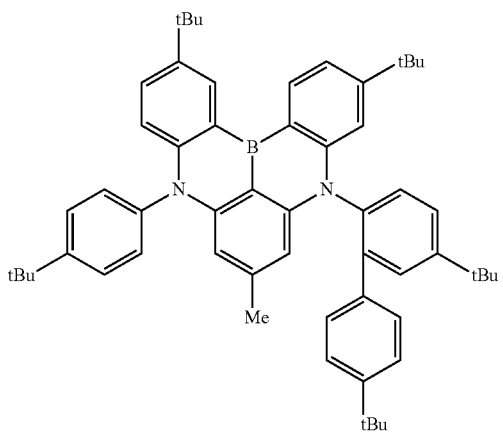

-continued
(1-384)
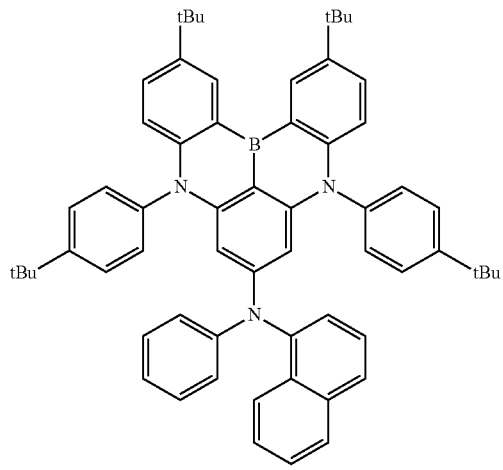
(1-385)
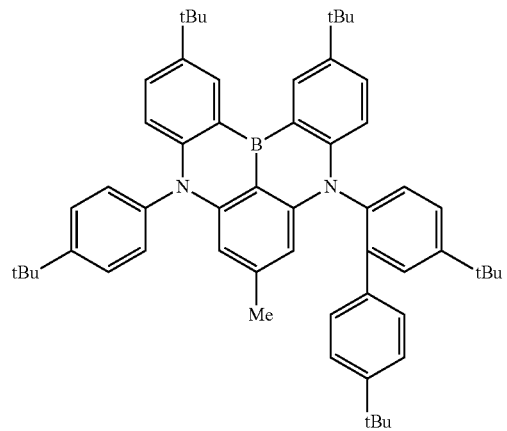
(1-386)
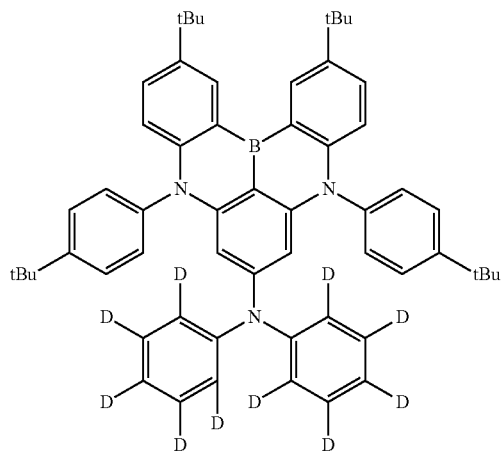
(1-387)
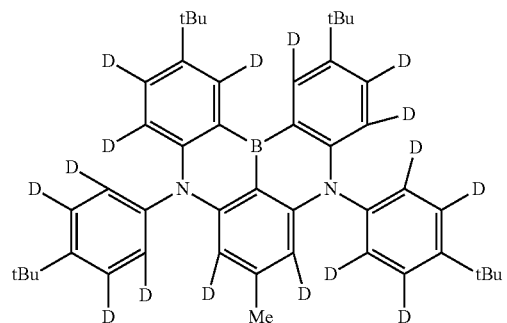
(1-388)
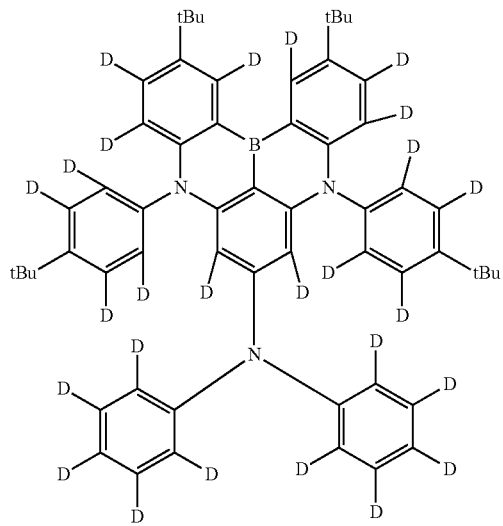

3. Process for Manufacturing Polycyclic Aromatic Compound Represented by Formula (1) and Multimer Thereof A polycyclic aromatic compound represented by general formula (1) or (1') and a multimer thereof can be manufactured according to methods described in many known literatures such as WO 2015/102118 A. For reference, a specific method for manufacturing the polycyclic aromatic compound will be described in Synthesis Example described later.

Basically, first, an intermediate is manufactured by bonding the ring A (ring a), ring B (ring b), and ring C (ring c) with bonding groups (groups containing $X^1$ or $X^2$) (first reaction), and then a final product can be manufactured by bonding the ring A (ring a), ring B (ring b), and ring C (ring c) with bonding groups (groups containing central element B (boron)) (second reaction). In the first reaction, for example, in an etherification reaction, a general reaction such as a nucleophilic substitution reaction or an Ullmann reaction can be utilized, and in an amination reaction, a general reaction such as a Buchwald-Hartwig reaction can be utilized. In the second reaction, a Tandem Hetero-Friedel-Crafts reaction (continuous aromatic electrophilic substitution reaction, the same hereinafter) can be utilized. Furthermore, by using a raw material halogenated, cyanated, or deuterated, or adding a step of halogenation, cyanation, or deuteration anywhere in these reaction steps, it is possible to manufacture a compound in which a desired position is halogenated, cyanated, or deuterated.

The second reaction is a reaction for introducing central element B (boron) that bonds ring A (ring a), ring B (ring b), and ring C (ring c) as illustrated in the following scheme (1) or (2), and as an example, a case in which $X^1$ and $X^2$ represent >O is indicated below. First, a hydrogen atom between $X^1$ and $X^2$ is ortho-metalated with n-butyllithium, sec-butyllithium, t-butyllithium, or the like. Subsequently, boron trichloride, boron tribromide, or the like is added thereto to perform lithium-boron metal exchange, and then a Brønsted base such as N,N-diisopropylethylamine is added thereto to induce a Tandem Bora-Friedel-Crafts reaction. Thus, a desired product can be obtained. In the second reaction, a Lewis acid such as aluminum trichloride may be added in order to accelerate the reaction. The definitions of the reference signs in the following schemes (1) and (2) are the same as the definitions described above.

Scheme (1)

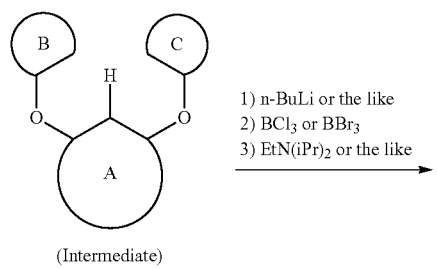

(Intermediate)

1) n-BuLi or the like
2) BCl$_3$ or BBr$_3$
3) EtN(iPr)$_2$ or the like

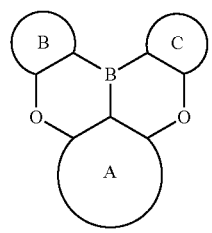

General formula (1)-based compound

Scheme (2)

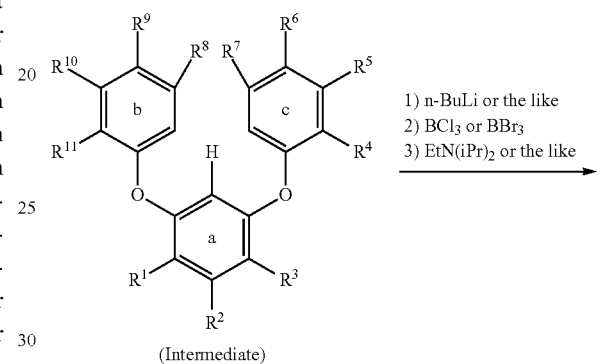

(Intermediate)

1) n-BuLi or the like
2) BCl$_3$ or BBr$_3$
3) EtN(iPr)$_2$ or the like

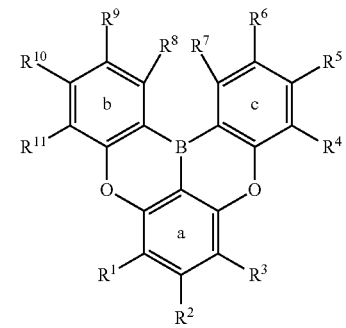

General formula (1')-based compound

Incidentally, the scheme (1) or (2) mainly illustrates a method for manufacturing a polycyclic aromatic compound represented by general formula (1) or (1'). However, a multimer thereof can be manufactured using an intermediate having a plurality of ring A's (ring a's), ring B's (ring b's), and ring C's (ring c's). More specifically, the manufacturing method will be described with the following schemes (3) to (5). In this case, a desired product can be obtained by increasing the amount of a reagent used therein such as butyllithium to a double amount or a triple amount.

Scheme (3)

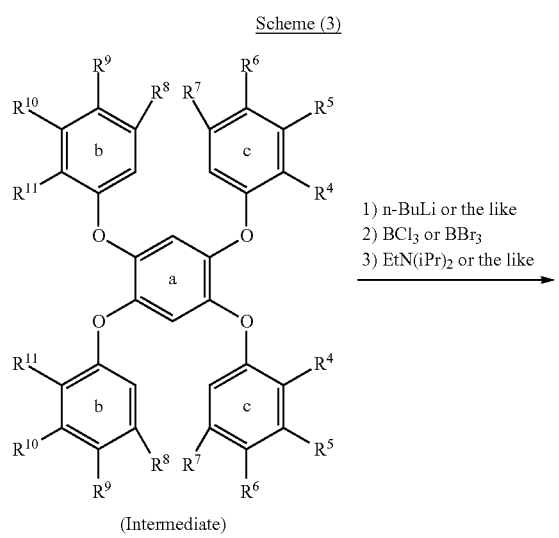

(Intermediate)

1) n-BuLi or the like
2) BCl$_3$ or BBr$_3$
3) EtN(iPr)$_2$ or the like

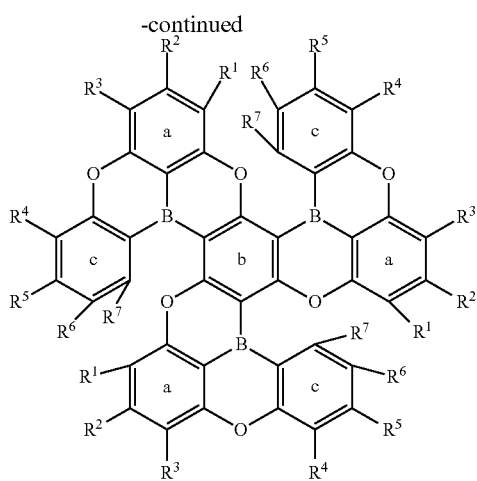

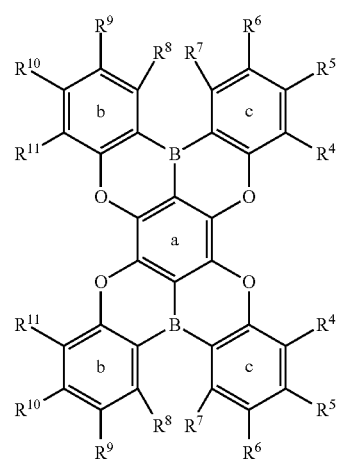

Scheme (4)

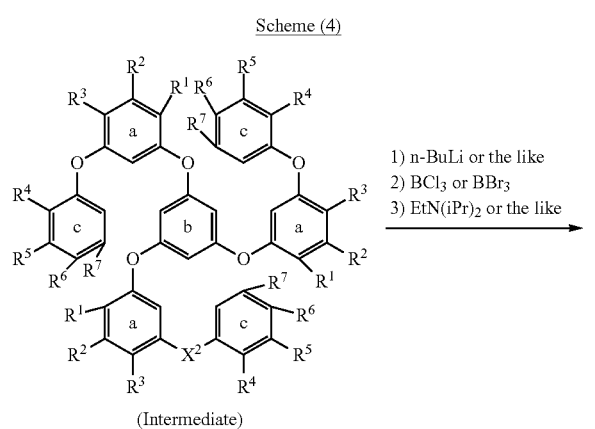

(Intermediate)

1) n-BuLi or the like
2) BCl$_3$ or BBr$_3$
3) EtN(iPr)$_2$ or the like

Scheme (5)

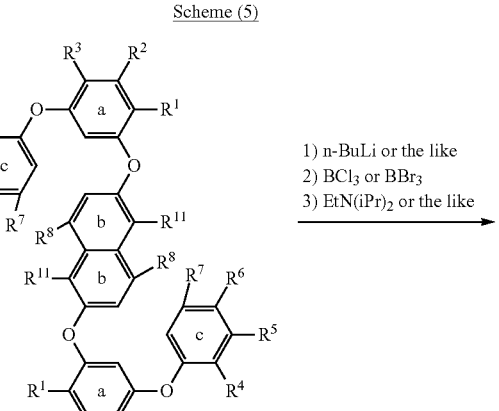

(Intermediate)

1) n-BuLi or the like
2) BCl$_3$ or BBr$_3$
3) EtN(iPr)$_2$ or the like

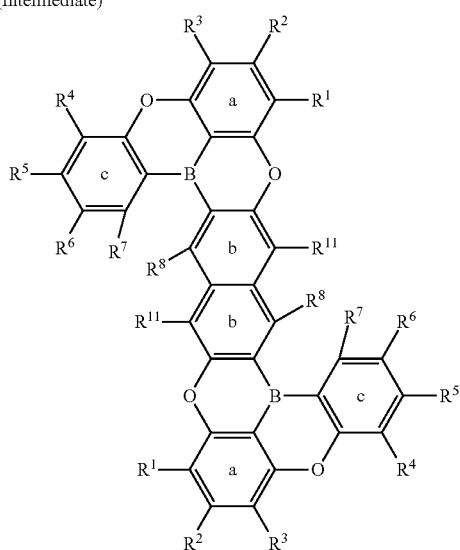

Incidentally, in a case where $X^1$ and $X^2$ each represent >N—R or in a case where either $X^1$ or $X^2$ represents >N—R, the polycyclic aromatic compound can be manufactured in a similar manner to the method described above by using an amine-based compound as an intermediate.

Specific examples of a solvent used in the above schemes include t-butylbenzene and xylene.

Note that examples of an ortho-metalation reagent include an alkyllithium such as methyllithium, n-butyllithium, sec-butyllithium, or t-butyllithium; and an organic alkali compound such as lithium diisopropylamide, lithium tetramethylpiperidide, lithium hexamethyldisilazide, or potassium hexamethyldisilazide.

Furthermore, examples of the Brønsted base include N,N-diisopropylethylamine, triethylamine, 2,2,6,6-tetramethylpiperidine, 1,2,2,6,6-pentamethylpiperidine, N,N-dimethylaniline, N,N-dimethyltoluidine, 2,6-lutidine, sodium tetraphenylborate, potassium tetraphenylborate, triphenylborane, tetraphenylsilane, $Ar_4BNa$, $Ar_4BK$, $Ar_3B$, and $Ar_4Si$ (note that Ar represents an aryl such as phenyl).

Examples of the Lewis acid include $AlCl_3$, $AlBr_3$, $AlF_3$, $BF_3$ $OEt_2$, $BCl_3$, $BBr_3$, $GaCl_3$, $GaBr_3$, $InCl_3$, $InBr_3$, $In(OTf)_3$, $SnCl_4$, $SnBr_4$, $AgOTf$, $ScCl_3$, $Sc(OTf)_3$, $ZnCl_2$, $ZnBr_2$, $Zn(OTf)_2$, $MgCl_2$, $MgBr_2$, $Mg(OTf)_2$, $LiOTf$, $NaOTf$, $KOTf$, $Me_3SiOTf$, $Cu(OTf)_2$, $CuCl_2$, $YCl_3$, $Y(OTf)_3$, $TiCl_4$, $TiBr_4$, $ZrCl_4$, $ZrBr_4$, $FeCl_3$, $FeBr_3$, $CoCl_3$, and $CoBr_3$.

4. Pyrene-Based Compound Represented by General Formula (2)

Basically, a pyrene-based compound represented by general formula (2) functions as a host.

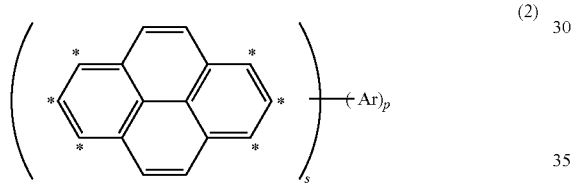

(2)

In the above formula (2), s pyrene moieties are bonded to p Ar moieties at any position of * in each of the pyrene moieties and any position in each of the Ar moieties, at least one hydrogen atom of the pyrene moieties may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, and at least one hydrogen atom in these substituents may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, Ar's each independently represent an aryl having 14 to 40 carbon atoms or a heteroaryl having 12 to 40 carbon atoms, and at least one hydrogen atom in these groups may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, s and p each independently represent an integer of 1 or 2, s and p do not simultaneously represent 2, when s represents 2, the two pyrene moieties including a substituent may be structurally the same or different, and when p represents 2, the two Ar moieties including a substituent may be structurally the same or different, and at least one hydrogen atom in the compound represented by formula (2) may be each independently substituted by a halogen atom, cyano, or a deuterium atom.

Ar represents an aryl having 14 to 40 carbon atoms or a heteroaryl having 12 to 40 carbon atoms, and various substituents can be bonded thereto. Specific examples of Ar include groups represented by the following general formula (Ar-1) and (Ar-2). $R^1$ to $R^8$ and $R^{10}$ to $R^{19}$ represent substituents.

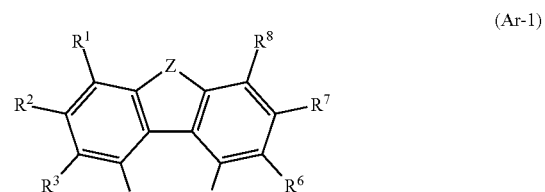

(Ar-1)

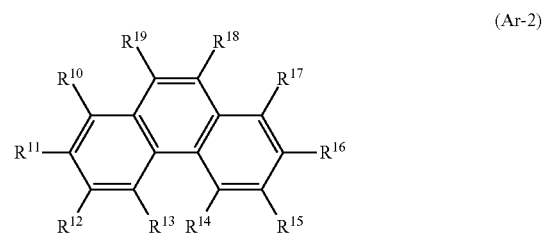

(Ar-2)

Furthermore, examples of a group in which adjacent $R^{18}$ and $R^{19}$ are bonded to each other to form a fused ring in the group represented by formula (Ar-2) include a group represented by the following general formula (Ar-3). $R^{20}$ to $R^{35}$ represent substituents.

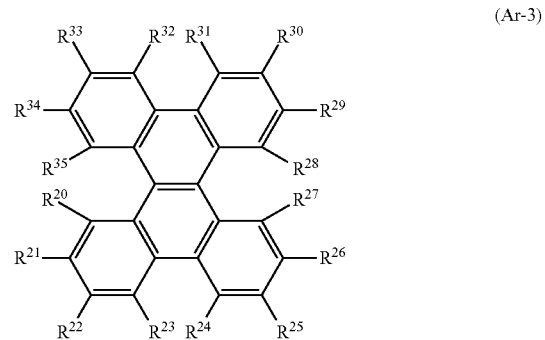

(Ar-3)

More specific examples of the group represented by formula (Ar-1) or (Ar-2) include groups represented by the following general formulas. Among these groups, the group represented by formula (Ar-1-1), (Ar-1-2), (Ar-3), (Ar-1-4), (Ar-2-2), or (Ar-2-4) is preferable, and the group represented by formula (Ar-1-2), (Ar-1-3), (Ar-1-4), or (Ar-2-4) is more preferable. In the following structural formulas, substituents are not explicitly illustrated, but at least one hydrogen atom in each of the structures may be substituted. Note that the group represented by the following formula (Ar-2-4) corresponds to the group represented by the above formula (Ar-3).

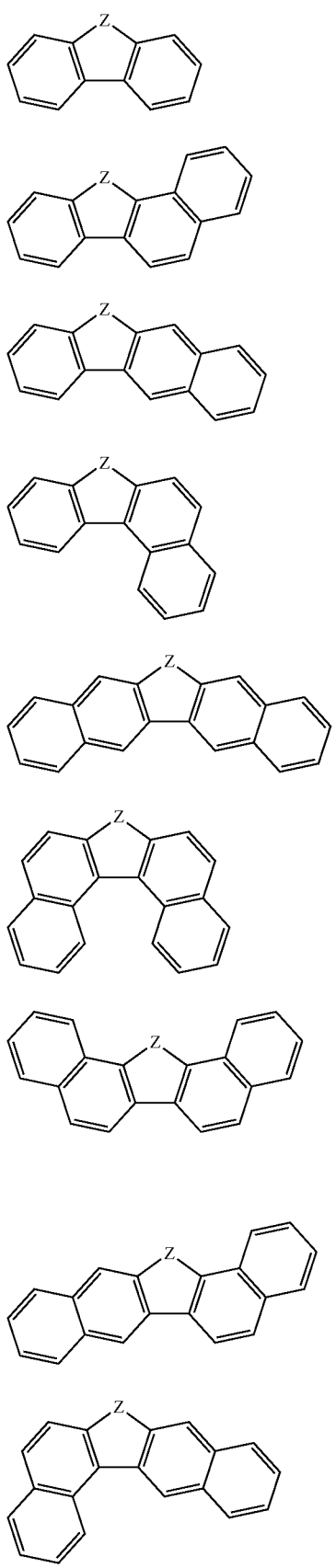
(Ar-1-1)
(Ar-1-2)
(Ar-1-3)
(Ar-1-4)
(Ar-1-5)
(Ar-1-6)
(Ar-1-7)
(Ar-1-8)
(Ar-1-9)
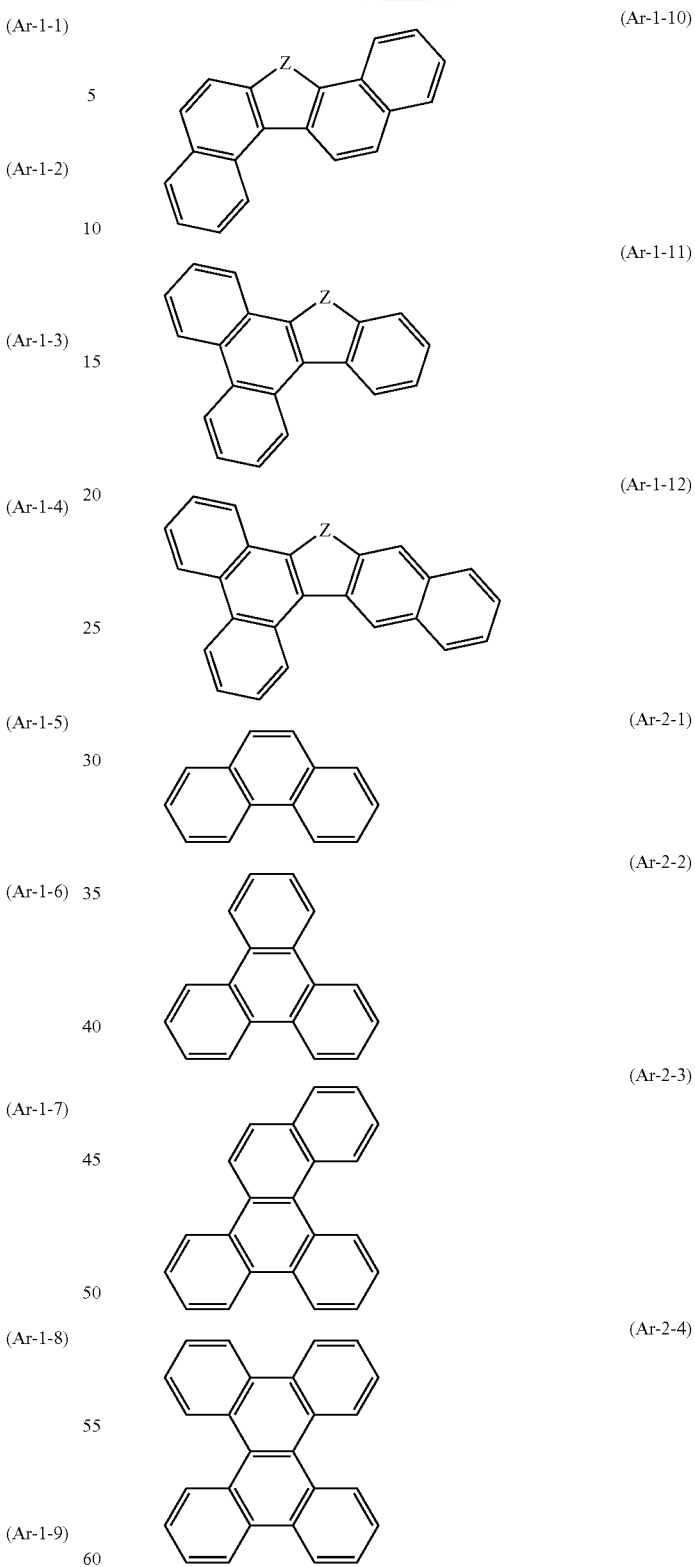
-continued
(Ar-1-10)
(Ar-1-11)
(Ar-1-12)
(Ar-2-1)
(Ar-2-2)
(Ar-2-3)
(Ar-2-4)
An aryl having 14 to 40 carbon atoms or a heteroaryl having 12 to 40 carbon atoms as Ar, a first substituent on the pyrene moiety (an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, preferably an aryl having 6 to 10 carbon atoms), a second substituent on the first substituent (an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, preferably an aryl having 6 to 10 carbon atoms), and a substituent on Ar ($R^1$ to $R^8$ in formula (Ar-1), $R^{10}$ to $R^{19}$ in formula (Ar-2), $R^{20}$ to $R^{35}$ in formula (Ar-3), and an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, preferably an alkyl having 1 to 30 carbon atoms, which is a substituent not explicitly represented by formulas (Ar-1-1) to (Ar-2-4)) will be described below collectively.

The aryl having 14 to 40 carbon atoms or the heteroaryl having 12 to 40 carbon atoms as Ar is preferably an aryl having 14 to 35 carbon atoms or a heteroaryl having 12 to 35 carbon atoms, more preferably an aryl having 14 to 30 carbon atoms or a heteroaryl having 12 to 30 carbon atoms, still more preferably an aryl having 14 to 25 carbon atoms or a heteroaryl of 12 to 25 carbon atoms, particularly preferably an aryl having 14 to 20 carbon atoms or a heteroaryl having 12 to 20 carbon atoms, and most preferably an aryl having 14 to 18 carbon atoms or a heteroaryl having 12 to 18 carbon atoms.

Specific examples of the aryl include phenyl which is a monocyclic system, biphenylyl which is a bicyclic system, naphthyl which is a fused bicyclic system, terphenylyl (m-terphenylyl, o-terphenylyl, or p-terphenylyl) which is a tricyclic system, anthracenyl, acenaphthylenyl, fluorenyl, phenalenyl, and phenanthrenyl which are fused tricyclic systems, triphenyleny and naphthacenyl which are fused tetracyclic systems, and perylenyl and pentacenyl which are fused pentacyclic systems.

Specific examples of the heteroaryl include pyrrolyl, oxazolyl, isoxazolyl, thiazolyl, isothiazolyl, imidazolyl, oxadiazolyl, thiadiazolyl, triazolyl, tetrazolyl, pyrazolyl, pyridyl, pyrimidinyl, pyridazinyl, pyrazinyl, triazinyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxathiinyl, phenoxazinyl, phenothiazinyl, phenazinyl, indolizinyl, furyl, benzofuranyl, isobenzofuranyl, dibenzofuranyl, thienyl, benzo[b]thienyl, dibenzothienyl, furazanyl, oxadiazolyl, thianthrenyl, naphthobenzofuranyl, and naphthobenzothienyl.

With regard to the first substituent on the pyrene moiety, the second substituent on the first substituent, and the substituent on Ar, specific examples of the aryl having 6 to 10 carbon atoms include phenyl and naphthyl. As specific examples of the heteroaryl having 2 to 11 carbon atoms, groups selected from the above-described heteroaryl groups can be cited.

The aryloxy having 6 to 30 carbon atoms is a group in which a hydrogen atom of the hydroxyl group is substituted by an aryl having 6 to 30 carbon atoms. The aryl is preferably an aryl having 6 to 25 carbon atoms, more preferably an aryl having 6 to 20 carbon atoms, still more preferably an aryl having 6 to 15 carbon atoms, and particularly preferably an aryl having 6 to 10 carbon atoms. As specific examples of the aryl, groups selected from the above-described aryl groups can be cited.

The alkyl having 1 to 30 carbon atoms may be either linear or branched, and is, for example, preferably a linear alkyl having 1 to 24 carbon atoms or a branched alkyl having 3 to 24 carbon atoms, more preferably an alkyl having 1 to 18 carbon atoms (a branched alkyl having 3 to 18 carbon atoms), still more preferably an alkyl having 1 to 12 carbon atoms (a branched alkyl having 3 to 12 carbon atoms), particularly preferably an alkyl having 1 to 6 carbon atoms (a branched alkyl having 3 to 6 carbon atoms), and most preferably an alkyl having 1 to 4 carbon atoms (a branched alkyl having 3 or 4 carbon atoms). Methyl, ethyl, isopropyl, or t-butyl is more preferable among these groups, and methyl or t-butyl is most preferable.

Specific examples of the alkyl include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

Examples of the cycloalkyl having 3 to 24 carbon atoms include a cycloalkyl having 3 to 20 carbon atoms, a cycloalkyl having 3 to 16 carbon atoms, a cycloalkyl having 3 to 14 carbon atoms, a cycloalkyl having 5 to 10 carbon atoms, a cycloalkyl having 5 to 8 carbon atoms, a cycloalkyl having 5 or 6 carbon atoms, and a cycloalkyl having 5 carbon atoms.

Specific examples of the cycloalkyl include cyclopropyl, methylcyclopropyl, cyclobutyl, methylcyclobutyl, cyclopentyl, methylcyclopentyl, cyclohexyl, methylcyclohexyl, cycloheptyl, methylcycloheptyl, cyclooctyl, methylcyclooctyl, cyclononyl, methylcyclononyl, cyclodecyl, methylcyclodecyl, bicyclo[1.0.1]butyl, bicyclo[1.1.1]pentyl, bicyclo[2.0.1]pentyl, bicyclo[1.2.1]hexyl, bicyclo[3.0.1]hexyl, bicyclo[2.1.2]heptyl, bicyclo[2.2.2]octyl, adamantyl, diamantyl, decahydronaphthalenyl, and decahydroazulenyl.

The alkenyl having 2 to 30 carbon atoms is, for example, preferably an alkenyl having 2 to 20 carbon atoms, more preferably an alkenyl having 2 to 10 carbon atoms, still more preferably an alkenyl having 2 to 6 carbon atoms, and particularly preferably an alkenyl having 2 to 4 carbon atoms.

Specific examples of the alkenyl include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

The alkoxy having 1 to 30 carbon atoms is, for example, preferably an alkoxy having 1 to 24 carbon atoms (a branched alkoxy having 3 to 24 carbon atoms), more preferably an alkoxy having 1 to 18 carbon atoms (a branched alkoxy having 3 to 18 carbon atoms), still more preferably an alkoxy having 1 to 12 carbon atoms (a branched alkoxy having 3 to 12 carbon atoms), particularly preferably an alkoxy having 1 to 6 carbon atoms (an alkoxy having 3 to 6 carbon atoms), and most preferably an alkoxy having 1 to 4 carbon atoms (a branched alkoxy having 3 or 4 carbon atoms).

Specific examples of the alkoxy include methoxy, ethoxy, propoxy, isopropoxy, butoxy, isobutoxy, s-butoxy, t-butoxy, pentyloxy, hexyloxy, heptyloxy, and octyloxy.

In formulas (Ar-1) and (Ar-2), adjacent groups among $R^1$ to $R^8$ or adjacent groups among $R^{10}$ to $R^{19}$ may be bonded to each other to form a fused ring. The term "adjacent groups" refers to a combination other than a combination of $R^4$ and $R^5$ or a combination of $R^{13}$ and $R^{14}$, and refers to, for example, a combination of $R^1$ and $R^2$. A structure in which a fused ring is formed in this way is the structure represented by each of the above formulas (Ar-1-2) to (Ar-1-12) and (Ar-2-2) to (Ar-2-4) ((Ar-3)). Meanwhile, the above formula (Ar-1-1) or (Ar-2-1) indicates a structure not containing a fused ring. Examples of the fused ring thus formed include a benzene ring, a naphthalene ring, a phenanthrene ring, a thiophene ring, a pyrrole ring, and a furan ring. A benzene ring, a naphthalene ring, or a phenanthrene ring, which is an aryl ring, is preferable, and a benzene ring is more preferable.

The fused ring formed by bonding adjacent groups to each other may be substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms. These substituents may be further substituted by an alkyl having 1 to 6 carbon atoms or a cycloalkyl having 3 to 14 carbon atoms. As detailed description of these groups, the above description can be cited.

Furthermore, Z represents $>CR_2$, $>N-R$, $>O$, or $>S$. Among these groups, Z preferably represents $>CR_2$ or $>O$, and more preferably represents $>CR_2$. With regard to R (an alkyl having 1 to 6 carbon atoms, a cycloalkyl having 3 to 14 carbon atoms, an aryl having 6 to 12 carbon atoms which may be substituted by an alkyl having 1 to 4 carbon atoms or a cycloalkyl having 5 to 10 carbon atoms, or a heteroaryl having 2 to 12 carbon atoms which may be substituted by an alkyl having 1 to 4 carbon atoms or a cycloalkyl having 5 to 10 carbon atoms) in $>CR_2$, and R (an alkyl having 1 to 4 carbon atoms, a cycloalkyl having 5 to 10 carbon atoms, an aryl having 6 to 12 carbon atoms which may be substituted by an alkyl having 1 to 4 carbon atoms or a cycloalkyl having 5 to 10 carbon atoms, or a heteroaryl having 2 to 12 carbon atoms which may be substituted by an alkyl having 1 to 4 carbon atoms or a cycloalkyl having 5 to 10 carbon atoms) in $>N-R$, as details of these groups, the above description of the alkyl, cycloalkyl, aryl, and heteroaryl can be cited.

With regard to $>CR_2$ which is Z, the R's may be bonded to each other to form a ring. In this case, a spiro structure is formed.

The above formula (2) means that s pyrene moieties are bonded to p Ar moieties at any position of * (1-position and/or 2-position) in each of the pyrene moieties. s and p each independently represent an integer of 1 or 2, and s and p do not simultaneously represent 2. The pyrene moiety has a symmetrical structure. Therefore, in a case of s=1 and p=1 or s=2 and p=1, the 1-position and the 2-position of the pyrene moiety can be indicated by * at two positions. In a case of s=1 and p=2, it is indicated that two Ar moieties can be bonded to 6 positions of the pyrene moiety by six symbols of *. When s represents 2, the two pyrene moieties including a substituents may be structurally the same or different. When p represents 2, the two Ar moieties including a substituent may be structurally the same or different. That is, in the pyrene moiety, as described above, various substituents may be bonded to the pyrene structure. When a substituent is bonded to the pyrene structure, the pyrene structure constitutes the pyrene moiety including the bonded substituent. Similarly, the Ar moiety constitutes the Ar moiety including a bonded substituent. When the pyrene-based compound represented by formula (2) contains a plurality of pyrene moieties or Ar moieties, the pyrene moiety including a substituent and the Ar moiety including a substituent may be structurally the same or different, and are preferably the same.

Incidentally, regarding a bond between the pyrene moiety and the Ar moiety, Ar is bonded at the position of (1-position and/or 2-position) in the pyrene moiety. Meanwhile, the pyrene moiety may be bonded at any position in the Ar moiety. For example, in formula (Ar-1) or (Ar-2) which is an example of Ar, the pyrene moiety may be bonded at any position of $R^1$ to $R^8$ and $R^{10}$ to $R^{19}$. Furthermore, when adjacent groups are bonded to each other to form a fused ring, the pyrene moiety may be bonded to the fused ring. When a substituent such as an aryl is selected as any one of $R^1$ to $R^8$ and $R^{10}$ to $R^{19}$, the pyrene moiety may be bonded at any position of the aryl. When a substituent such as an aryl is selected as R in $>CR_2$ and $>N-R$ as Z, the pyrene moiety may be bonded at any position of the aryl. Among these bonding positions, any position of $R^1$ to $R^8$ and $R^{10}$ to $R^{19}$ in formula (Ar-1) or (Ar-2) is preferable. This description also applies to lower formulas of the formulas (Ar-1) and (Ar-2).

All or some of hydrogen atoms in the pyrene-based compound represented by formula (2) may be substituted by halogen atoms, cyanos, or deuterium atoms. For example, in formula (2), a hydrogen atom in the pyrene moiety or the Ar moiety may be substituted by a halogen atom, cyano, or a deuterium atom. The halogen is fluorine, chlorine, bromine, or iodine, preferably fluorine, chlorine, or bromine, and more preferably fluorine.

Specific examples of the pyrene-based compound according to an embodiment of the present invention include compounds represented by the following structural formulas. Incidentally, in the following structural formulas, "Me" represents a methyl group, "Et" represents an ethyl group, "tBu" represents a tertiary butyl group, "iPr" represents an isopropyl group, and "D" represents a deuterium atom.

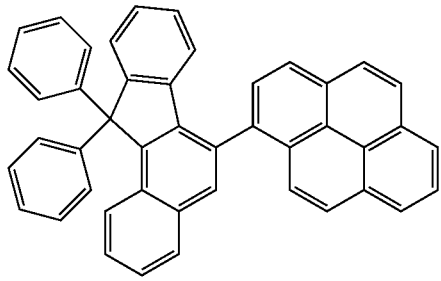

(2-1)

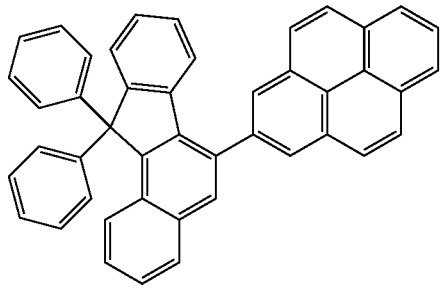

(2-2)

-continued
(2-3)
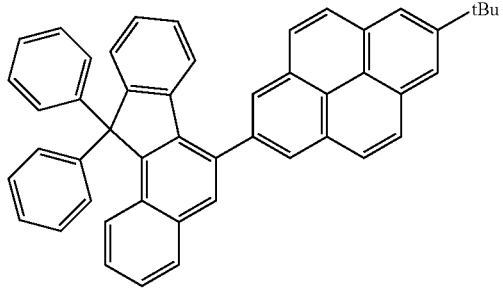
(2-4)
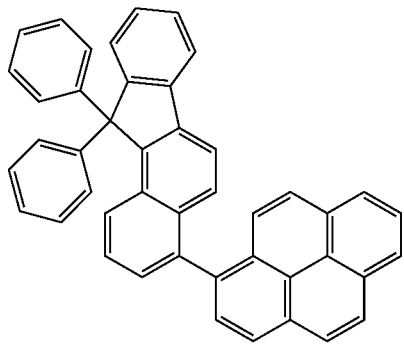
(2-5)
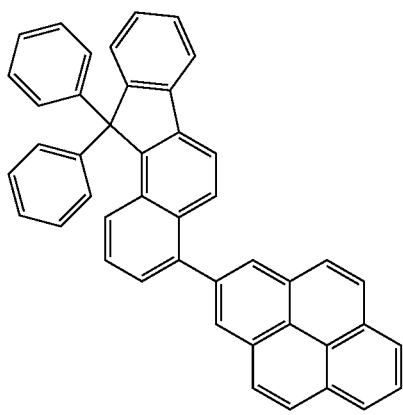
(2-6)
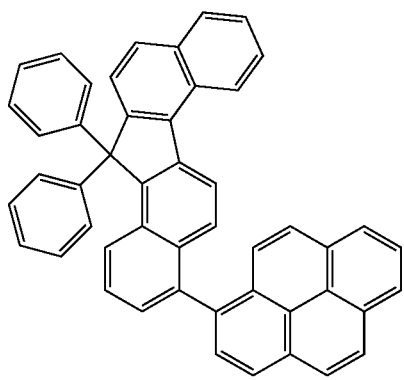
(2-7)
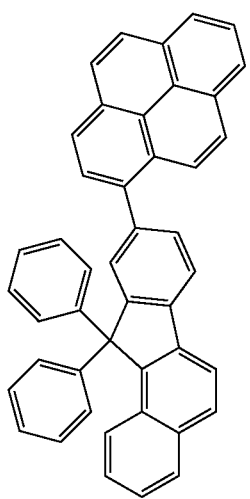
(2-8)
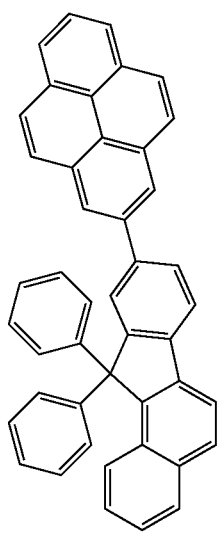

-continued
(2-9)
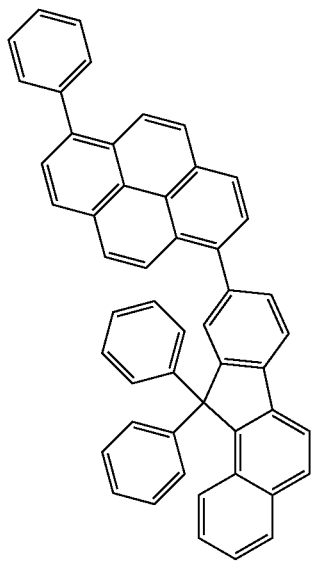
(2-10)
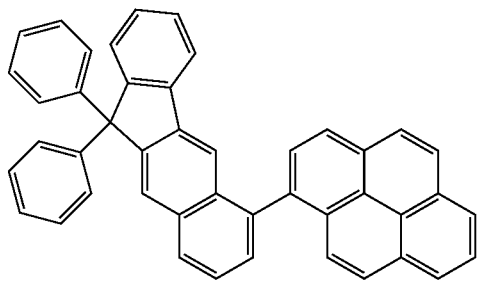
(2-11)
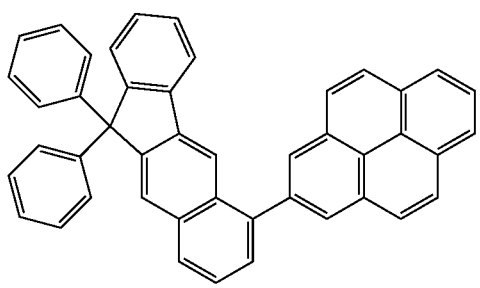
(2-12)
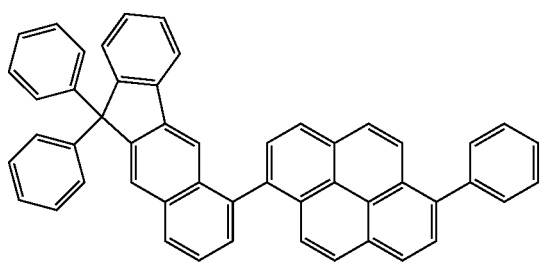
(2-13)
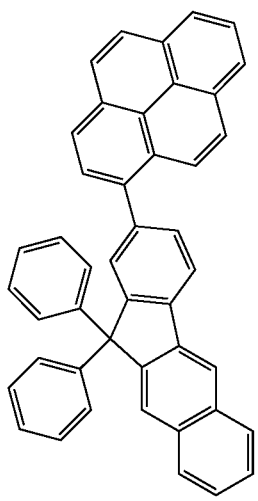
(2-14)
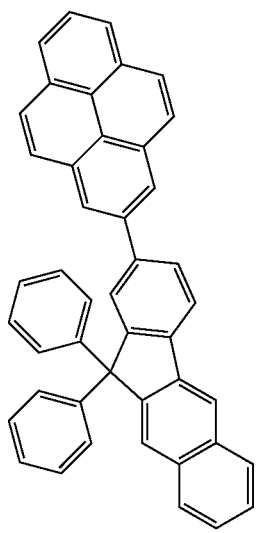

-continued
(2-15)
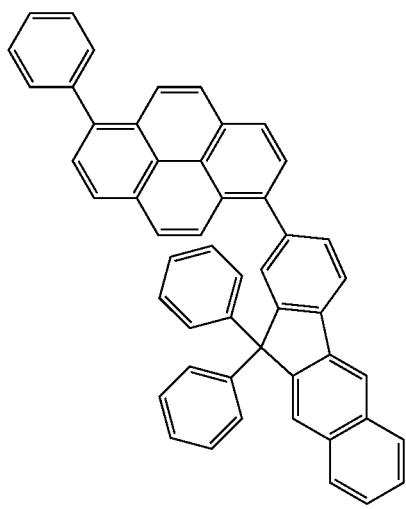
(2-16)
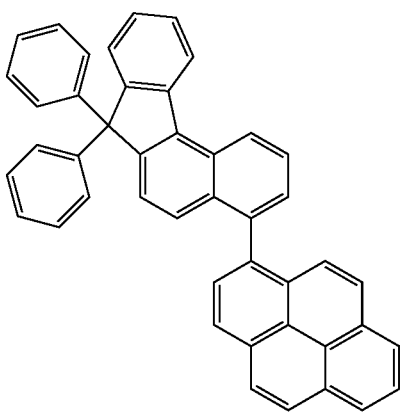
(2-17)
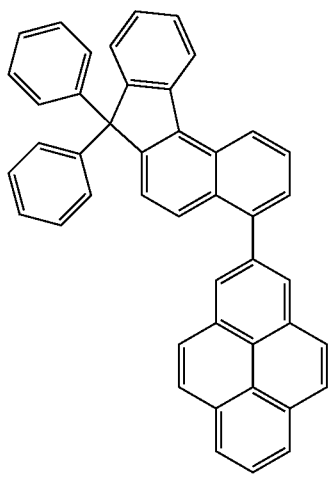
(2-18)
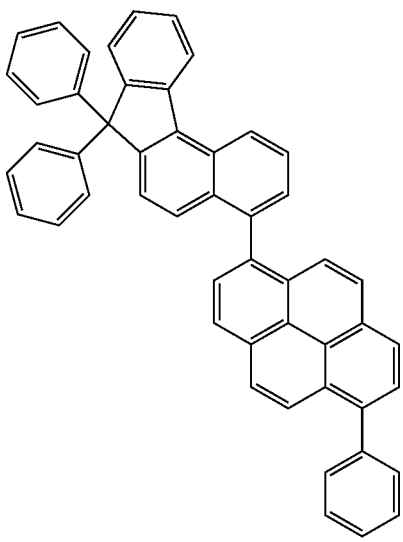
(2-19)
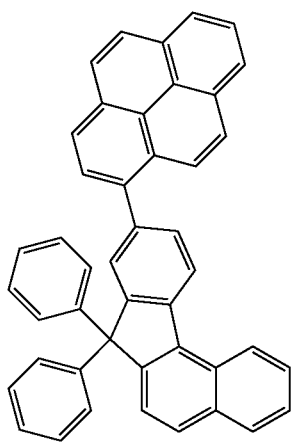
(2-20)
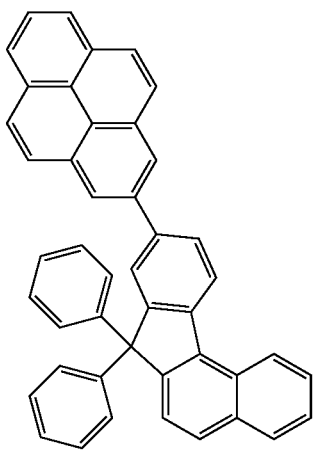

-continued
(2-40)
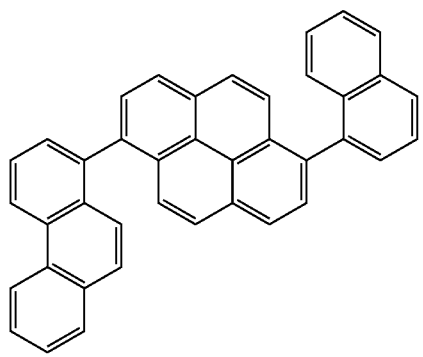
(2-41)
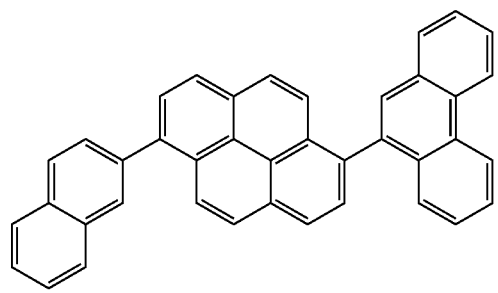
(2-42)
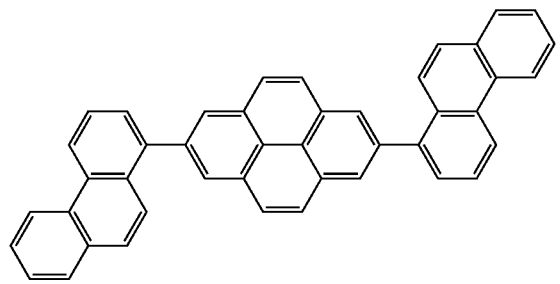
(2-43)
(2-46)
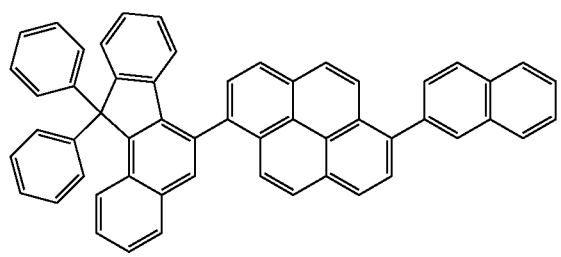
(2-47)
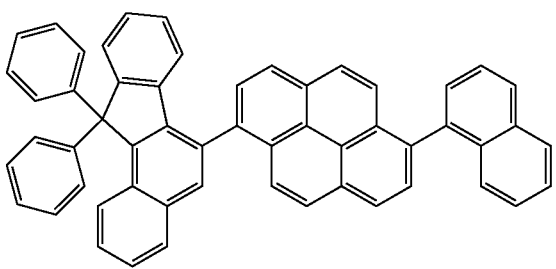
(2-48)
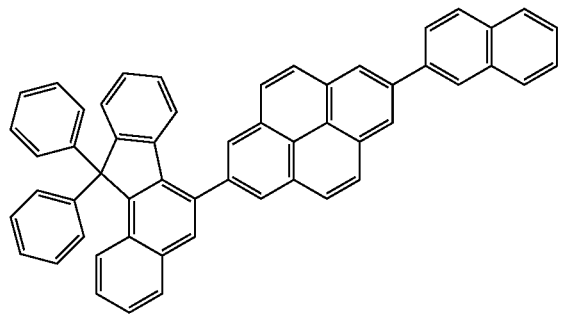
(2-49)
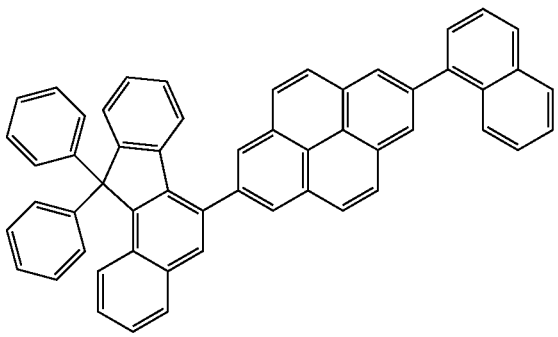

-continued
(2-50)
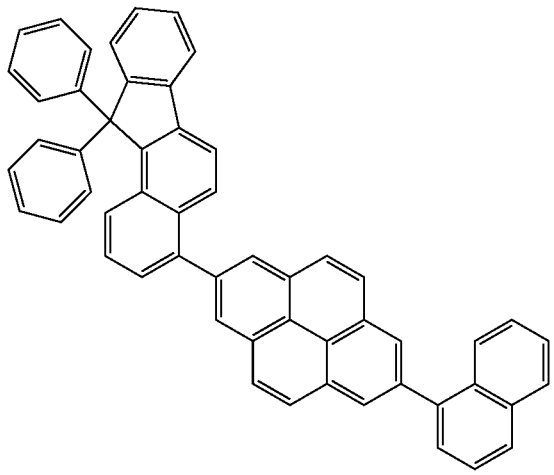
(2-52)
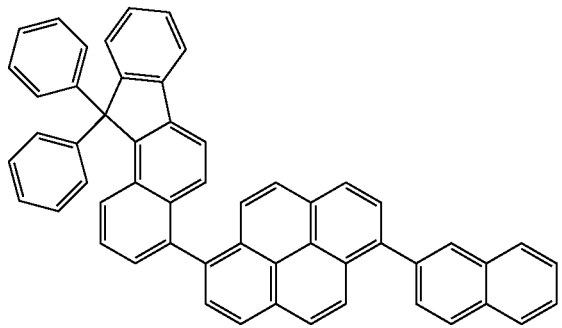
(2-53)
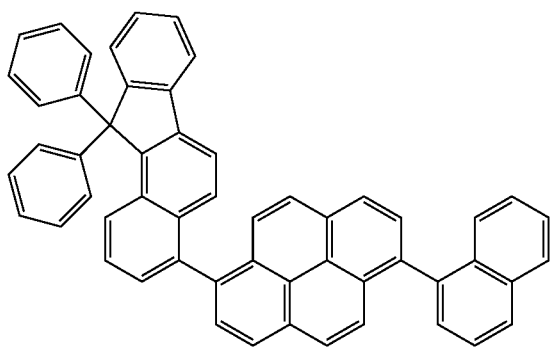
(2-54)
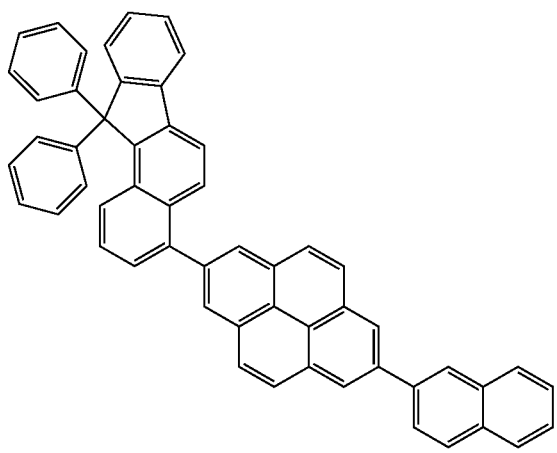
(2-110)
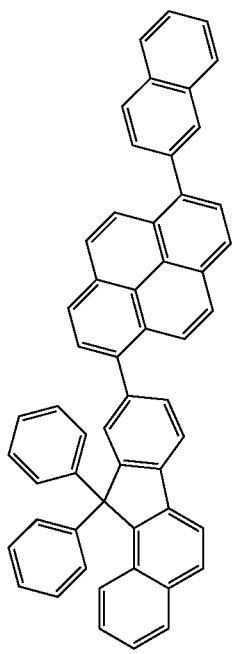
(2-111)

-continued
(2-112)
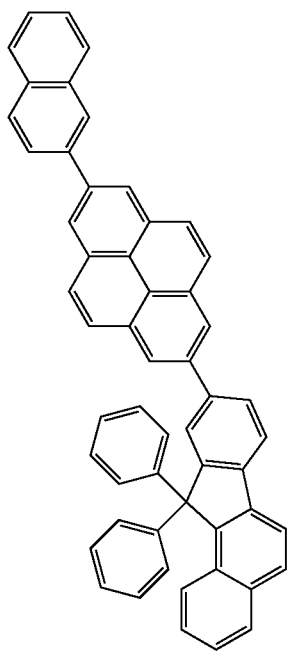
(2-113)
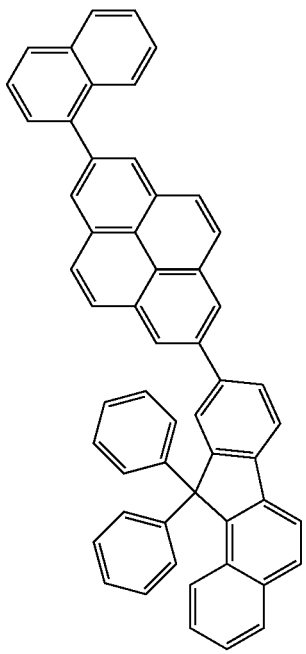
(2-116)
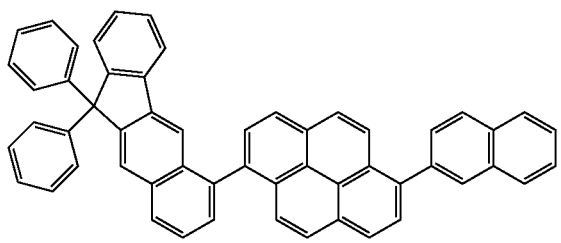
(2-117)
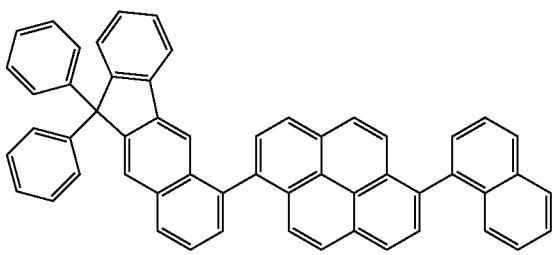
(2-118)
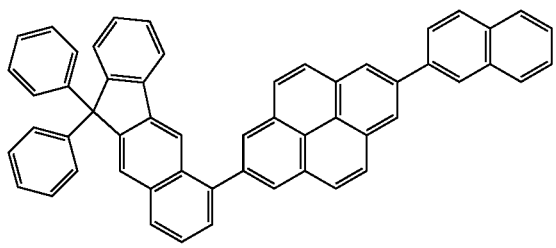
(2-119)
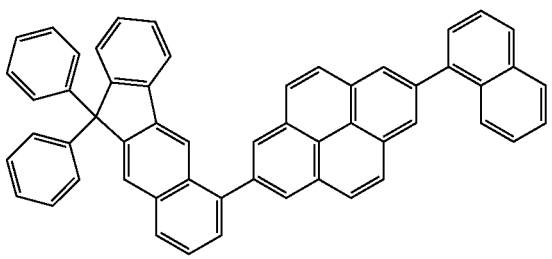

-continued
(2-122)
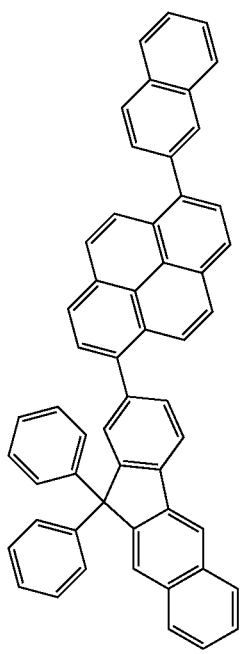
(2-123)
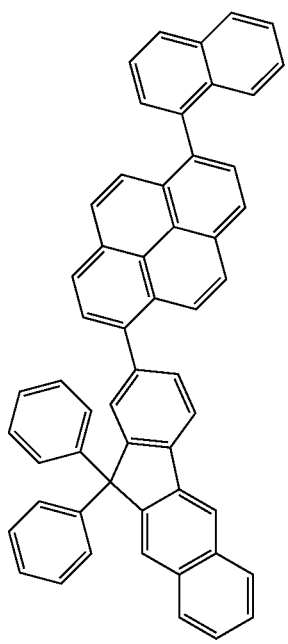
(2-124)
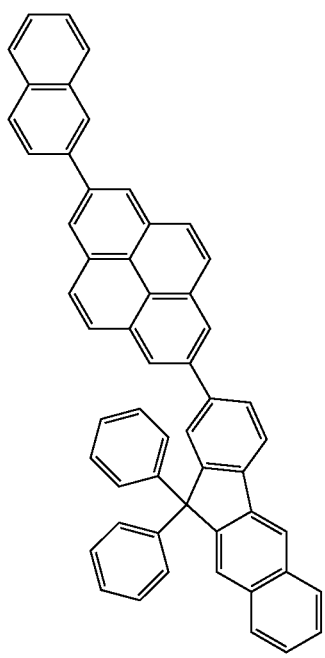
(2-125)

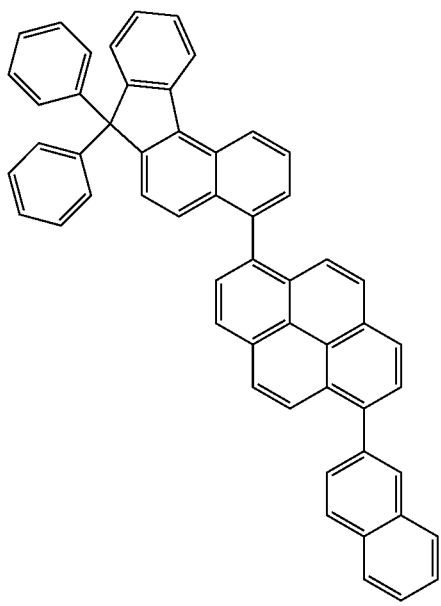
(2-140)
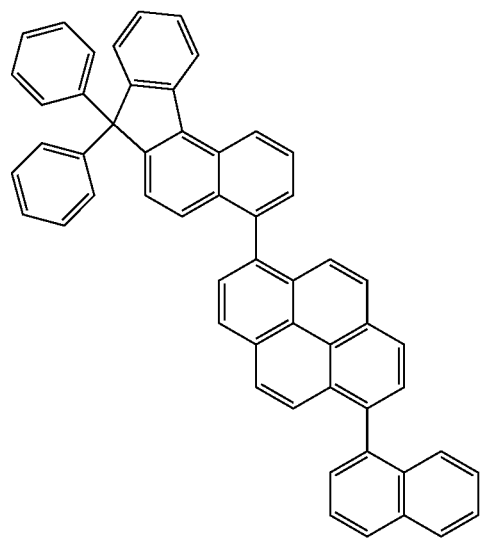
(2-141)
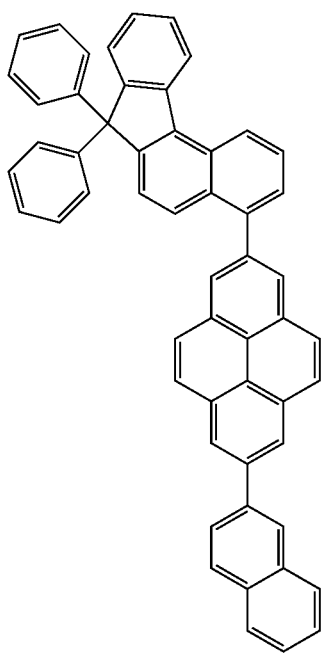
(2-142)
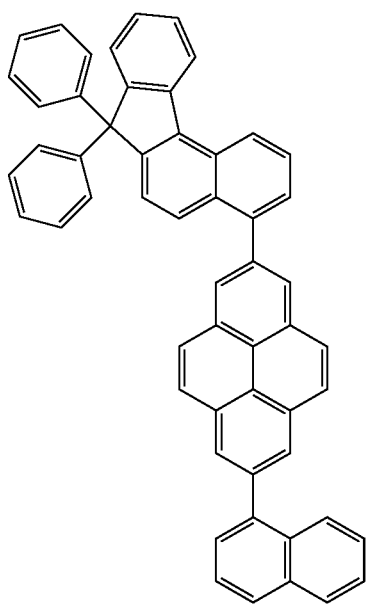
(2-143)

(2-146)
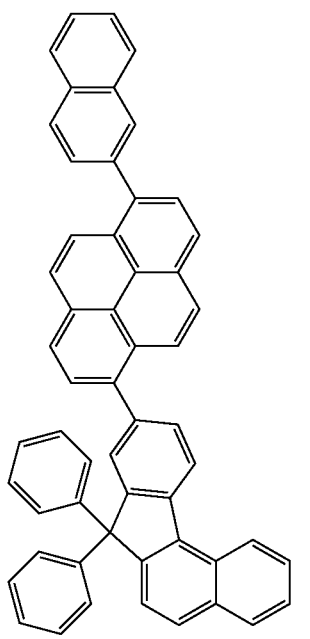
(2-147)
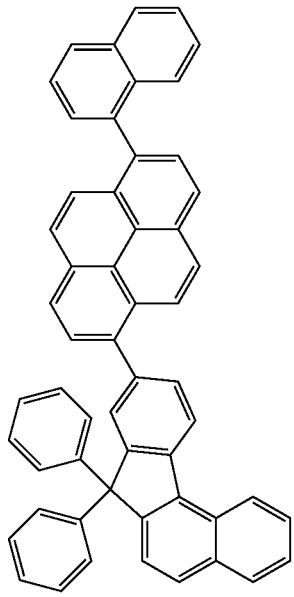
(2-148)
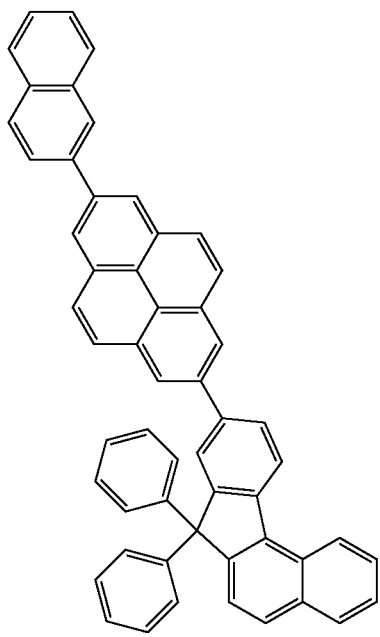
(2-149)
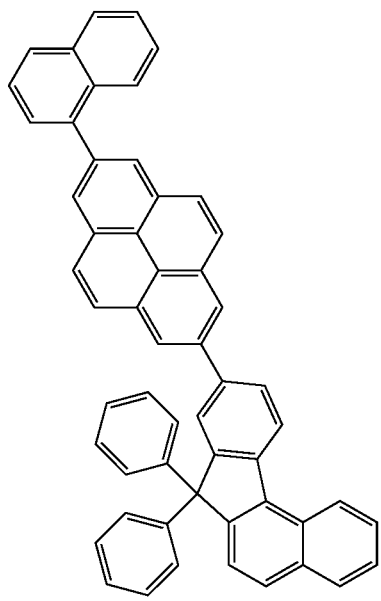
(2-152)
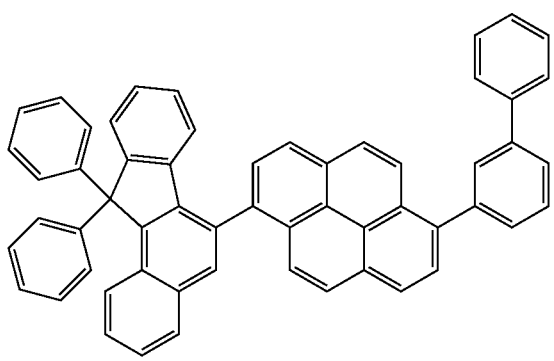
(2-153)
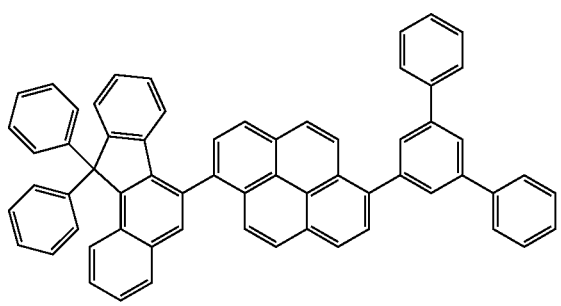

-continued
(2-154)
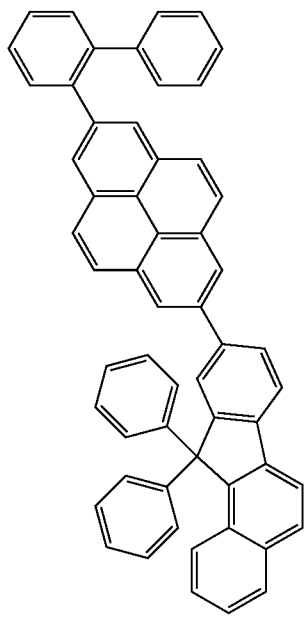
(2-155)
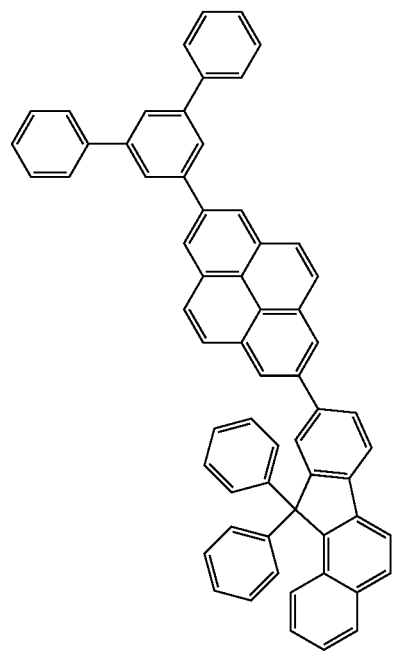
(2-170)
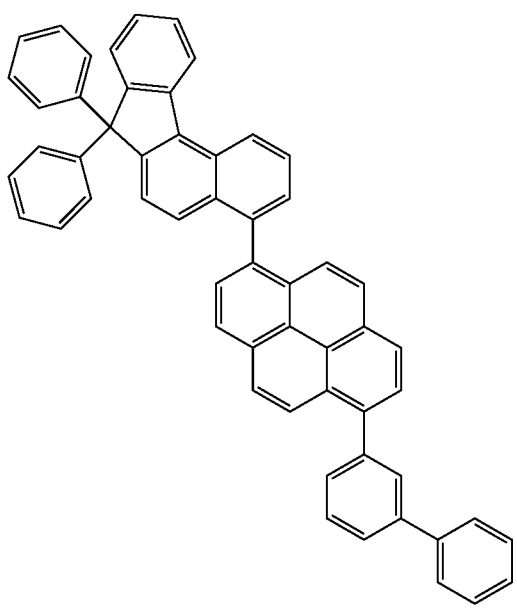
(2-171)
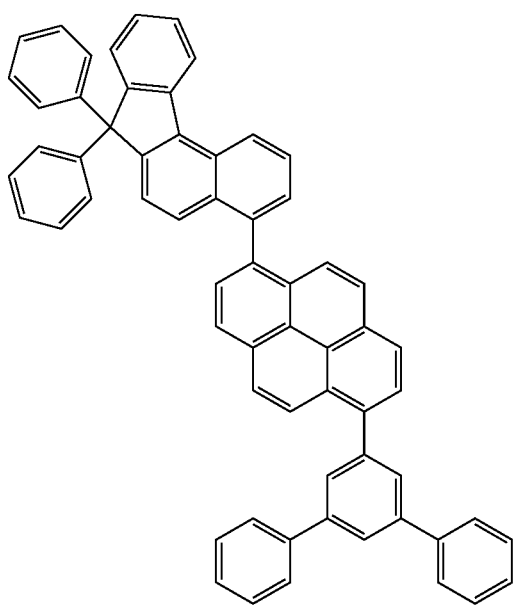

(2-173)
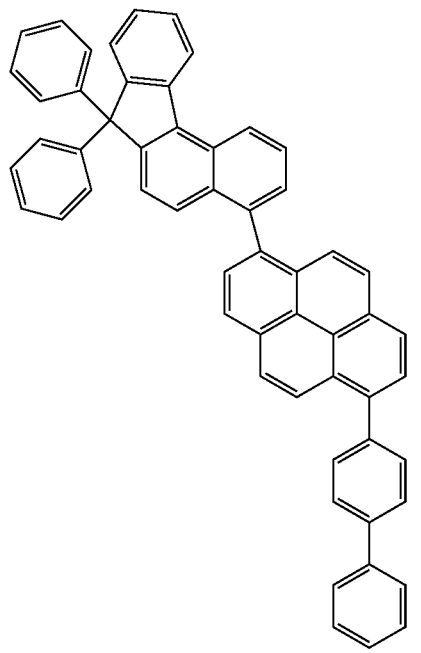
(2-174)
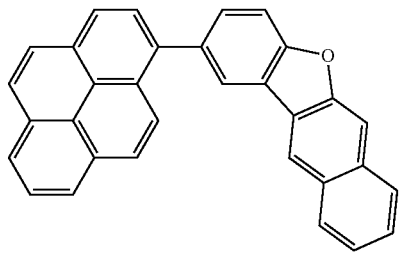
(2-175)
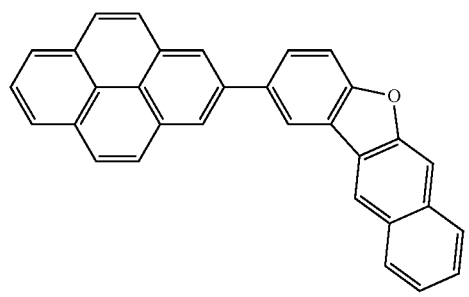
(2-176)
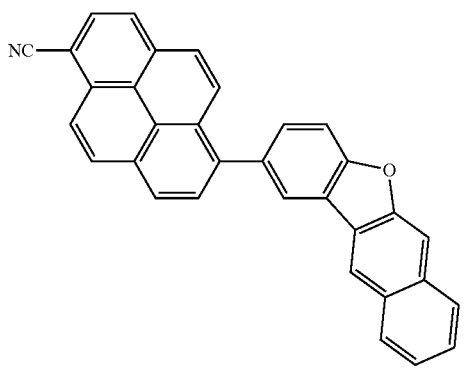
(2-177)
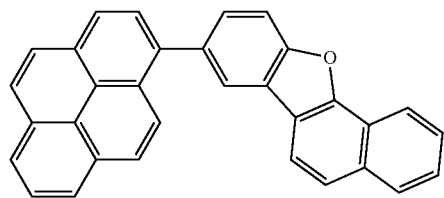
(2-178)
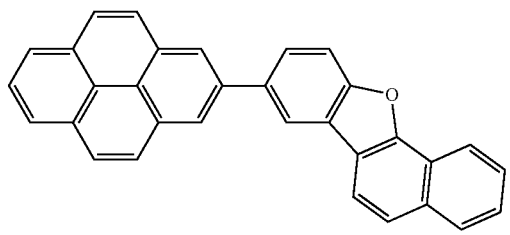
(2-181)
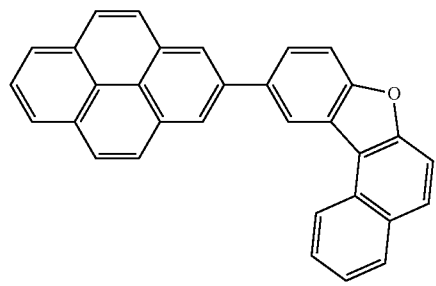
(2-182)
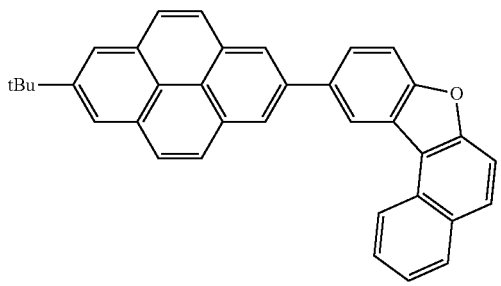

-continued
(2-183)
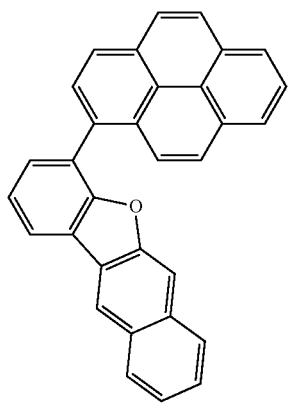
(2-184)
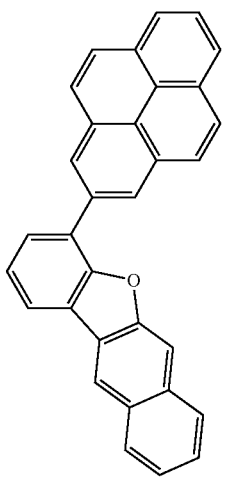
(2-186)
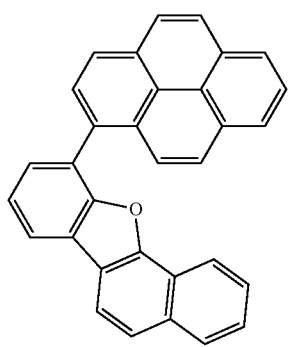
(2-187)
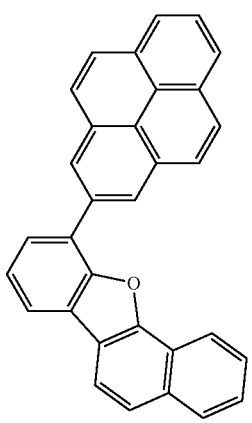
(2-189)
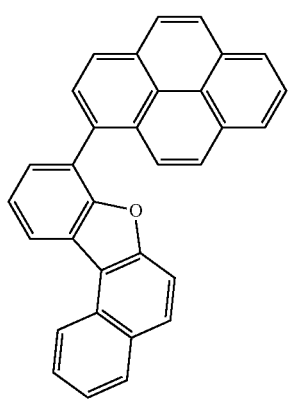
(2-190)
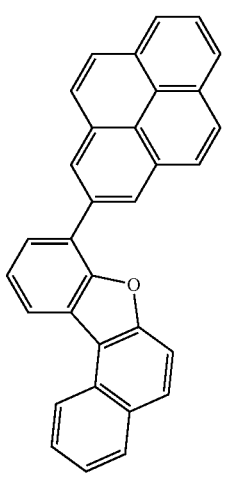

-continued
(2-192)
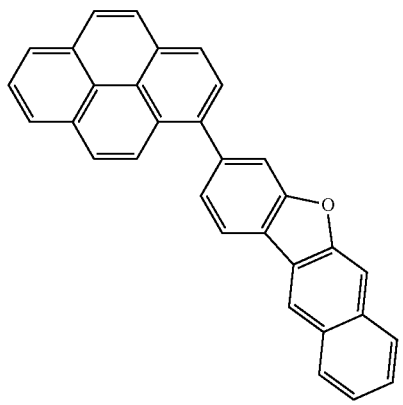
(2-193)
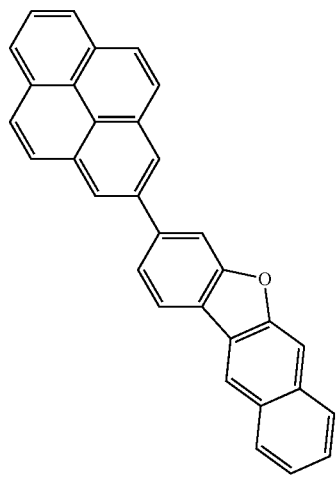
(2-210)
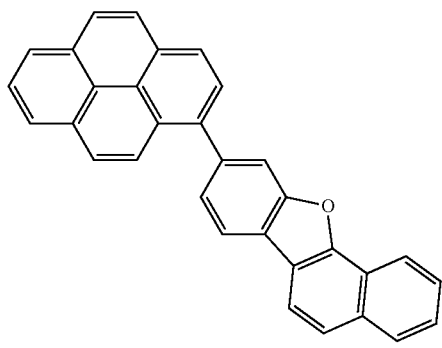
(2-211)
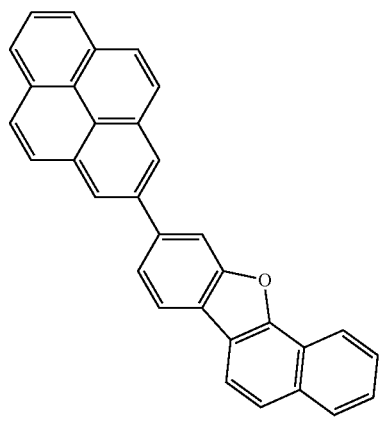
(2-212)
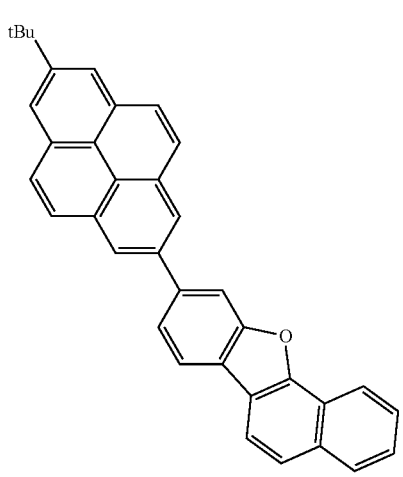
(2-213)
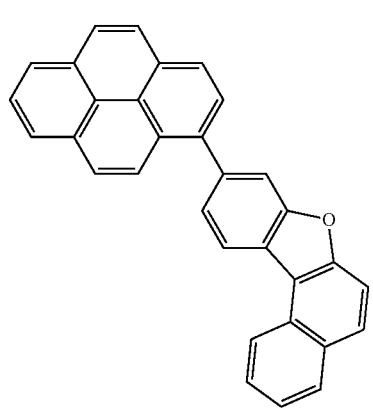

-continued
(2-214)
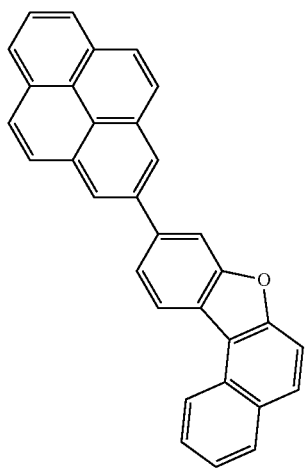
(2-215)
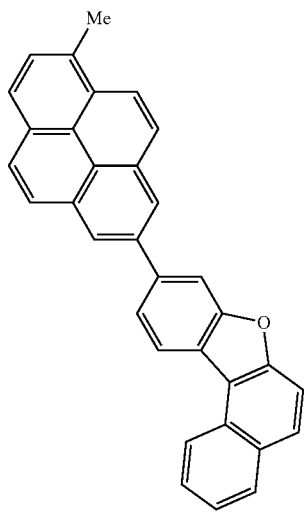
(2-216)
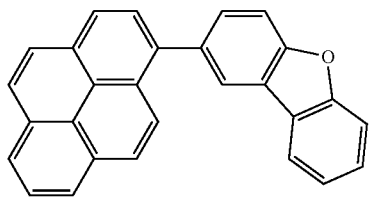
(2-217)
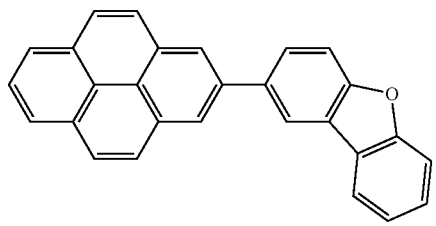
(2-218)
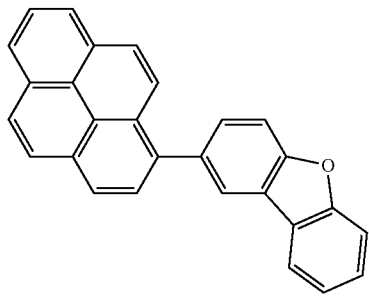
(2-219)
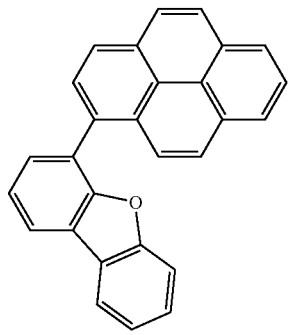
(2-220)
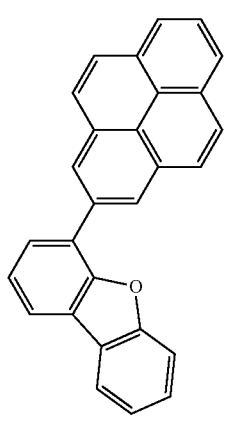
(2-221)
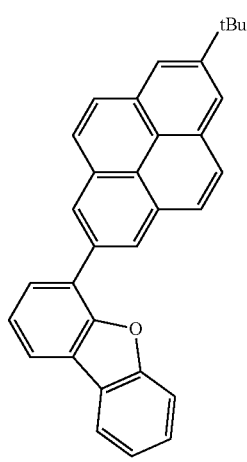

-continued
(2-222)
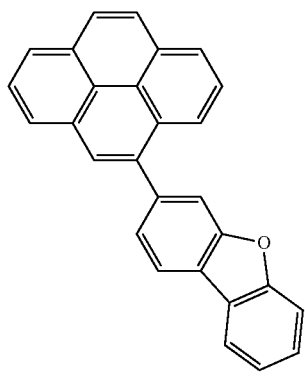
(2-223)
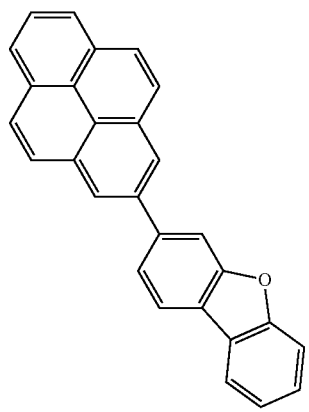
(2-224)
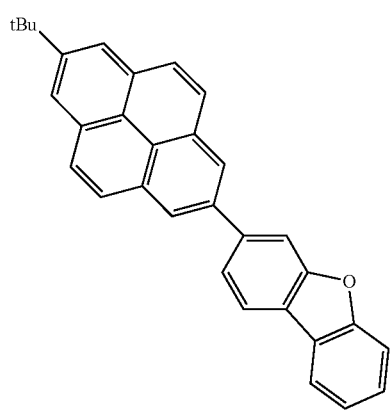
(2-225)
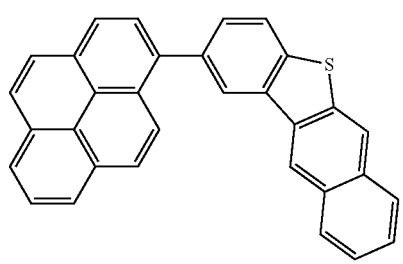
(2-226)
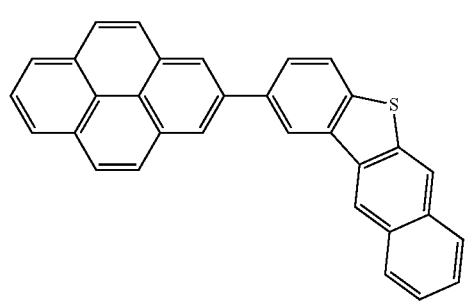
(2-228)
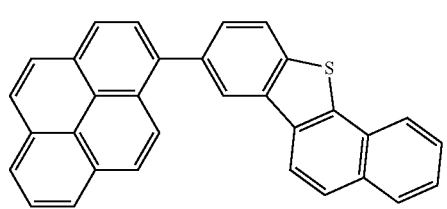
(2-229)
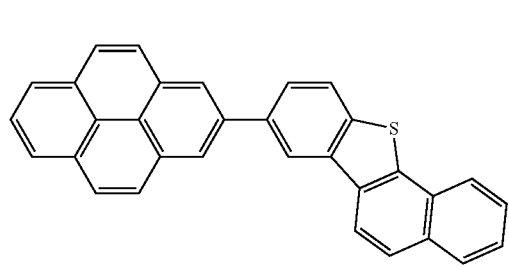
(2-231)
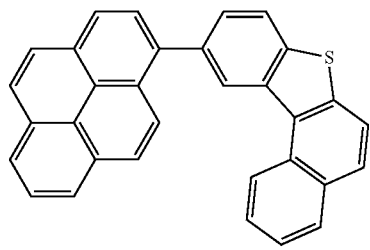

-continued
(2-232)
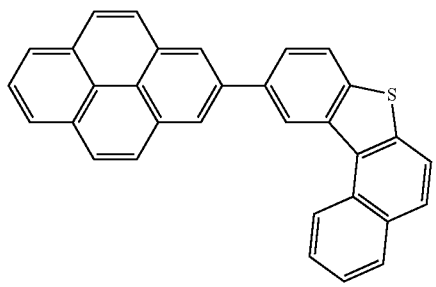
(2-233)
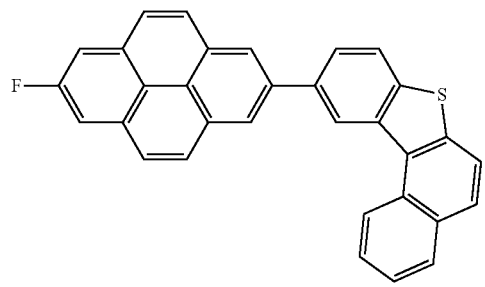
(2-234)
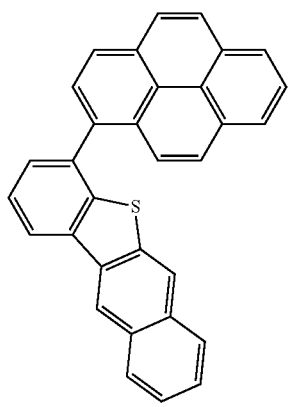
(2-235)
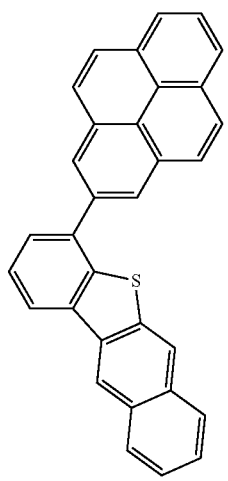
(2-237)
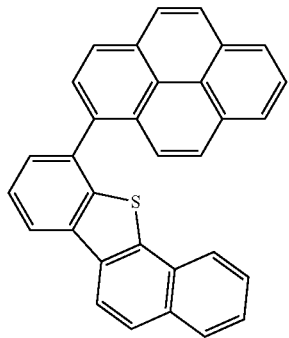
(2-238)
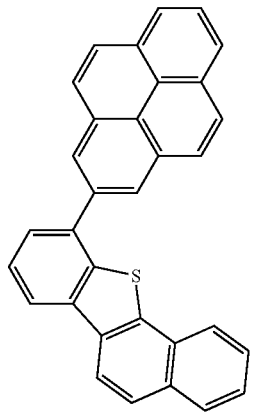
(2-260)
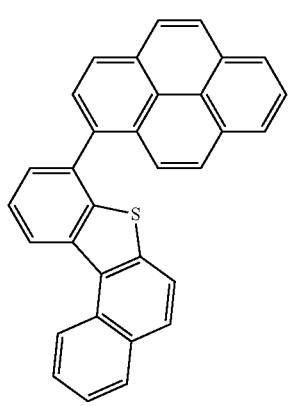
(2-261)
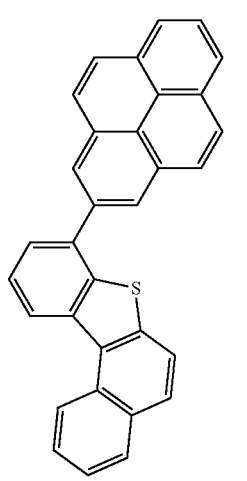

-continued
(2-263)
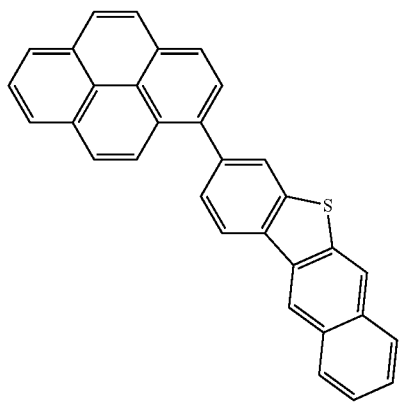
(2-264)
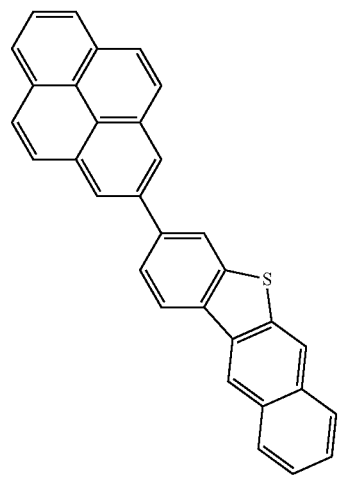
(2-266)
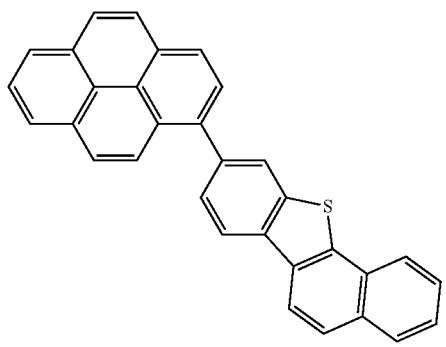
(2-267)
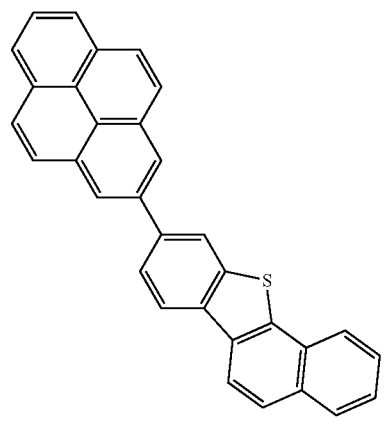
(2-269)
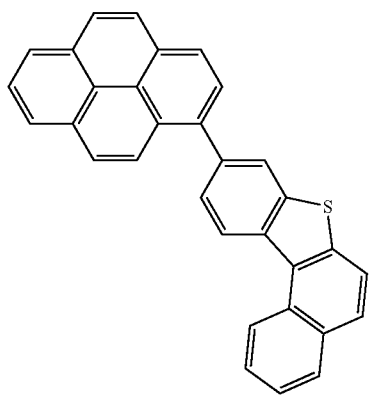
(2-270)
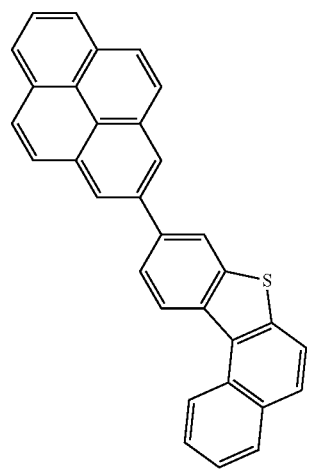
(2-272)
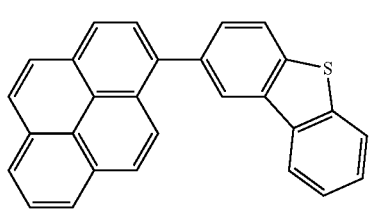
(2-273)
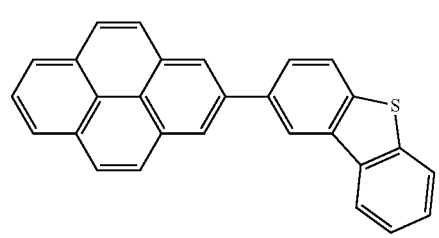

-continued
(2-275)
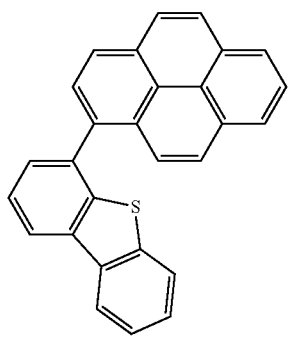
(2-276)
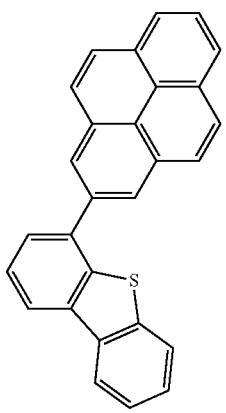
(2-278)
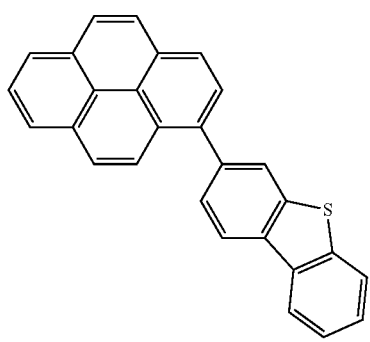
(2-279)
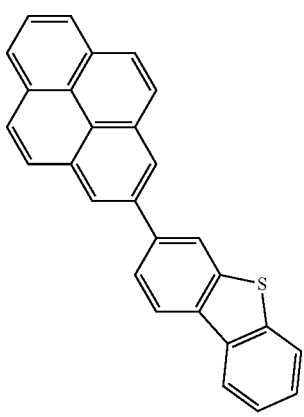
(2-281)
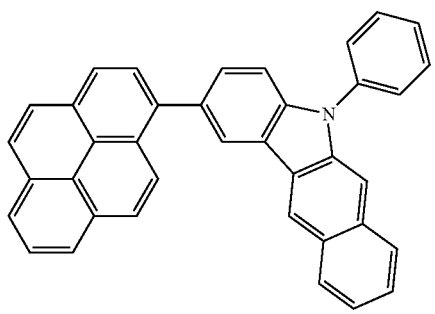
(2-282)
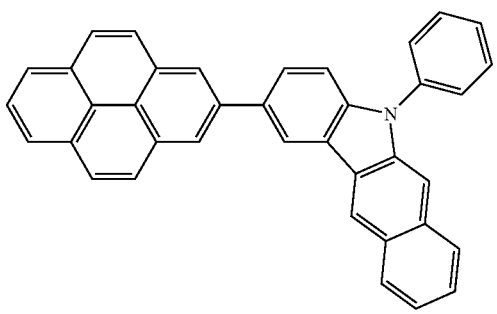
(2-284)
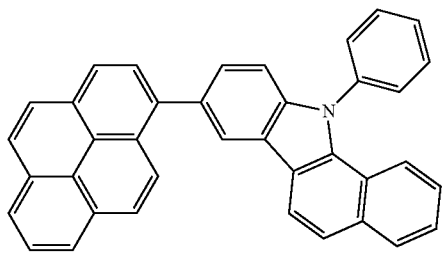
(2-285)
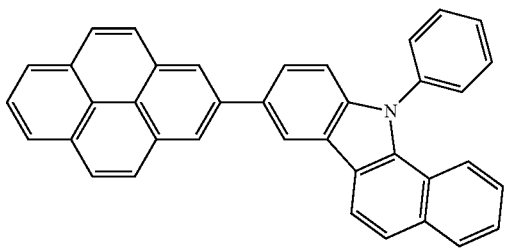

-continued
(2-287)
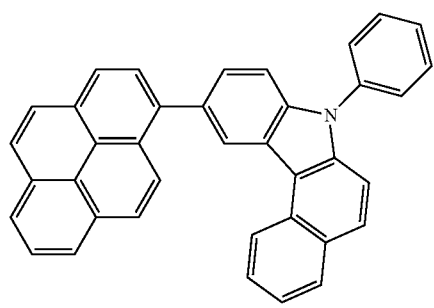
(2-288)
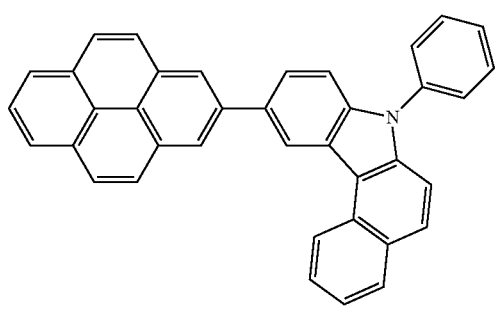
(2-311)
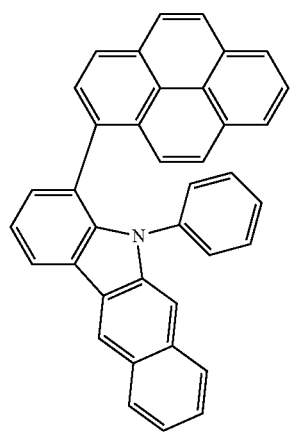
(2-312)
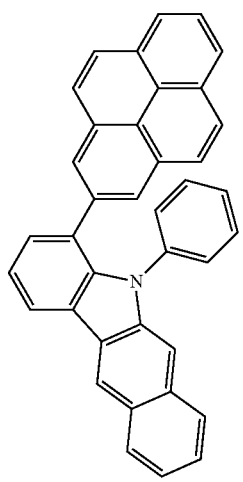
(2-314)
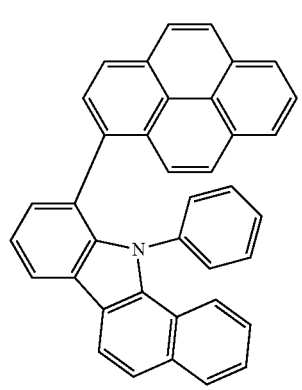
(2-315)
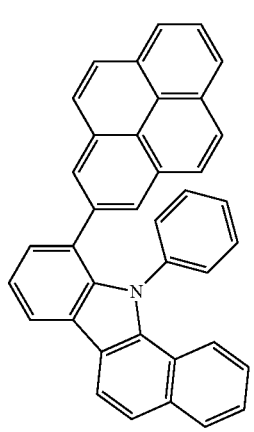

-continued
(2-317)
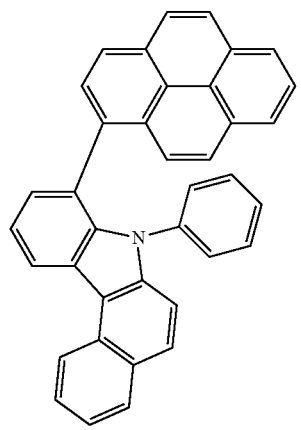
(2-318)
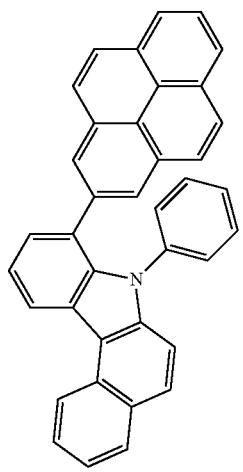
(2-320)
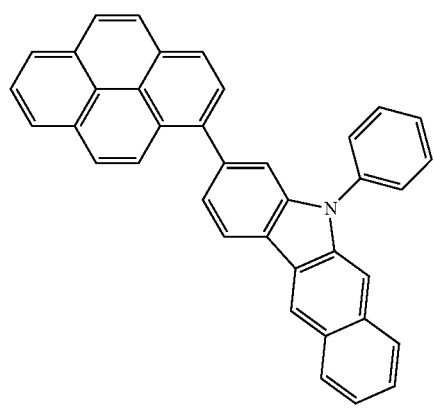
(2-321)
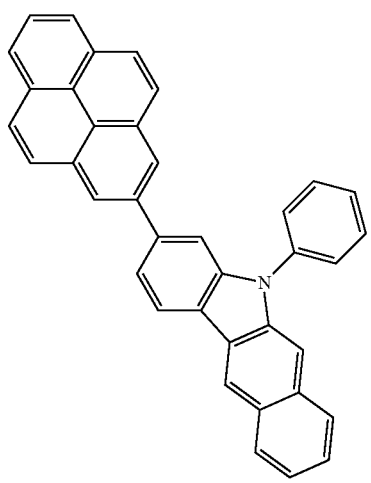
(2-323)
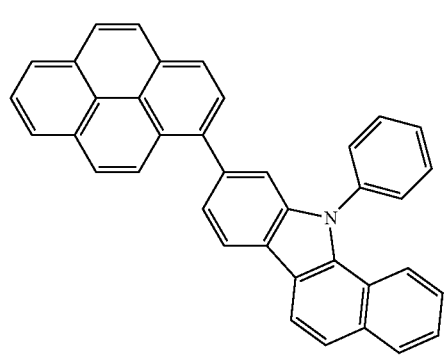
(2-324)
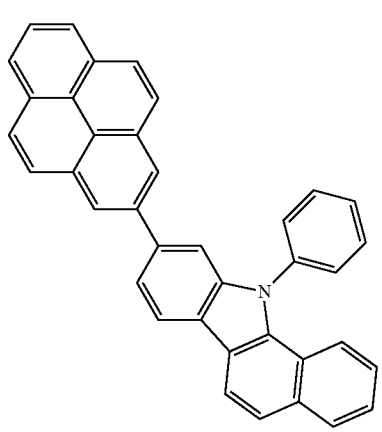

-continued
(2-326)
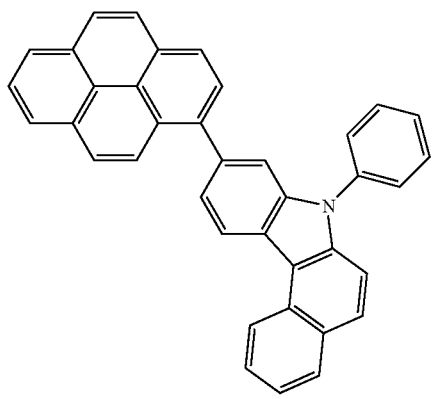
(2-327)
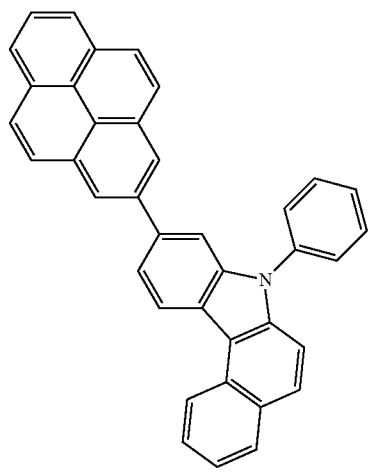
(2-329)
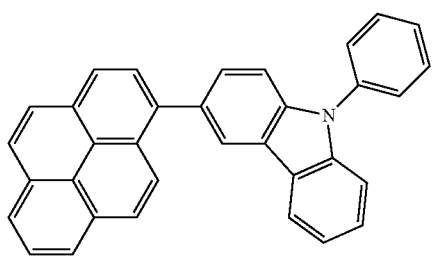
(2-330)
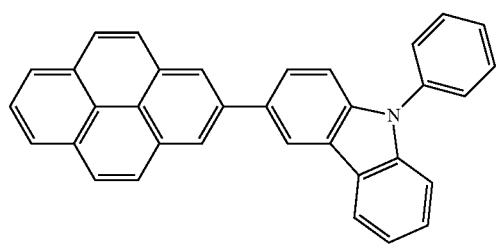
(2-332)
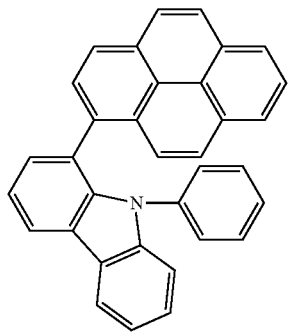
(2-333)
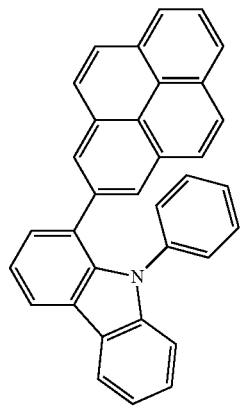
(2-335)
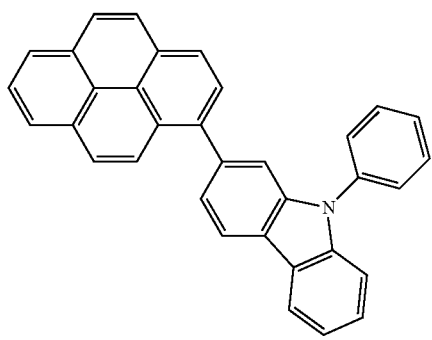
(2-336)
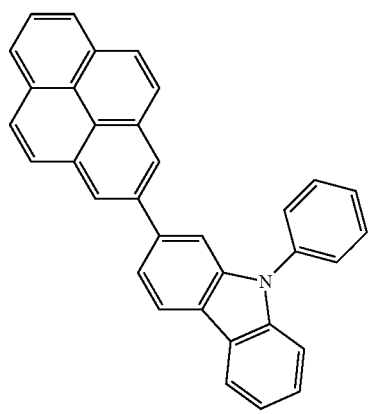

-continued
(2-337)
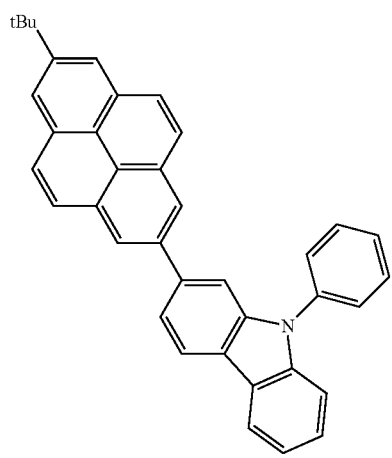
(2-350)
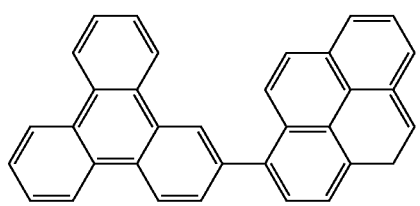
(2-351)
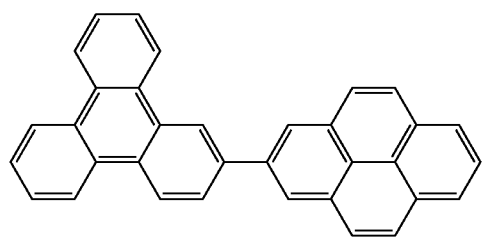
(2-353)
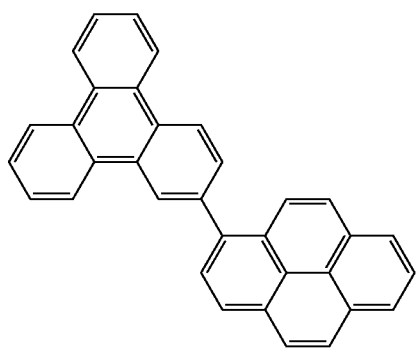
(2-354)
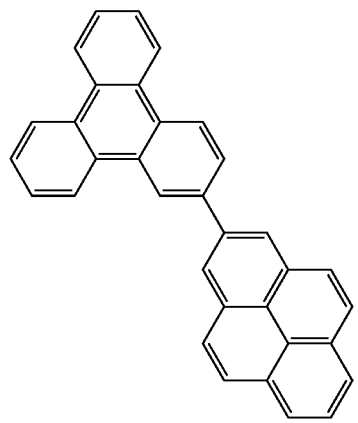
(2-356)
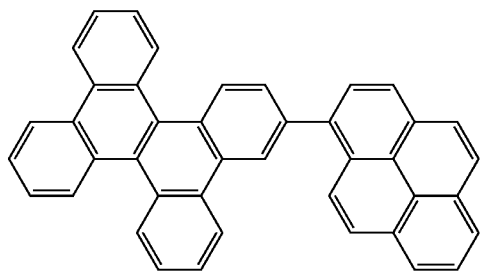
(2-357)
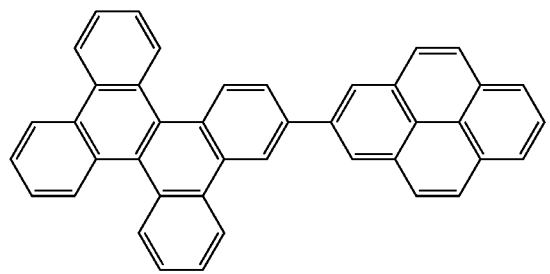
(2-358)
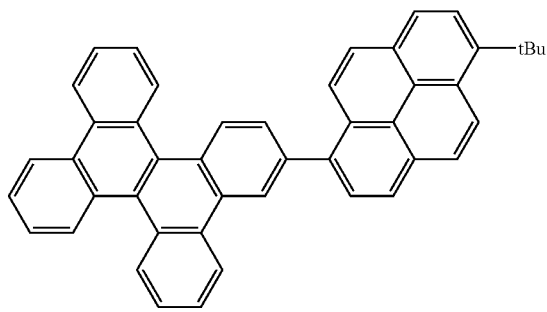

-continued
(2-359)
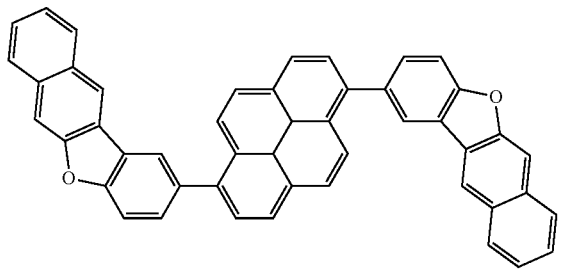
(2-360)
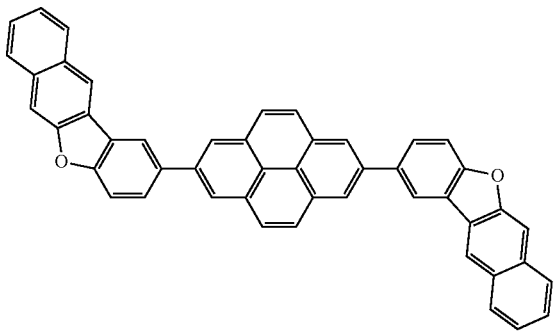
(2-361)
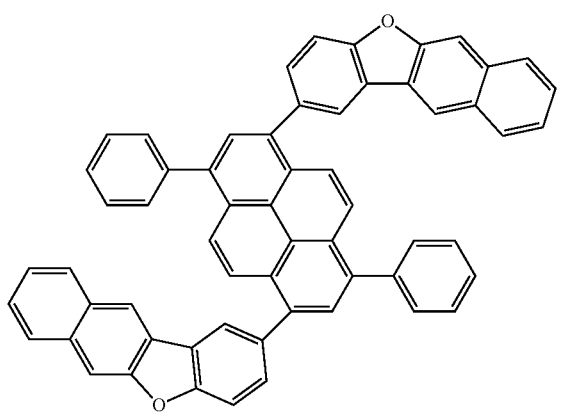
(2-362)
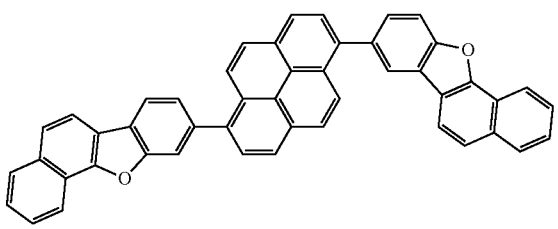
(2-363)
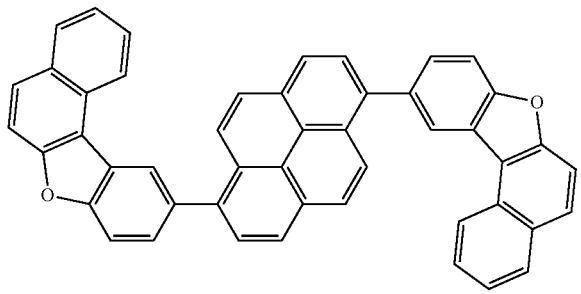
(2-364)
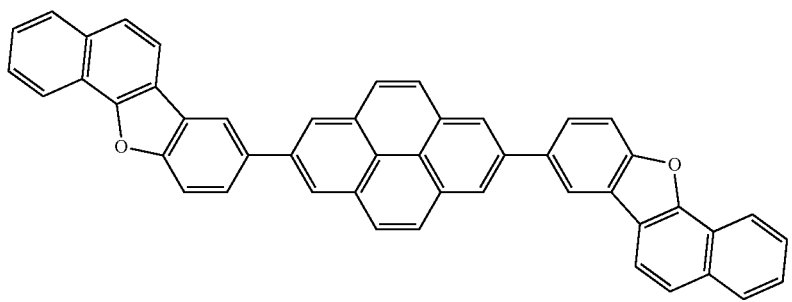

-continued
(2-366)
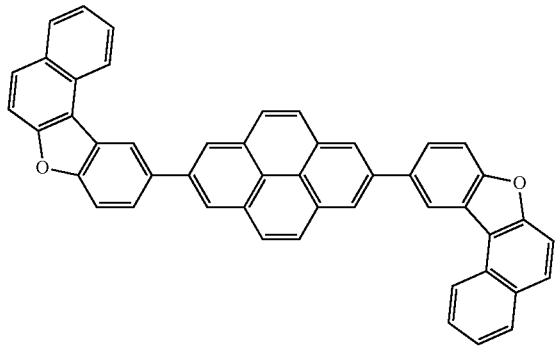
(2-367)
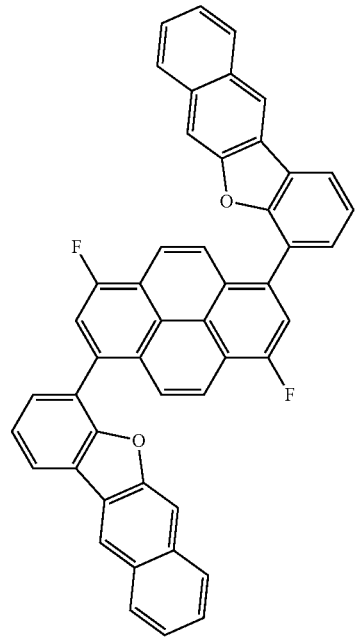
(2-368)
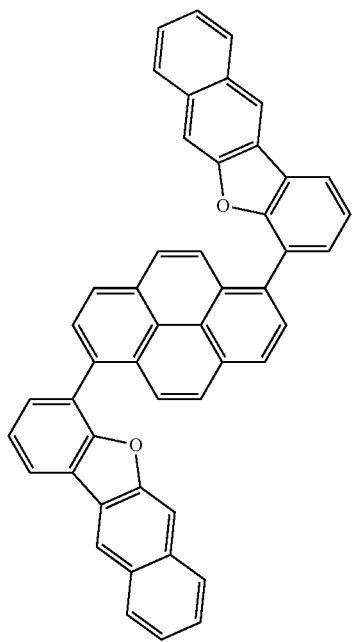
(2-369)
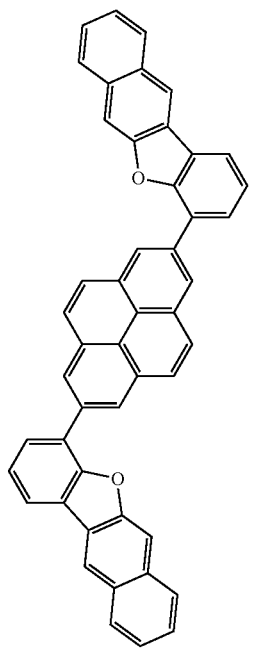

-continued
(2-370)
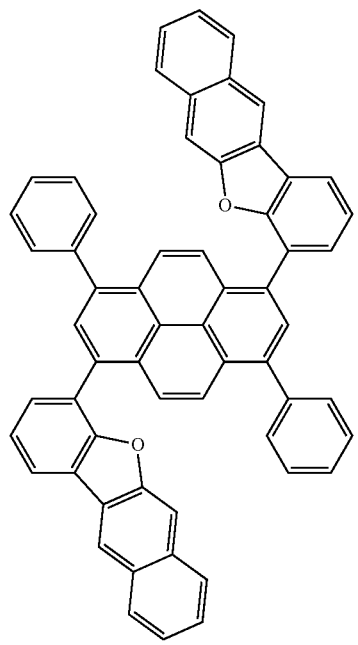
(2-421)
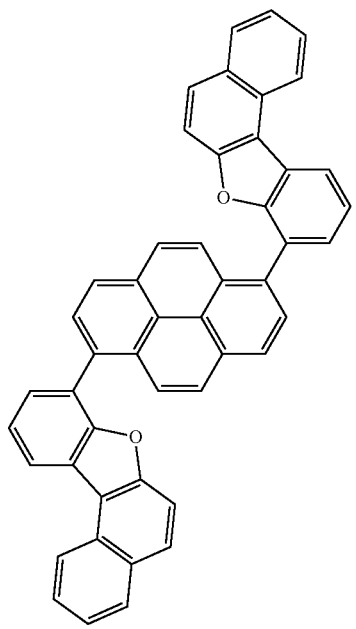
(2-422)
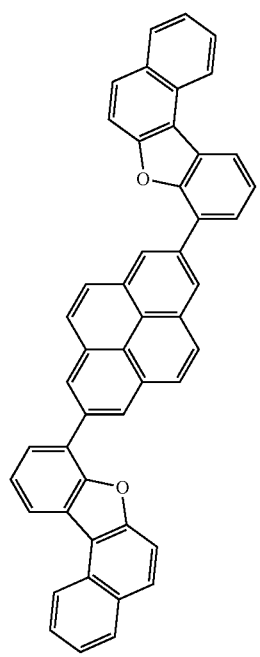
(2-424)
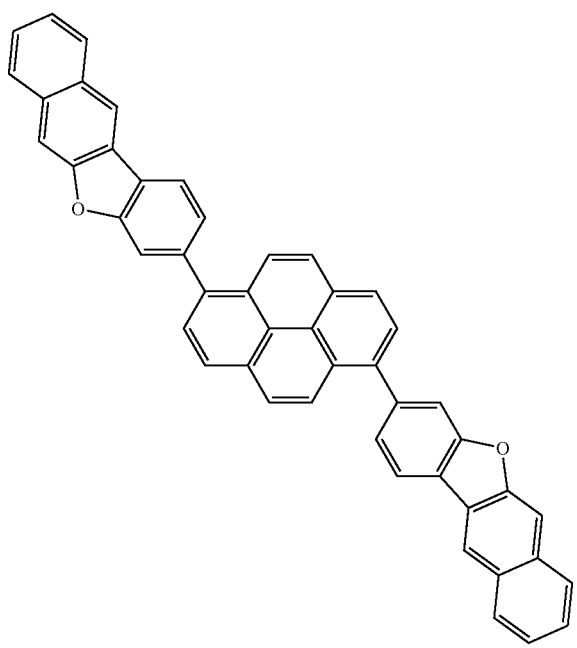

-continued
(2-425)
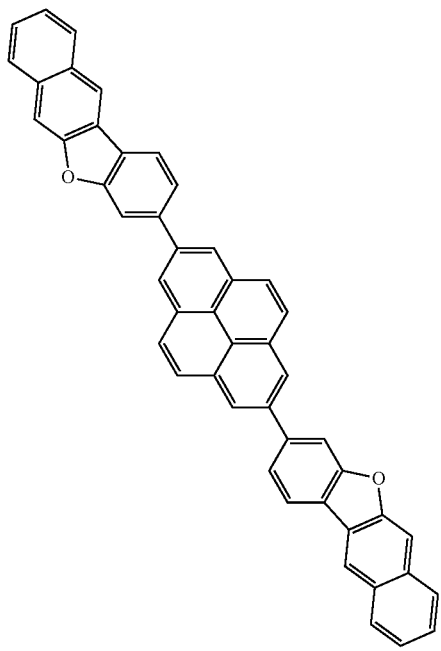
(2-427)
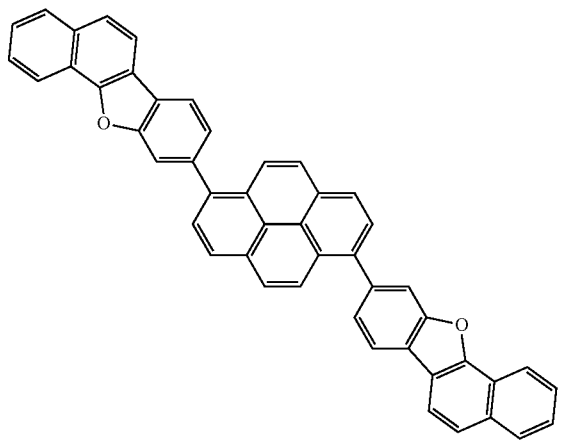
(2-428)
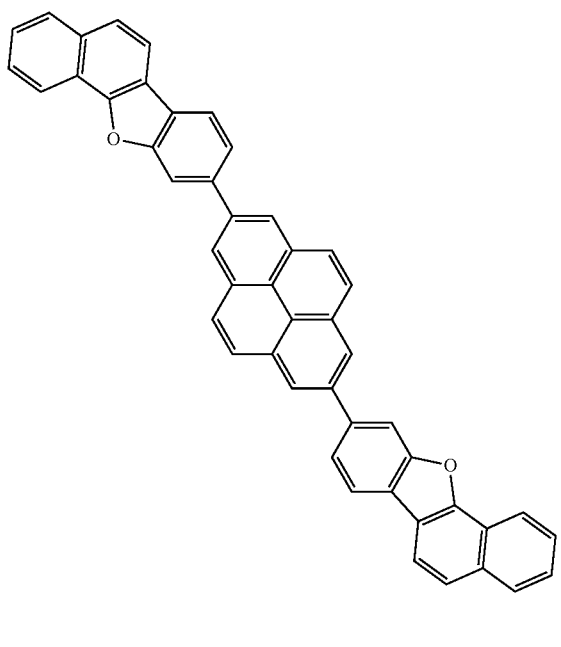
(2-430)
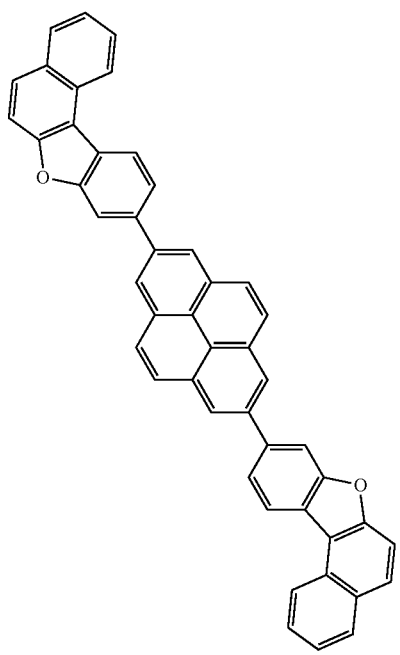

-continued
(2-432)
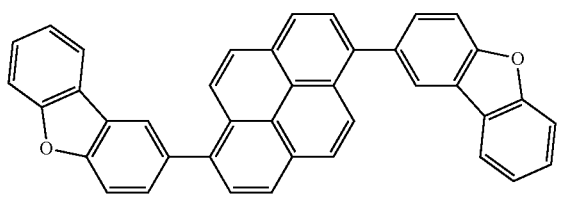
(2-434)
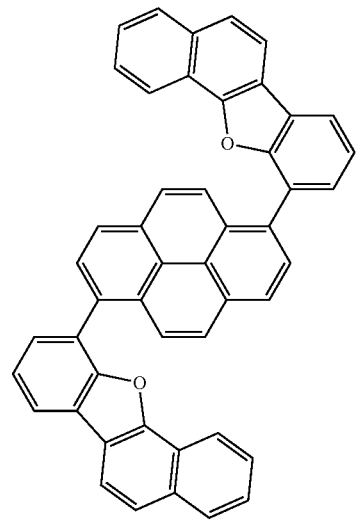
(2-435)
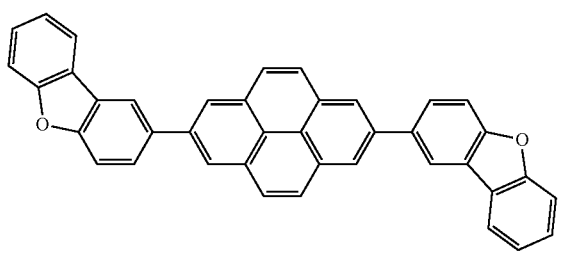
(2-436)
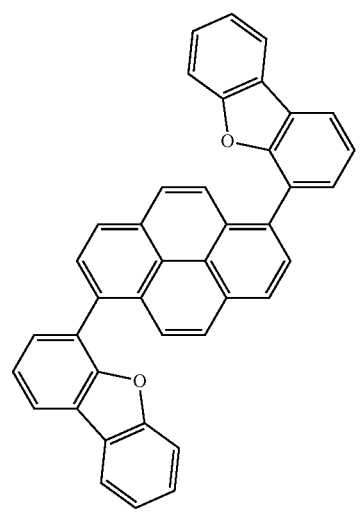

-continued
(2-437)
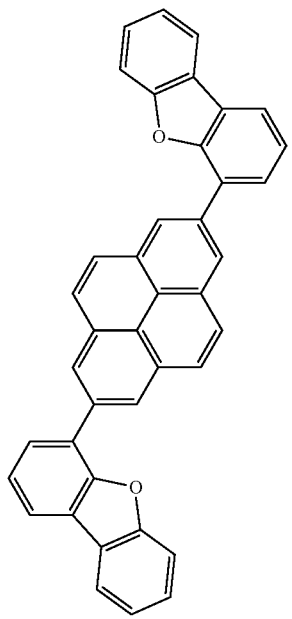
(2-460)
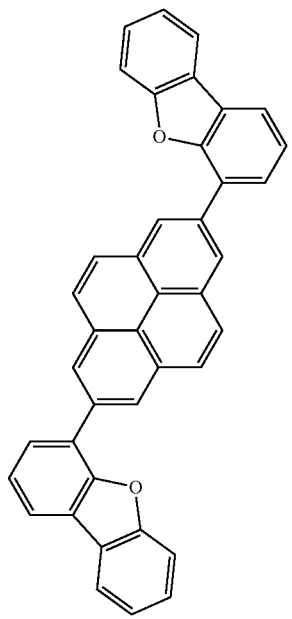
(2-461)
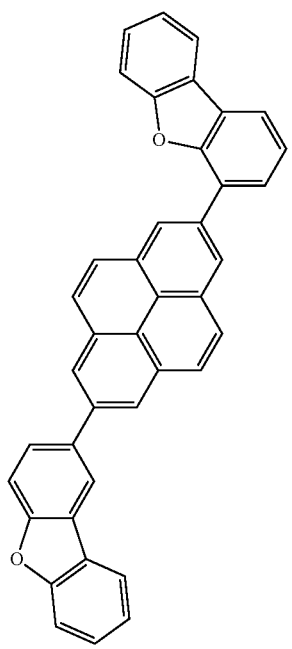
(2-462)
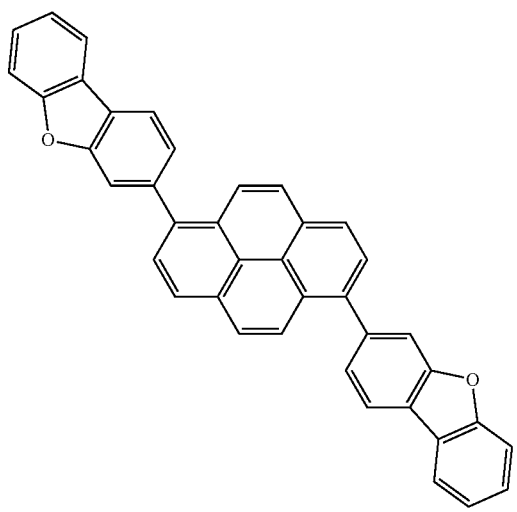

-continued
(2-463)
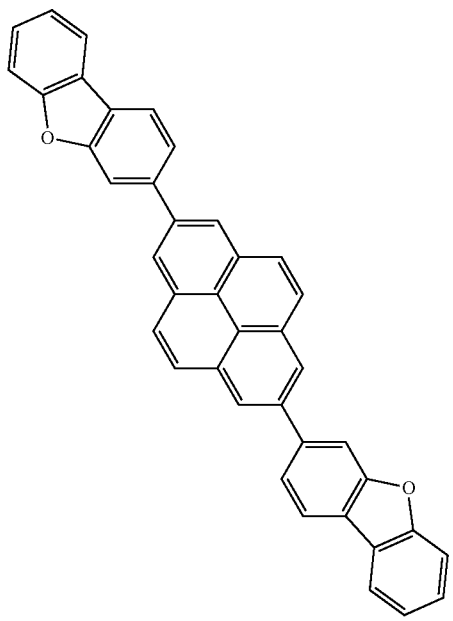
(2-464)
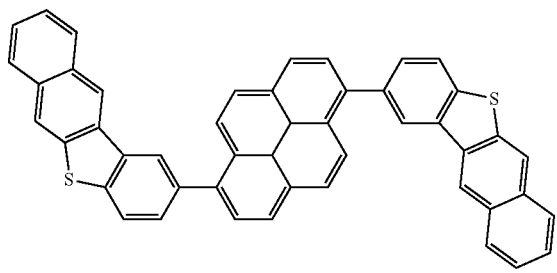
(2-465)
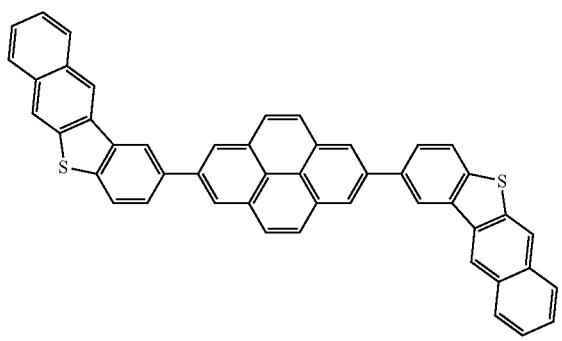
(2-466)
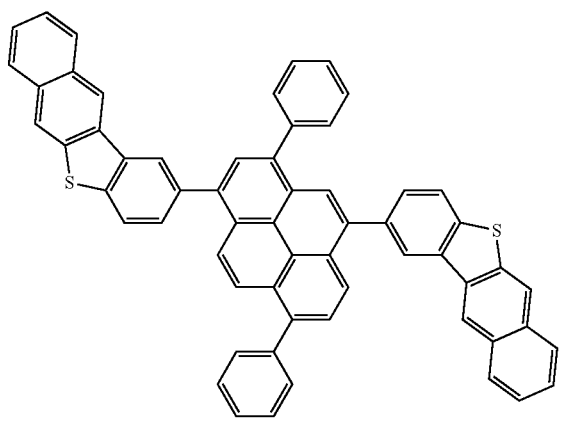
(2-467)
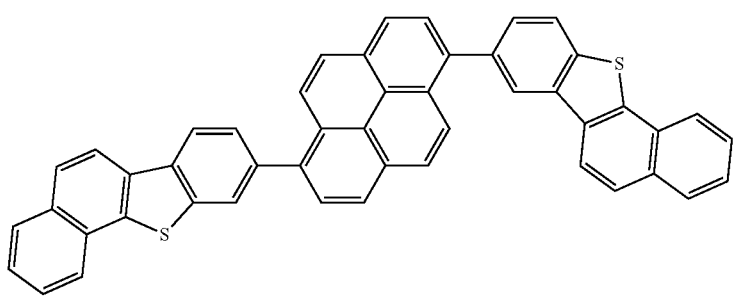

(2-468)
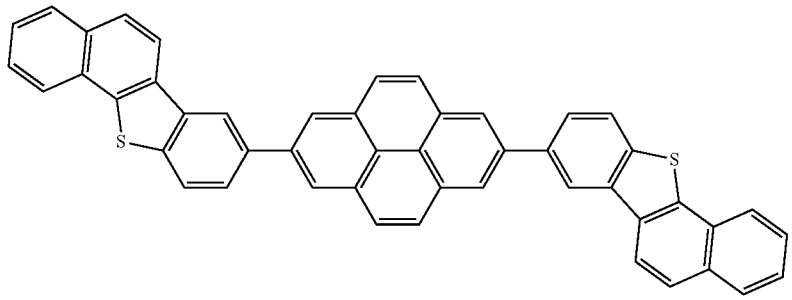
(2-469)
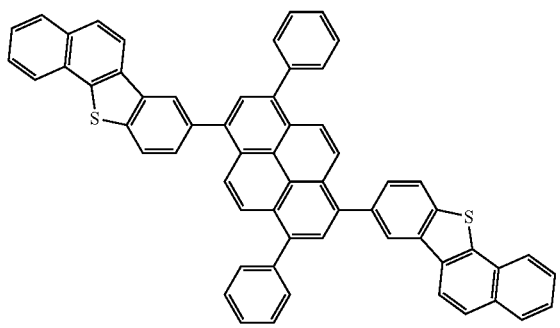
(2-470)
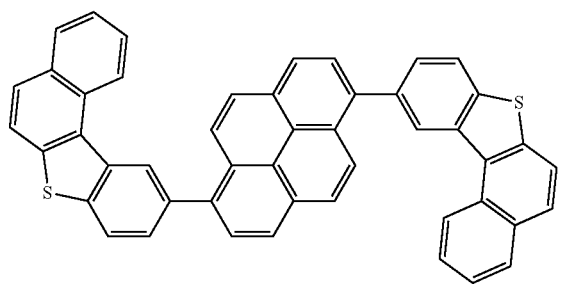
(2-471)
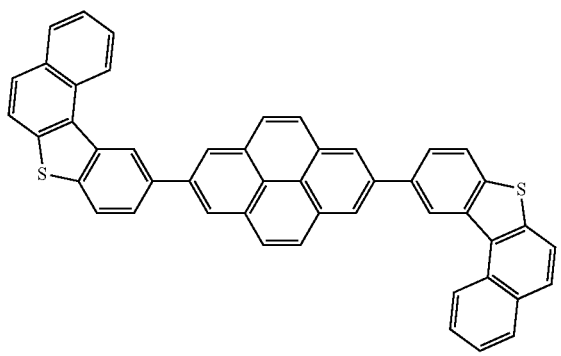
(2-472)
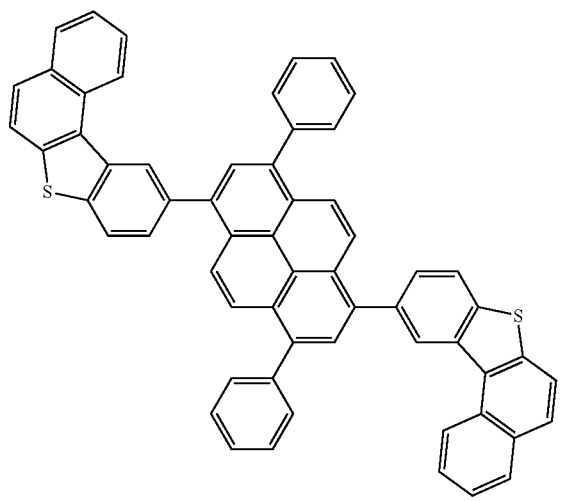

(2-473)
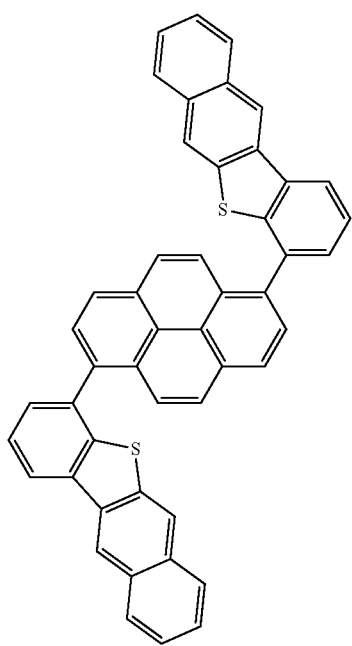
(2-474)
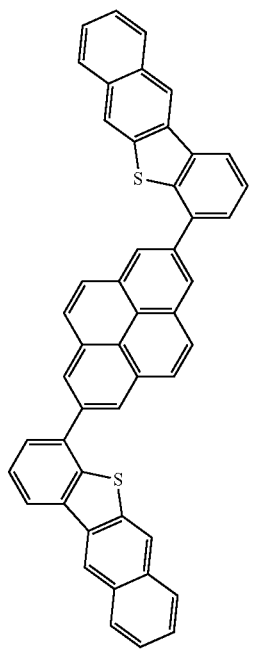
(2-476)
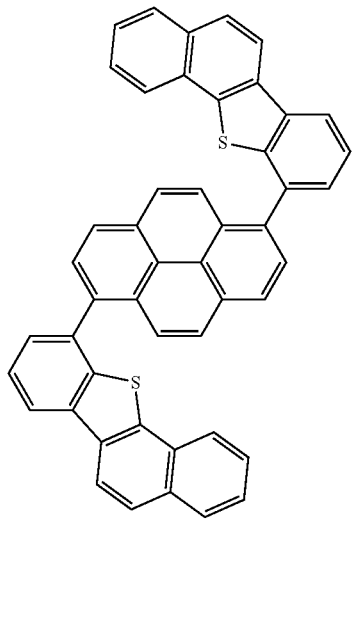
(2-500)
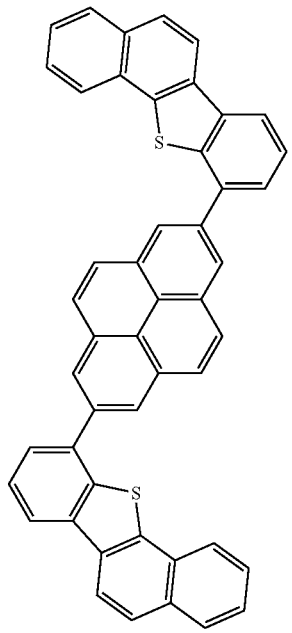

-continued
(2-502)
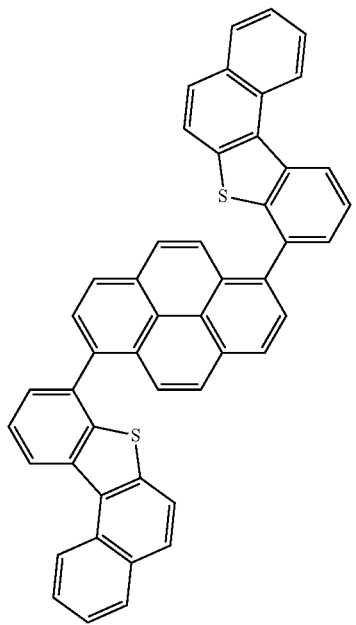
(2-503)
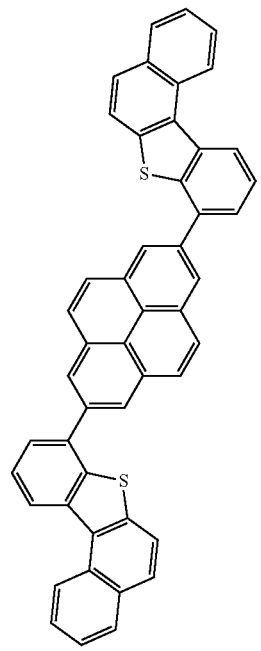
(2-505)
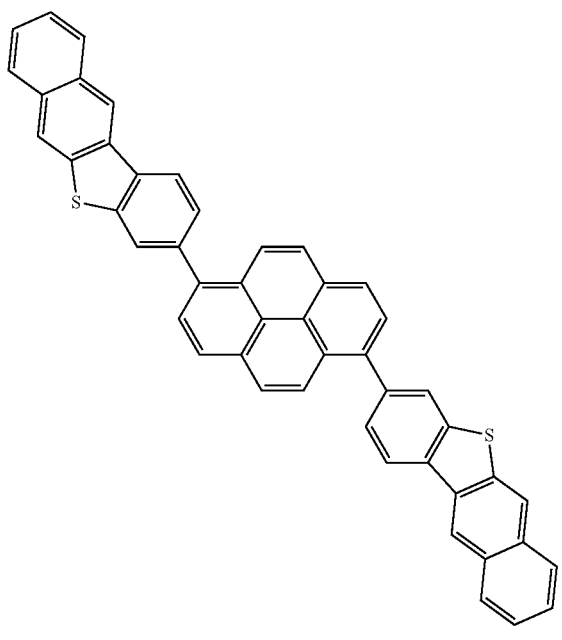
(2-506)
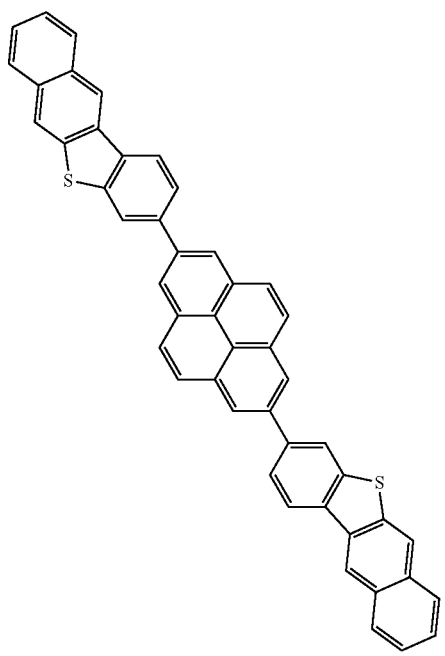

-continued
(2-508)
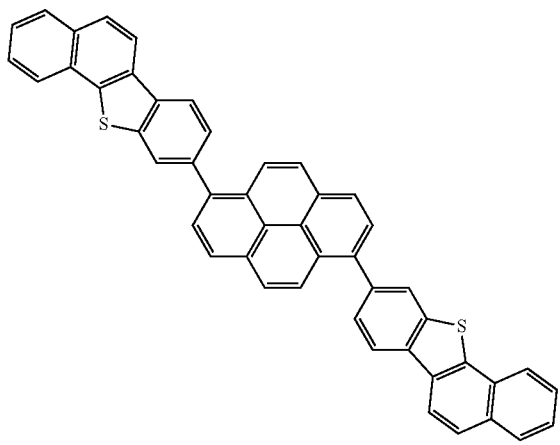
(2-509)
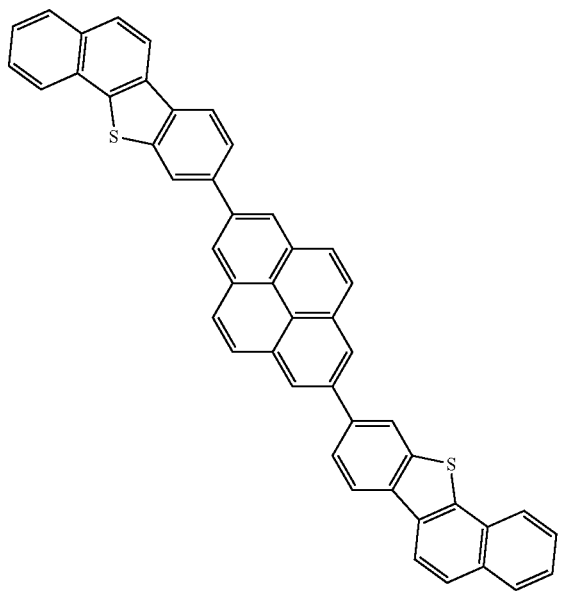
(2-511)
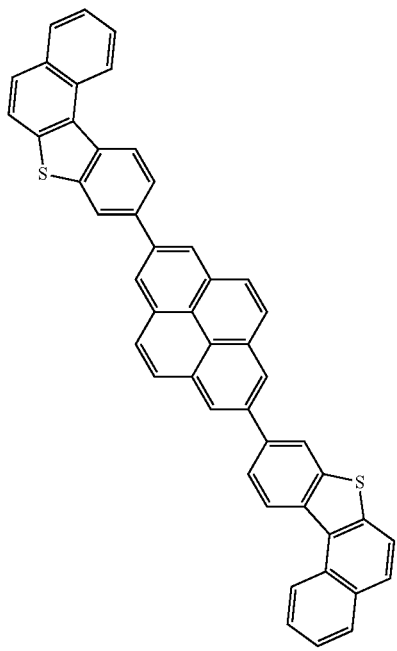
(2-513)
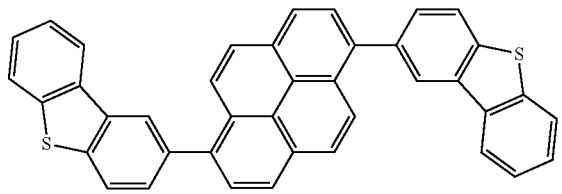

-continued
(2-514)
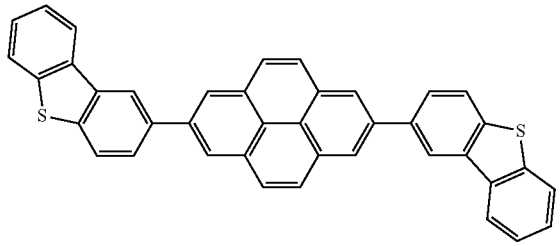
(2-515)
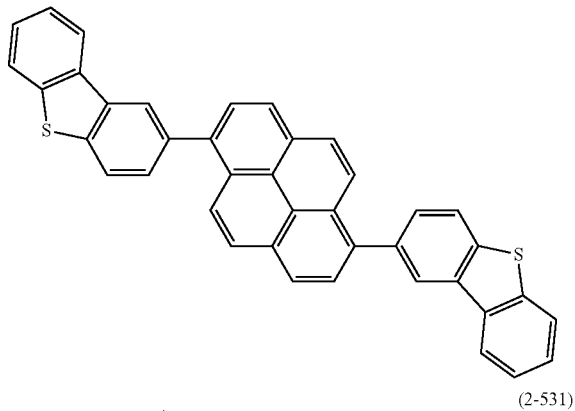
(2-530)
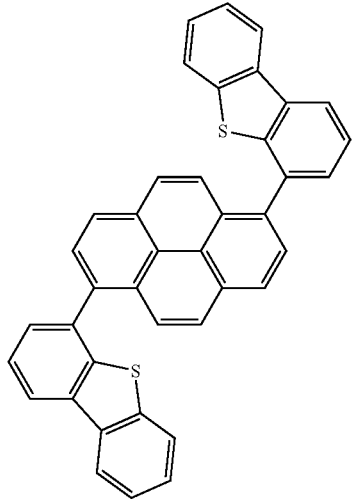
(2-531)
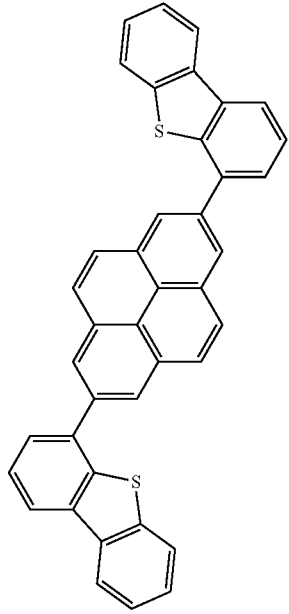
(2-533)
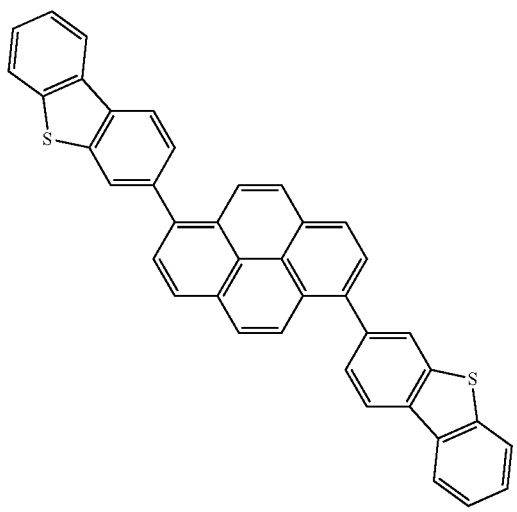
(2-534)
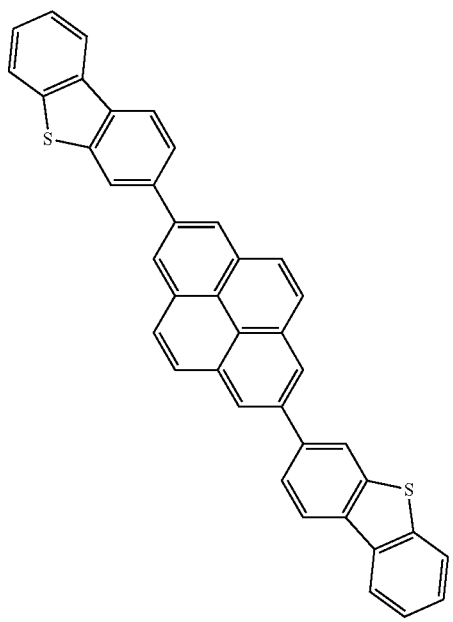

-continued
(2-535)
(2-536)
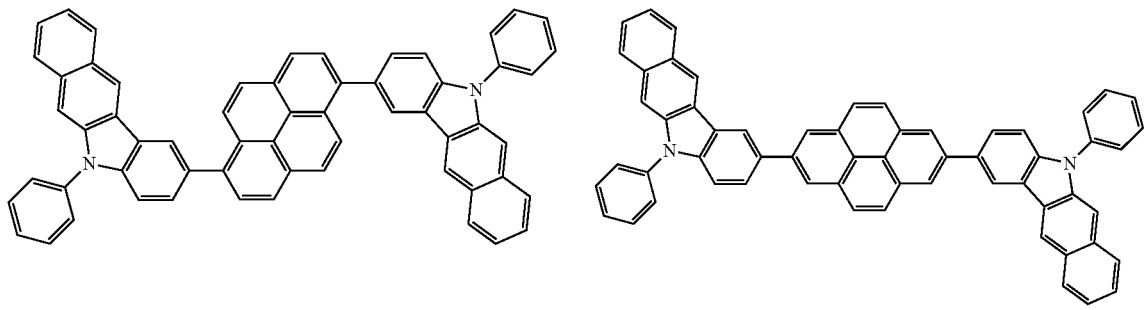
(2-537)
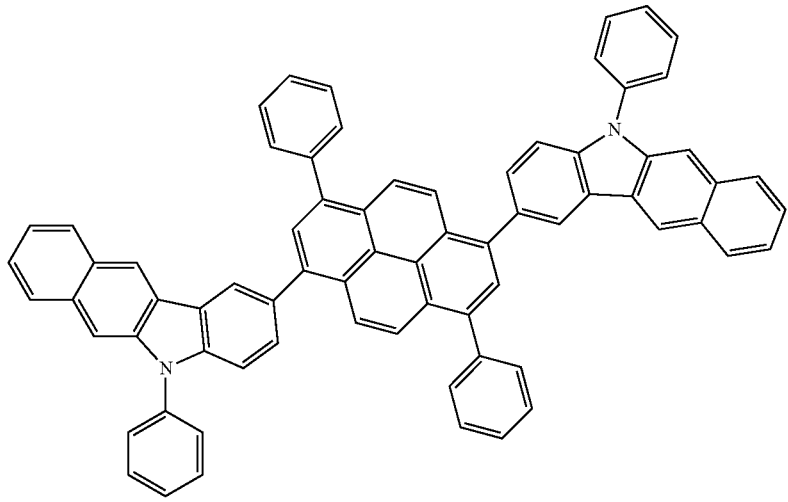
(2-538)
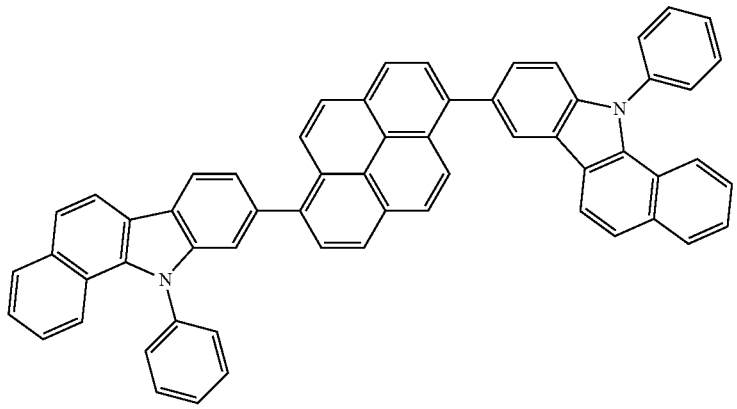
(2-539)
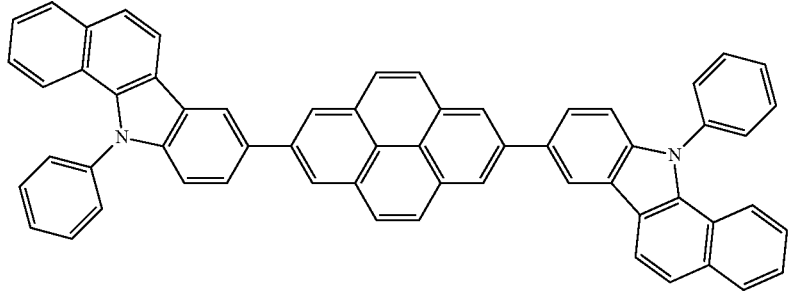

-continued
(2-540)
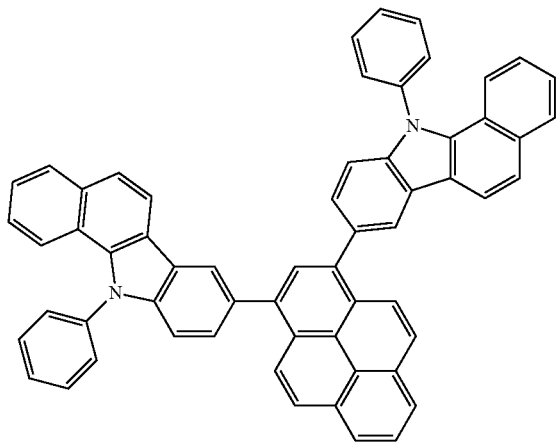
(2-541)
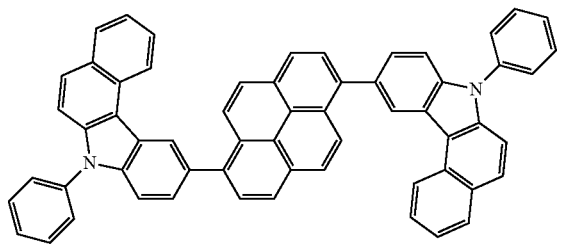
(2-542)
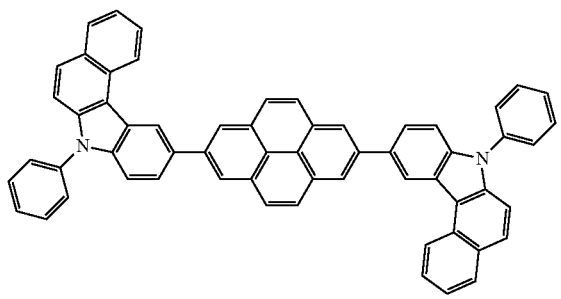
(2-543)
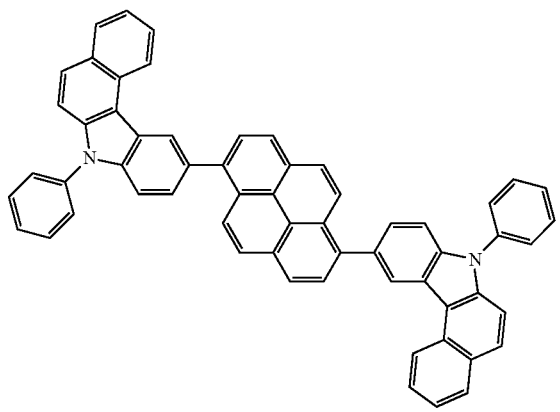
(2-544)
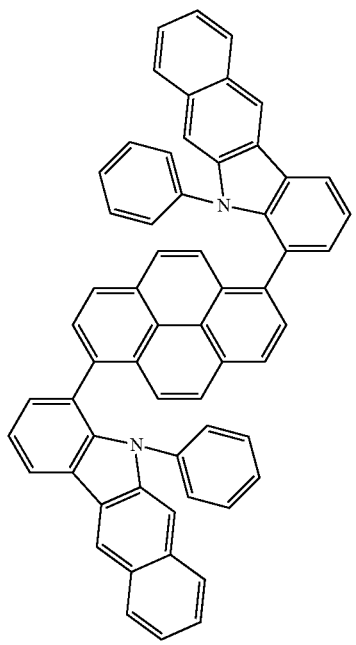
(2-570)
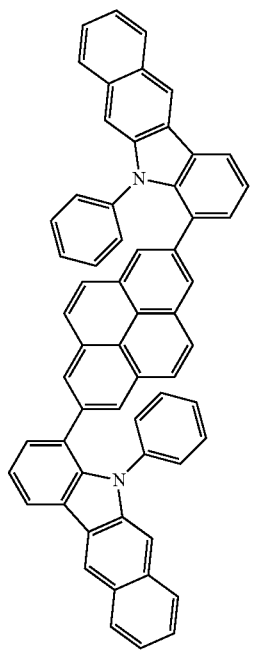

-continued
(2-572)
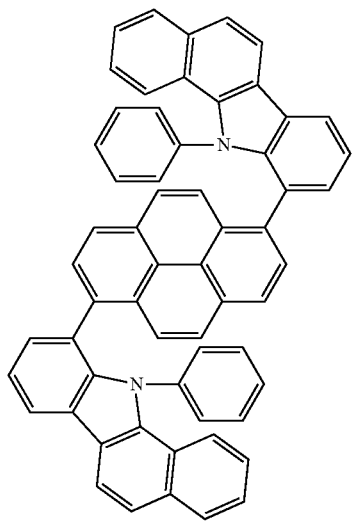
(2-573)
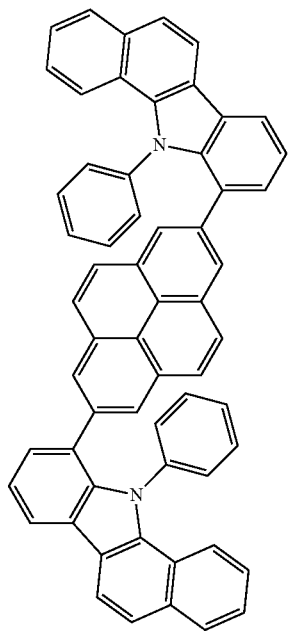
(2-575)
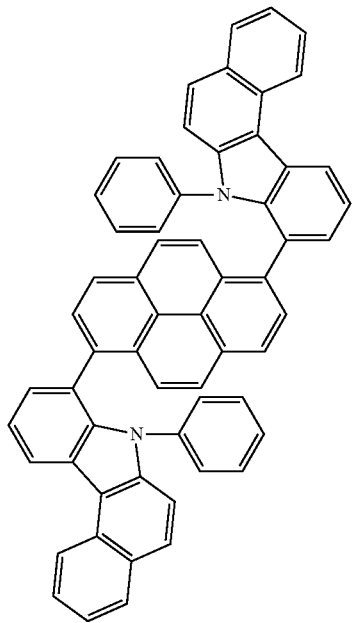
(2-576)
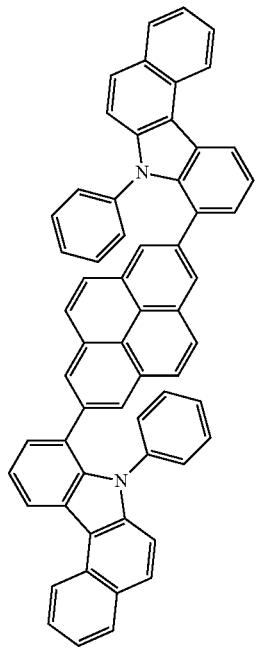

(2-578)
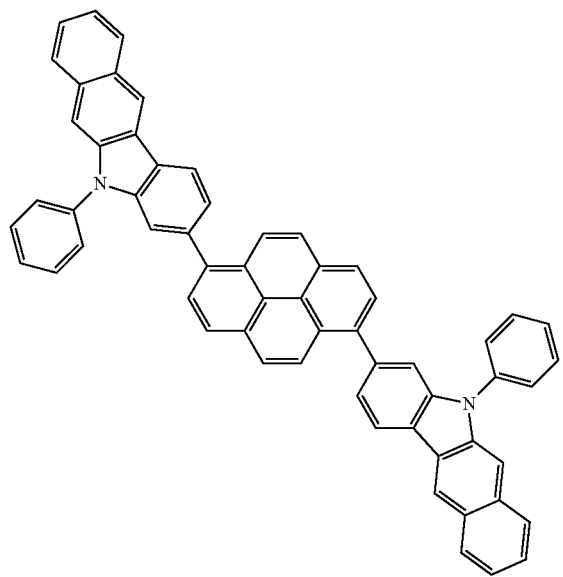
(2-579)
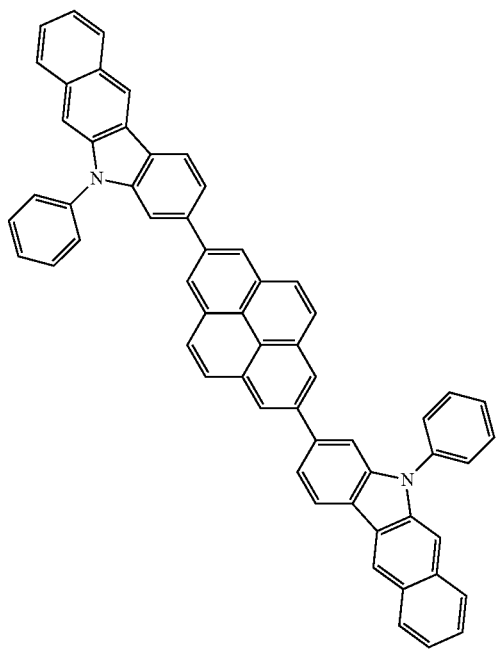
(2-581)
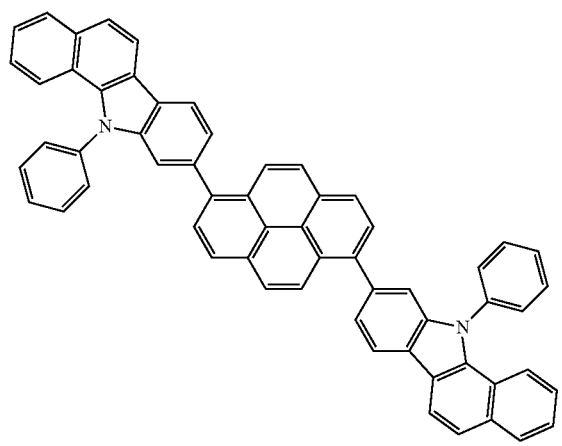
(2-582)
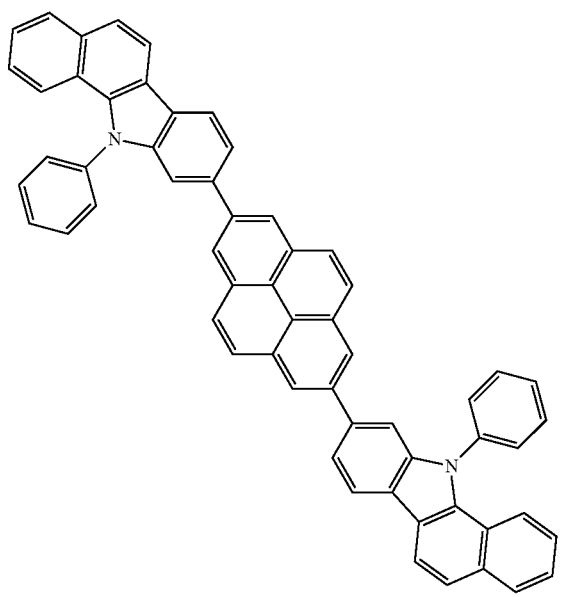

-continued
(2-600)
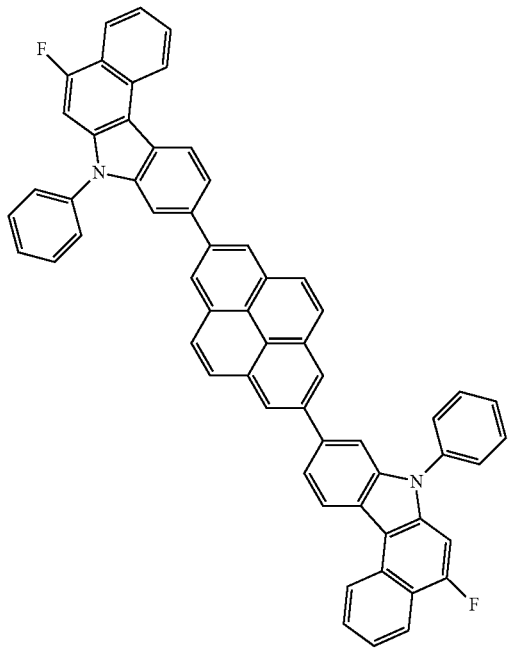
(2-601)
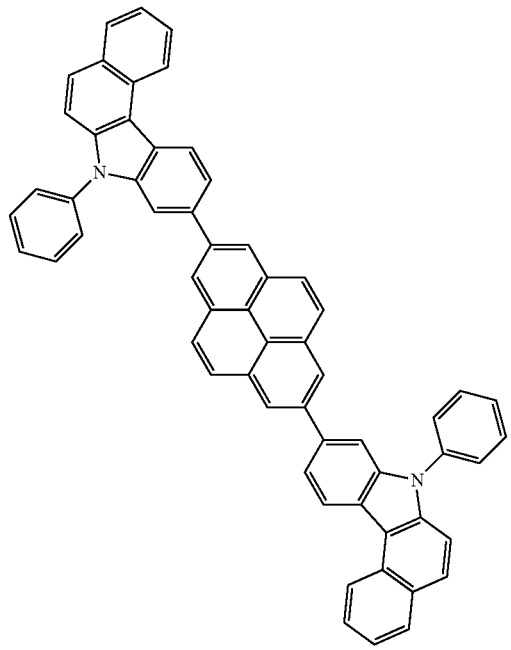
(2-603)
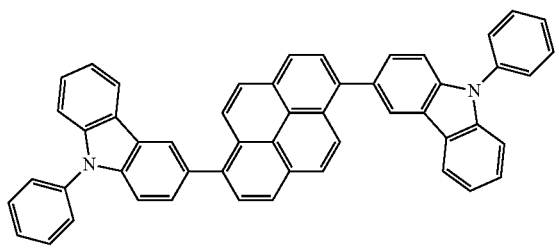
(2-604)
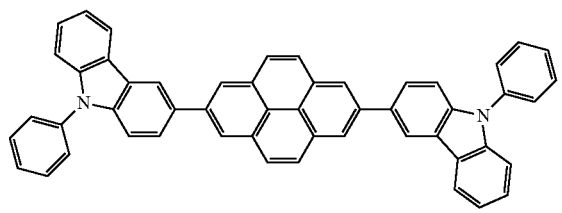
(2-605)
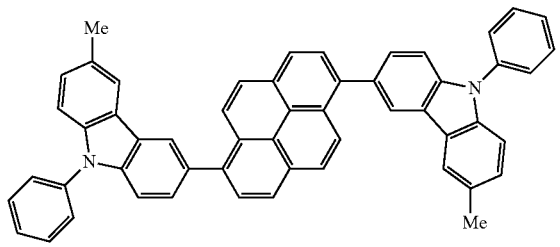
(2-606)
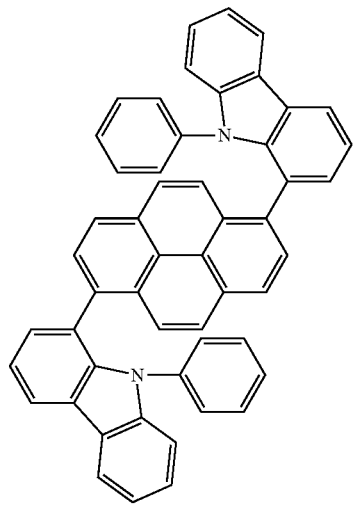

-continued
(2-607)
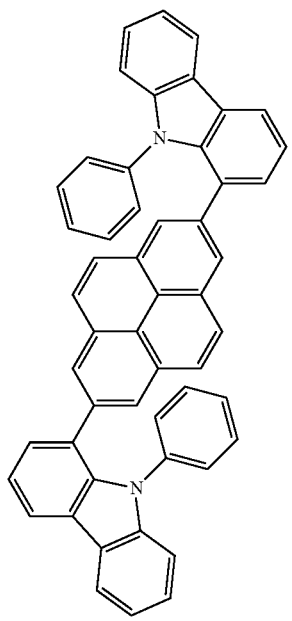
(2-609)
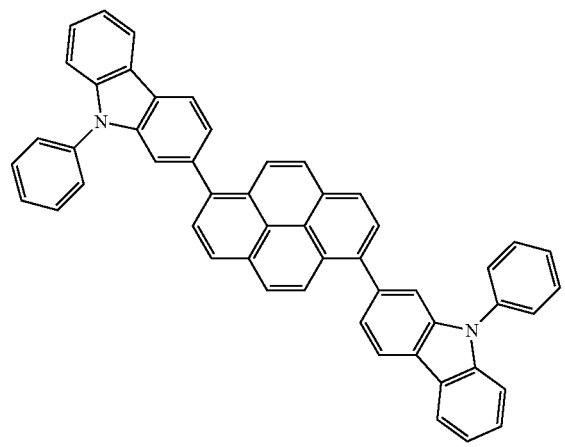
(2-610)
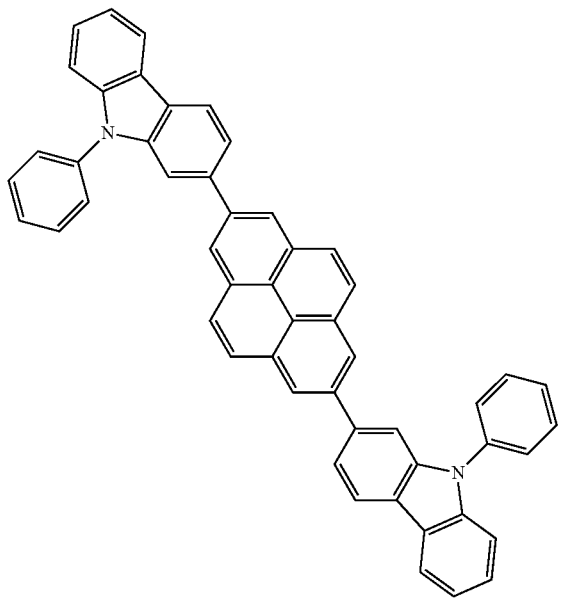
(2-624)
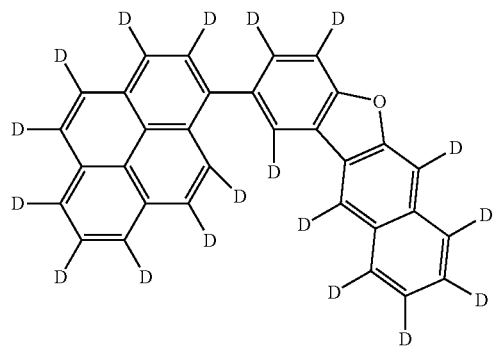
(2-625)
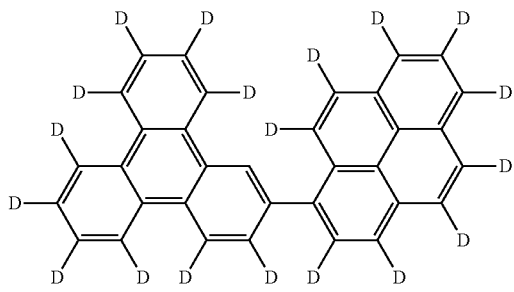
(2-626)
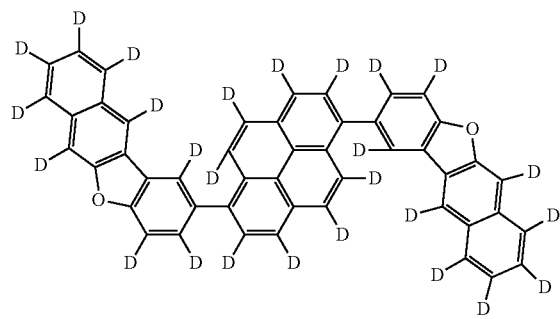

(2-627)
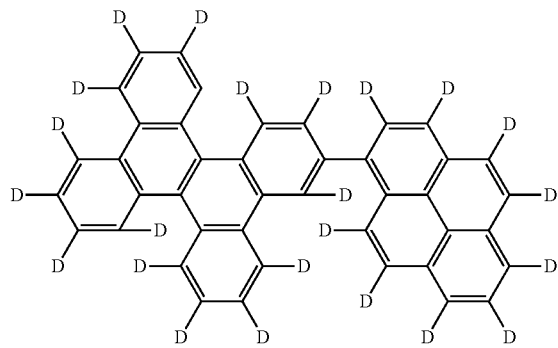
(2-1001)
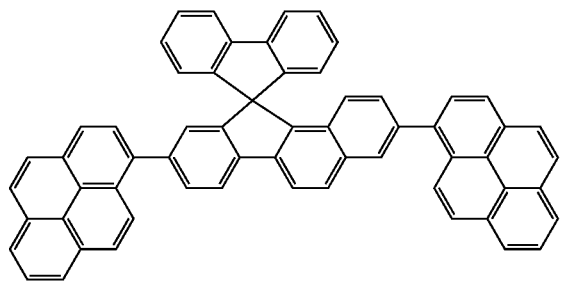
(2-1002)
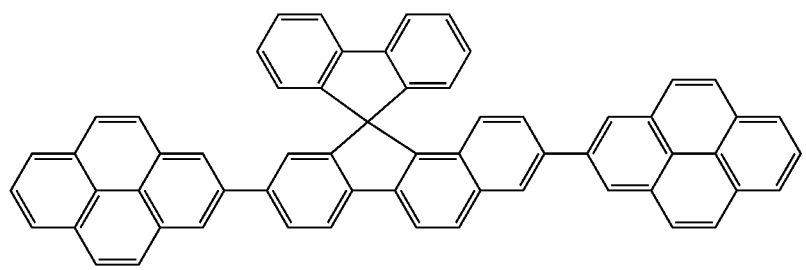
(2-1003)
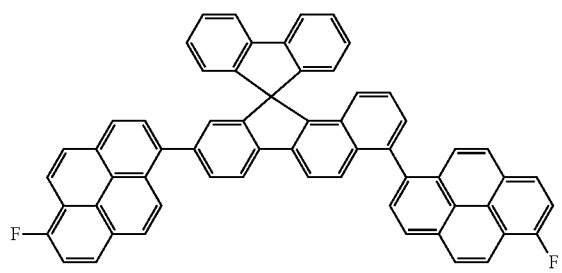
(2-1004)
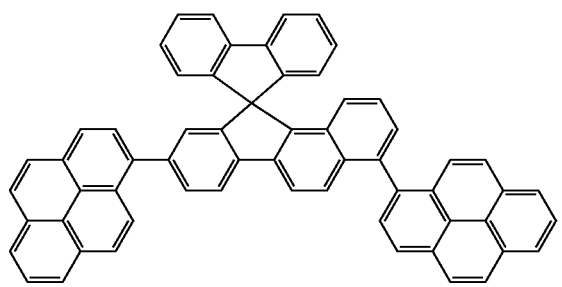
(2-1006)
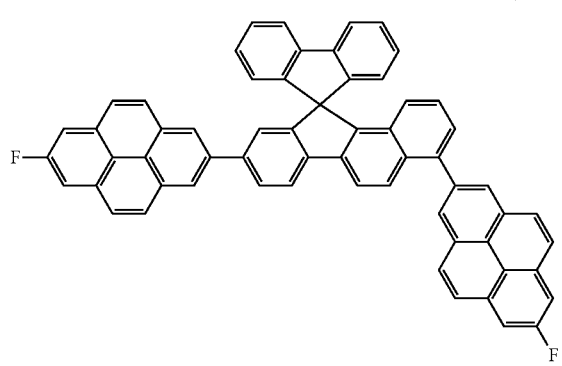
(2-1005)
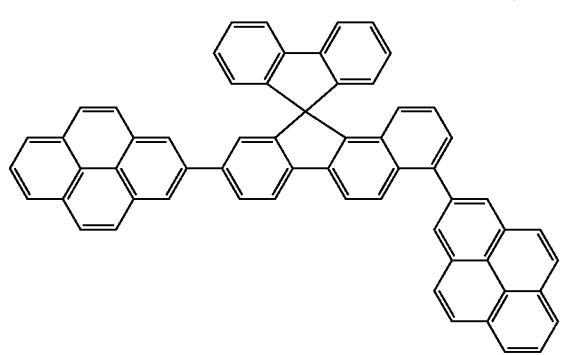
(2-1008)
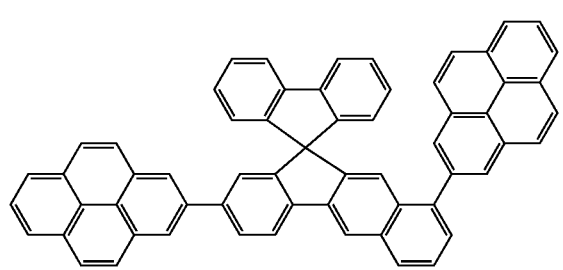
(2-1007)
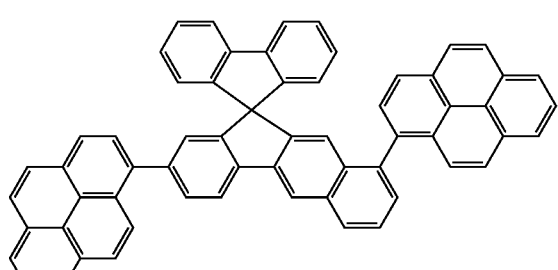

-continued
(2-1009)
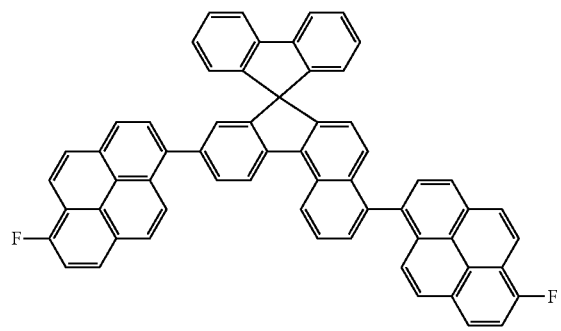
(2-1010)
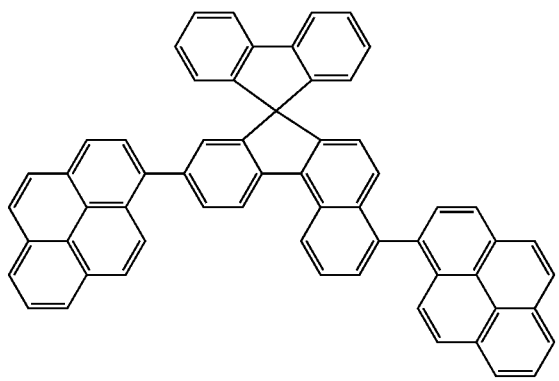
(2-1011)
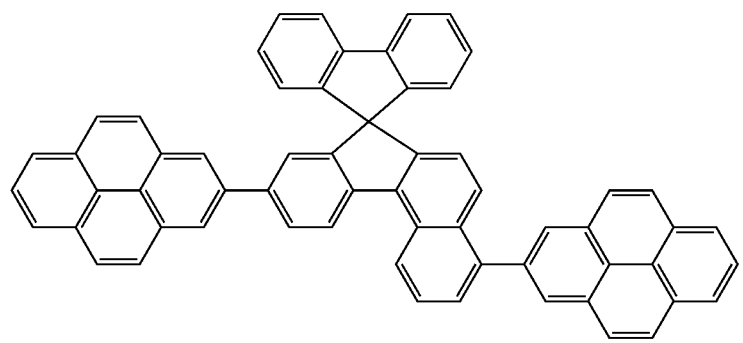
(2-1012)
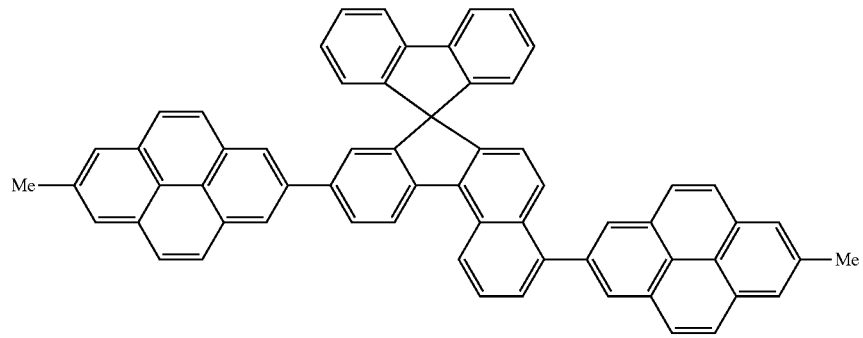
(2-1020)
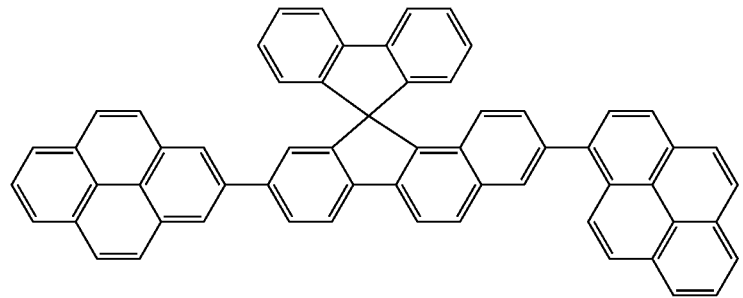

-continued
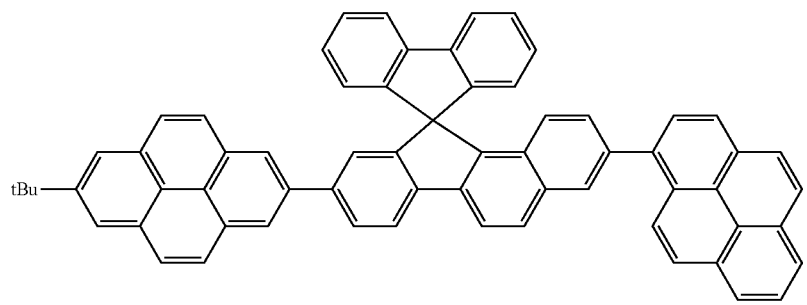
(2-1021)
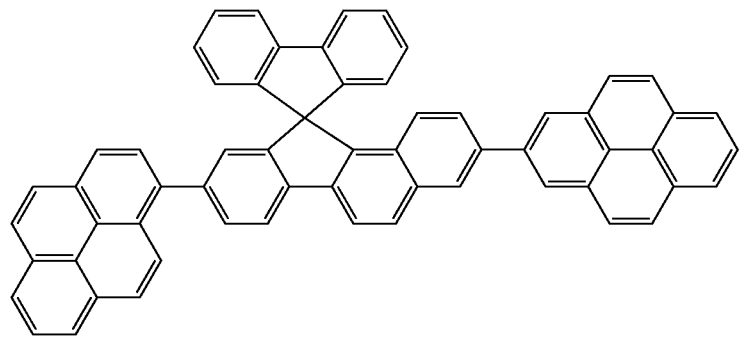
(2-1022)
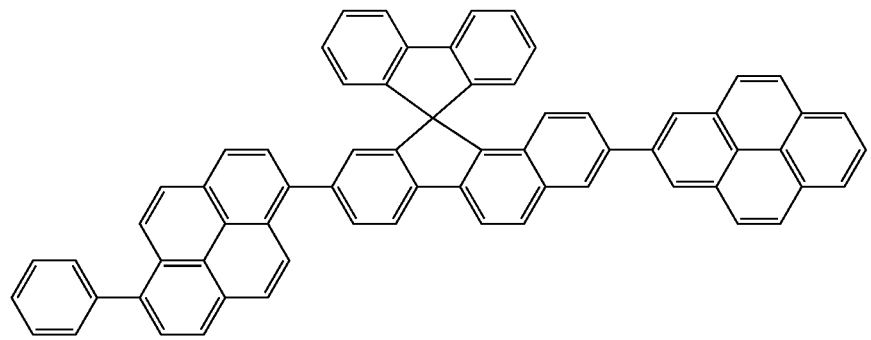
(2-1023)
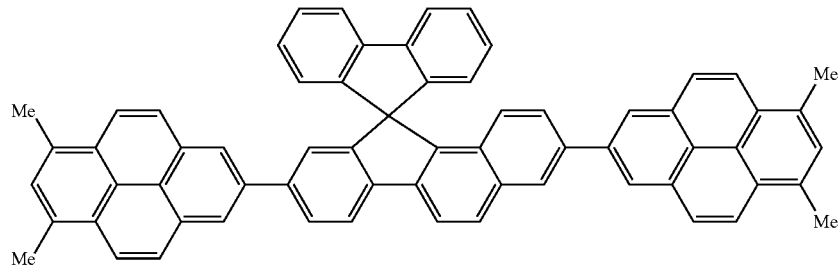
(2-1024)
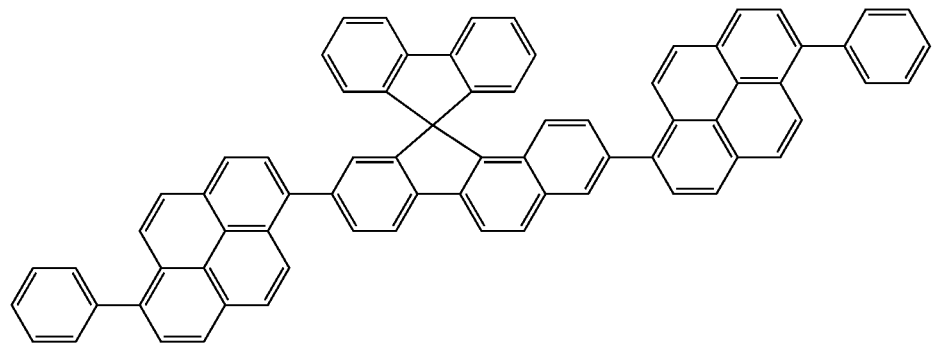
(2-1025)

-continued
(2-1026)
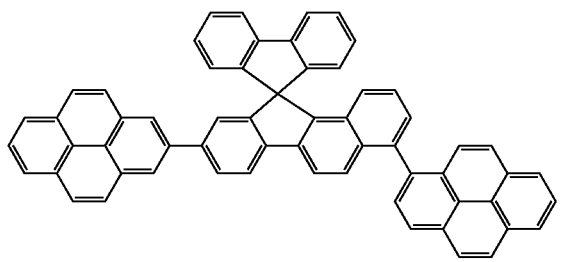
(2-1027)
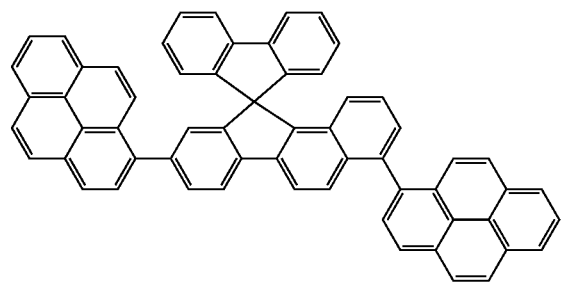
(2-1028)
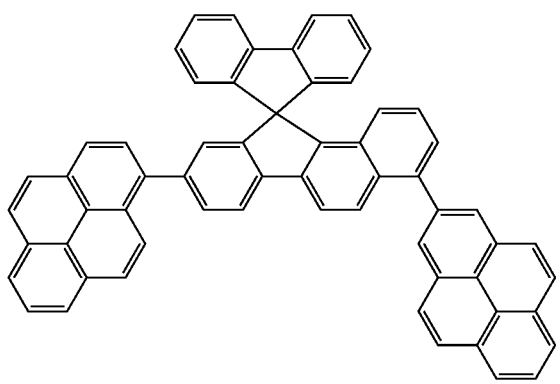
(2-1029)
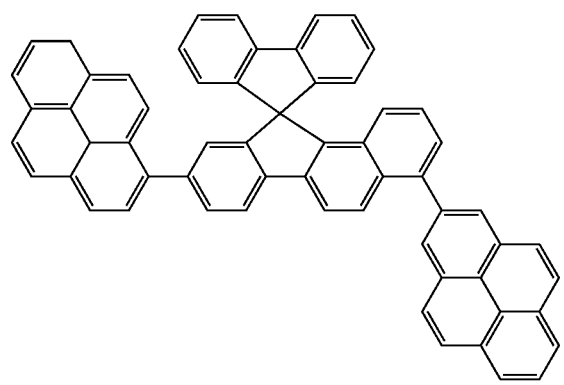
(2-1050)
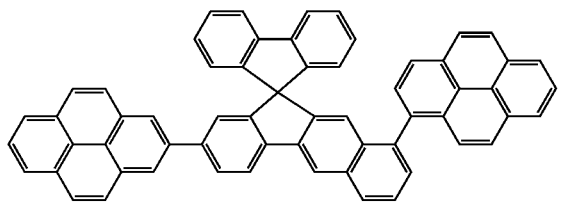
(2-1051)
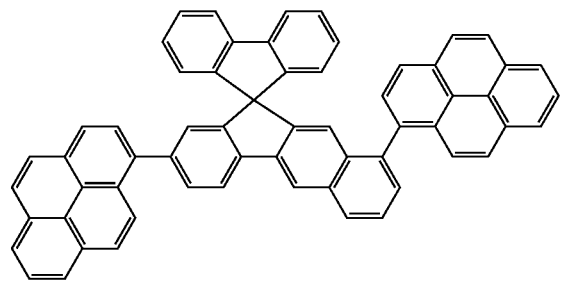
(2-1052)
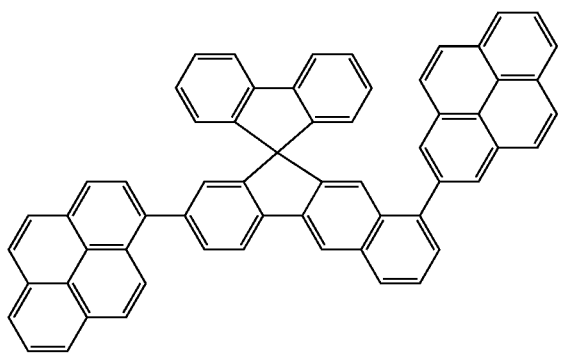
(2-1053)
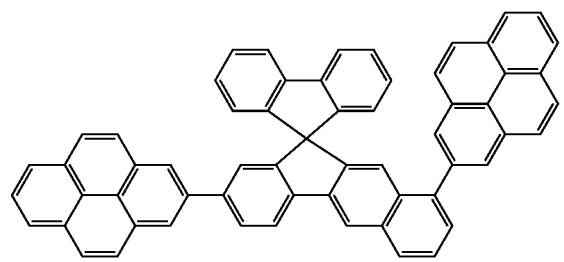

-continued
(2-1056)
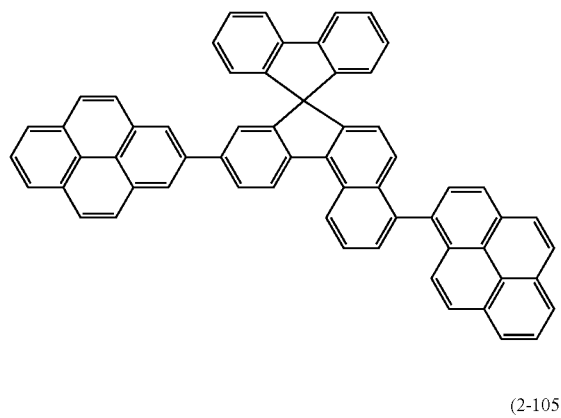
(2-1057)
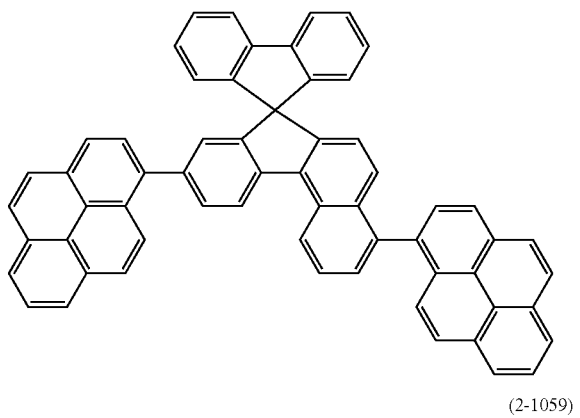
(2-1058)
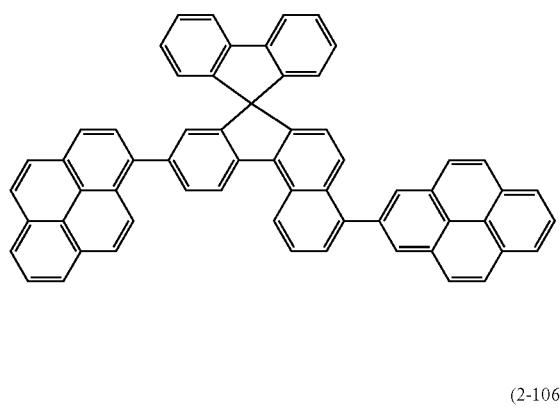
(2-1059)
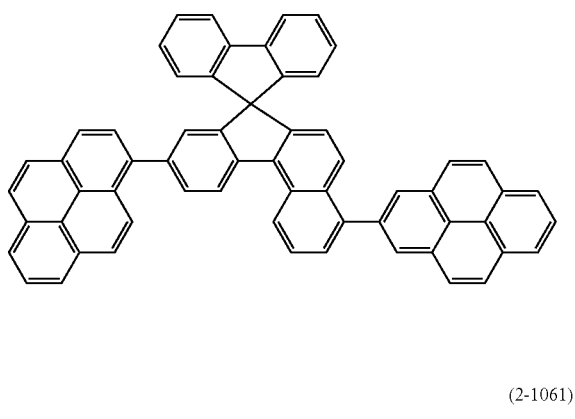
(2-1060)
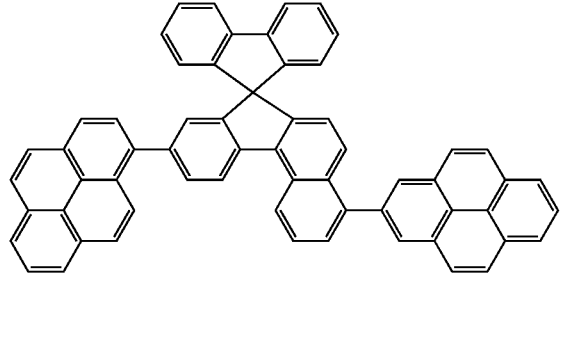
(2-1061)
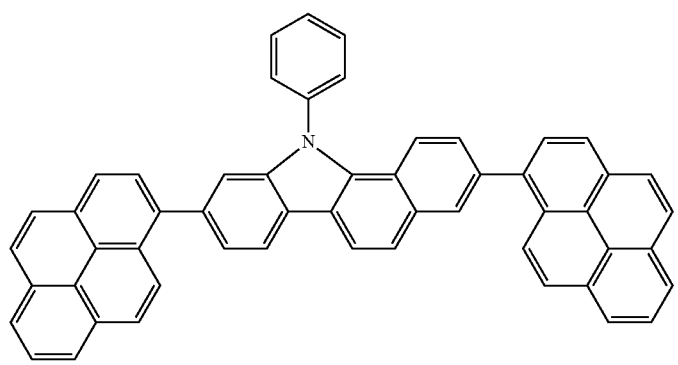
(2-1062)

(2-1063)
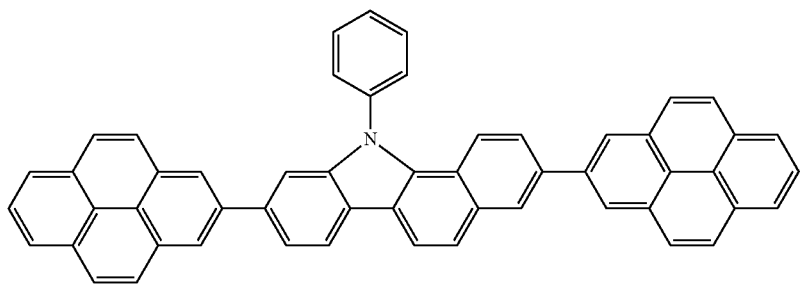
(2-1064)
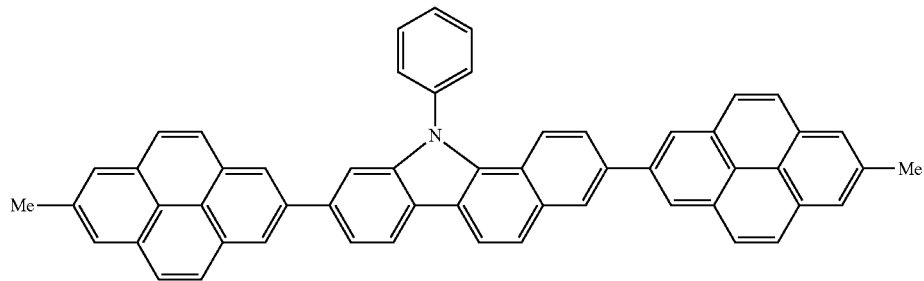
(2-1065)
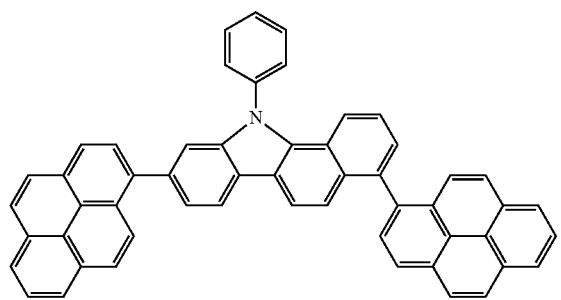
(2-1066)
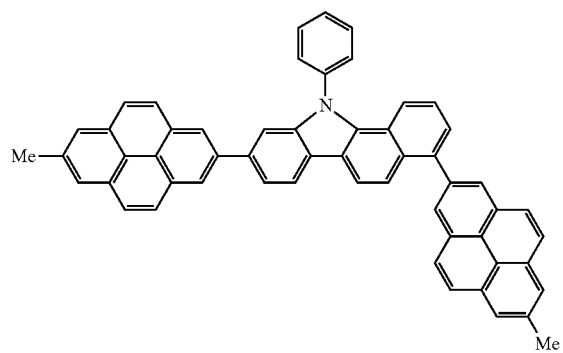
(2-1067)
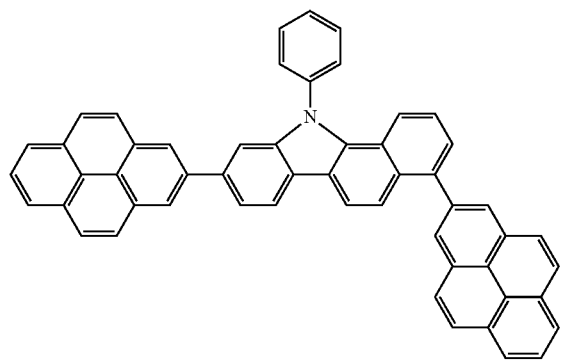
(2-1068)
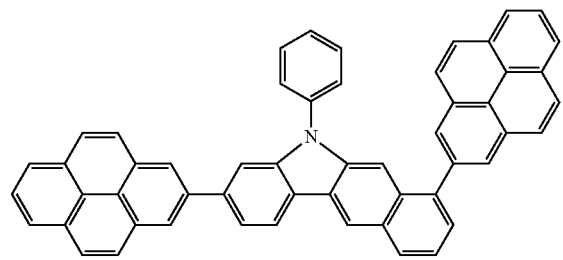

(2-1069)
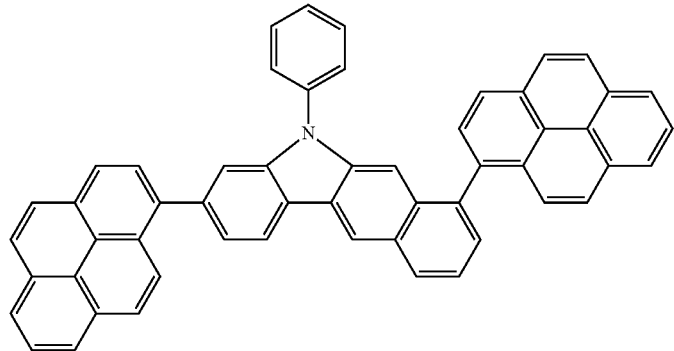
(2-1070)
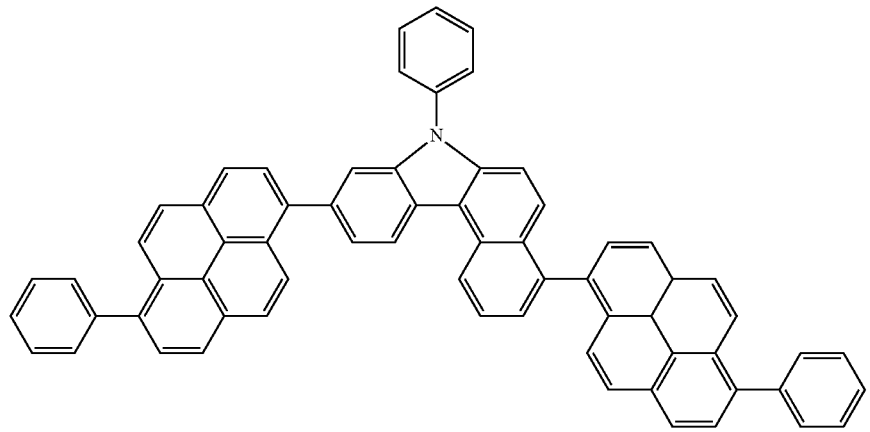
(2-1071)
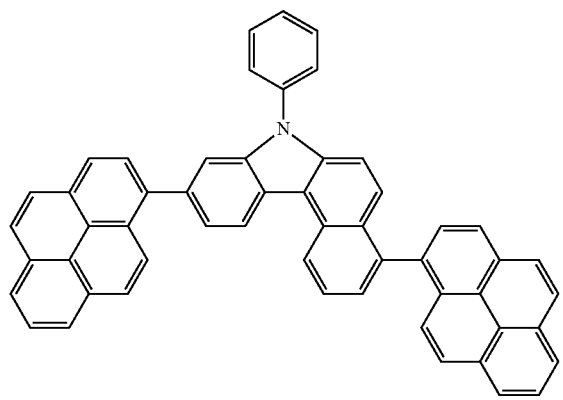
(2-1072)
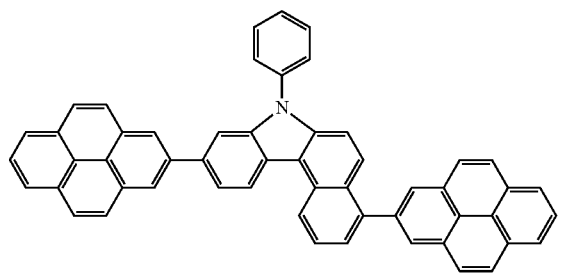
(2-1072)
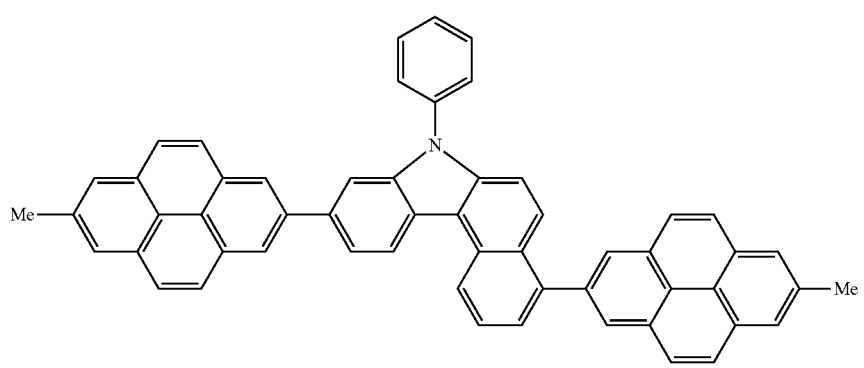

-continued
(2-1080)
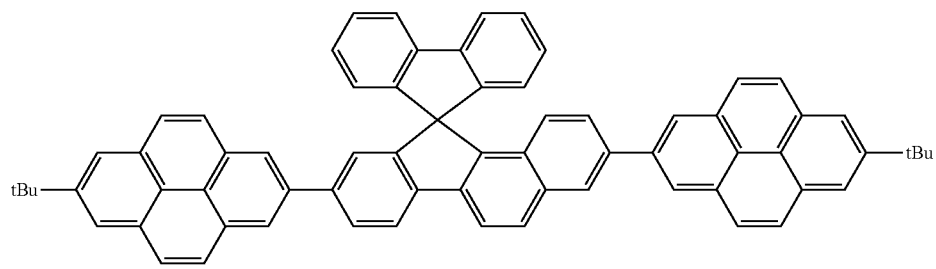
(2-1081)
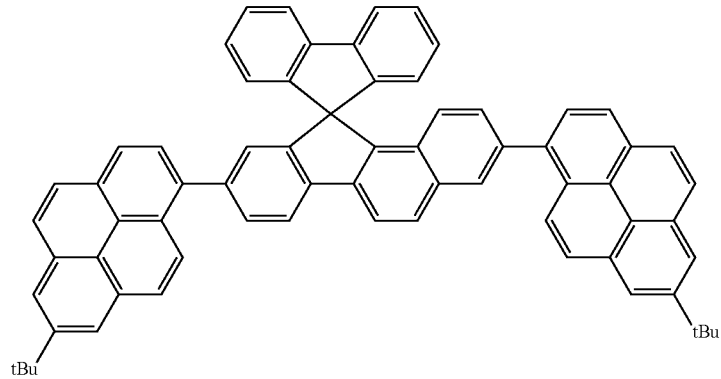
(2-1082)
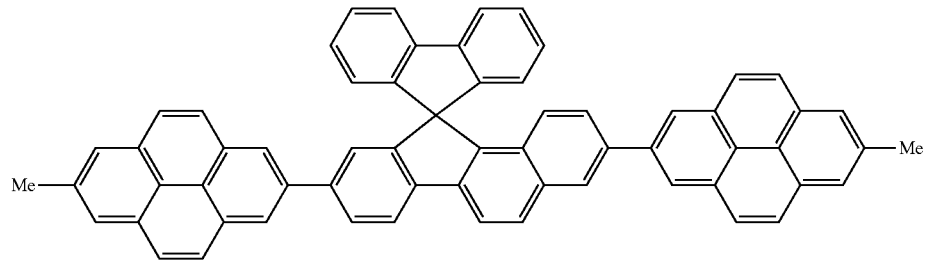
(2-1083)
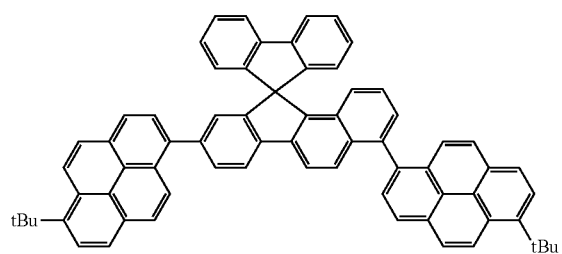
(2-1084)
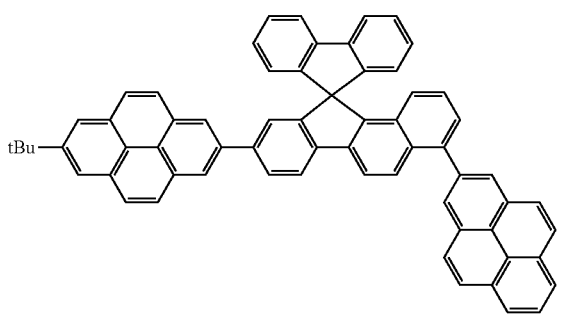
(2-1085)
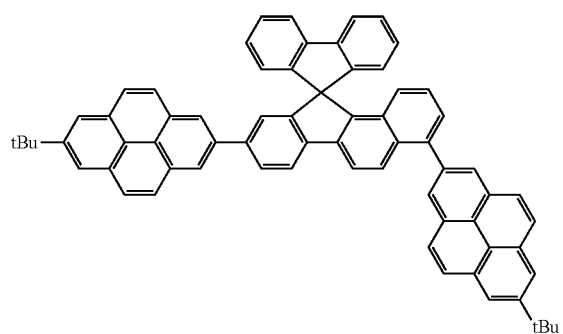

(2-1087)
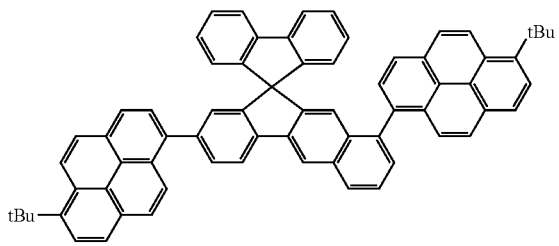
(2-1088)
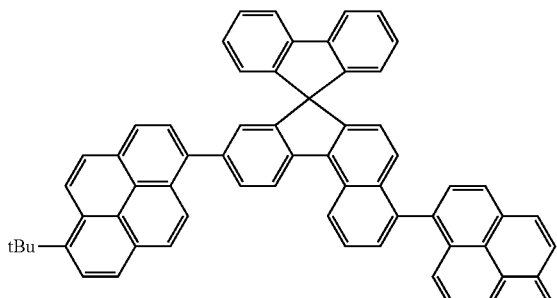
(2-1089)
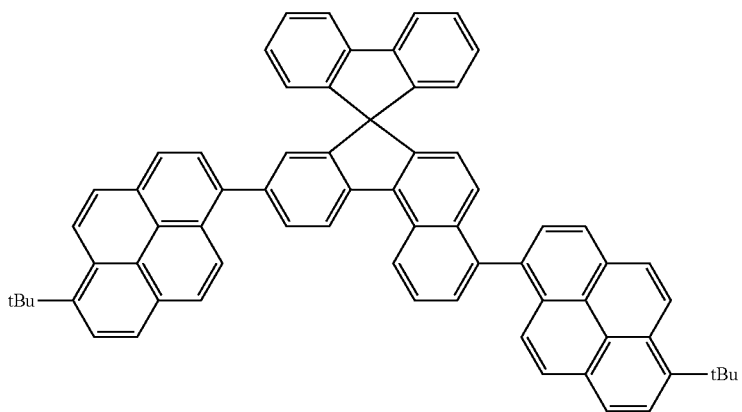
(2-1090)
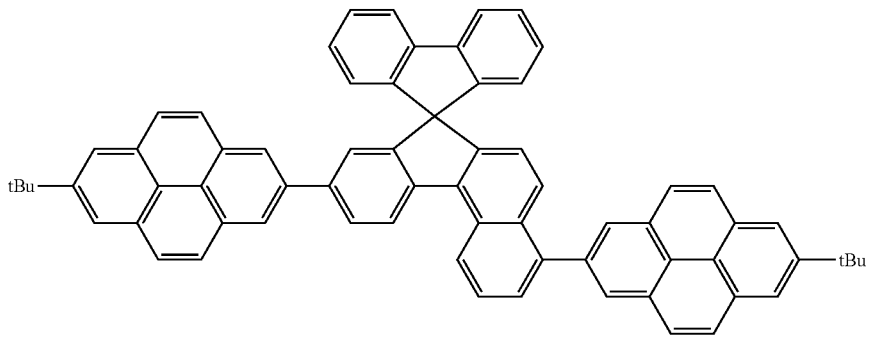
(2-1091)
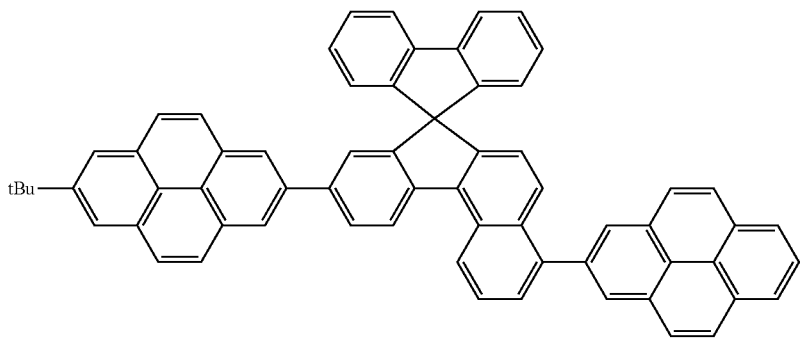

-continued
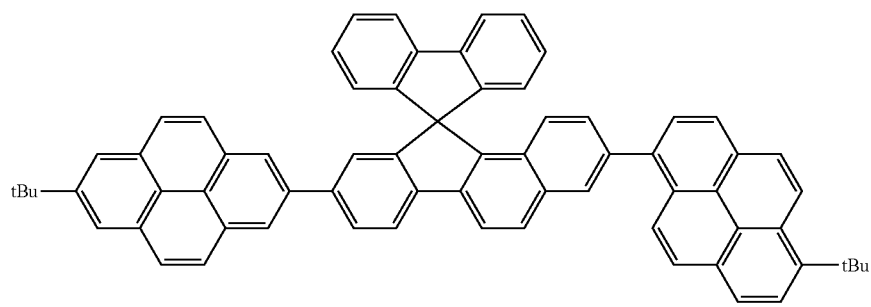
(2-1110)
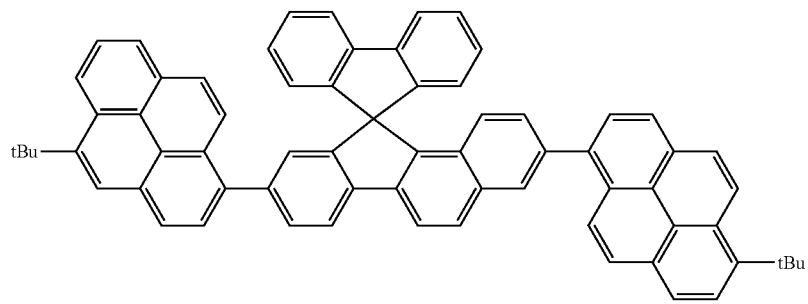
(2-1111)
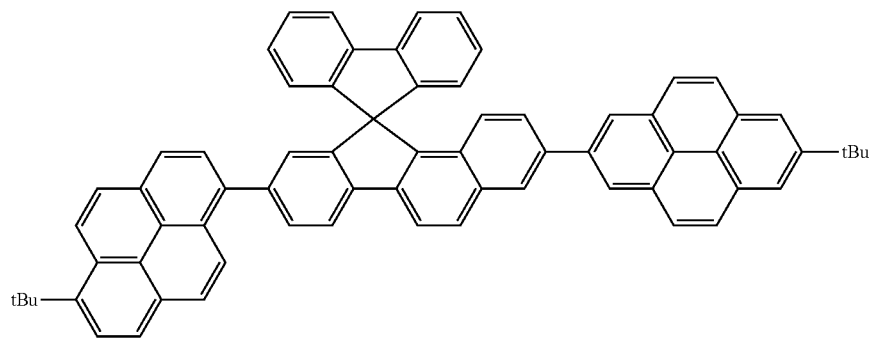
(2-1112)
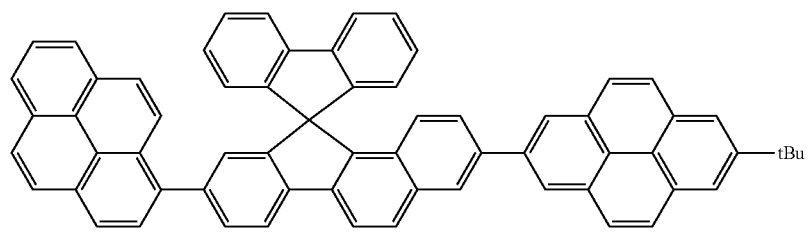
(2-1113)
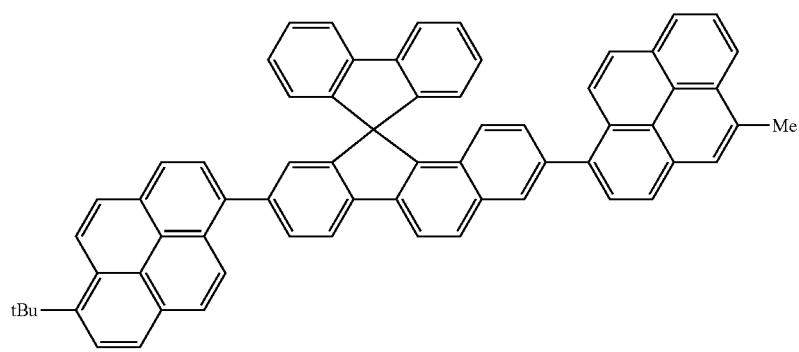
(2-1114)

-continued
(2-1115)
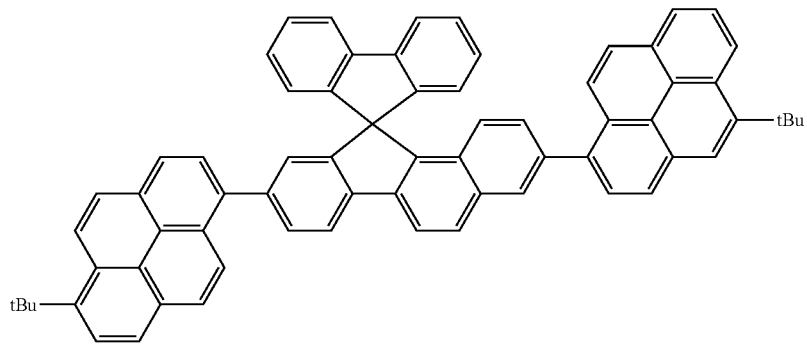
(2-1116)
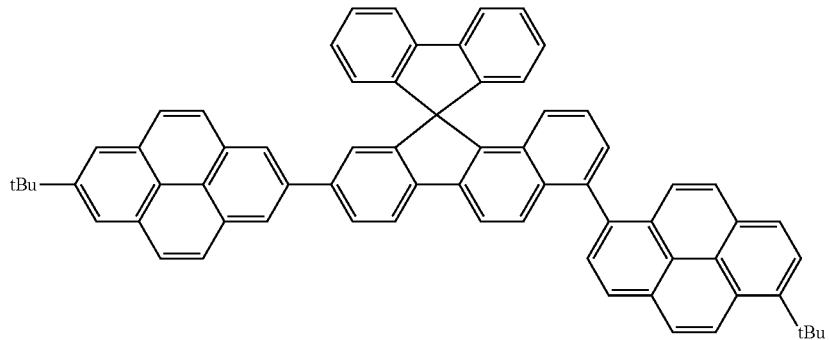
(2-1117)
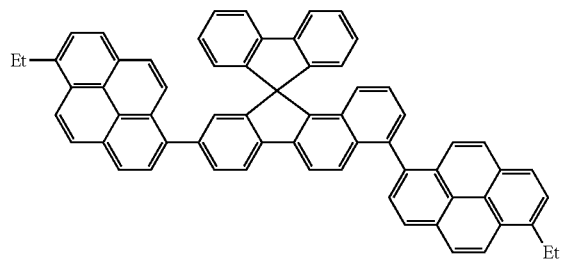
(2-1118)
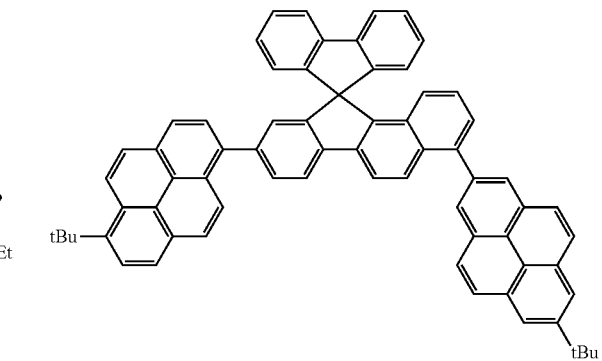
(2-1119)
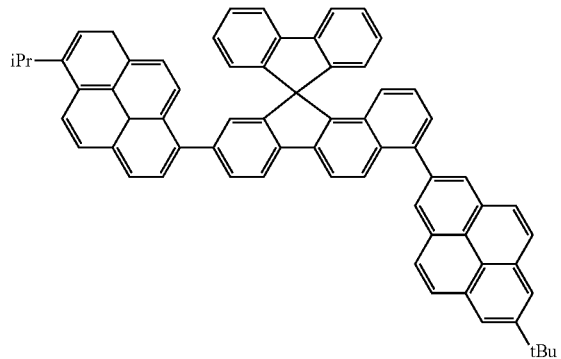
(2-1120)
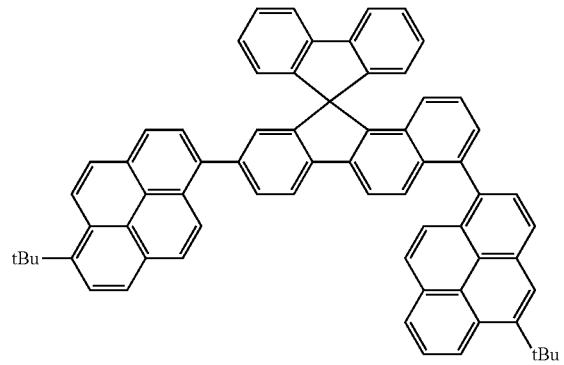

(2-1121)
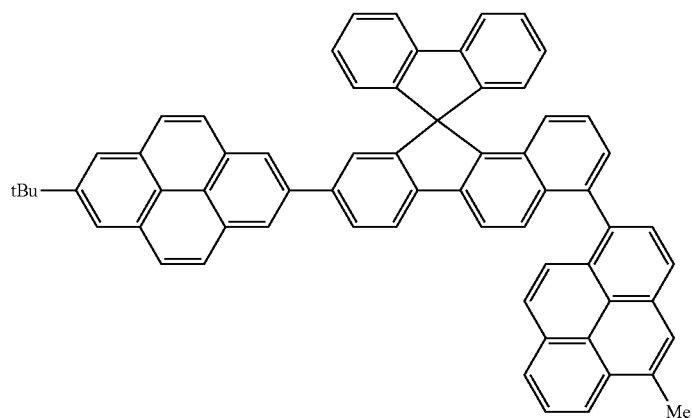
(2-1140)
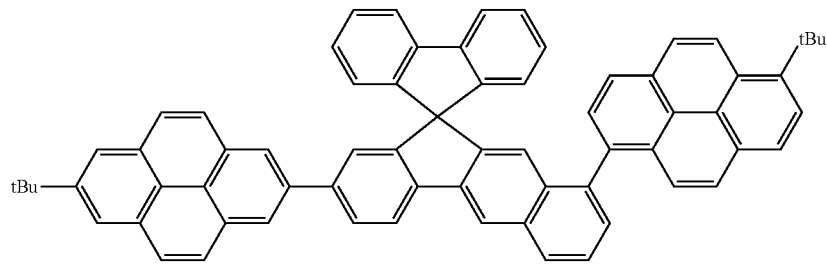
(2-1141)
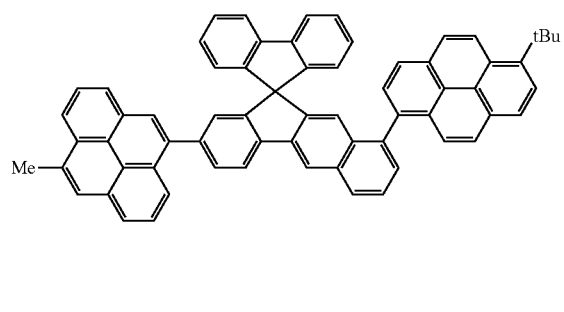
(2-1142)
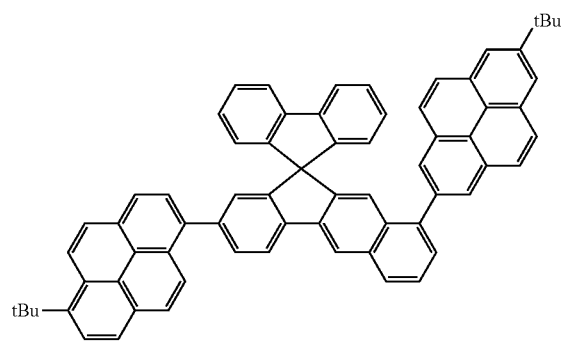
(2-1143)
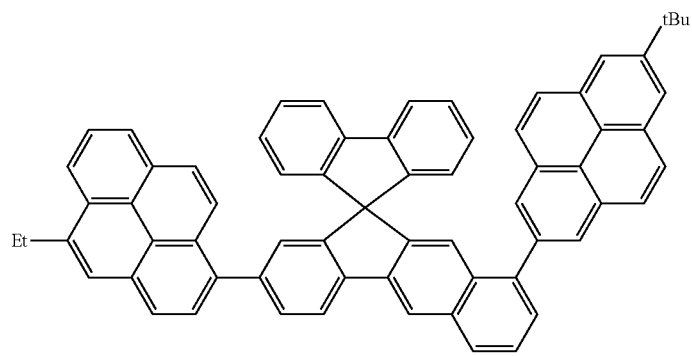

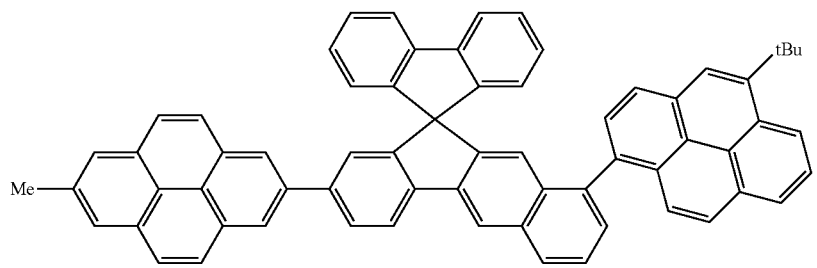
(2-1144)
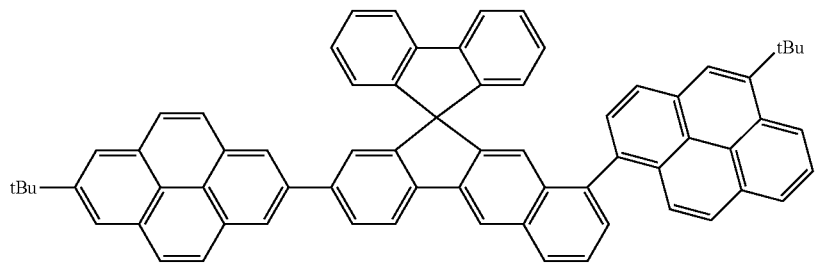
(2-1145)
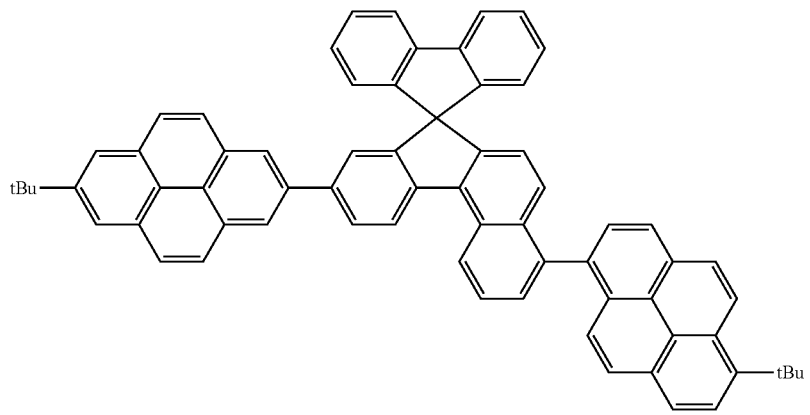
(2-1146)
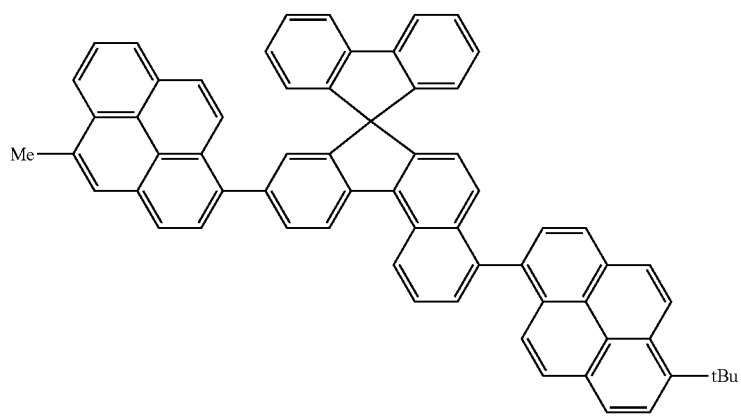
(2-1147)

-continued
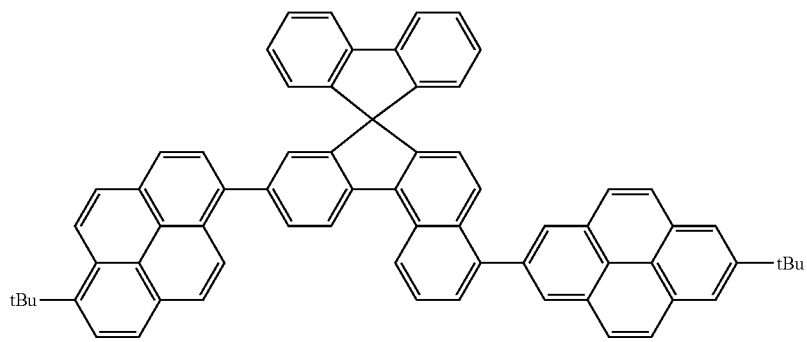
(2-1148)
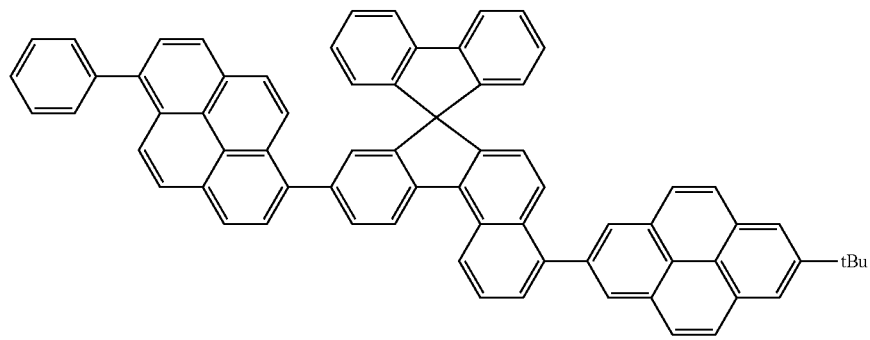
(2-1149)
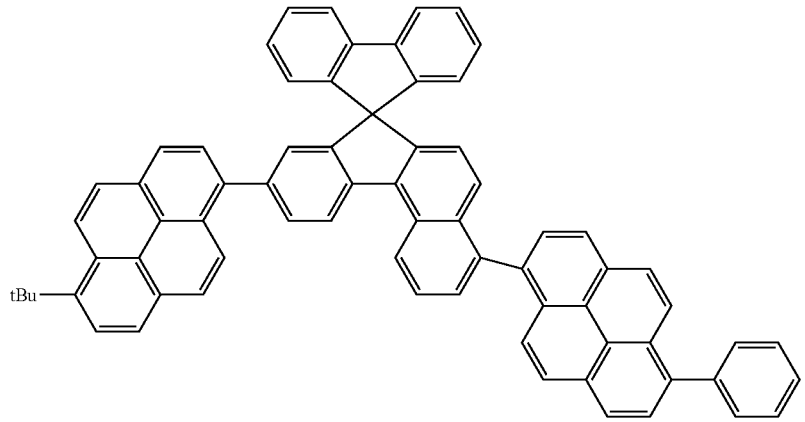
(2-1150)
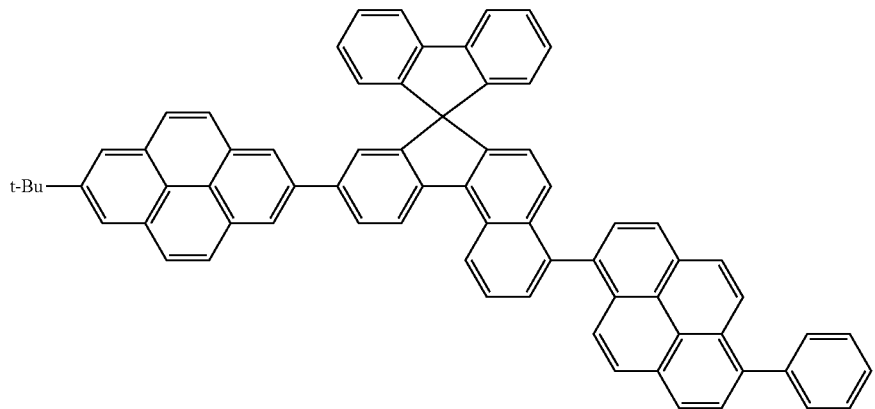
(2-1151)

-continued
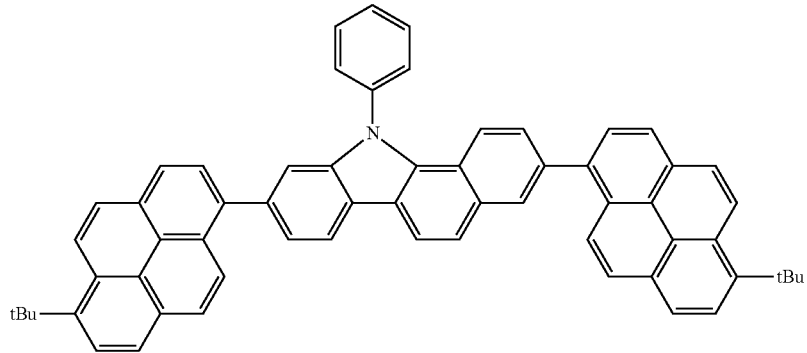
(2-1170)
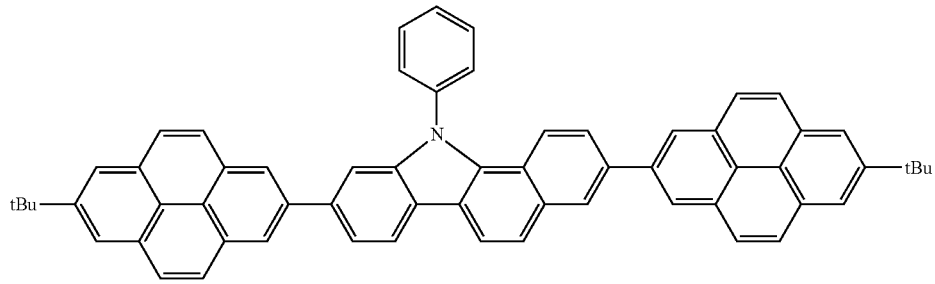
(2-1171)
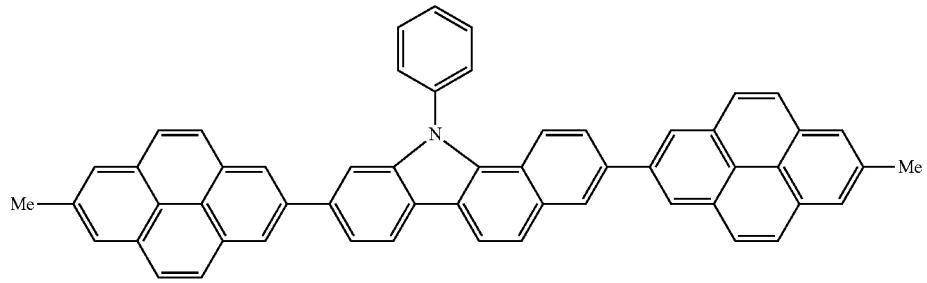
(2-1172)
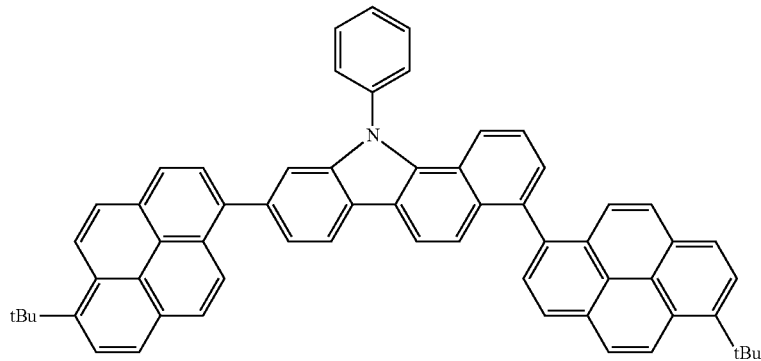
(2-1173)

-continued
(2-1174)
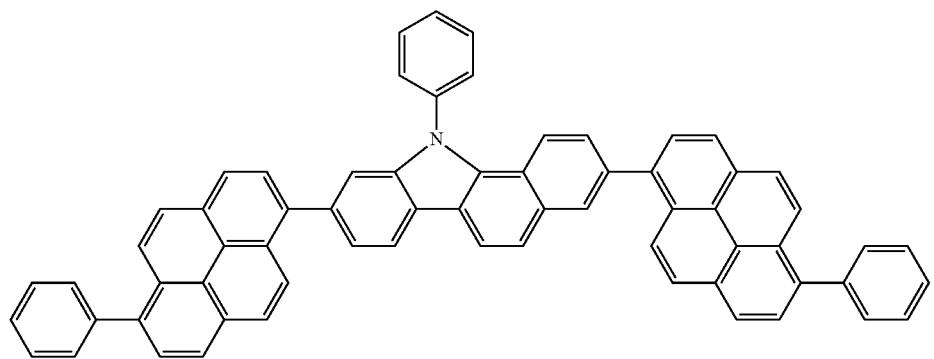
(2-1175)
(2-1176)
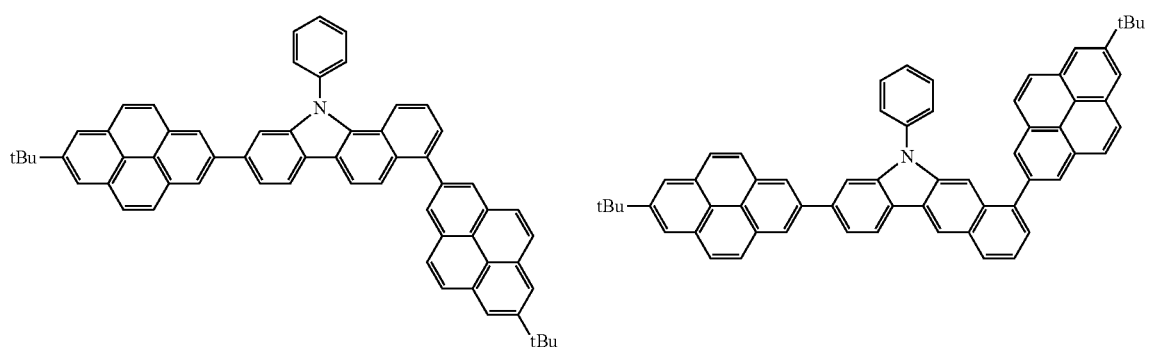
(2-1177)
(2-1178)
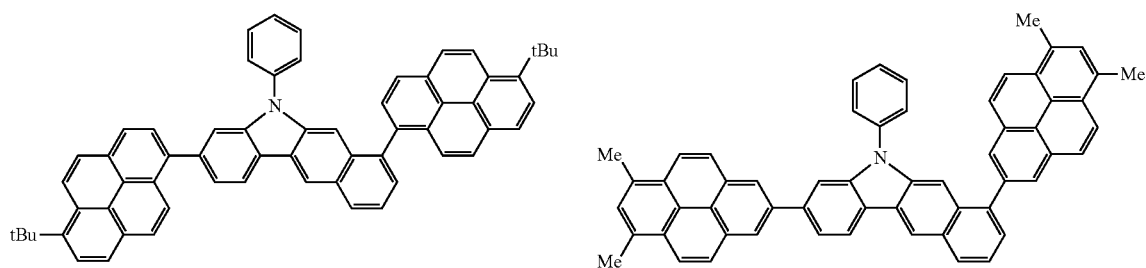
(2-1179)
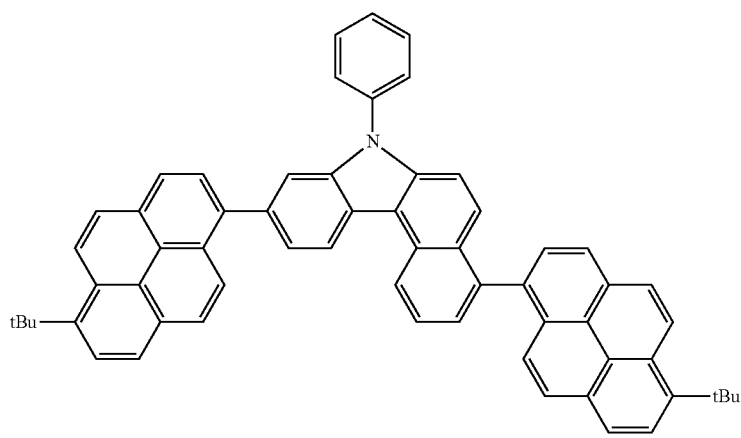

-continued
(2-1180)
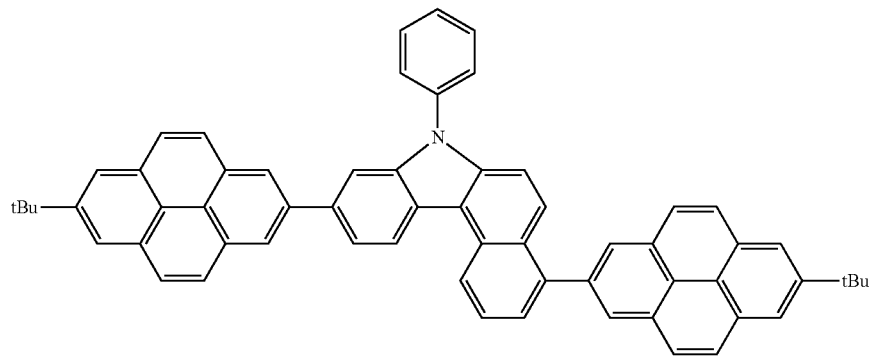
(2-1221)
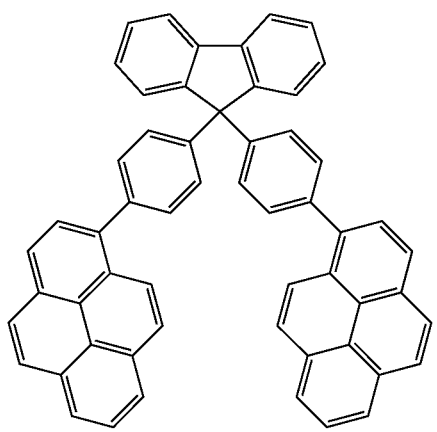
(2-1222)
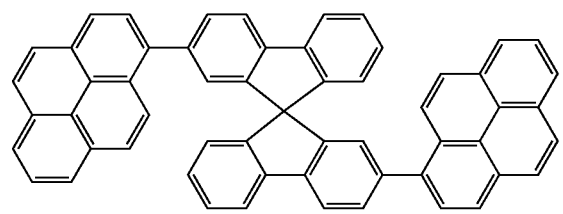
(2-1223)
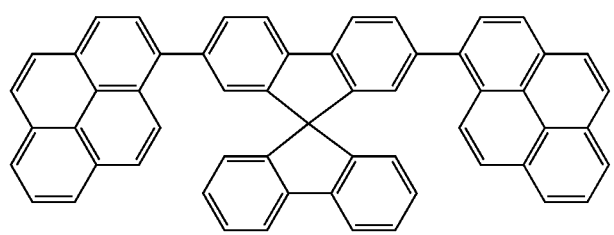
(2-1225)
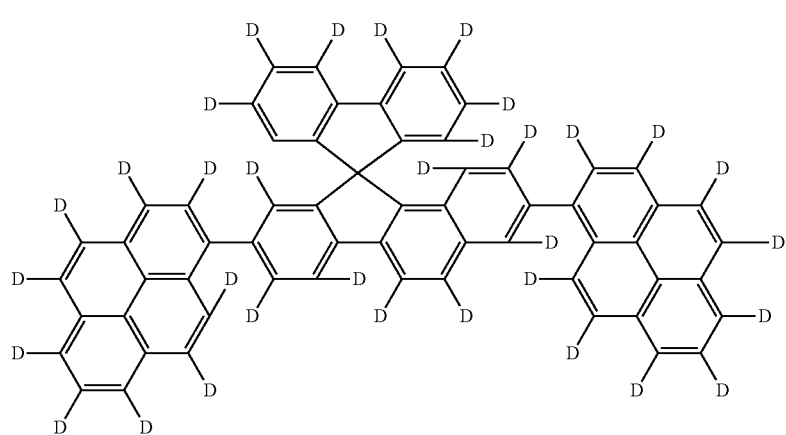

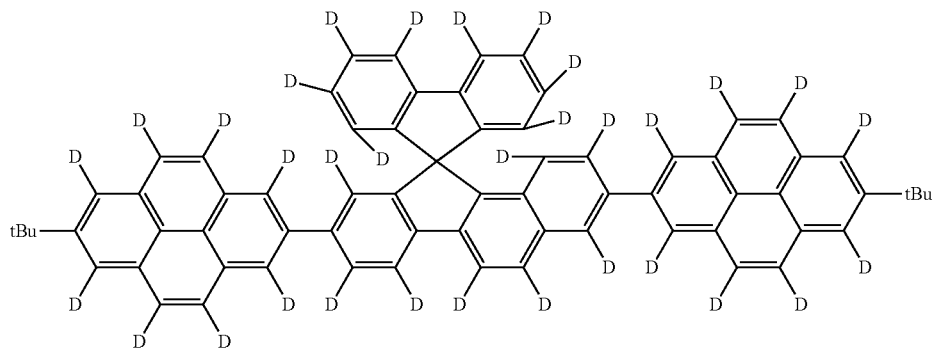

(2-1226)

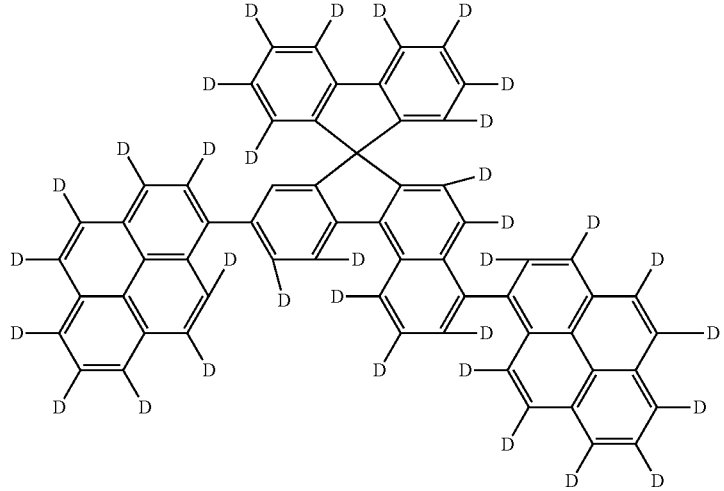

(2-1227)

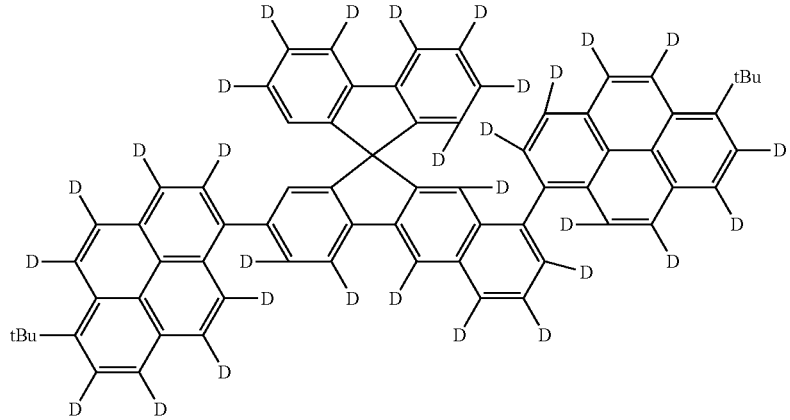

(2-1228)

Among the above compounds, the compounds represented by formulas (2-1), (2-2) to (2-20), (2-41) to (2-43), (2-46), (2-47) to (2-173), (2-174), (2-175) to (2-215), (2-351) to (2-354), (2-356), (2-357), (2-358), (2-359), (2-360) to (2-430), (2-1001), (2-1002) to (2-1012), (2-1080), and (2-1081) to (2-1091) are preferable.

Compounds represented by formulas (2-1), (2-46), (2-174), (2-350), (2-356), (2-359), (2-1001), and (2-1080) are more preferable.

5. Method for Manufacturing Pyrene-Based Compound Represented by Formula (2)

The pyrene-based compound represented by formula (2) has a structure in which various substituents are bonded to a pyrene skeleton, a skeleton of a compound represented by Ar, or the like, and can be manufactured by a known method. By manufacturing an intermediate by a halogenation reaction, a boron oxidation reaction, or a boronic acid esterification reaction, which is usually used, subjecting the manufactured intermediate to a Suzuki coupling reaction, another metalation reaction, or a cross coupling reaction via metal species (a Negishi coupling reaction, a Kumada-Tamao coupling reaction, a Kosugi-Migita-Stille coupling reaction, or the like), the pyrene-based compound represented by formula (2) can be appropriately manufactured. Alternatively, by manufacturing an intermediate having a substituent, for example, an alkoxy group such as a methoxy group, converting the intermediate into an —OH form by a demethylation reaction using a pyridine hydrochloride or the like, then converting the —OH form into a sulfonate using a reagent such as trifluoromethanesulfonic anhydride, and subjecting the sulfonate to a cross coupling reaction such as a Suzuki coupling reaction, the pyrene-based compound represented by formula (2) can be manufactured. Commercially available materials can also be used as these intermediates including a halogen, boronic acid, boronate, and sulfonate. For reference, a specific method for manufacturing the pyrene-based compound will be described in Synthesis Example described later.

6. Organic Electroluminescent Element

Hereinafter, an organic EL element according to the present embodiment will be described in detail based on the drawings. FIG. 1 is a schematic cross-sectional view illustrating the organic EL element according to the present embodiment.

<Structure of Organic Electroluminescent Element>

An organic EL element 100 illustrated in FIG. 1 includes a substrate 101, a positive electrode 102 provided on the substrate 101, a hole injection layer 103 provided on the positive electrode 102, a hole transport layer 104 provided on the hole injection layer 103, a light emitting layer 105 provided on the hole transport layer 104, an electron transport layer 106 provided on the light emitting layer 105, an electron injection layer 107 provided on the electron transport layer 106, and a negative electrode 108 provided on the electron injection layer 107.

Incidentally, the organic EL element 100 may be configured, by reversing the manufacturing order, to include, for example, the substrate 101, the negative electrode 108 provided on the substrate 101, the electron injection layer 107 provided on the negative electrode 108, the electron transport layer 106 provided on the electron injection layer 107, the light emitting layer 105 provided on the electron transport layer 106, the hole transport layer 104 provided on the light emitting layer 105, the hole injection layer 103 provided on the hole transport layer 104, and the positive electrode 102 provided on the hole injection layer 103.

Not all of the above layers are essential. The configuration includes the positive electrode 102, the light emitting layer 105, and the negative electrode 108 as a minimum constituent unit, and optionally includes the hole injection layer 103, the hole transport layer 104, the electron transport layer 106, and the electron injection layer 107. Each of the above layers may be formed of a single layer or a plurality of layers.

A form of layers constituting the organic EL element may be, in addition to the above structure form of "substrate/positive electrode/hole injection layer/hole transport layer/light emitting layer/electron transport layer/electron injection layer/negative electrode", a structure form of "substrate/positive electrode/hole transport layer/light emitting layer/electron transport layer/electron injection layer/negative electrode", "substrate/positive electrode/hole injection layer/light emitting layer/electron transport layer/electron injection layer/negative electrode", "substrate/positive electrode/hole injection layer/hole transport layer/light emitting layer/electron injection layer/negative electrode", "substrate/positive electrode/hole injection layer/hole transport layer/light emitting layer/electron transport layer/negative electrode", "substrate/positive electrode/light emitting layer/electron transport layer/electron injection layer/negative electrode", "substrate/positive electrode/hole transport layer/light emitting layer/electron injection layer/negative electrode", "substrate/positive electrode/hole transport layer/light emitting layer/electron transport layer/negative electrode", "substrate/positive electrode/hole injection layer/light emitting layer/electron injection layer/negative electrode", "substrate/positive electrode/hole injection layer/light emitting layer/electron transport layer/negative electrode", "substrate/positive electrode/light emitting layer/electron transport layer/negative electrode", or "substrate/positive electrode/light emitting layer/electron injection layer/negative electrode".

<Substrate in Organic Electroluminescent Element>

The substrate 101 serves as a support of the organic EL element 100, and usually, quartz, glass, metals, plastics, and the like are used therefor. The substrate 101 is formed into a plate shape, a film shape, or a sheet shape according to a purpose, and for example, a glass plate, a metal plate, a metal foil, a plastic film, and a plastic sheet are used therefor. Among these examples, a glass plate and a plate made of a transparent synthetic resin such as polyester, polymethacrylate, polycarbonate, or polysulfone are preferable. For a glass substrate, soda lime glass, alkali-free glass, and the like are used. The thickness is only required to be sufficient for maintaining mechanical strength. Therefore, the thickness is only required to be 0.2 mm or more, for example. An upper limit value of the thickness is, for example, 2 mm or less, and preferably 1 mm or less. Regarding a material of glass, glass having fewer ions eluted from the glass is desirable, and therefore alkali-free glass is preferable. However, soda lime glass which has been subjected to barrier coating with $SiO_2$ or the like is also commercially available, and therefore this soda lime glass can be used. Furthermore, the substrate 101 may be provided with a gas barrier film such as a dense silicon oxide film on at least one surface in order to increase a gas barrier property. Particularly in a case of using a plate, a film, or a sheet made of a synthetic resin having a low gas barrier property as the substrate 101, a gas barrier film is preferably provided.

<Positive Electrode in Organic Electroluminescent Element>

The positive electrode 102 plays a role of injecting a hole into the light emitting layer 105. Incidentally, in a case where the hole injection layer 103 and/or the hole transport layer 104 are/is disposed between the positive electrode 102 and the light emitting layer 105, a hole is injected into the light emitting layer 105 through these layers.

Examples of a material to form the positive electrode 102 include an inorganic compound and an organic compound. Examples of the inorganic compound include a metal (aluminum, gold, silver, nickel, palladium, chromium, and the like), a metal oxide (indium oxide, tin oxide, indium-tin oxide (ITO), indium-zinc oxide (IZO), and the like), a metal halide (copper iodide and the like), copper sulfide, carbon black, ITO glass, and Nesa glass. Examples of the organic compound include an electrically conductive polymer such as polythiophene such as poly(3-methylthiophene), polypyrrole, or polyaniline. In addition to these compounds, a material can be appropriately selected for use from materials used as a positive electrode of an organic EL element.

A resistance of a transparent electrode is not limited as long as a sufficient current can be supplied for light emission of a luminescent element. However, a low resistance is desirable from a viewpoint of consumption power of the luminescent element. For example, an ITO substrate having a resistance of 300Ω/☐ or less functions as an element electrode. However, a substrate having a resistance of about 10Ω/☐ can be also supplied at present, and therefore it is particularly desirable to use a low resistance product having a resistance of, for example, 100 to 5Ω/☐, preferably 50 to 5Ω/☐. The thickness of ITO can be arbitrarily selected according to a resistance value, but an ITO having a thickness of 50 to 300 nm is often used.

<Hole Injection Layer and Hole Transport Layer in Organic Electroluminescent Element>

The hole injection layer 103 plays a role of efficiently injecting a hole that migrates from the positive electrode 102 into the light emitting layer 105 or the hole transport layer 104. The hole transport layer 104 plays a role of efficiently transporting a hole injected from the positive electrode 102 or a hole injected from the positive electrode 102 through the hole injection layer 103 to the light emitting layer 105. The hole injection layer 103 and the hole transport layer 104 are each formed by laminating and mixing one or more kinds of hole injection/transport materials, or by a mixture of a hole injection/transport material and a polymer binder. Furthermore, a layer may be formed by adding an inorganic salt such as iron(III) chloride to the hole injection/transport material.

A hole injection/transport substance needs to efficiently inject/transport a hole coming from a positive electrode between electrodes to which an electric field is applied, and desirably has a high hole injection efficiency and transports an injected hole efficiently. For this purpose, a substance which has low ionization potential, large hole mobility, and further has excellent stability, and in which impurities serving as traps are not easily generated at the time of manufacturing and at the time of use, is preferable.

As a material to form the hole injection layer 103 and the hole transport layer 104, any compound can be selected for use among compounds that have been conventionally used as charge transporting materials for holes, p-type semiconductors, and known compounds used in a hole injection layer and a hole transport layer of an organic EL element. Specific examples thereof include a heterocyclic compound including a carbazole derivative (N-phenylcarbazole, polyvinylcarbazole, and the like), a biscarbazole derivative such as bis(N-arylcarbazole) or bis(N-alkylcarbazole), a triarylamine derivative (a polymer having an aromatic tertiary amino in a main chain or a side chain, 1,1-bis(4-di-p-tolylaminophenyl) cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-dphenyl-1,1'-diamine, $N^4,N^{4'}$-diphenyl-$N^4,N^{4'}$-bis (9-phenyl-9H-carbazol-3-yl)-[1,1'-biphenyl]-4,4'-diamine, $N^4,N^4,N^{4'},N^{4'}$-tetra[1,1'-biphenyl]-4-yl)-[1,1'-biphenyl]-4,4'-diamine, a triphenylamine derivative such as 4,4',4"-tris(3-methylphenyl(phenyl) amino) triphenylamine, a starburst amine derivative, and the like), a stilbene derivative, a phthalocyanine derivative (non-metal, copper phthalocyanine, and the like), a pyrazoline derivative, a hydrazone-based compound, a benzofuran derivative, a thiophene derivative, an oxadiazole derivative, a quinoxaline derivative (for example, 1,4,5,8,9,12-hexaazatriphenylene-2,3,6,7,10,11-hexacarbonitrile, and the like), and a porphyrin derivative, and a polysilane. Among the polymer-based materials, a polycarbonate, a styrene derivative, a polyvinylcarbazole, a polysilane, and the like having the above monomers in side chains are preferable. However, there is no particular limitation as long as a compound can form a thin film required for manufacturing a luminescent element, can inject a hole from a positive electrode, and can further transport a hole.

Furthermore, it is also known that electroconductivity of an organic semiconductor is strongly affected by doping into the organic semiconductor. Such an organic semiconductor matrix substance is formed of a compound having a good electron-donating property, or a compound having a good electron-accepting property. For doping with an electron-donating substance, a strong electron acceptor such as tetracyanoquinonedimethane (TCNQ) or 2,3,5,6-tetrafluorotetracyano-1,4-benzoquinonedimethane (F4TCNQ) is known (see, for example, literature "M. Pfeiffer, A. Beyer, T. Fritz, K. Leo, Appl. Phys. Lett., 73(22), 3202-3204 (1998)" and literature "J. Blochwitz, M. Pheiffer, T. Fritz, K. Leo, Appl. Phys. Lett., 73(6), 729-731 (1998)"). These compounds generate a so-called hole by an electron migrating process in an electron-donating type base substance (hole transport substance). Electroconductivity of the base substance depends on the number and mobility of the holes fairly significantly. Known examples of a matrix substance having a hole transporting characteristic include a benzidine derivative (TPD and the like), a starburst amine derivative (TDATA and the like), and a specific metal phthalocyanine (particularly, zinc phthalocyanine (ZnPc) and the like) (JP 2005-167175 A).

<Light Emitting Layer in Organic Electroluminescent Element>

The light emitting layer 105 emits light by recombining a hole injected from the positive electrode 102 and an electron injected from the negative electrode 108 between electrodes to which an electric field is applied. A material to form the light emitting layer 105 is only required to be a compound which is excited by recombination between a hole and an electron and emits light (luminescent compound), and is preferably a compound which can form a stable thin film shape and exhibits a strong light emission (fluorescence) efficiency in a solid state. In the present invention, as a material for a light emitting layer, for example, a pyrene-based compound represented by the above general formula (2) as a host material and, for example, a polycyclic aromatic compound represented by the above general formula (1) and a multimer thereof as a dopant material can be used.

The light emitting layer may be formed of a single layer or a plurality of layers, and each layer is formed of a material for a light emitting layer (a host material and a dopant material). Each of the host material and the dopant material may be formed of a single kind, or a combination of a plurality of kinds. The dopant material may be included in the host material wholly or partially. Regarding a doping method, doping can be performed by a co-deposition method with a host material, or alternatively, a dopant material may be mixed in advance with a host material, and then vapor deposition may be performed simultaneously.

The amount of use of a host material depends on the kind of the host material, and is only required to be determined according to a characteristic of the host material. The reference of the amount of use of a host material is preferably from 50 to 99.999% by weight, more preferably from 80 to 99.95% by weight, and still more preferably from 90 to 99.9% by weight with respect to the total amount of a material for a light emitting layer.

The amount of use of a dopant material depends on the kind of the dopant material, and is only required to be determined according to a characteristic of the dopant material. The reference of the amount of use of a dopant is preferably from 0.001 to 50% by weight, more preferably from 0.05 to 20% by weight, and still more preferably from 0.1 to 10% by weight with respect to the total amount of a material for a light emitting layer. The amount of use within the above range is preferable, for example, from a viewpoint of being able to prevent a concentration quenching phenomenon.

Examples of a host material that can be used in combination with a pyrene-based compound represented by formula (2) include a fused ring derivative such as anthracene conventionally known as a luminous body, a bisstyryl derivative such as a bisstyrylanthracene derivative or a distyrylbenzene derivative, a tetraphenylbutadiene derivative, a cyclopentadiene derivative, a fluorene derivative, and a benzofluorene derivative.

A dopant material that can be used in combination with a polycyclic aromatic compound represented by formula (1) and a multimer thereof is not particularly limited, and existing compounds can be used. The dopant material can be selected from various materials depending on a desired color of emitted light. Specific examples of the dopant material include a fused ring derivative of phenanthrene, anthracene, tetracene, pentacene, perylene, rubrene, chrysene, or the like, a benzoxazole derivative, a benzothiazole derivative, a benzimidazole derivative, a benzotriazole derivative, an oxazole derivative, an oxadiazole derivative, a thiazole derivative, an imidazole derivative, a thiadiazole derivative, a triazole derivative, a pyrazoline derivative, a stilbene derivative, a thiophene derivative, a tetraphenylbutadiene derivative, a cyclopentadiene derivative, a bisstyryl derivative such as a bisstyrylanthracene derivative or a distyrylbenzene derivative (JP 1-245087 A), a bisstyrylarylene derivative (JP 2-247278 A), a diazaindacene derivative, a furan derivative, a benzofuran derivative, an isobenzofuran derivative such as phenylisobenzofuran, dimesitylisobenzofuran, di(2-methylphenyl)isobenzofuran, di(2-trifluoromethylphenyl)isobenzofuran, or phenylisobenzofuran, a dibenzofuran derivative, a coumarin derivative such as a 7-dialkylaminocoumarin derivative, a 7-piperidinocoumarin derivative, a 7-hydroxycoumarin derivative, a 7-methoxycoumarin derivative, a 7-acetoxycoumarin derivative, a 3-benzothiazolylcoumarin derivative, a 3-benzimidazolylcoumarin derivative, or a 3-benzoxazolylcoumarin derivative, a dicyanomethylenepyran derivative, a dicyanomethylenethiopyran derivative, a polymethine derivative, a cyanine derivative, an oxobenzoanthracene derivative, a xanthene derivative, a rhodamine derivative, a fluorescein derivative, a pyrylium derivative, a carbostyryl derivative, an acridine derivative, an oxazine derivative, a phenylene oxide derivative, a quinacridone derivative, a quinazoline derivative, a pyrrolopyridine derivative, a furopyridine derivative, a pyromethene derivative, a perinone derivative, a pyrrolopyrrole derivative, a squarylium derivative, a violanthrone derivative, a phenazine derivative, an acridone derivative, a deazaflavine derivative, a fluorene derivative, and a benzofluorene derivative.

<Electron Injection Layer and Electron Transport Layer in Organic Electroluminescent Element>

The electron injection layer 107 plays a role of efficiently injecting an electron migrating from the negative electrode 108 into the light emitting layer 105 or the electron transport layer 106. The electron transport layer 106 plays a role of efficiently transporting an electron injected from the negative electrode 108, or an electron injected from the negative electrode 108 through the electron injection layer 107 to the light emitting layer 105. The electron transport layer 106 and the electron injection layer 107 are each formed by laminating and mixing one or more kinds of electron transport/injection materials, or by a mixture of an electron transport/injection material and a polymer binder.

The electron injection/transport layer manages injection of an electron from a negative electrode and further manages transport of an electron, and desirably has a high electron injection efficiency and can efficiently transport an injected electron. For this purpose, a substance which has high electron affinity and large electron mobility, and further has excellent stability, and in which impurities serving as traps are not easily generated at the time of manufacturing and at the time of use, is preferable. However, when a transport balance between a hole and an electron is considered, in a case where the electron injection/transport layer mainly plays a role of efficiently preventing a hole coming from a positive electrode from flowing toward a negative electrode side without being recombined, even if electron transport ability is not so high, the electron injection/transport layer has an effect of enhancing a light emission efficiency equally to a material having high electron transport ability. Therefore, the electron injection/transport layer in the present embodiment may also include a function of a layer capable of efficiently preventing migration of a hole.

A material (electron transport material) for forming the electron transport layer 106 or the electron injection layer 107 can be arbitrarily selected for use from compounds conventionally used as electron transfer compounds in a photoconductive material, and known compounds that are used in an electron injection layer and an electron transport layer of an organic EL element.

A material used in an electron transport layer or an electron injection layer preferably includes at least one selected from a compound formed of an aromatic ring or a heteroaromatic ring including one or more kinds of atoms selected from carbon, hydrogen, oxygen, sulfur, silicon, and phosphorus atoms, a pyrrole derivative and a fused ring derivative thereof, and a metal complex having an electron-accepting nitrogen atom. Specific examples of the material include a fused ring-based aromatic ring derivative of naphthalene, anthracene, or the like, a styryl-based aromatic ring derivative represented by 4,4'-bis(diphenylethenyl)biphenyl, a perinone derivative, a coumarin derivative, a naphthalimide derivative, a quinone derivative such as anthraquinone or diphenoquinone, a phosphorus oxide derivative, a carbazole derivative, and an indole derivative. Examples of the metal complex having an electron-accepting nitrogen atom include a hydroxyazole complex such as a hydroxyphenyloxazole complex, an azomethine complex, a tropolone metal complex, a flavonol metal complex, and a benzoquinoline metal complex. These materials are used singly, but may also be used in a mixture with other materials.

Furthermore, specific examples of other electron transfer compounds include a pyridine derivative, a naphthalene derivative, an anthracene derivative, a phenanthroline derivative, a perinone derivative, a coumarin derivative, a naphthalimide derivative, an anthraquinone derivative, a diphenoquinone derivative, a diphenylquinone derivative, a perylene derivative, an oxadiazole derivative (1,3-bis[(4-t-butylphenyl)-1,3,4-oxadiazolyl]phenylene and the like), a thiophene derivative, a triazole derivative (N-naphthyl-2,5-diphenyl-1,3,4-triazole and the like), a thiadiazole derivative, a metal complex of an oxine derivative, a quinolinol-based metal complex, a quinoxaline derivative, a polymer of a quinoxaline derivative, a benzazole compound, a gallium complex, a pyrazole derivative, a perfluorinated phenylene derivative, a triazine derivative, a pyrazine derivative, a benzoquinoline derivative (2,2'-bis(benzo[h]quinolin-2-yl)-9,9'-spirobifluorene and the like), an imidazopyridine derivative, a borane derivative, a benzimidazole derivative (tris(N-phenylbenzimidazol-2-yl)benzene and the like), a benzoxazole derivative, a benzothiazole derivative, a quinoline derivative, an oligopyridine derivative such as terpyridine, a bipyridine derivative, a terpyridine derivative (1,3-bis(4'-(2,2':6'2''-terpyridinyl))benzene and the like), a naphthyridine derivative (bis(1-naphthyl)-4-(1,8-naphthyridin-2-yl)phenylphosphine oxide and the like), an aldazine derivative, a carbazole derivative, an indole derivative, a phosphorus oxide derivative, and a bisstyryl derivative.

Furthermore, a metal complex having an electron-accepting nitrogen atom can be also used, and examples thereof include a quinolinol-based metal complex, a hydroxyazole complex such as a hydroxyphenyloxazole complex, an azomethine complex, a tropolone metal complex, a flavonol metal complex, and a benzoquinoline metal complex.

The materials described above are used singly, but may also be used in a mixture with other materials.

Among the above materials, a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, a quinolinol-based metal complex are preferable.

<Borane Derivative>

The borane derivative is, for example, a compound represented by the following general formula (ETM-1), and specifically disclosed in JP 2007-27587 A.

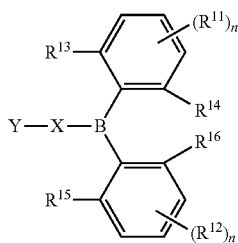

(ETM-1)

In the above formula (ETM-1), $R^{11}$ and $R^{12}$ each independently represent at least one of a hydrogen atom, an alkyl, a cycloalkyl, an optionally substituted aryl, a substituted silyl, an optionally substituted nitrogen-containing heterocyclic ring, and a cyano, $R^{13}$ to $R^{16}$ each independently represent an optionally substituted alkyl, an optionally substituted cycloalkyl, or an optionally substituted aryl, X represents an optionally substituted arylene, Y represents an optionally substituted aryl having 16 or fewer carbon atoms, a substituted boryl, or an optionally substituted carbazolyl, and n's each independently represent an integer of 0 to 3. Examples of a substituent in a case of being "optionally substituted" or "substituted" include an aryl, a heteroaryl, an alkyl, and a cycloalkyl.

Among compounds represented by the above general formula (ETM-1), a compound represented by the following general formula (ETM-1-1) and a compound represented by the following general formula (ETM-1-2) are preferable.

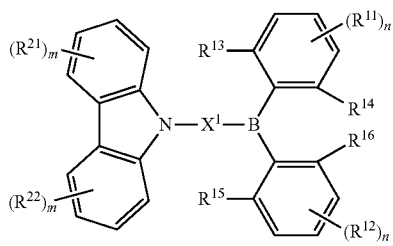

(ETM-1-1)

In formula (ETM-1-1), $R^{11}$ and $R^{12}$ each independently represent at least one of a hydrogen atom, an alkyl, a cycloalkyl, an optionally substituted aryl, a substituted silyl, an optionally substituted nitrogen-containing heterocyclic ring, and a cyano, $R^{13}$ to $R^{16}$ each independently represent an optionally substituted alkyl, an optionally substituted cycloalkyl, or an optionally substituted aryl, $R^{21}$ and $R^{22}$ each independently represent at least one of a hydrogen atom, an alkyl, a cycloalkyl, an optionally substituted aryl, a substituted silyl, an optionally substituted nitrogen-containing heterocyclic ring, and a cyano, $X^1$ represents an optionally substituted arylene having 20 or fewer carbon atoms, n's each independently represent an integer of 0 to 3, and m's each independently represent an integer of 0 to 4. Examples of a substituent in a case of being "optionally substituted" or "substituted" include an aryl, a heteroaryl, an alkyl, and a cycloalkyl.

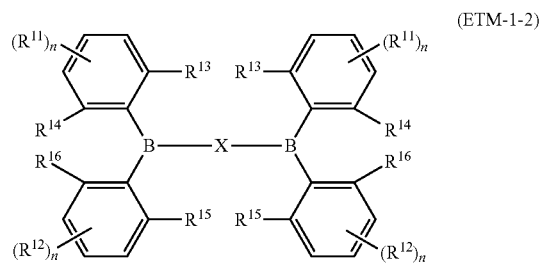

(ETM-1-2)

In formula (ETM-1-2), $R^{11}$ and $R^{12}$ each independently represent at least one of a hydrogen atom, an alkyl, a cycloalkyl, an optionally substituted aryl, a substituted silyl, an optionally substituted nitrogen-containing heterocyclic ring, and cyano, $R^{13}$ to $R^{16}$ each independently represent an optionally substituted alkyl, an optionally substituted cycloalkyl, or an optionally substituted aryl, $X^1$ represents an optionally substituted arylene having 20 or fewer carbon atoms, and n's each independently represent an integer of 0 to 3. Examples of a substituent in a case of being "optionally substituted" or "substituted" include an aryl, a heteroaryl, an alkyl, and a cycloalkyl.

Specific examples of $X^1$ include divalent groups represented by the following formulas (X-1) to (X-9).

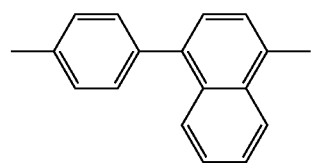

(X-1)

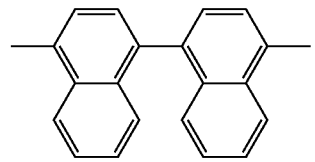

(X-2)

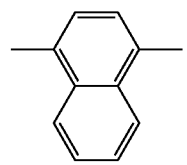

(X-3)

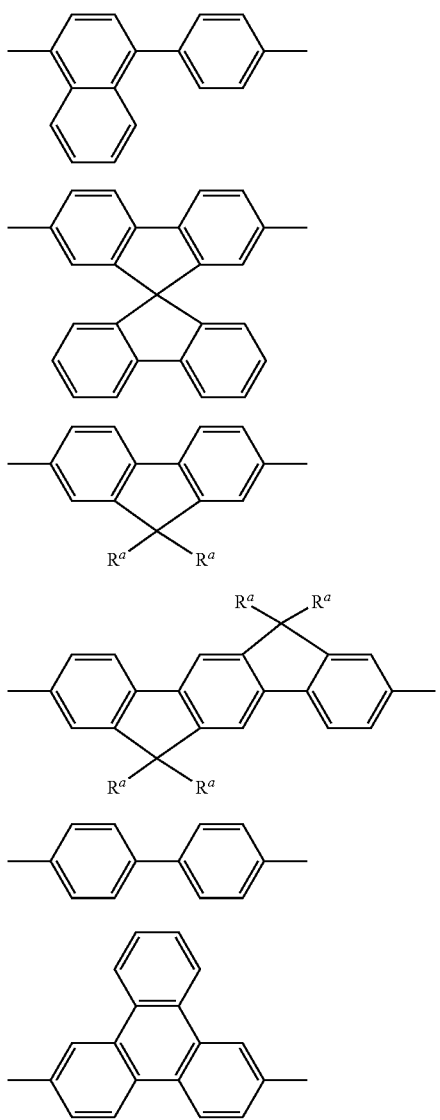

(In each formula, $R^a$'s each independently represent an alkyl group, a cycloalkyl group, or an optionally substituted phenyl group.)

Specific examples of this borane derivative include the following compounds.

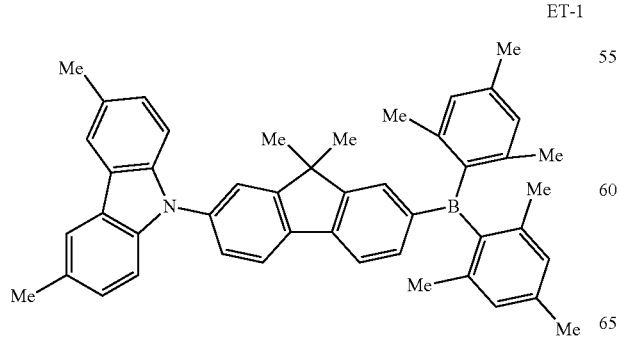

This borane derivative can be manufactured using known raw materials and known synthesis methods.

<Pyridine Derivative>

A pyridine derivative is, for example, a compound represented by the following formula (ETM-2), and preferably a compound represented by formula (ETM-2-1) or (ETM-2-2).

$$\varphi\text{—(Pyridine-based substituent)}_n \quad \text{(ETM-2)}$$

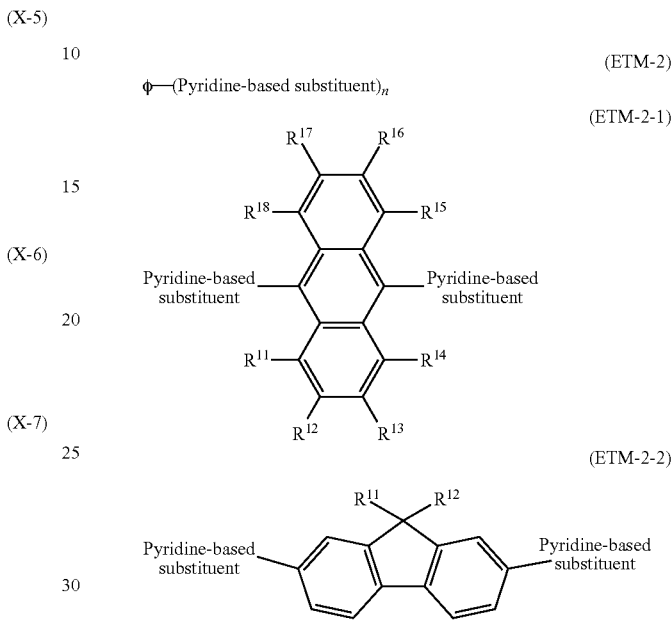

φ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4.

In the above formula (ETM-2-1), $R^{11}$ to $R^{18}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms).

In the above formula (ETM-2-2), $R^{11}$ and $R^{12}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms), and $R^{11}$ and $R^{12}$ may be bonded to each other to form a ring.

In each formula, the "pyridine-based substituent" is any one of the following formulas (Py-1) to (Py-15), and the pyridine-based substituents may be each independently substituted by an alkyl having 1 to 4 carbon atoms or a cycloalkyl having 5 to 10 carbon atoms. The pyridine-based substituent may be bonded to p, an anthracene ring, or a fluorene ring in each formula via a phenylene group or a naphthylene group.

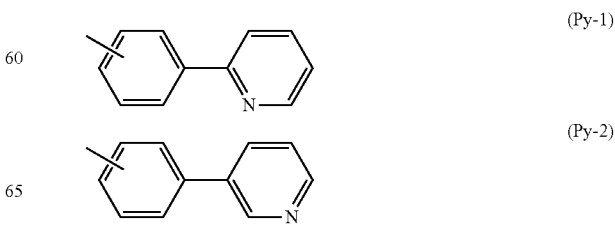

(Py-3) 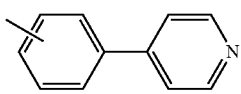
(Py-4) 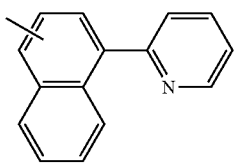
(Py-5) 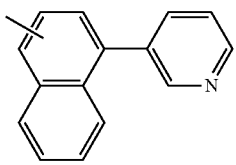
(Py-6) 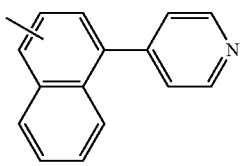
(Py-7) 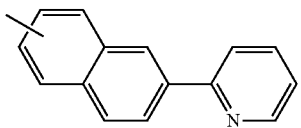
(Py-8) 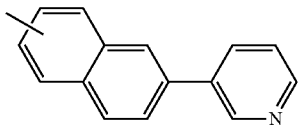
(Py-9) 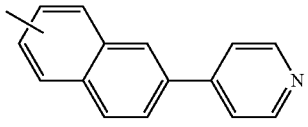
(Py-10) 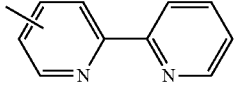
(Py-11) 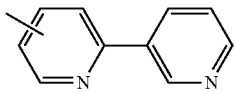
(Py-12) 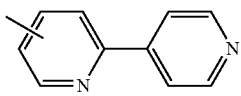
(Py-13) 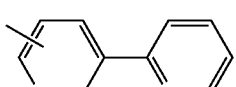
(Py-14) 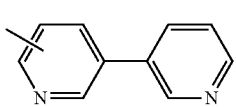
(Py-15) 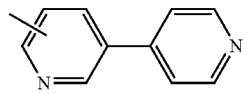
The pyridine-based substituent is any one of the above-formulas (Py-1) to (Py-15). However, among these formulas, the pyridine-based substituent is preferably any one of the following formulas (Py-21) to (Py-44).
(Py-21) 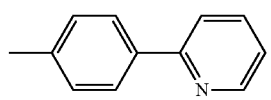
(Py-22) 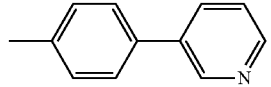
(Py-23) 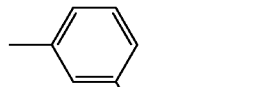
(Py-24) 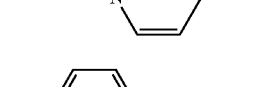
(Py-25) 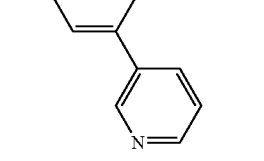
(Py-26) 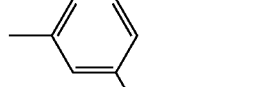
(Py-27) 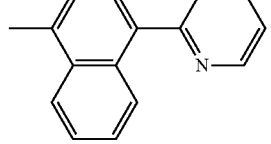
(Py-28) 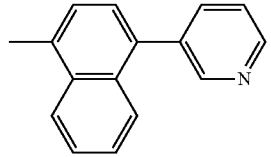

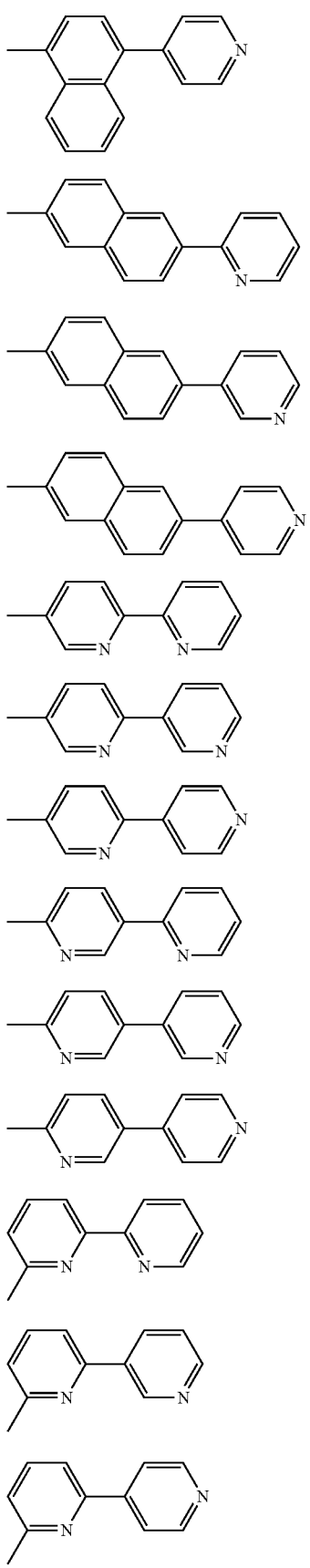

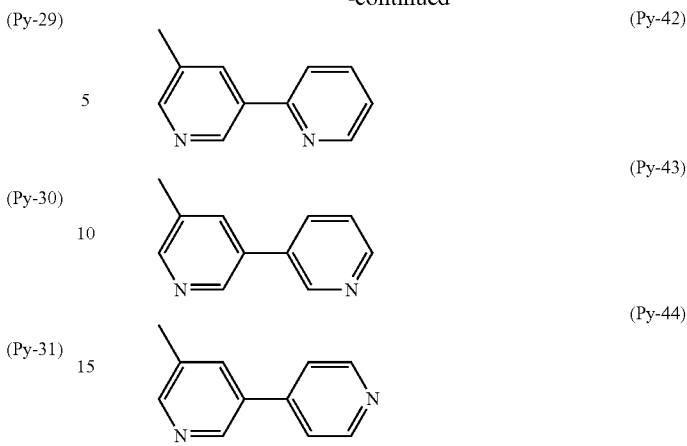

At least one hydrogen atom in each pyridine derivative may be substituted by a deuterium atom. One of the two "pyridine-based substituents" in the above formulas (ETM-2-1) and (ETM-2-2) may be substituted by an aryl.

The alkyl in $R^{11}$ to $R^{18}$ may be either linear or branched, and examples thereof include a linear alkyl having 1 to 24 carbon atoms and a branched alkyl having 3 to 24 carbon atoms. A preferable "alkyl" is an alkyl having 1 to 18 carbon atoms (branched alkyl having 3 to 18 carbon atoms). A more preferable "alkyl" is an alkyl having 1 to 12 carbon atoms (branched alkyl having 3 to 12 carbon atoms). A still more preferable "alkyl" is an alkyl having 1 to 6 carbon atoms (branched alkyl having 3 to 6 carbon atoms). A particularly preferable "alkyl" is an alkyl having 1 to 4 carbon atoms (branched alkyl having 3 or 4 carbon atoms).

Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, 1-methylhexyl, n-octyl, t-octyl, 1-methylheptyl, 2-ethylhexyl, 2-propylpentyl, n-nonyl, 2,2-dimethylheptyl, 2,6-dimethyl-4-heptyl, 3,5,5-trimethylhexyl, n-decyl, n-undecyl, 1-methyldecyl, n-dodecyl, n-tridecyl, 1-hexylheptyl, n-tetradecyl, n-pentadecyl, n-hexadecyl, n-heptadecyl, n-octadecyl, and n-eicosyl.

As the alkyl having 1 to 4 carbon atoms by which the pyridine-based substituent is substituted, the above description of the alkyl can be cited.

Examples of the "cycloalkyl" in $R^{11}$ to $R^{18}$ include a cycloalkyl having 3 to 12 carbon atoms. A preferable "cycloalkyl" is a cycloalkyl having 3 to 10 carbon atoms. A more preferable "cycloalkyl" is a cycloalkyl having 3 to 8 carbon atoms. A still more preferable "cycloalkyl" is a cycloalkyl having 3 to 6 carbon atoms.

Specific examples of the "cycloalkyl" include cyclopropyl, cyclobutyl, cyclopentyl, cyclohexyl, methylcyclopentyl, cycloheptyl, methylcyclohexyl, cyclooctyl, and dimethylcyclohexyl.

As the cycloalkyl having 5 to 10 carbon atoms by which the pyridine-based substituent is substituted, the above description of the cycloalkyl can be cited.

As the "aryl" in $R^{11}$ to $R^{18}$, a preferable aryl is an aryl having 6 to 30 carbon atoms, a more preferable aryl is an aryl having 6 to 18 carbon atoms, a still more preferable aryl is an aryl having 6 to 14 carbon atoms, and a particularly preferable aryl is an aryl having 6 to 12 carbon atoms.

Specific examples of the "aryl having 6 to 30 carbon atoms" include phenyl which is a monocyclic aryl; (1-,2-)

naphthyl which is a fused bicyclic aryl; acenaphthylene-(1-, 3-,4-,5-)yl, a fluorene-(1-,2-,3-,4-,9-)yl, phenalene-(1-, 2-)yl, and (1-,2-,3-,4-,9-)phenanthryl which are fused tricyclic aryls; triphenylene-(1-, 2-)yl, pyrene-(1-,2-, 4-)yl, and naphthacene-(1-, 2-, 5-)yl which are fused tetracyclic aryls; and perylene-(1-,2-,3-)yl and pentacene-(1-, 2-, 5-, 6-)yl which are fused pentacyclic aryls.

Preferable examples of the "aryl having 6 to 30 carbon atoms" include a phenyl, a naphthyl, a phenanthryl, a chrysenyl, and a triphenylenyl. More preferable examples thereof include a phenyl, a 1-naphthyl, a 2-naphthyl, and a phenanthryl. Particularly preferable examples thereof include a phenyl, a 1-naphthyl, and a 2-naphthyl.

$R^{11}$ and $R^{12}$ in the above formula (ETM-2-2) may be bonded to each other to form a ring. As a result, cyclobutane, cyclopentane, cyclopentene, cyclopentadiene, cyclohexane, fluorene, indene, or the like may be spiro-bonded to a 5-membered ring of a fluorene skeleton.

Specific examples of this pyridine derivative include the following compounds.

ET-2

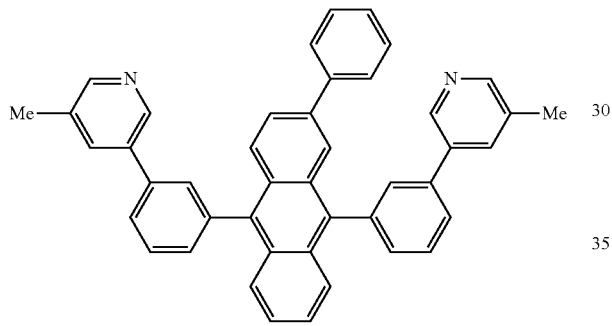

ET-3

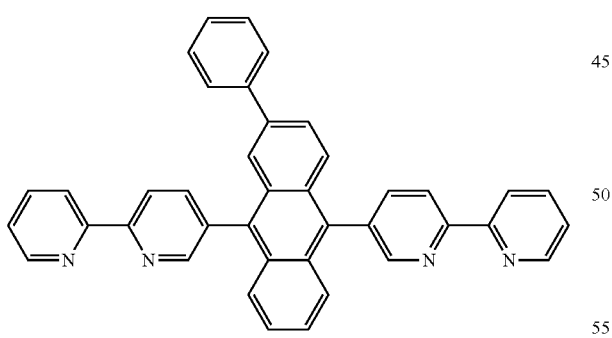

ET-6

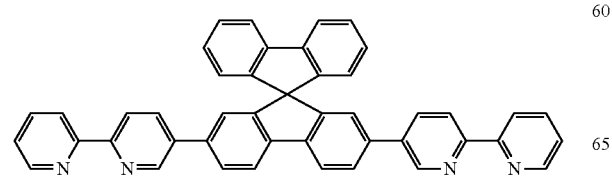

ET-7

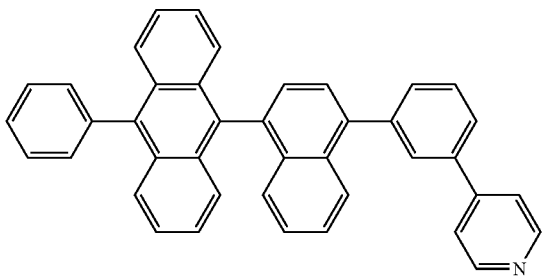

This pyridine derivative can be manufactured using known raw materials and known synthesis methods.

<Fluoranthene Derivative>

The fluoranthene derivative is, for example, a compound represented by the following general formula (ETM-3), and specifically disclosed in WO 2010/134352 A.

(ETM-3)

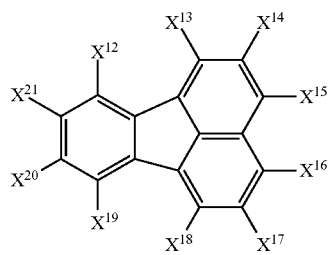

In the above formula (ETM-3), $X^{12}$ to $X^{21}$ each represent a hydrogen atom, a halogen atom, a linear, branched or cyclic alkyl, a linear, branched or cyclic alkoxy, a substituted or unsubstituted aryl, or a substituted or unsubstituted heteroaryl. Here, examples of a substituent in a case of being substituted include an aryl, a heteroaryl, an alkyl, and a cycloalkyl.

Specific examples of this fluoranthene derivative include the following compounds.

(ETM-3-1)

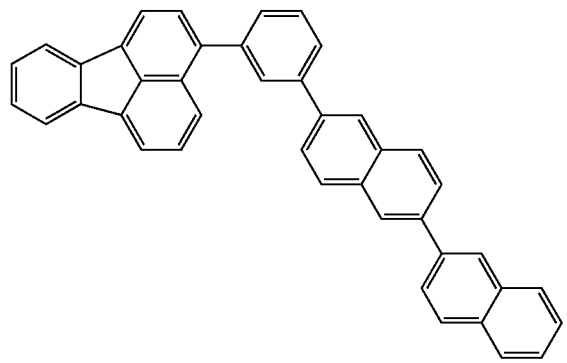

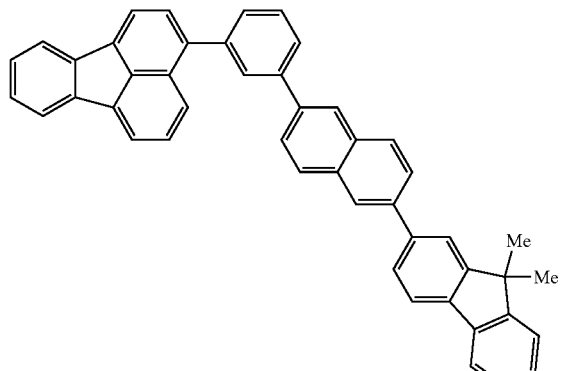

(ETM-3-2)

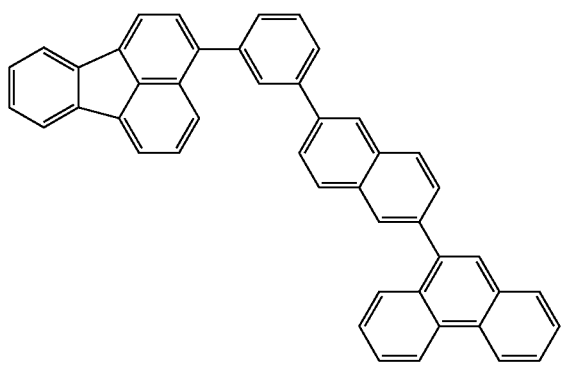

(ETM-3-3)

<BO-Based Derivative>

The BO-based derivative is, for example, a polycyclic aromatic compound represented by the following formula (ETM-4) or a polycyclic aromatic compound multimer having a plurality of structures represented by the following formula (ETM-4).

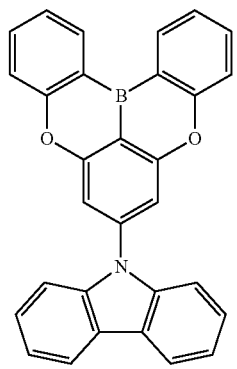

(ETM-4)

$R^1$ to $R^{11}$ each independently represent a hydrogen atom, an aryl, a heteroaryl, a diarylamino, a diheteroarylamino, an arylheteroarylamino, an alkyl, a cycloalkyl, an alkoxy, or an aryloxy, and at least one hydrogen atom in these substituents may be substituted by an aryl, a heteroaryl, an alkyl, or a cycloalkyl.

Adjacent groups among $R^1$ to $R^{11}$ may be bonded to each other to form an aryl ring or a heteroaryl ring together with the ring a, ring b, or ring c, and at least one hydrogen atom in the ring thus formed may be substituted by an aryl, a heteroaryl, a diarylamino, a diheteroarylamino, an arylheteroarylamino, an alkyl, a cycloalkyl, an alkoxy, or an aryloxy, while at least one hydrogen atom in these substituents may be substituted by an aryl, a heteroaryl, an alkyl, or a cycloalkyl.

At least one hydrogen atom in a compound or structure represented by formula (ETM-4) may be substituted by a halogen atom or a deuterium atom.

For description of a substituent in formula (ETM-4) and a form of ring formation, the description of a polycyclic aromatic compound represented by the above general formula (1) can be cited.

Specific examples of this BO-based derivative include the following compounds.

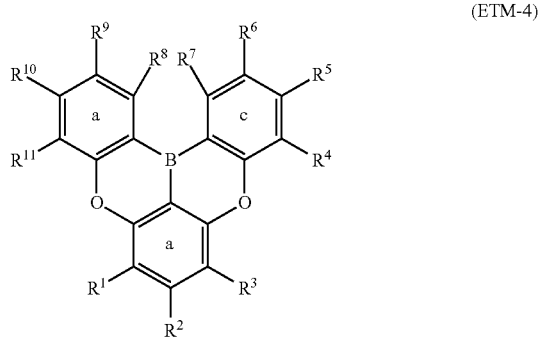

ET-5

This BO-based derivative can be manufactured using known raw materials and known synthesis methods.

<Anthracene Derivative>

One of the anthracene derivatives is, for example, a compound represented by the following formula (ETM-5-1).

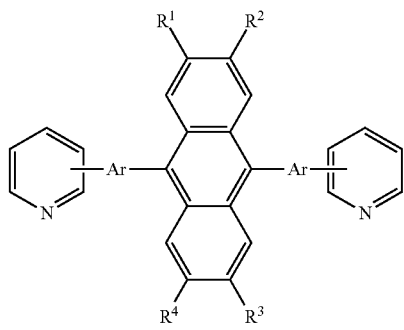

(ETM-5-1)

Ar's each independently represent a divalent benzene or naphthalene, $R^1$ to $R^4$ each independently represent a hydrogen atom, an alkyl having 1 to 6 carbon atoms, a cycloalkyl having 3 to 6 carbon atoms, or an aryl having 6 to 20 carbon atoms.

Ar's can be each independently selected from a divalent benzene and naphthalene appropriately. Two Ar's may be different from or the same as each other, but are preferably the same from a viewpoint of easiness of synthesis of an anthracene derivative. Ar is bonded to pyridine to form "a moiety formed of Ar and pyridine". For example, this moiety is bonded to anthracene as a group represented by any one of the following formulas (Py-1) to (Py-12).

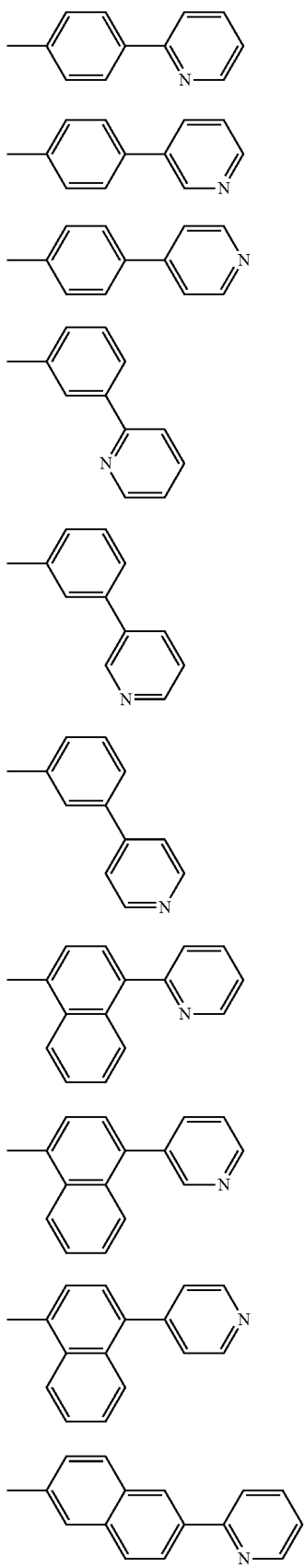

(Py-1)
(Py-2)
(Py-3)
(Py-4)
(Py-5)
(Py-6)
(Py-7)
(Py-8)
(Py-9)
(Py-10)

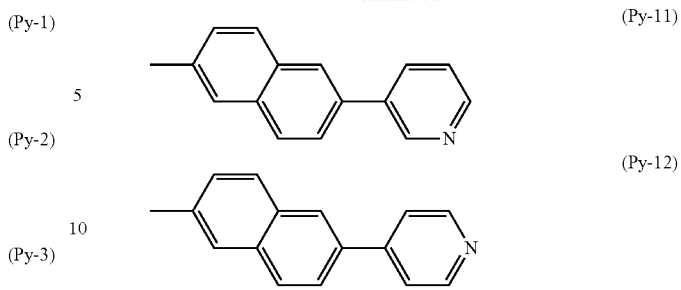

(Py-11)
(Py-12)

Among these groups, a group represented by any one of the above formulas (Py-1) to (Py-9) is preferable, and a group represented by any one of the above formulas (Py-1) to (Py-6) is more preferable. Two "moieties formed of Ar and pyridine" bonded to anthracene may have the same structure as or different structures from each other, but preferably have the same structure from a viewpoint of easiness of synthesis of an anthracene derivative. However, two "moieties formed of Ar and pyridine" preferably have the same structure or different structures from a viewpoint of element characteristics.

The alkyl having 1 to 6 carbon atoms in $R^1$ to $R^4$ may be either linear or branched. That is, the alkyl having 1 to 6 carbon atoms is a linear alkyl having 1 to 6 carbon atoms or a branched alkyl having 3 to 6 carbon atoms. More preferably, the alkyl having 1 to 6 carbon atoms is an alkyl having 1 to 4 carbon atoms (branched alkyl having 3 to 4 carbon atoms). Specific examples thereof include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, and 2-ethylbutyl. Methyl, ethyl, n-propyl, isopropyl, n-butyl, isobutyl, s-butyl, and t-butyl are preferable. Methyl, ethyl, and a t-butyl are more preferable.

Specific examples of the cycloalkyl having 3 to 6 carbon atoms in $R^1$ to $R^4$ include cyclopropyl, cyclobutyl, cyclopentyl, cyclohexyl, methylcyclopentyl, cycloheptyl, methylcyclohexyl, cyclooctyl, and dimethylcyclohexyl.

For the aryl having 6 to 20 carbon atoms in $R^1$ to $R^4$, an aryl having 6 to 16 carbon atoms is preferable, an aryl having 6 to 12 carbon atoms is more preferable, and an aryl having 6 to 10 carbon atoms is particularly preferable.

Specific examples of the "aryl having 6 to 20 carbon atoms" include phenyl, (o-, m-, p-) tolyl, (2,3-, 2,4-, 2,5-, 2,6-, 3,4-, 3,5-) xylyl, mesityl (2,4,6-trimethylphenyl), and (o-, m-, p-)cumenyl which are monocyclic aryls; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; anthracene-(1-, 2-, 9-)yl, acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; triphenylene-(1-, 2-)yl, pyrene-(1-, 2-, 4-)yl, and tetracene-(1-, 2-, 5-)yl which are fused tetracyclic aryls; and perylene-(1-, 2-, 3-)yl which is a fused pentacyclic aryl.

The "aryl having 6 to 20 carbon atoms" is preferably a phenyl, a biphenylyl, a terphenylyl, or a naphthyl, more preferably a phenyl, a biphenylyl, a 1-naphthyl, a 2-naphthyl, or an m-terphenyl-5'-yl, still more preferably a phenyl, a biphenylyl, a 1-naphthyl, or a 2-naphthyl, and most preferably a phenyl.

One of the anthracene derivatives is, for example, a compound represented by the following formula (ETM-5-2).

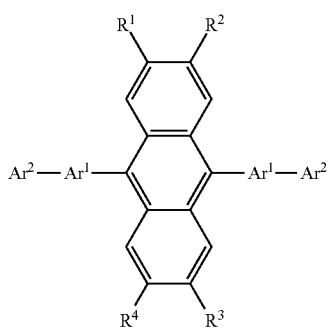

(ETM-5-2)

Ar$^1$'s each independently represent a single bond, a divalent benzene, naphthalene, anthracene, fluorene, or phenalene.

Ar$^2$'s each independently represent an aryl having 6 to 20 carbon atoms. The same description as the "aryl having 6 to 20 carbon atoms" in the above formula (ETM-5-1) can be cited. An aryl having 6 to 16 carbon atoms is preferable, an aryl having 6 to 12 carbon atoms is more preferable, and an aryl having 6 to 10 carbon atoms is particularly preferable. Specific examples thereof include phenyl, biphenylyl, naphthyl, terphenylyl, anthracenyl, acenaphthylenyl, fluorenyl, phenalenyl, phenanthryl, triphenylenyl, pyrenyl, etracenyl, and perylenyl.

R$^1$ to R$^4$ each independently represent a hydrogen atom, an alkyl having 1 to 6 carbon atoms, a cycloalkyl having 3 to 6 carbon atoms, or an aryl having 6 to 20 carbon atoms. The description in the above formula (ETM-5-1) can be cited.

Specific examples of these anthracene derivatives include the following compounds.

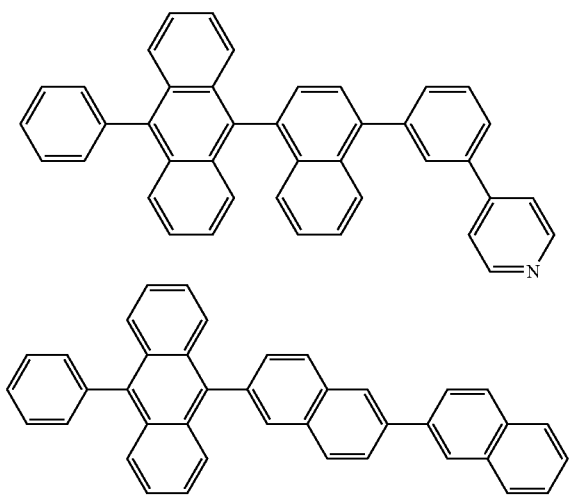

ET-7

These anthracene derivatives can be manufactured using known raw materials and known synthesis methods.

<Benzofluorene Derivative>

The benzofluorene derivative is, for example, a compound represented by the following formula (ETM-6).

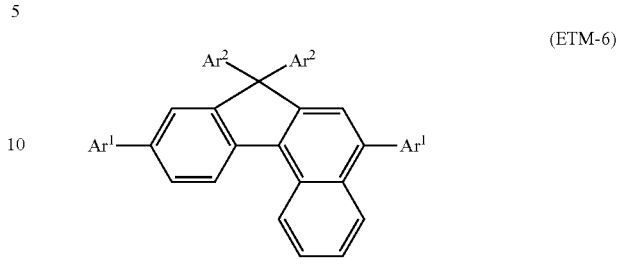

(ETM-6)

Ar$^1$'s each independently represent an aryl having 6 to 20 carbon atoms. The same description as the "aryl having 6 to 20 carbon atoms" in the above formula (ETM-5-1) can be cited. An aryl having 6 to 16 carbon atoms is preferable, an aryl having 6 to 12 carbon atoms is more preferable, and an aryl having 6 to 10 carbon atoms is particularly preferable. Specific examples thereof include phenyl, biphenylyl, naphthyl, terphenylyl, anthracenyl, acenaphthylenyl, fluorenyl, phenalenyl, phenanthryl, triphenylenyl, pyrenyl, etracenyl, and perylenyl.

Ar$^2$'s each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms), and two Ar$^2$'s may be bonded to each other to form a ring.

The alkyl as Ar$^2$ may be either linear or branched, and examples thereof include a linear alkyl having 1 to 24 carbon atoms and a branched alkyl having 3 to 24 carbon atoms. A preferable "alkyl" is an alkyl having 1 to 18 carbon atoms (branched alkyl having 3 to 18 carbon atoms). A more preferable "alkyl" is an alkyl having 1 to 12 carbon atoms (branched alkyl having 3 to 12 carbon atoms). A still more preferable "alkyl" is an alkyl having 1 to 6 carbon atoms (branched alkyl having 3 to 6 carbon atoms). A particularly preferable "alkyl" is an alkyl having 1 to 4 carbon atoms (branched alkyl having 3 or 4 carbon atoms). Specific examples of the "alkyl" include methyl, ethyl, n-propyl, isopropyl, n-butyl, isobutyl, s-butyl, t-butyl, n-pentyl, isopentyl, neopentyl, t-pentyl, n-hexyl, 1-methylpentyl, 4-methyl-2-pentyl, 3,3-dimethylbutyl, 2-ethylbutyl, n-heptyl, and 1-methylhexyl.

Examples of the "cycloalkyl" in Ar$^2$ include a cycloalkyl having 3 to 12 carbon atoms. A preferable "cycloalkyl" is a cycloalkyl having 3 to 10 carbon atoms. A more preferable "cycloalkyl" is a cycloalkyl having 3 to 8 carbon atoms. A still more preferable "cycloalkyl" is a cycloalkyl having 3 to 6 carbon atoms. Specific examples of the "cycloalkyl" include cyclopropyl, cyclobutyl, cyclopentyl, cyclohexyl, methylcyclopentyl, cycloheptyl, methylcyclohexyl, cyclooctyl, and dimethylcyclohexyl.

As the "aryl" in Ar$^2$, a preferable aryl is an aryl having 6 to 30 carbon atoms, a more preferable aryl is an aryl having 6 to 18 carbon atoms, a still more preferable aryl is an aryl having 6 to 14 carbon atoms, and a particularly preferable aryl is an aryl having 6 to 12 carbon atoms.

Specific examples of the "aryl having 6 to 30 carbon atoms" include phenyl, naphthyl, acenaphthylenyl, fluorenyl, phenalenyl, phenanthryl, triphenylenyl, pyrenyl, naphthacenyl, perylenyl, and pentacenyl.

Two Ar²'s may be bonded to each other to form a ring. As a result, cyclobutane, cyclopentane, cyclopentene, cyclopentadiene, cyclohexane, fluorene, indene, or the like may be spiro-bonded to a 5-membered ring of a fluorene skeleton.

Specific examples of this benzofluorene derivative include the following compounds.

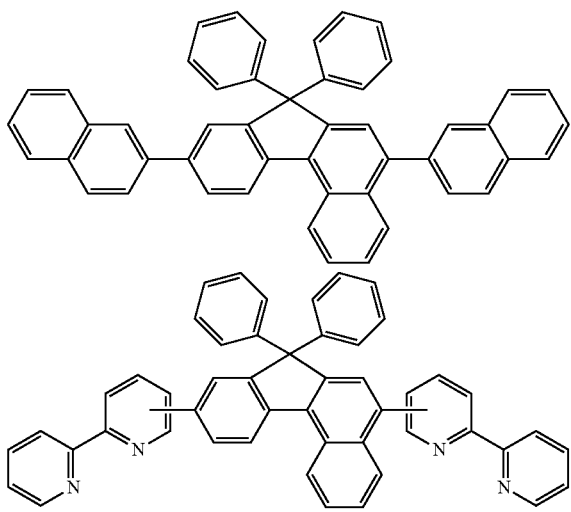

This benzofluorene derivative can be manufactured using known raw materials and known synthesis methods.

<Phosphine Oxide Derivative>

The phosphine oxide derivative is, for example, a compound represented by the following formula (ETM-7-1). Details are also described in WO 2013/079217 A.

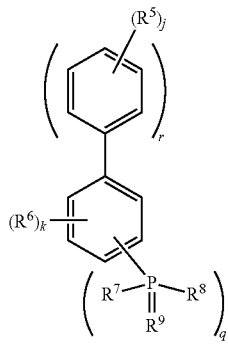

(ETM-7-1)

$R^5$ represents a substituted or unsubstituted alkyl having 1 to 20 carbon atoms, a substituted or unsubstituted cycloalkyl having 3 to 20 carbon atoms, a substituted or unsubstituted aryl having 6 to 20 carbon atoms, or a substituted or unsubstituted heteroaryl having 5 to 20 carbon atoms, $R^6$ represents CN, a substituted or unsubstituted alkyl having 1 to 20 carbon atoms, a substituted or unsubstituted cycloalkyl having 3 to 20 carbon atoms, a substituted or unsubstituted heteroalkyl having 1 to 20 carbon atoms, a substituted or unsubstituted aryl having 6 to 20 carbon atoms, a substituted or unsubstituted heteroaryl having 5 to 20 carbon atoms, a substituted or unsubstituted alkoxy having 1 to 20 carbon atoms, or a substituted or unsubstituted aryloxy having 6 to 20 carbon atoms, $R^7$ and $R^8$ each independently represent a substituted or unsubstituted aryl having 6 to 20 carbon atoms or a substituted or unsubstituted heteroaryl having 5 to 20 carbon atoms, $R^9$ represents an oxygen atom or a sulfur atom, j represents 0 or 1, k represents 0 or 1, r represents an integer of 0 to 4, and q represents an integer of 1 to 3.

Here, examples of a substituent in a case of being substituted include an aryl, a heteroaryl, an alkyl, and a cycloalkyl.

The phosphine oxide derivative may be, for example, a compound represented by the following formula (ETM-7-2).

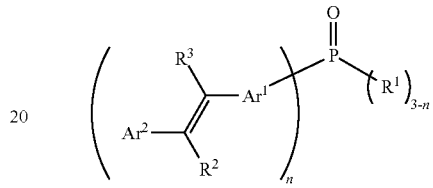

(ETM-7-2)

$R^1$ to $R^3$ may be the same as or different from each other and are selected from a hydrogen atom, an alkyl group, a cycloalkyl group, an aralkyl group, an alkenyl group, a cycloalkenyl group, an alkynyl group, an alkoxy group, an alkylthio group, a cycloalkylthio group, an aryl ether group, an aryl thioether group, an aryl group, a heterocyclic group, a halogen atom, a cyano group, an aldehyde group, a carbonyl group, a carboxyl group, an amino group, a nitro group, a silyl group, and a fused ring formed with an adjacent substituent.

$Ar^1$'s may be the same as or different from each other, and represents an arylene group or a heteroarylene group. $Ar^2$'s may be the same as or different from each other, and represents an aryl group or a heteroaryl group. However, at least one of $Ar^1$ and $Ar^2$ has a substituent or forms a fused ring with an adjacent substituent. n represents an integer of 0 to 3. When n is 0, no unsaturated structure portion is present. When n is 3, $R^1$ is not present.

Among these substituents, the alkyl group represents a saturated aliphatic hydrocarbon group such as a methyl group, an ethyl group, a propyl group, or a butyl group. This saturated aliphatic hydrocarbon group may be unsubstituted or substituted. The substituent in a case of being substituted is not particularly limited, and examples thereof include an alkyl group, an aryl group, and a heterocyclic group, and this point is also common to the following description. The number of carbon atoms in the alkyl group is not particularly limited, but is usually in a range of 1 to 20 from a viewpoint of availability and cost.

The cycloalkyl group represents a saturated alicyclic hydrocarbon group such as a cyclopropyl, a cyclohexyl, a norbornyl, or an adamanty. This saturated alicyclic hydrocarbon group may be unsubstituted or substituted. The carbon number of the alkyl group moiety is not particularly limited, but is usually in a range of 3 to 20.

Furthermore, the aralkyl group represents an aromatic hydrocarbon group via an aliphatic hydrocarbon, such as a benzyl group or a phenylethyl group. Both the aliphatic hydrocarbon and the aromatic hydrocarbon may be unsubstituted or substituted. The carbon number of the aliphatic moiety is not particularly limited, but is usually in a range of 1 to 20.

The alkenyl group represents an unsaturated aliphatic hydrocarbon group containing a double bond, such as a vinyl group, an allyl group, or a butadienyl group. This unsaturated aliphatic hydrocarbon group may be unsubstituted or substituted. The carbon number of the alkenyl group is not particularly limited, but is usually in a range of 2 to 20.

The cycloalkenyl group represents an unsaturated alicyclic hydrocarbon group containing a double bond, such as a cyclopentenyl group, a cyclopentadienyl group, or a cyclohexene group. This unsaturated alicyclic hydrocarbon group may be unsubstituted or substituted.

The alkynyl group represents an unsaturated aliphatic hydrocarbon group containing a triple bond, such as an acetylenyl group. This unsaturated aliphatic hydrocarbon group may be unsubstituted or substituted. The carbon number of the alkynyl group is not particularly limited, but is usually in a range of 2 to 20.

The alkoxy group represents an aliphatic hydrocarbon group via an ether bond, such as a methoxy group. The aliphatic hydrocarbon group may be unsubstituted or substituted. The carbon number of the alkoxy group is not particularly limited, but is usually in a range of 1 to 20.

The alkylthio group is a group in which an oxygen atom of an ether bond of an alkoxy group is substituted by a sulfur atom.

The cycloalkylthio group is a group in which an oxygen atom of an ether bond of a cycloalkoxy group is substituted by a sulfur atom.

The aryl ether group represents an aromatic hydrocarbon group via an ether bond, such as a phenoxy group. The aromatic hydrocarbon group may be unsubstituted or substituted. The carbon number of the aryl ether group is not particularly limited, but is usually in a range of 6 to 40.

The aryl thioether group is a group in which an oxygen atom of an ether bond of an aryl ether group is substituted by a sulfur atom.

Furthermore, the aryl group represents an aromatic hydrocarbon group such as a phenyl group, a naphthyl group, a biphenyl group, a phenanthryl group, a terphenyl group, or a pyrenyl group. The aryl group may be unsubstituted or substituted. The carbon number of the aryl group is not particularly limited, but is usually in a range of 6 to 40.

Furthermore, the heterocyclic group represents a cyclic structural group having an atom other than a carbon atom, such as a furanyl group, a thiophenyl group, an oxazolyl group, a pyridyl group, a quinolinyl group, or a carbazolyl group. This cyclic structural group may be unsubstituted or substituted. The carbon number of the heterocyclic group is not particularly limited, but is usually in a range of 2 to 30.

Halogen refers to fluorine, chlorine, bromine, and iodine.

The aldehyde group, the carbonyl group, and the amino group can include those substituted by an aliphatic hydrocarbon, an alicyclic hydrocarbon, an aromatic hydrocarbon, a heterocyclic ring, or the like.

Furthermore, the aliphatic hydrocarbon, the alicyclic hydrocarbon, the aromatic hydrocarbon, and the heterocyclic ring may be unsubstituted or substituted.

The silyl group represents, for example, a silicon compound group such as a trimethylsilyl group. This silicon compound group may be unsubstituted or substituted. The number of carbon atoms of the silyl group is not particularly limited, but is usually in a range of 3 to 20. The number of silicon atoms is usually 1 to 6.

The fused ring formed with an adjacent substituent is, for example, a conjugated or unconjugated fused ring formed between $Ar^1$ and $R^2$, $Ar^1$ and $R^3$, $Ar^2$ and $R^2$, $Ar^2$ and $R^3$, $R^2$ and $R^3$, or $Ar^1$ and $Ar^2$. Here, when n is 1, two $R^{11}$'s may form a conjugated or nonconjugated fused ring. These fused rings may contain a nitrogen atom, an oxygen atom, or a sulfur atom in the ring structure, or may be fused with another ring.

Specific examples of this phosphine oxide derivative include the following compounds.

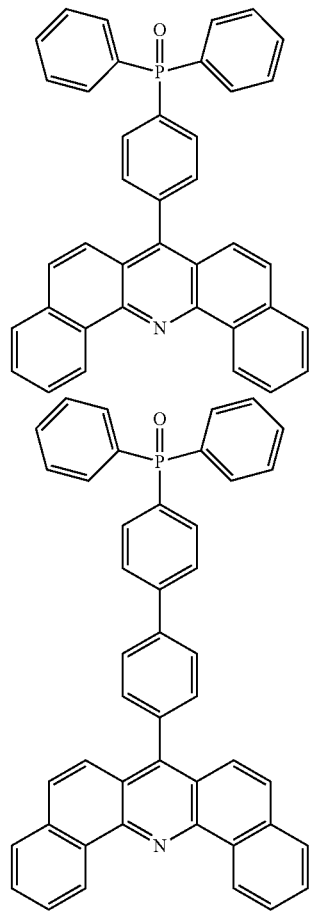

This phosphine oxide derivative can be manufactured using known raw materials and known synthesis methods.

<Pyrimidine Derivative>

The pyrimidine derivative is, for example, a compound represented by the following formula (ETM-8), and preferably a compound represented by the following formula (ETM-8-1). Details are also described in WO 2011/021689 A.

(ETM-8)

(ETM-8-1)

Ar's each independently represent an optionally substituted aryl or an optionally substituted heteroaryl. n represents an integer of 1 to 4, preferably an integer of 1 to 3, and more preferably 2 or 3.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

Specific examples of this pyrimidine derivative include the following compounds.

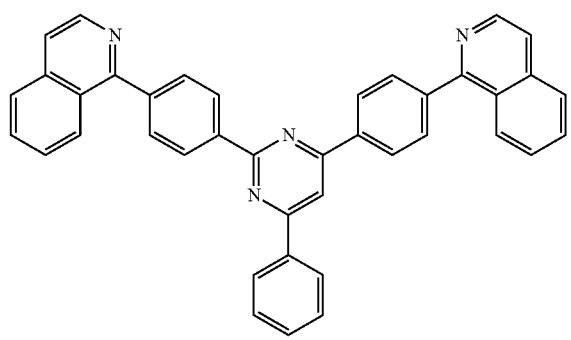 [SMILES: c1ccc(-c2cc(-c3ccc(-c4nccc5ccccc45)cc3)nc(-c3ccc(-c4nccc5ccccc45)cc3)n2)cc1]

This pyrimidine derivative can be manufactured using known raw materials and known synthesis methods.

<Carbazole Derivative>

The carbazole derivative is, for example, a compound represented by the following formula (ETM-9), or a multimer obtained by bonding a plurality of the compounds with a single bond or the like. Details are described in US 2014/0197386 A.

(ETM-9)

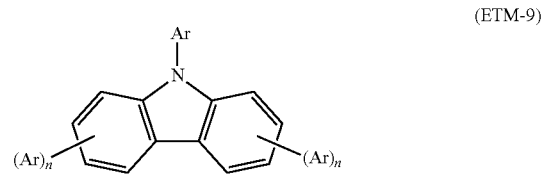

Ar's each independently represent an optionally substituted aryl or an optionally substituted heteroaryl. n's each independently represent an integer of 0 to 4, preferably an integer of 0 to 3, and more preferably 0 or 1.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

The carbazole derivative may be a multimer obtained by bonding a plurality of compounds represented by the above formula (ETM-9) with a single bond or the like. In this case, the compounds may be bonded with an aryl ring (preferably, a polyvalent benzene ring, naphthalene ring, anthracene ring, fluorene ring, benzofluorene ring, phenalene ring, phenanthrene ring or triphenylene ring) in addition to a single bond.

Specific examples of this carbazole derivative include the following compounds.

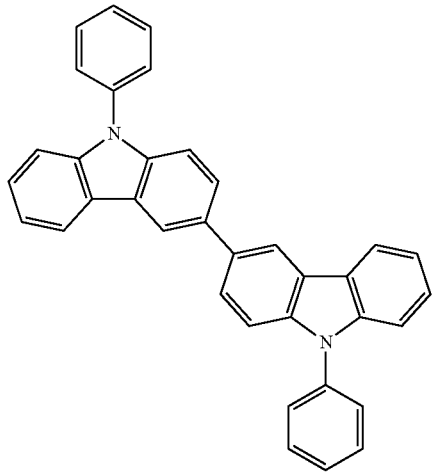

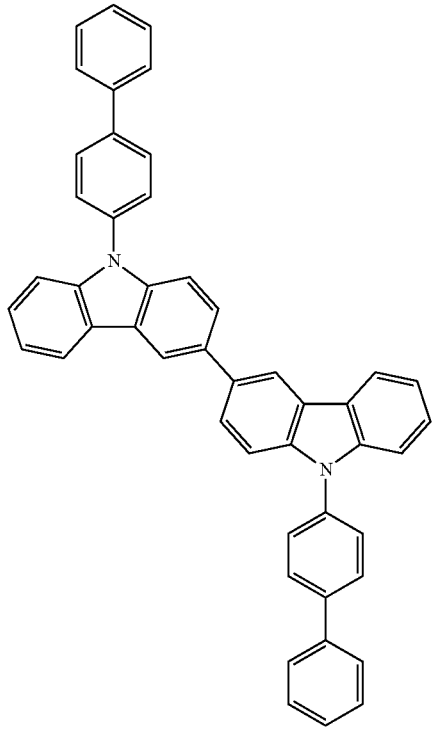

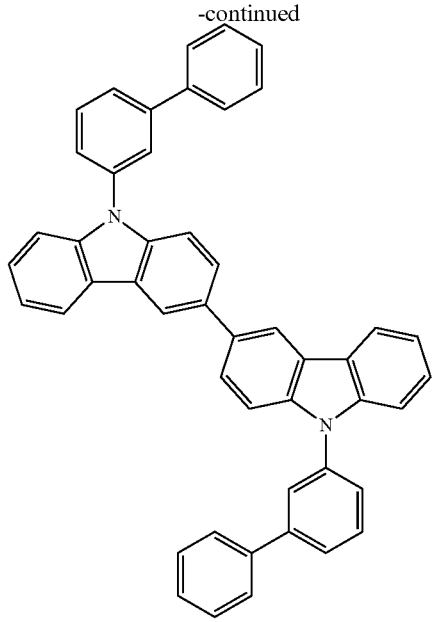

This carbazole derivative can be manufactured using known raw materials and known synthesis methods.

<Triazine Derivative>

The triazine derivative is, for example, a compound represented by the following formula (ETM-10), and preferably a compound represented by the following formula (ETM-10-1). Details are described in US 2011/0156013 A.

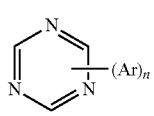

(ETM-10)

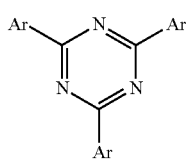

(ETM-10-1)

Ar's each independently represent an optionally substituted aryl or an optionally substituted heteroaryl. n represents an integer of 1 to 3, preferably 2 or 3.

Examples of the "aryl" as the "optionally substituted aryl" include an aryl having 6 to 30 carbon atoms. An aryl having 6 to 24 carbon atoms is preferable, an aryl having 6 to 20 carbon atoms is more preferable, and an aryl having 6 to 12 carbon atoms is still more preferable.

Specific examples of the "aryl" include phenyl which is a monocyclic aryl; (2-, 3-, 4-)biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; quaterphenylyl-(5'-phenyl-m-terphenyl-2-yl, 5'-phenyl-m-terphenyl-3-yl, 5'-phenyl-m-terphenyl-4-yl, m-quaterphenylyl) which is a tetracyclic aryl; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls.

Examples of the "heteroaryl" as the "optionally substituted heteroaryl" include a heteroaryl having 2 to 30 carbon atoms. A heteroaryl having 2 to 25 carbon atoms is preferable, a heteroaryl having 2 to 20 carbon atoms is more preferable, a heteroaryl having 2 to 15 carbon atoms is still more preferable, and a heteroaryl having 2 to 10 carbon atoms is particularly preferable. In addition, examples of the "heteroaryl" include a heterocyclic ring containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl.

The above aryl and heteroaryl may be substituted, and may be each substituted by, for example, the above aryl or heteroaryl.

Specific examples of this triazine derivative include the following compounds.

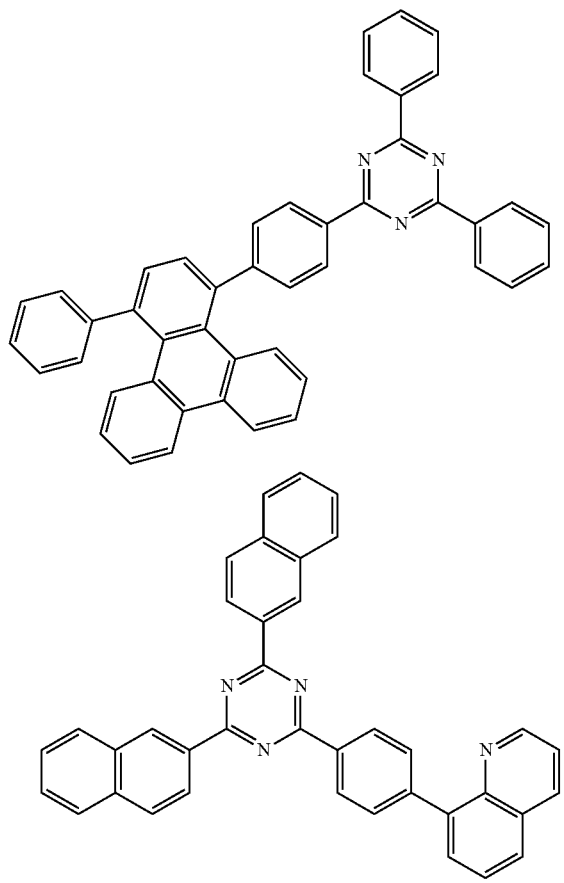

This triazine derivative can be manufactured using known raw materials and known synthesis methods.

<Benzimidazole Derivative>

The benzimidazole derivative is, for example, a compound represented by the following formula (ETM-11).

φ-(Benzimidazole-based substituent)$_n$      (ETM-11)

φ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4. A benzimidazole-based substituent" is a substituent in which the pyridyl group in the "pyridine-based substituent" in the formulas (ETM-2), (ETM-2-1), and (ETM-2-2) is substituted by a benzimidazole group, and at least one hydrogen atom in the benzimidazole derivative may be substituted by a deuterium atom.

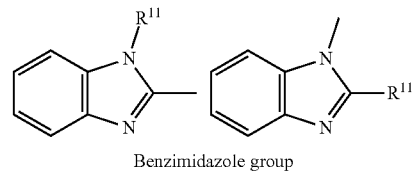

Benzimidazole group $R^{11}$ in the above benzimidazole represents a hydrogen atom, an alkyl having 1 to 24 carbon atoms, a cycloalkyl having 3 to 12 carbon atoms, or an aryl having 6 to 30 carbon atoms. The description of $R^{11}$ in the above formulas (ETM-2-1), and (ETM-2-2) can be cited.

Furthermore, p is preferably an anthracene ring or a fluorene ring. For the structure in this case, the description of the above formula (ETM-2-1) or (ETM-2-2) can be cited. For $R^{11}$ to $R^{18}$ in each formula, the description of the above formula (ETM-2-1) or (ETM-2-2) can be cited. In the above formula (ETM-2-1) or (ETM-2-2), a form in which two pyridine-based substituents are bonded has been described. However, when these substituents are substituted by benzimidazole-based substituents, both the pyridine-based substituents may be substituted by benzimidazole-based substituents (that is, n=2), or one of the pyridine-based substituents may be substituted by a benzimidazole-based substituent and the other pyridine-based substituent may be substituted by any one of $R^{11}$ to $R^{18}$ (that is, n=1). Furthermore, for example, at least one of $R^{11}$ to $R^{18}$ in the above formula (ETM-2-1) may be substituted by a benzimidazole-based substituent and the "pyridine-based substituent" may be substituted by any one of $R^{11}$ to $R^{18}$.

Specific examples of this benzimidazole derivative include 1-phenyl-2-(4-(10-phenylanthracen-9-yl)phenyl)-1H-benzo[d]imidazole, 2-(4-(10-(naphthalen-2-yl)anthracen-9-yl)phenyl)-1-phenyl-1H-benzo[d]imidazole, 2-(3-(10-(naphthalen-2-yl)anthracen-9-yl)phenyl)-1-phenyl-1H-benzo[d]imidazole, 5-(10-(naphthlen-2-yl)anthracen-9-yl)-1,2-diphenyl-1H-benzo[d]imidazole, 1-(4-(10-(naphthalen-2-yl)anthracen-9-yl)phenyl)-2-phenyl-1H-benzo[d]imidazole, 2-(4-(9,10-di(naphthalen-2-yl)anthracen-2-yl)phenyl)-1-phenyl-1H-benzo[d]imidazole, 1-(4-(9,10-di(naphthalen-2-yl)anthracen-2-yl)phenyl)-2-phenyl-1H-benzo[d]imidazole, and 5-(9,10-di(naphthalen-2-yl)anthracen-2-yl)-1,2-diphenyl-1H-benzo[d]imidazole.

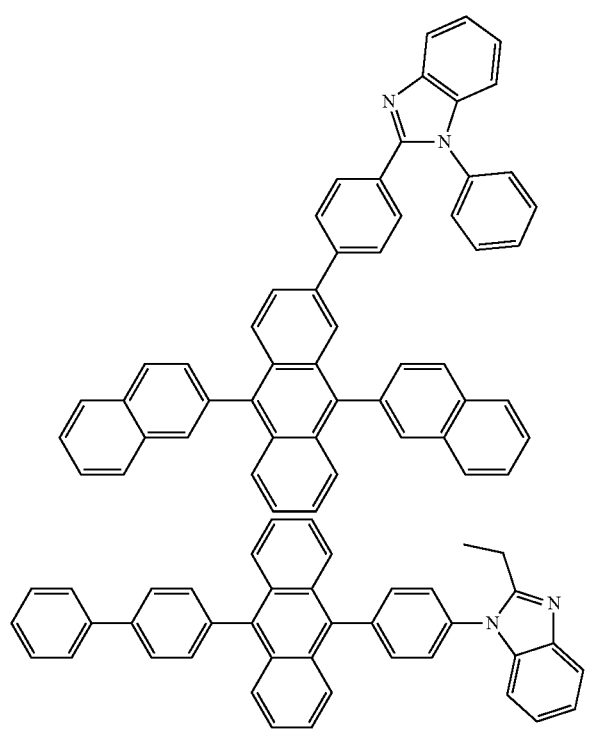

This benzimidazole derivative can be manufactured using known raw materials and known synthesis methods.

<Phenanthroline Derivative>

The phenanthroline derivative is, for example, a compound represented by the following formula (ETM-12) or (ETM-12-1). Details are described in WO 2006/021982 A.

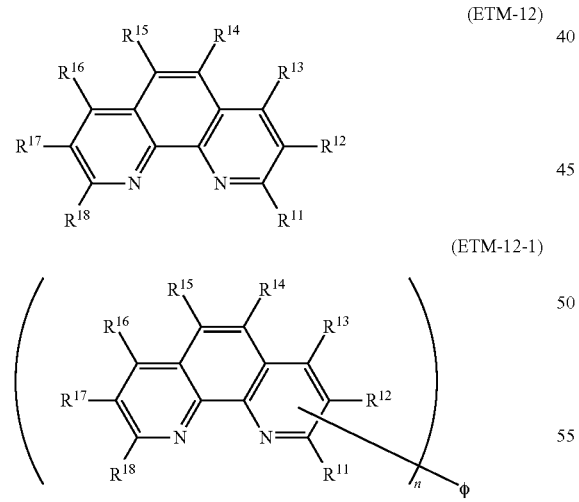

$\varphi$ represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4.

In each formula, $R^{11}$ to $R^{18}$ each independently represent a hydrogen atom, an alkyl (preferably, an alkyl having 1 to 24 carbon atoms), a cycloalkyl (preferably, a cycloalkyl having 3 to 12 carbon atoms), or an aryl (preferably, an aryl having 6 to 30 carbon atoms). In the above formula (ETM-12-1), any one of $R^{11}$ to $R^{18}$ is bonded to c which is an aryl ring.

At least one hydrogen atom in each phenanthroline derivative may be substituted by a deuterium atom.

For the alkyl, cycloalkyl, and aryl in $R^{11}$ to $R^{18}$, the description of $R^{11}$ to $R^{18}$ in the above formula (ETM-2) can be cited. In addition to the above examples, examples of the p include those having the following structural formulas. Note that R's in the following structural formulas each independently represent a hydrogen atom, a methyl, an ethyl, an isopropyl, a cyclohexyl, a phenyl, a 1-naphthyl, a 2-naphthyl, a biphenylyl, or a terphenylyl.

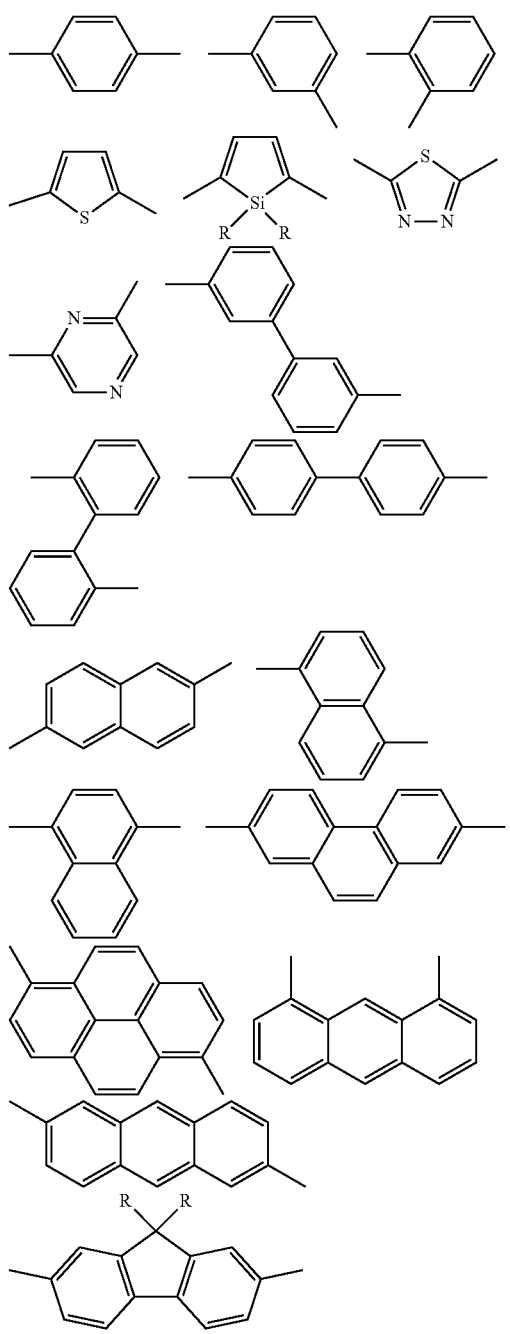

-continued

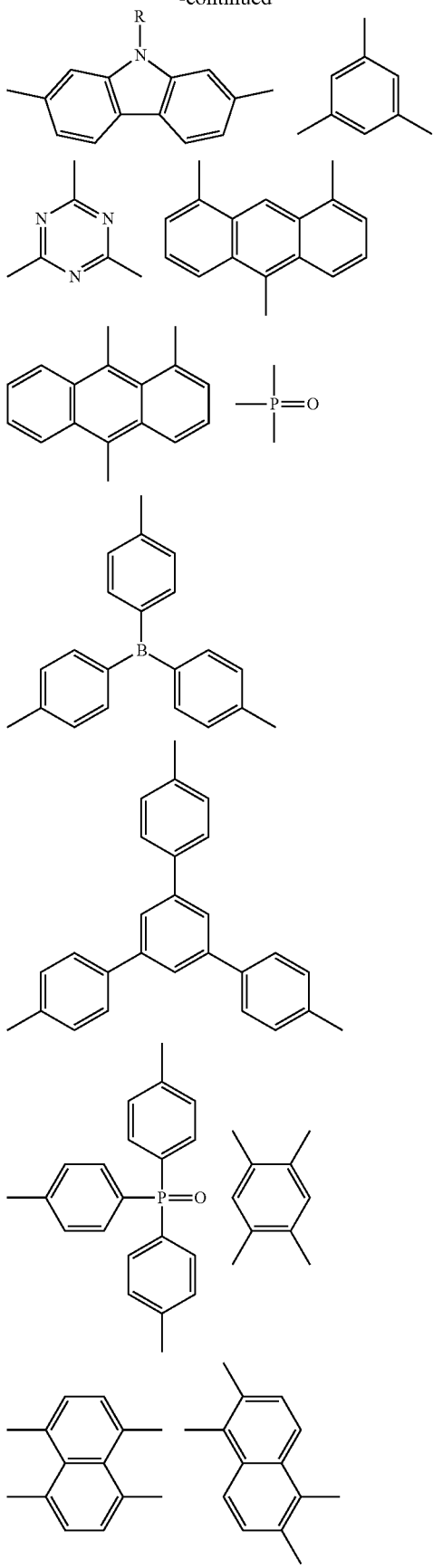

-continued

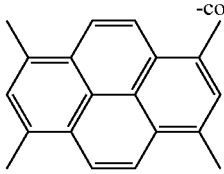

Specific examples of this phenanthroline derivative include 4,7-diphenyl-1,10-phenanthroline, 2,9-dimethyl-4,7-diphenyl-1,10-phenanthroline, 9,10-di(1,10-phenanthrolin-2-yl)anthracene, 2,6-di(1,10-phenanthrolin-5-yl)pyridine, 1,3,5-tri(1,10-phenanthrolin-5-yl)benzene, 9,9'-difluoro-bis(1,10-phenanthrolin-5-yl), bathocuproine, 1,3-bis(2-phenyl-1,10-phenanthrolin-9-yl)benzene, and a compound represented by the following structural formula.

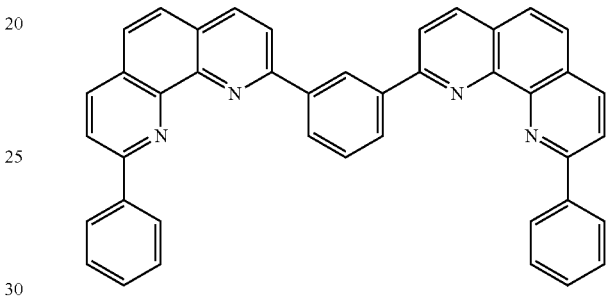

This phenanthroline derivative can be manufactured using known raw materials and known synthesis methods.

<Quinolinol-Based Metal Complex>

The quinolinol-based metal complex is, for example, a compound represented by the following general formula (ETM-13).

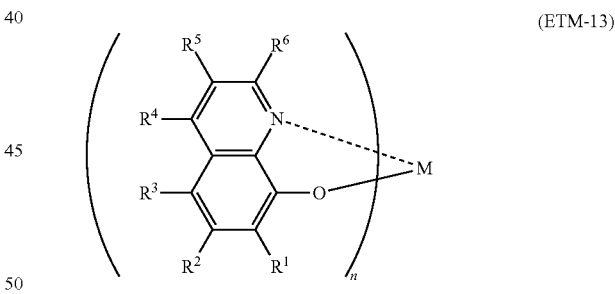

(ETM-13)

In the formula, $R^1$ to $R^6$ each independently represent a hydrogen atom, a fluorine atom, an alkyl, a cycloalkyl, an aralkyl, an alkenyl, a cyano, an alkoxy, or an aryl, M represents Li, Al, Ga, Be, or Zn, and n represents an integer of 1 to 3.

Specific examples of the quinolinol-based metal complex include 8-quinolinollithium, tris(8-quinolinolato)aluminum, tris(4-methyl-8-quinolinolato)aluminum, tris(5-methyl-8-quinolinolato)aluminum, tris(3,4-dimethyl-8-quiolinolato) aluminum, tris(4,5-dimethyl-8-quinolinolato)aluminum, tris (4,6-dimethyl-8-quinolinolato)aluminum, bis(2-methyl-8-quinolinolato) (phenolato)aluminum, bis(2-methyl-8-quinolinolato) (2-methylphenolato)aluminum, bis(2-methyl-8-quinolinolato) (3-methylphenolato)aluminum, bis (2-methyl-8-quinolinolato) (4-methylphenolato)aluminum, bis(2-methyl-8-quinolinolato) (2-phenylphenolato)aluminum, bis(2-methyl-8-quinolinolato) (3-phenylphenolato) aluminum, bis(2-methyl-8-quinolinolato) (4-phenylphenolato)aluminum, bis(2-methyl-8-quinolinolato) (2,3-dimethylphenolato)aluminum, bis(2-methyl-8-quinolinolato) (2,6-dimethylphenolato)aluminum, bis(2-methyl-8-quinolinolato) (3,4-dimethylphenolato)aluminum, bis(2-methyl-8-quinolinolato) (3,5-dimethylphenolato)aluminum, bis(2-methyl-8-quinolinolato) (3,5-di-t-butylphenolato)aluminum, bis(2-methyl-8-quinolinolato) (2,6-diphenylphenolato)aluminum, bis(2-methyl-8-quinolinolato) (2,4,6-triphenylphenolato)aluminum, bis(2-methyl-8-quinolinolato) (2,4,6-trimethylphenolato)aluminum, bis(2-methyl-8-quinolinolato) (2,4,5,6-tetramethylphenolato)aluminum, bis(2-methyl-8-quinolinolato) (1-naphtholato) aluminum, bis(2-methyl-8-quinolinolato) (2-naphtholato) aluminum, bis(2,4-dimethyl-8-quinolinolato) (2-phenylphenolato)aluminum, bis(2,4-dimethyl-8-quinolinolato) (3-phenylphenolato)aluminum, bis(2,4-dimethyl-8-quinolinolato) (4-phenylphenolato)aluminum, bis(2,4-dimethyl-8-quinolinolato) (3,5-dimethylphenolato)aluminum, bis(2,4-dimethyl-8-quinolinolato) (3,5-di-t-butylphenolato) aluminum, bis(2-methyl-8-quinolinolato)aluminum-p-oxo-bis(2-methyl-8-quinolinolato)aluminum, bis(2,4-dimethyl-8-quinolinolato)aluminum-µ-oxo-bis(2,4-dimethyl-8-quinolinolato)aluminum, bis(2-methyl-4-ethyl-8-quinolinolato)aluminum-µ-oxo-bis(2-methyl-4-ethyl-8-quinolinolato)aluminum, bis(2-methyl-4-methoxy-8-quinolinolato)aluminum-µ-oxo-bis(2-methyl-4-methoxy-8-quinolinolato)aluminum, bis(2-methyl-5-cyano-8-quinolinolato)aluminum-µ-oxo-bis(2-methyl-5-cyano-8-quinolinolato)aluminum, bis(2-methyl-5-trifluoromethyl-8-quinolinolato)aluminum-µ-oxo-bis(2-methyl-5-trifluoromethyl-8-quiolinolato)aluminum, and bis(10-hydroxybenzo[h]quinoline)beryllium.

This quinolinol-based metal complex can be manufactured using known raw materials and known synthesis methods.

<Thiazole Derivative and Benzothiazole Derivative>

The thiazole derivative is, for example, a compound represented by the following formula (ETM-14-1).

$\phi$-(Thiazole-based substituent)$_n$ (ETM-14-1)

The benzothiazole derivative is, for example, a compound represented by the following formula (ETM-14-2).

$\phi$-(Benzothiazole-based substituent)$_n$ (ETM-14-2)

φ in each formula represents an n-valent aryl ring (preferably, an n-valent benzene ring, naphthalene ring, anthracene ring, fluorene ring, benzofluorene ring, phenalene ring, phenanthrene ring, or triphenylene ring), and n represents an integer of 1 to 4. A "thiazole-based substituent" or a "benzothiazole-based substituent" is a substituent in which the pyridyl group in the "pyridine-based substituent" in the formulas (ETM-2), (ETM-2-1), and (ETM-2-2) is substituted by the following thiazole group or benzothiazole group, and at least one hydrogen atom in the thiazole derivative and the benzothiazole derivative may be substituted by a deuterium atom.

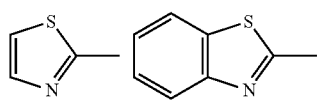

Thiazole group    Benzothiazole group

Furthermore, φ is preferably an anthracene ring or a fluorene ring. For the structure in this case, the description of the above formula (ETM-2-1) or (ETM-2-2) can be cited. For $R^{11}$ to $R^{18}$ in each formula, the description of the above formula (ETM-2-1) or (ETM-2-2) can be cited. In the above formula (ETM-2-1) or (ETM-2-2), a form in which two pyridine-based substituents are bonded has been described. However, when these substituents are substituted by thiazole-based substituents (or benzothiazole-based substituents), both the pyridine-based substituents may be substituted by thiazole-based substituents (or benzothiazole-based substituents) (that is, n=2), or one of the pyridine-based substituents may be substituted by a thiazole-based substituent (or benzothiazole-based substituent) and the other pyridine-based substituent may be substituted by any one of $R^{11}$ to $R^{18}$ (that is, n=1). Furthermore, for example, at least one of $R^{11}$ to $R^{18}$ in the above formula (ETM-2-1) may be substituted by a thiazole-based substituent (or benzothiazole-based substituent) and the "pyridine-based substituent" may be substituted by any one of $R^{11}$ to $R^{18}$.

These thiazole derivatives or benzothiazole derivatives can be manufactured using known raw materials and known synthesis methods.

The electron transport layer or the electron injection layer may further contain a substance capable of reducing a material to form the electron transport layer or the electron injection layer. As this reducing substance, various substances are used as long as having reducibility to a certain extent. For example, at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal, can be suitably used.

Preferable examples of the reducing substance include an alkali metal such as Na (work function 2.36 eV), K (work function 2.28 eV), Rb (work function 2.16 eV), or Cs (work function 1.95 eV); and an alkaline earth metal such as Ca (work function 2.9 eV), Sr (work function 2.0 to 2.5 eV), or Ba (work function 2.52 eV). A substance having a work function of 2.9 eV or less is particularly preferable. Among these substances, an alkali metal such as K, Rb, or Cs is a more preferable reducing substance, Rb or Cs is a still more preferable reducing substance, and Cs is the most preferable reducing substance. These alkali metals have particularly high reducing ability, and can enhance emission luminance of an organic EL element or can lengthen a lifetime thereof by adding the alkali metals in a relatively small amount to a material to form an electron transport layer or an electron injection layer. Furthermore, as the reducing substance having a work function of 2.9 eV or less, a combination of two or more kinds of these alkali metals is also preferable, and particularly, a combination including Cs, for example, a combination of Cs with Na, a combination of Cs with K, a combination of Cs with Rb, or a combination of Cs with Na and K, is preferable. By inclusion of Cs, reducing ability can be efficiently exhibited, and emission luminance of an organic EL element is enhanced or a lifetime thereof is lengthened by adding Cs to a material to form an electron transport layer or an electron injection layer.

<Negative Electrode in Organic Electroluminescent Element>

The negative electrode 108 plays a role of injecting an electron to the light emitting layer 105 through the electron injection layer 107 and the electron transport layer 106.

A material to form the negative electrode 108 is not particularly limited as long as being a substance capable of efficiently injecting an electron to an organic layer. However, a material similar to a material to form the positive electrode 102 can be used. Among these materials, a metal such as tin, indium, calcium, aluminum, silver, copper, nickel, chromium, gold, platinum, iron, zinc, lithium, sodium, potassium, cesium, or magnesium, and an alloy thereof (a magnesium-silver alloy, a magnesium-indium alloy, an aluminum-lithium alloy such as lithium fluoride/aluminum, or the like) are preferable. In order to enhance element characteristics by increasing an electron injection efficiency, lithium, sodium, potassium, cesium, calcium, magnesium, or an alloy containing these low work function-metals is effective. However, many of these low work function-metals are generally unstable in air. In order to ameliorate this problem, for example, a method using an electrode having high stability obtained by doping an organic layer with a trace amount of lithium, cesium, or magnesium is known. Other examples of a dopant that can be used include an inorganic salt such as lithium fluoride, cesium fluoride, lithium oxide, or cesium oxide. However, the dopant is not limited thereto.

Furthermore, in order to protect an electrode, a metal such as platinum, gold, silver, copper, iron, tin, aluminum, or indium, an alloy using these metals, an inorganic substance such as silica, titania, or silicon nitride, polyvinyl alcohol, vinyl chloride, a hydrocarbon-based polymer compound, or the like may be laminated as a preferable example. A method for manufacturing these electrodes is not particularly limited as long as being able to obtain conduction, such as resistance heating, electron beam deposition, sputtering, ion plating, or coating.

<Binder that May be Used in Each Layer>

The materials used in the above-described hole injection layer, hole transport layer, light emitting layer, electron transport layer, and electron injection layer can form each layer by being used singly. However, it is also possible to use the materials by dispersing the materials in a solvent-soluble resin such as polyvinyl chloride, polycarbonate, polystyrene, poly(N-vinylcarbazole), polymethyl methacrylate, polybutyl methacrylate, polyester, polysulfone, polyphenylene oxide, polybutadiene, a hydrocarbon resin, a ketone resin, a phenoxy resin, polyamide, ethyl cellulose, a vinyl acetate resin, an ABS resin, or a polyurethane resin; or a curable resin such as a phenolic resin, a xylene resin, a petroleum resin, a urea resin, a melamine resin, an unsaturated polyester resin, an alkyd resin, an epoxy resin, or a silicone resin, as a polymer binder.

<Method for Manufacturing Organic Electroluminescent Element>

Each layer constituting an organic EL element can be formed by forming thin films of the materials to constitute each layer by methods such as a vapor deposition method, resistance heating deposition, electron beam deposition, sputtering, a molecular lamination method, a printing method, a spin coating method, a casting method, and a coating method. The film thickness of each layer thus formed is not particularly limited, and can be appropriately set according to a property of a material, but is usually within a range of 2 nm to 5000 nm. The film thickness can be usually measured using a crystal oscillation type film thickness measuring apparatus or the like. In a case of forming a thin film using a vapor deposition method, vapor deposition conditions depend on the kind of a material, an intended crystal structure of a film, an association structure, and the like. It is preferable to appropriately set the vapor deposition conditions generally in ranges of a boat heating temperature of +50 to +400° C., a degree of vacuum of $10^{-6}$ to $10^{-3}$ Pa, a rate of vapor deposition of 0.01 to 50 nm/sec, a substrate temperature of −150 to +300° C., and a film thickness of 2 nm to 5 μm.

Next, as an example of a method for manufacturing an organic EL element, a method for manufacturing an organic EL element formed of positive electrode/hole injection layer/hole transport layer/light emitting layer including a host material and a dopant material/electron transport layer/electron injection layer/negative electrode will be described. A thin film of a positive electrode material is formed on an appropriate substrate by a vapor deposition method or the like to manufacture a positive electrode, and then thin films of a hole injection layer and a hole transport layer are formed on this positive electrode. A thin film is formed thereon by co-depositing a host material and a dopant material to obtain a light emitting layer. An electron transport layer and an electron injection layer are formed on this light emitting layer, and a thin film formed of a substance for a negative electrode is formed by a vapor deposition method or the like to obtain a negative electrode. An intended organic EL element is thereby obtained. Incidentally, in manufacturing the above organic EL element, it is also possible to manufacture the element by reversing the manufacturing order, that is, in order of a negative electrode, an electron injection layer, an electron transport layer, a light emitting layer, a hole transport layer, a hole injection layer, and a positive electrode.

In a case where a direct current voltage is applied to the organic EL element thus obtained, it is only required to apply the voltage by assuming a positive electrode as a positive polarity and assuming a negative electrode as a negative polarity. By applying a voltage of about 2 to 40 V, light emission can be observed from a transparent or semi-transparent electrode side (the positive electrode or the negative electrode, or both the electrodes). This organic EL element also emits light even in a case where a pulse current or an alternating current is applied. Note that a waveform of an alternating current applied may be any waveform.

Application Examples of Organic Electroluminescent Element

The present invention can also be applied to a display apparatus including an organic EL element, a lighting apparatus including an organic EL element, or the like.

The display apparatus or lighting apparatus including an organic EL element can be manufactured by a known method such as connecting the organic EL element according to the present embodiment to a known driving apparatus, and can be driven by appropriately using a known driving method such as direct driving, pulse driving, or alternating driving.

Examples of the display apparatus include a panel display such as a color flat panel display; and a flexible display such as a flexible color organic electroluminescent (EL) display (see, for example, JP 10-335066 A, JP 2003-321546 A, and JP 2004-281086 A). Examples of a display method of the display include a matrix method and/or a segment method. Note that the matrix display and the segment display may co-exist in the same panel.

In the matrix, pixels for display are arranged two-dimensionally as in a lattice form or a mosaic form, and characters or images are displayed by an assembly of pixels. The shape or size of a pixel depends on intended use. For example, for display of images and characters of a personal computer, a monitor, or a television, square pixels each having a size of 300 μm or less on each side are usually used, and in a case of a large-sized display such as a display panel, pixels having a size in the order of millimeters on each side are used. In a case of monochromic display, it is only required to arrange pixels of the same color. However, in a case of color display, display is performed by arranging pixels of red, green, and blue. In this case, typically, delta type display and stripe type display are available. For this matrix driving method, either a line sequential driving method or an active matrix method may be employed. The line sequential driving method has an advantage of having a simpler structure. However, in consideration of operation characteristics, the active matrix method may be superior. Therefore, it is necessary to use the line sequential driving method and the active matrix method properly according to intended use.

In the segment method (type), a pattern is formed so as to display predetermined information, and a determined region emits light. Examples of the segment method include display of time or temperature in a digital clock or a digital thermometer, display of a state of operation in an audio instrument or an electromagnetic cooker, and panel display in an automobile.

Examples of the lighting apparatus include a lighting apparatuses for indoor lighting or the like, and a backlight of a liquid crystal display apparatus (see, for example, JP 2003-257621 A, JP 2003-277741 A, and JP 2004-A). The backlight is mainly used for enhancing visibility of a display apparatus that is not self-luminous, and is used in a liquid crystal display apparatus, a timepiece, an audio apparatus, an automotive panel, a display plate, a sign, and the like. Particularly, in a backlight for use in a liquid crystal display apparatus, among the liquid crystal display apparatuses, for use in a personal computer in which thickness reduction has been a problem to be solved, in consideration of difficulty in thickness reduction because a conventional type backlight is formed from a fluorescent lamp or a light guide plate, a backlight using the luminescent element according to the present embodiment is characterized by its thinness and lightweightness.

EXAMPLES

Hereinafter, the present invention will be described more specifically by way of Examples, but the present invention is not limited thereto. First, Synthesis Examples of a polycyclic aromatic compound and a pyrene-based compound will be described below.

Synthesis Example (1): Synthesis of Compound (1-290)

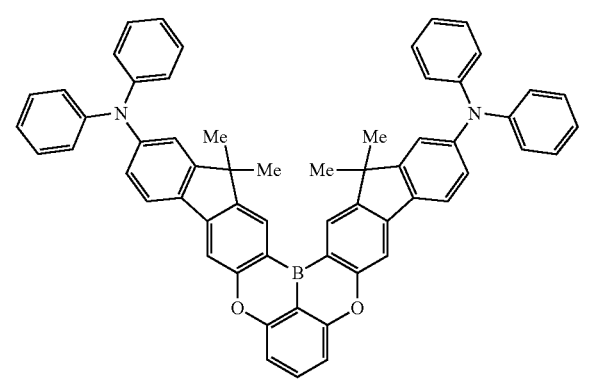

(1-290)

In a nitrogen atmosphere, a flask containing methyl 4-methoxysalicylate (50.0 g) and pyridine (dehydrated) (350 ml) was cooled in an ice bath. Subsequently, trifluoromethanesulfonic anhydride (154.9 g) was dropwise added to this solution. After completion of the dropwise addition, the ice bath was removed, the solution was stirred at room temperature for two hours, and water was added thereto to stop the reaction. Toluene was added thereto, and the organic layer was separated. Thereafter, purification was performed with a silica gel short pass column (eluent: toluene) to obtain methyl 4-methoxy-2-(((trifluoromethyl) sulfonyl) oxy) benzoate (86.0 g).

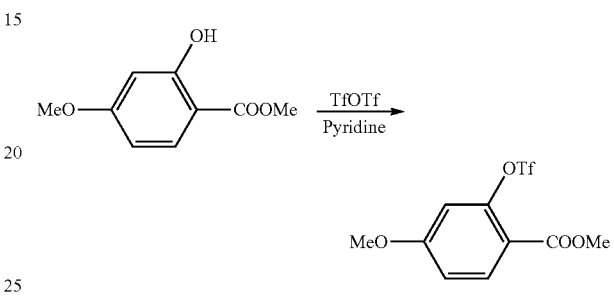

In a nitrogen atmosphere, Pd(PPh$_3$)$_4$ (2.5 g) was added to a suspension solution of methyl 4-methoxy-2-(((trifluoromethyl) sulfonyl) oxy) benzoate (23.0 g), (4-(diphenylamino) phenyl) boronic acid (25.4 g), tripotassium phosphate (31.1 g), toluene (184 ml), ethanol (27.6 ml), and water (27.6 ml), and the resulting mixture was stirred at a reflux temperature for three hours. The reaction liquid was cooled to room temperature, water and toluene were added thereto, and the organic layer was separated. A solvent of the organic layer was distilled off under reduced pressure. The obtained solid was purified with a silica gel column (eluent: mixed solvent of heptane/toluene) to obtain methyl 4'-(diphenylamino)-5-methoxy-[1,1'-biphenyl]-2-carboxylate (29.7 g). In this case, referring to the method described on page 94 of "Guide to Organic Chemistry Experiment (1)—Substance Handling Method and Separation and Purification Method", Kagaku-Dojin Publishing Company, INC., the proportion of toluene in an eluent was gradually increased, and an intended product was thereby eluted.

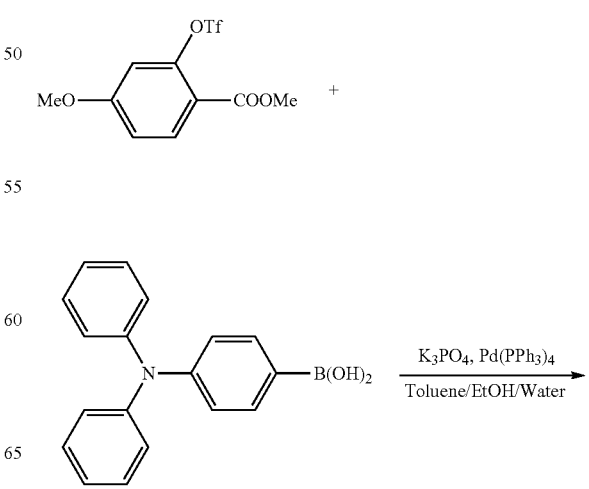

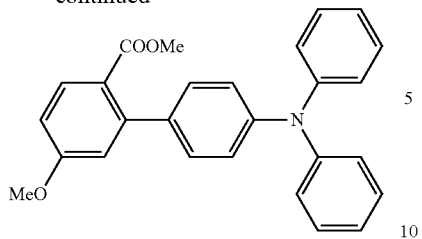

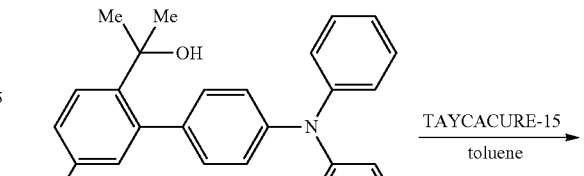

In a nitrogen atmosphere, a THF (111.4 ml) solution having methyl 4'-(diphenylamino)-5-methoxy-[1,1'-biphenyl]-2-carboxylate (11.4 g) dissolved therein was cooled in a water bath. To the solution, a methyl magnesium bromide THF solution (1.0 M, 295 ml) was dropwise added. After completion of the dropwise addition, the water bath was removed, and the solution was heated to a reflux temperature, and stirred for four hours. Thereafter, the solution was cooled in an ice bath, an ammonium chloride aqueous solution was added thereto to stop the reaction, ethyl acetate was added thereto, and the organic layer was separated. Thereafter, a solvent was distilled off under reduced pressure. The obtained solid was purified with a silica gel column (eluent: toluene) to obtain 2-(4'-(diphenylamino)-5-methoxy-[1,1'-biphenyl]-2-yl) propan-2-ol (8.3 g).

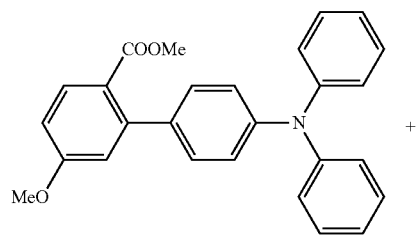

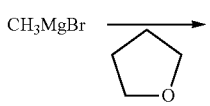

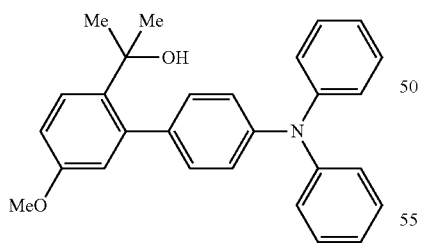

In a nitrogen atmosphere, a flask containing 2-(4'-(diphenylamino)-5-methoxy-[1,1'-biphenyl]-2-yl) propan-2-ol (27.0 g), TAYCACURE-15 (13.5 g), and toluene (162 ml) was stirred at a reflux temperature for two hours. The reaction liquid was cooled to room temperature and caused to pass through a silica gel short pass column (eluent: toluene) to remove TAYCACURE-15. Thereafter, a solvent was distilled off under reduced pressure to obtain 6-methoxy-9,9'-dimethyl-N,N-diphenyl-9H-fluoren-2-amine (25.8 g).

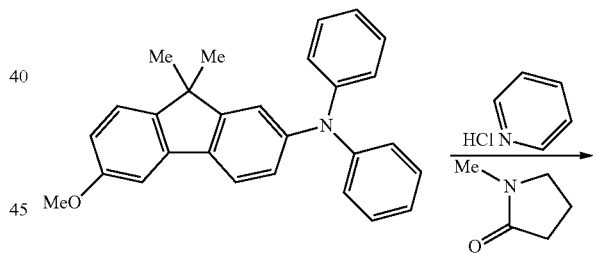

In a nitrogen atmosphere, a flask containing 6-methoxy-9,9'-dimethyl-N,N-diphenyl-9H-fluoren-2-amine (25.0 g), pyridine hydrochloride (36.9 g), and N-methyl-2-pyrrolidone (NMP) (22.5 ml) was stirred at a reflux temperature for six hours. The reaction liquid was cooled to room temperature. Thereafter, water and ethyl acetate were added thereto, and the organic layer was separated. The solvent was distilled off under reduced pressure. Thereafter, the residue was purified with a silica gel column (eluent: toluene) to obtain 7-(diphenylamino)-9,9'-dimethyl-9H-fluoren-3-ol (22.0 g).

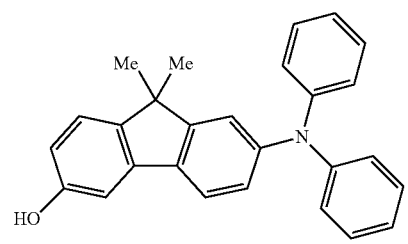

In a nitrogen atmosphere, a flask containing 7-(diphenylamino)-9,9'-dimethyl-9H-fluoren-3-ol (14.1 g), 2-bromo-1,3-difluorobenzene (3.6 g), potassium carbonate (12.9 g), and NMP (30 ml) was heated and stirred at a reflux temperature for five hours. After the reaction was stopped, the reaction liquid was cooled to room temperature, and water was added thereto. A precipitate thus precipitated was collected by suction filtration. The obtained precipitate was washed with water and then with methanol and then purified with a silica gel column (eluent: heptane/toluene mixed solvent) to obtain 6,6'-((2-bromo-1,3-phenylene) bis(oxy)) bis(9,9-dimethyl-N,N-diphenyl-9H-fluoren-2-amine) (12.6 g). At this time, the proportion of toluene in the eluent was gradually increased, and an intended product was thereby eluted.

+

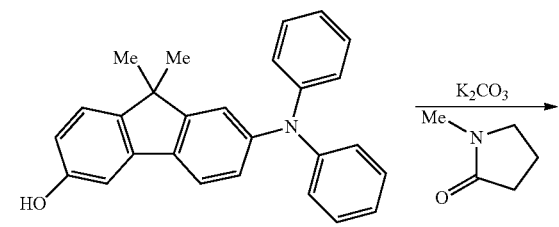

-continued

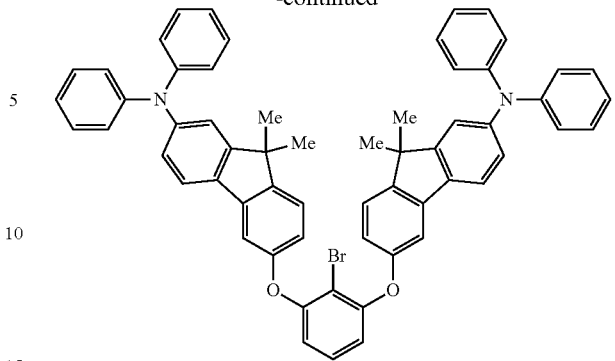

In a nitrogen atmosphere, a flask containing 6,6'-((2-bromo-1,3-phenylene) bis(oxy)) bis(9,9-dimethyl-N,N-diphenyl-9H-fluoren-2-amine) (11.0 g) and xylene (60.5 ml) was cooled to −40° C., and a 2.6 M n-butyllithium hexane solution (5.1 ml) was dropwise added thereto. After completion of the dropwise addition, the solution was stirred at this temperature for 0.5 hours. Thereafter, the solution was heated to 60° C., and stirred for three hours. Thereafter, the reaction liquid was depressurized to distill off a component having a low boiling point. Thereafter, the residue was cooled to −40° C., and boron tribromide (4.3 g) was added thereto. The solution was heated to room temperature, and stirred for 0.5 hours. Thereafter, the solution was cooled to 0° C., N-ethyl-N-isopropylpropan-2-amine (3.8 g) was added thereto, and the solution was heated and stirred at 125° C. for eight hours. The reaction liquid was cooled to room temperature, and a sodium acetate aqueous solution was added thereto to stop the reaction. Thereafter, toluene was added thereto, and the organic layer was separated. The organic layer was purified with a silica gel short pass column, then with a silica gel column (eluent: heptane/toluene=4 (volume ratio)), and further with an activated carbon column (eluent: toluene) to obtain compound (1-290) (1.2 g).

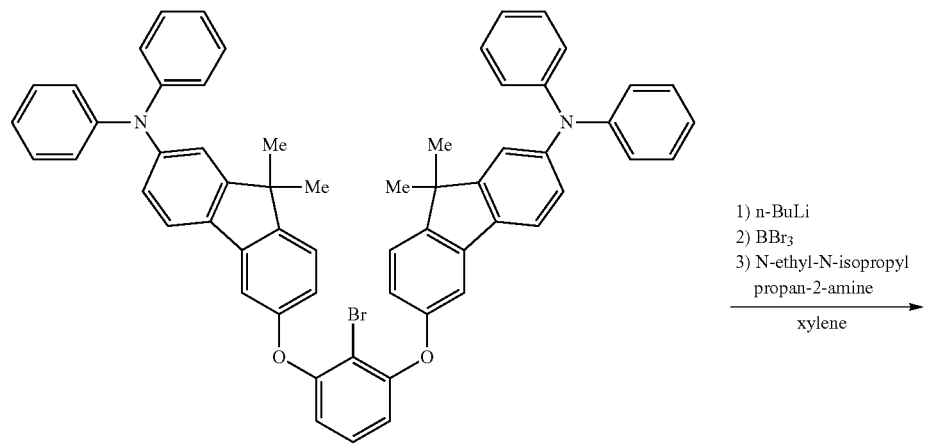

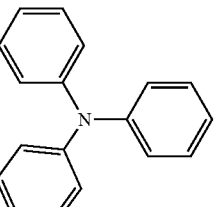
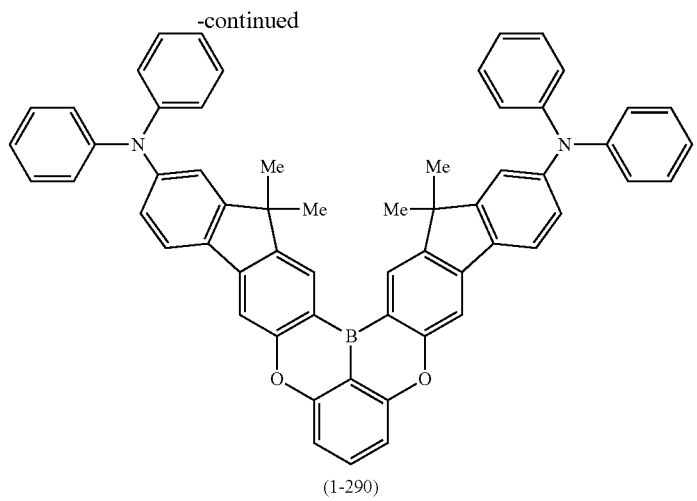

(1-290)

The structure of compound (1-290) thus obtained was identified by NMR measurement.

¹H-NMR (400 MHz, CDCl₃): δ=8.64 (s, 2H), 7.75 (m, 3H), 7.69 (d, 2H), 7.30 (t, 8H), 7.25 (s, 2H), 7.20 (m, 10H), 7.08 (m, 6H), 1.58 (s, 12H)

Synthesis Example (2): Synthesis of Compound (1-139)

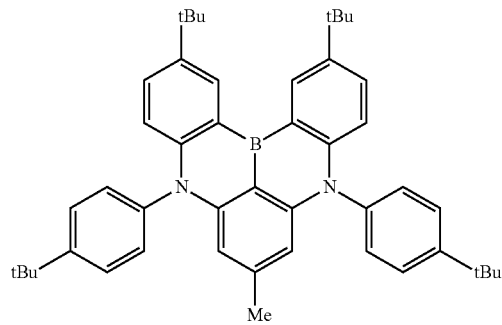

(1-139)

Compound (1-139) was synthesized using a similar method to that in the Synthesis Example described above.

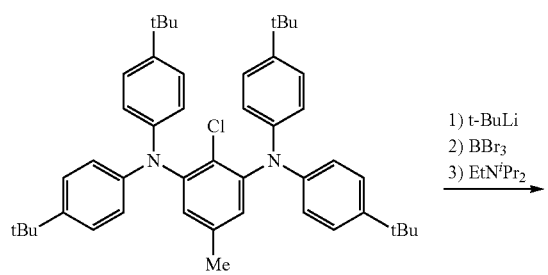

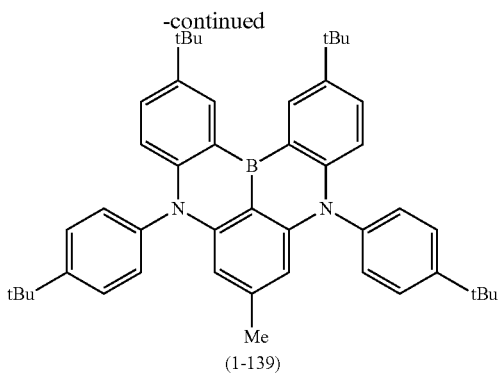

(1-139)

The structure of compound (1-139) thus obtained was identified by NMR measurement.

¹H-NMR (500 MHz, CDCl₃): δ=1.47 (s, 36H), 2.17 (s, 3H), 5.97 (s, 2H), 6.68 (d, 2H), 7.28 (d, 4H), 7.49 (dd, 2H), 7.67 (d, 4H), 8.97 (d, 2H).

Synthesis Example (3): Synthesis of Compound (1-151)

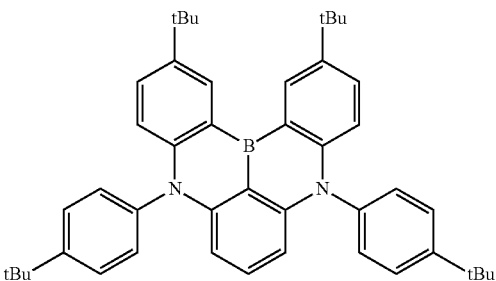

(1-151)

Compound (1-151) was synthesized using a similar method to that in the Synthesis Example described above.

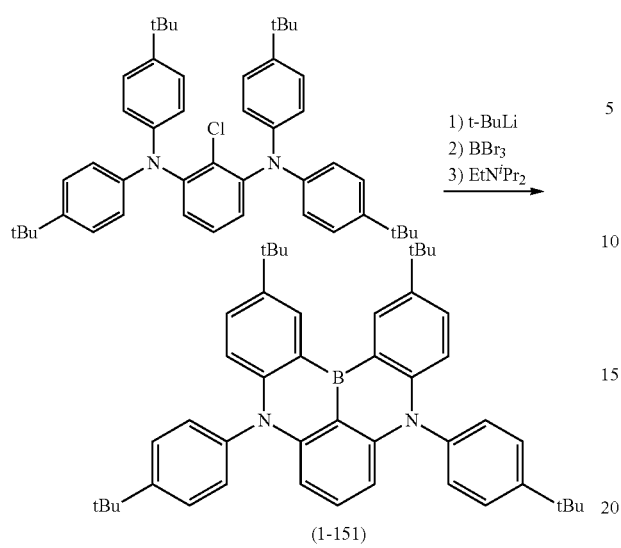

1) t-BuLi
2) BBr₃
3) EtN$^i$Pr₂

(1-151)

The structure of compound (1-151) thus obtained was identified by NMR measurement.

¹H-NMR (500 MHz, CDCl₃): δ=1.46 (s, 18H), 1.47 (s, 18H), 6.14 (d, 2H), 6.75 (d, 2H), 7.24 (t, 1H), 7.29 (d, 4H), 7.52 (dd, 2H), 7.67 (d, 4H), 8.99 (d, 2H).

Synthesis Example (4): Synthesis of Compound (2-1)

11,11-diphenyl-6-(pyren-1-yl)-11H-benzo[a]fluorene

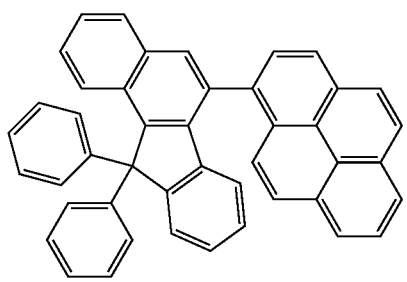

(2-1)

In a nitrogen atmosphere, 1-bromo-2-methoxynaphthalene (9.5 g), bis(pinacolato) diboron (12.2 g), potassium acetate (11.8 g), a (1,1'-bis(diphenylphosphino) ferrocene) palladium(II) dichloride.dichloromethane complex (0.98 g) as a palladium catalyst, and cyclopentyl methyl ether (CPME, 143 mL) were put in a flask, and were stirred at a reflux temperature for four hours in a nitrogen atmosphere. The reaction solution was cooled to room temperature, water was added thereto, and ethyl acetate was further added thereto for liquid separation extraction. The organic layer was separated, then dried, concentrated and purified with an activated carbon short pass column (eluent: toluene) to obtain intermediate A (11.3 g).

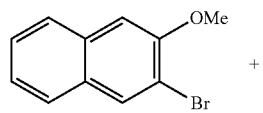

+

-continued

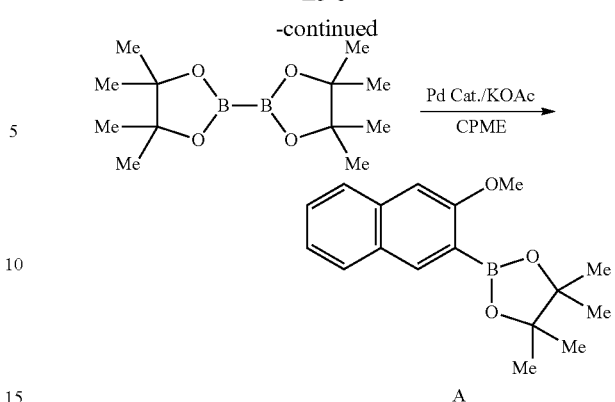

A

In a nitrogen atmosphere, intermediate A (11.3 g), methyl 2-bromobenzoate (8.6 g), potassium phosphate (16.9 g), tetrakis(triphenylphosphine) palladium (1.4 g) as a palladium catalyst, toluene (85 mL), ethanol (17 mL), and water (9 mL) were put in a flask and stirred at a reflux temperature for seven hours in a nitrogen atmosphere. The reaction solution was cooled to room temperature, water was added thereto, and toluene was further added thereto for liquid separation extraction. The organic layer was separated, and was then dried and concentrated. The crude product was purified with a silica gel column (eluent: toluene) to obtain intermediate B (9.1 g).

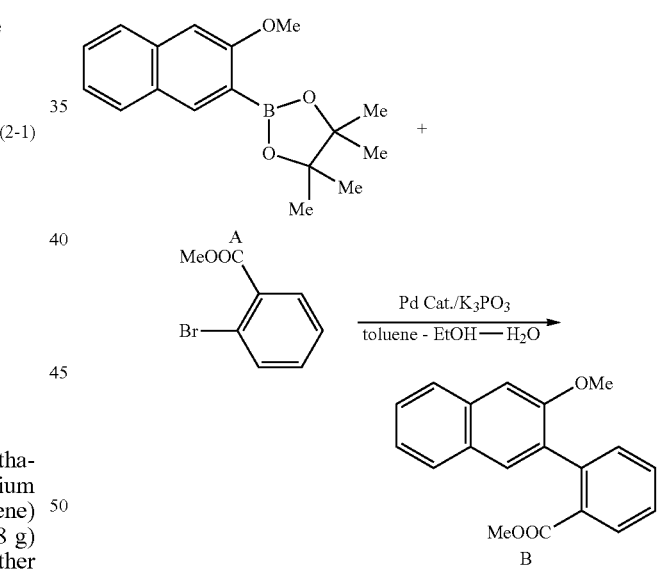

In a nitrogen atmosphere, intermediate B (9.1 g) and tetrahydrofuran (THF, 21 mL) were put in a flask and cooled in an ice bath. Thereafter, a 1 M phenylmagnesium bromide/THF solution (94 mL) was added dropwise thereto in a nitrogen atmosphere, and the resulting mixture was stirred at a reflux temperature for three hours. The solution was cooled. Thereafter, a saturated ammonium chloride aqueous solution was added thereto to stop the reaction, and then ethyl acetate was added thereto, and the solvent was extracted. The organic layer was separated, and was then dried and concentrated. The crude product was purified with a silica gel column (eluent: toluene) to obtain intermediate C (12.3 g).

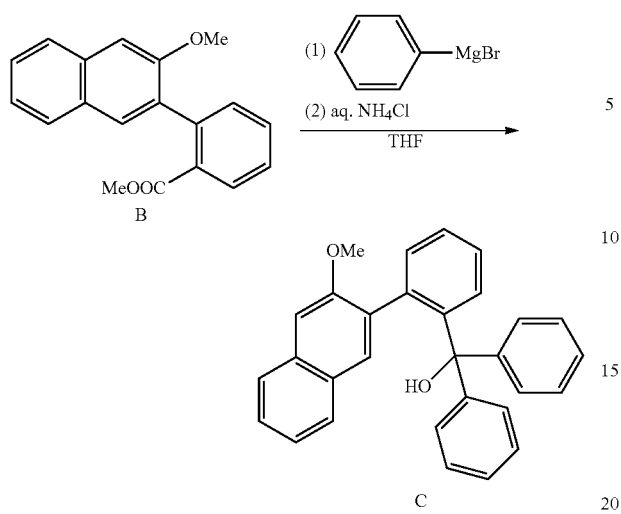

In a nitrogen atmosphere, intermediate C (12.3 g) and acetic acid (117 mL) were put in a flask. One drop of concentrated sulfuric acid was added thereto, and then the resulting mixture was stirred at 90° C. for three hours in a nitrogen atmosphere. The solution was cooled. Thereafter, water was added thereto. Thereafter, the precipitate was filtered, washed with water, and dried to obtain intermediate D (10.6 g).

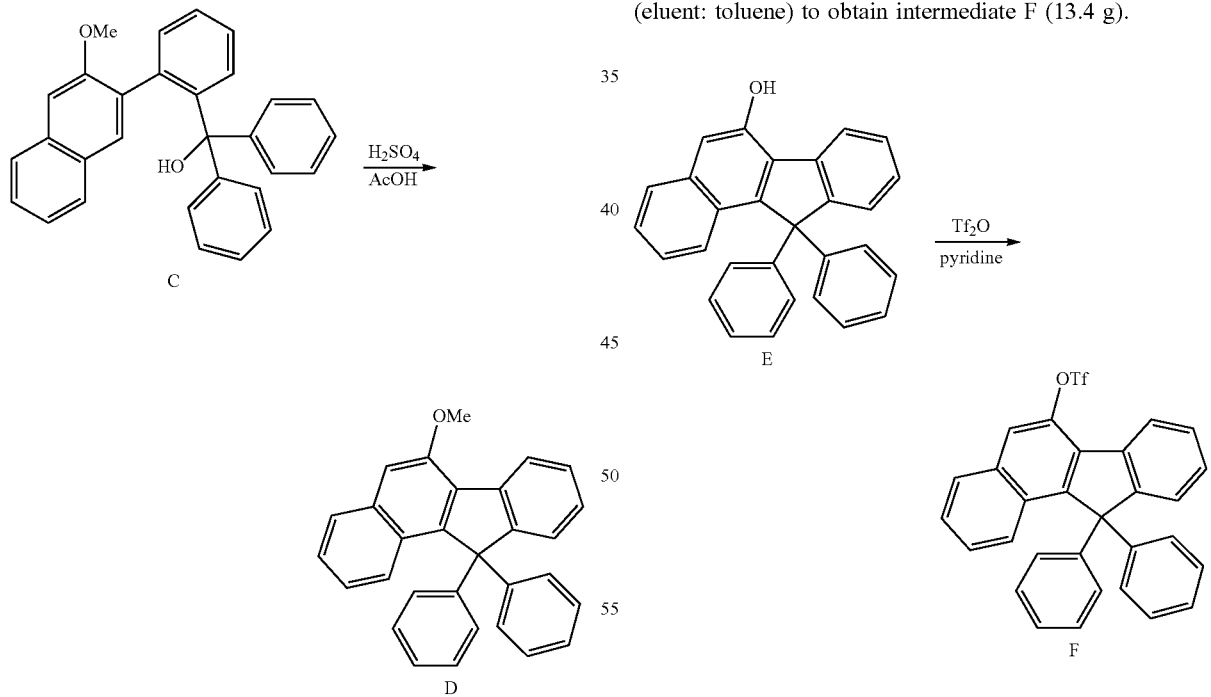

In a nitrogen atmosphere, intermediate D (10.6 g), pyridine hydrochloride (15.4 g), and N-methylpyrrolidone (NMP, 10 mL) were put in a flask and stirred in a nitrogen atmosphere at 185° C. for four hours. The solution was cooled. Thereafter, water was added thereto. Thereafter, the precipitate was filtered, washed with water, and dried to obtain intermediate E (10.1 g).

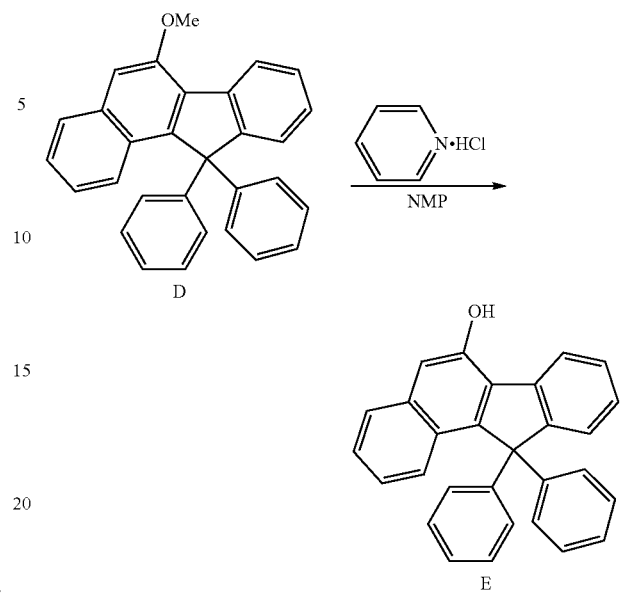

In a nitrogen atmosphere, intermediate E (10 g) and pyridine (100 mL) were put in a flask and cooled in an ice bath. Thereafter, trifluoromethanesulfonic anhydride (18.3 g) was added dropwise thereto in a nitrogen atmosphere. The solution was stirred for three hours as it was. Thereafter, water was added thereto to stop the reaction. The precipitate was filtered and purified with a silica gel short pass column (eluent: toluene) to obtain intermediate F (13.4 g).

In a nitrogen atmosphere, intermediate F (3 g), 1-pyreneboronic acid (2.1 g), potassium phosphate (2.5 g), tetrakis (triphenylphosphine) palladium (0.2 g) as a palladium catalyst, 1,2,4-trimethyl benzene (24 mL), t-butyl alcohol (3 mL), and water (1.5 mL) were put in a flask and stirred at a reflux temperature for four hours in a nitrogen atmosphere. The reaction solution was cooled to room temperature, water was added thereto, and toluene was further added thereto for liquid separation extraction. The organic layer was separated, and was then dried and concentrated. The crude product was purified with a silica gel column (eluent: toluene/heptane=3/1 (volume ratio)), and then was purified by sublimation to obtain compound (2-1) (1.2 g).

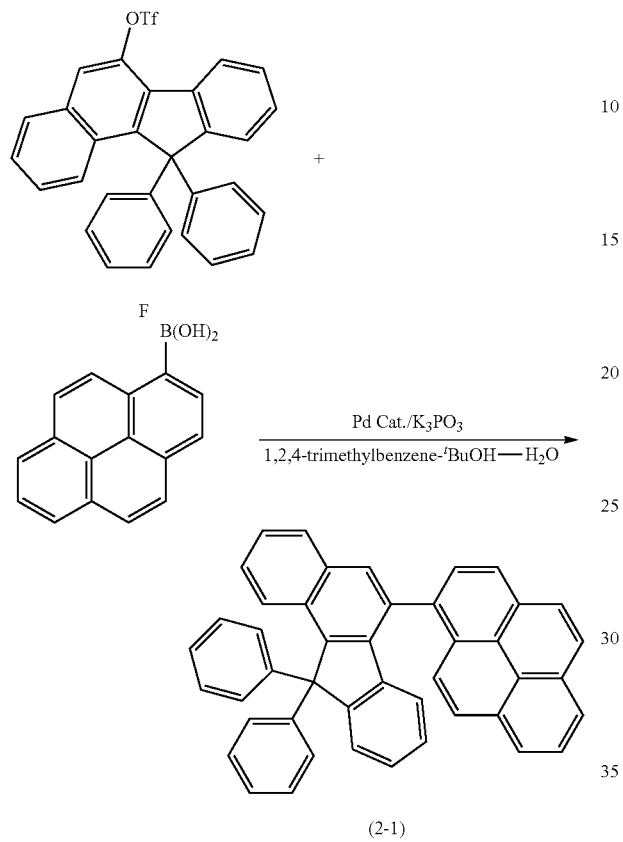

(2-1)

The structure of compound (2-1) thus obtained was identified by NMR measurement.

$^1$H-NMR (CDCl$_3$): 6.0 (d, 1H), 6.6 (dt, 1H), 7.0 (dt, 1H), 7.2 to 7.5 (m, 13H), 7.9 to 8.0 (m, 5H), 8.0 (t, 1H), 8.2 to 8.3 (m, 5H), 8.4 (d, 1H)

Synthesis Example (5): Synthesis of Compound (2-46)

6-(6-(naphthalen-2-yl) pyren-1-yl)-11,11-diphenyl-11H-benzo[a]fluorene

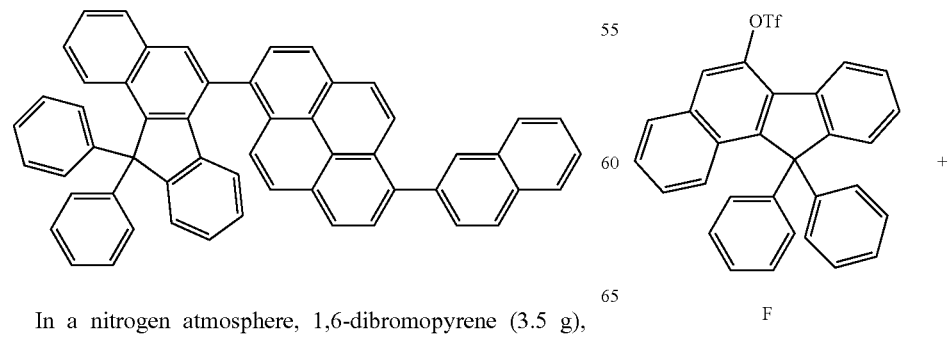

(2-46)

In a nitrogen atmosphere, 1,6-dibromopyrene (3.5 g), 2-naphthylboronic acid (1.7 g), potassium carbonate (2.7 g), tetrakis(triphenylphosphine) palladium (0.3 g) as a palladium catalyst, toluene (35 mL), and water (9 mL) were put in a flask and stirred at a reflux temperature for three hours in a nitrogen atmosphere. The reaction solution was cooled to room temperature, water was added thereto, and toluene was further added thereto for liquid separation extraction. The organic layer was separated, and was then dried and concentrated. The crude product was purified with a silica gel column (eluent: toluene/heptane=6/1 (volume ratio)) to obtain intermediate G (2.1 g).

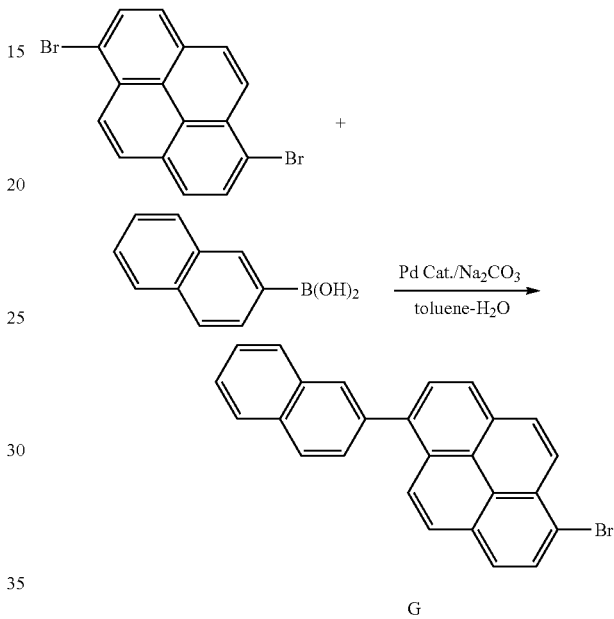

G

In a nitrogen atmosphere, intermediate F (7 g), bis(pinacolato) diboron (4.1 g), potassium acetate (4.0 g), a (1,1'-bis(diphenylphosphino) ferrocene) palladium(II) dichloride.dichloromethane complex (0.3 g) as a palladium catalyst, and cyclopentyl methyl ether (CPME, 67 mL) were put into a flask, and were stirred at a reflux temperature for four hours in a nitrogen atmosphere. The reaction solution was cooled to room temperature, water was added thereto, and ethyl acetate was further added thereto for liquid separation extraction. The organic layer was separated, then dried, concentrated and purified with an activated carbon short pass column (eluent: toluene) to obtain intermediate H (4.6 g).

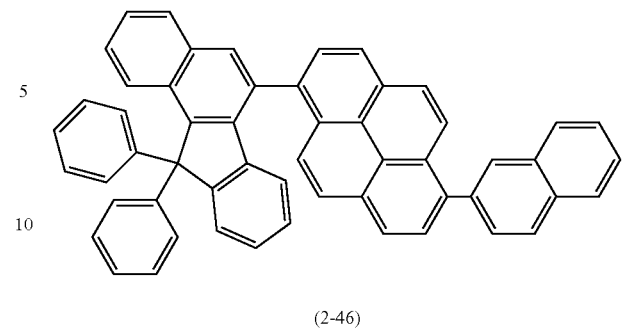

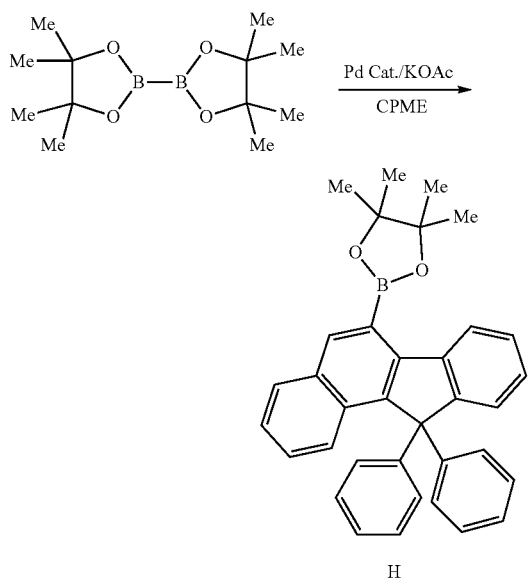

In a nitrogen atmosphere, intermediate G (0.8 g), intermediate H (0.9 g), potassium phosphate (0.9 g), tetrakis(triphenylphosphine) palladium (0.1 g) as a palladium catalyst, 1,2,4-trimethyl benzene (12 mL), t-butyl alcohol (2 mL), and water (1 mL) were put in a flask and stirred at a reflux temperature for 14 hours in a nitrogen atmosphere. The reaction solution was cooled to room temperature, water was added thereto, and toluene was further added thereto for liquid separation extraction. The organic layer was separated, and was then dried and concentrated. The crude product was purified with a silica gel column (eluent: toluene/heptane=⅓ (volume ratio)), and then was purified by sublimation to obtain compound (2-46) (1.0 g).

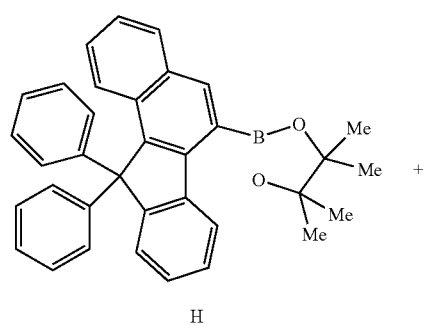

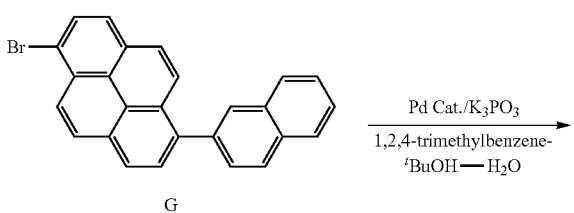

(2-46)

The structure of compound (2-46) thus obtained was identified by NMR measurement.

$^1$H-NMR (CDCl$_3$): 6.0 (d, 1H), 6.6 (dt, 1H), 7.0 (dt, 1H), 7.2 to 7.6 (m, 15H), 7.8 to 8.2 (m, 14H), 8.2 to 8.3 (m, 2H).

Synthesis Example (6): Synthesis of Compound (2-1001)

3,9-di(pyren-1-yl) spiro[benzo[a]fluorene-11,9'-fluorene]

(2-1001)

In a nitrogen atmosphere, a flask containing pyrene-1-boronic acid (5 g), ethylene glycol (3.8 g), and toluene (30 mL) was stirred at a reflux temperature for three hours. After the reaction, the solution was cooled. Water was added thereto, and the resulting mixture was stirred. The organic layer was separated, and was then concentrated under reduced pressure to obtain a crude product. The crude product was caused to pass through a silica gel short pass column (eluent: toluene). Thereafter, the eluate was concentrated to obtain 2-(pyren-1-yl)-1,3,2-dioxaborolane (4.2 g).

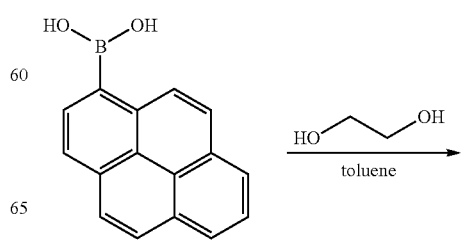

-continued

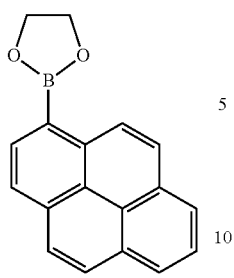

In a nitrogen atmosphere, intermediate I (3.8 g) synthesized by a method described in JP 2009-184993 A, 2-(pyren-1-yl)-1,3,2-dioxaborolane (3.3 g), chlorophenylallyl [1,3-bis(2,6-diisopropylphenyl) imidazol-2-ylidene]palladium(II) (19 mg) as a palladium catalyst, potassium carbonate (3.2 g), tetrabutylammonium bromide (TBAB, 0.6 g), cyclopentyl methyl ether (CPME, 20 mL), and water (2 mL) were put in a flask and heated and stirred at a reflux temperature for nine hours. After the reaction, the reaction solution was cooled. Water was added thereto, and the resulting mixture was stirred. Thereafter, the precipitate was filtered. The precipitate was dried, then heated and dissolved in chlorobenzene, and then filtered through a silica gel short pass column (eluent: toluene). The eluate was concentrated to obtain a solid. The solid was filtered and dried, and then subjected to sublimation purification to obtain compound (2-1001) (2.2 g).

Synthesis Example (7): Synthesis of Compound (2-350)

2-(pyren-1-yl) triphenylene

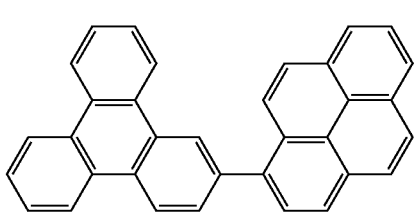

In a nitrogen atmosphere, 4,4,5,5-tetramethyl-2-(triphenylen-2-yl)-1,3,2-dioxaborolane (3.0 g), 1-bromopyrene (2.2 g), chlorophenylallyl [1,3-bis(2,6-diisopropylphenyl) imidazol-2-ylidene] palladium(II) (25 mg) as a palladium catalyst, potassium carbonate (2.2 g), tetrabutylammonium bromide (TBAB, 0.8 g), cyclopentyl methyl ether (CPME, 20 mL), and water (2 mL) were put in a flask and heated and stirred at a reflux temperature for two hours. After the reaction, the reaction solution was cooled. Water was added thereto, and the resulting mixture was stirred. Thereafter, the precipitate was filtered. The precipitate was dried, then heated and dissolved in chlorobenzene, and then filtered through a silica gel short pass column (eluent: toluene). The eluate was concentrated to obtain a solid. The solid was filtered and dried, and then subjected to sublimation purification to obtain compound (2-350) (3.3 g).

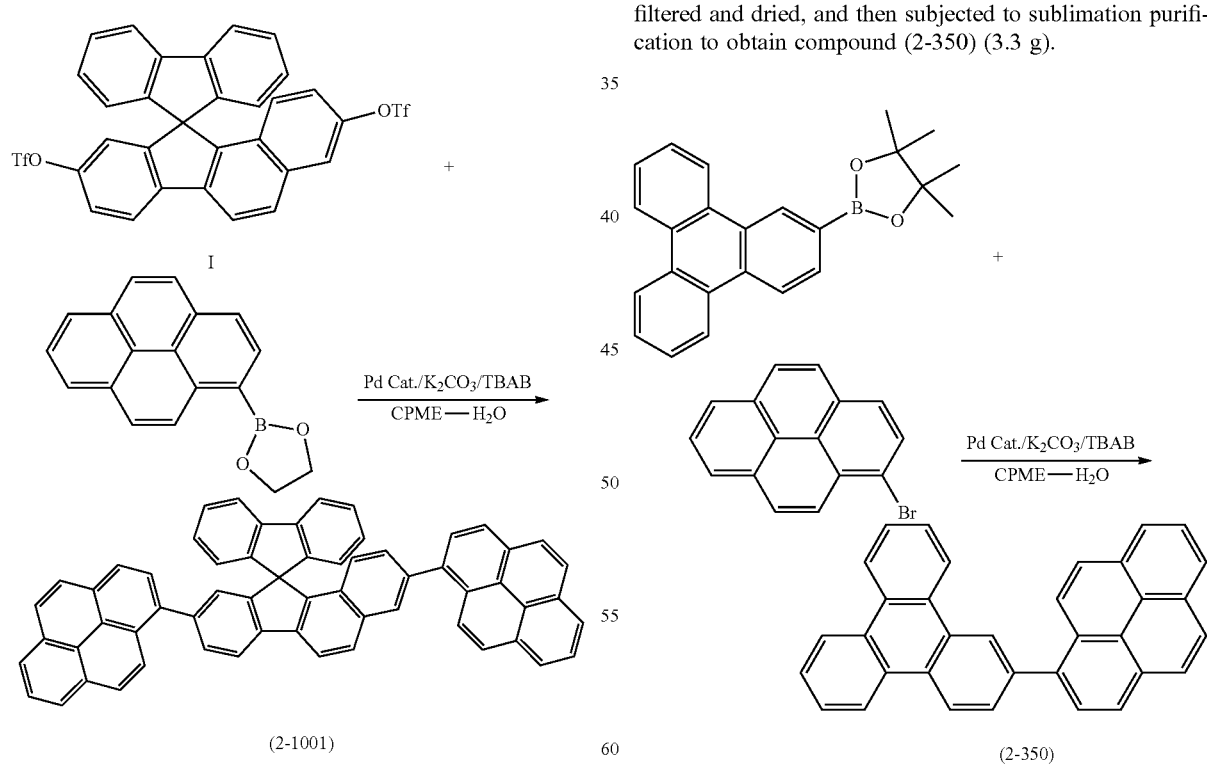

The structure of compound (2-1001) thus obtained was identified by NMR measurement.

$^1$H-NMR (CDCl$_3$): 6.9 to 7.0 (m, 4H), 7.2 (t, 2H), 7.4 (dd, 1H), 7.4 (dt, 2H), 7.7 (dd, 1H), 7.8 to 7.9 (m, 2H), 7.9 to 8.1 (m, 9H), 8.1 to 8.2 (m, 13H)

The structure of compound (2-350) thus obtained was identified by NMR measurement.

$^1$H-NMR (CDCl$_3$): 7.6 to 7.7 (m, 4H), 7.9 (dd, 1H), 8.0 (m, 2H), 8.1 to 8.2 (m, 4H), 8.2 (m, 1H), 8.3 (m, 2H), 8.7 to 8.8 (m, 4H), 8.8 (d, 1H), 8.9 (d, 1H)

Synthesis Example (8): Synthesis of Compound (2-1080)

3,9-bis(7-(t-butyl)pyren-2-yl) spiro[benzo[a]fluorene-11,9'-fluorene]

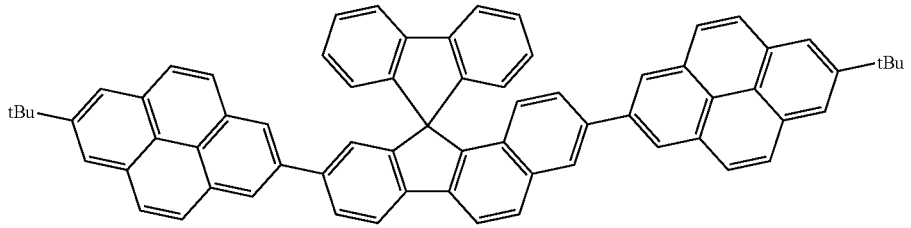

(2-1080)

In a nitrogen atmosphere, intermediate J (1.7 g) synthesized by a method described in WO 2015/141608 A, 2-bromo-7-(t-butyl) pyrene (2 g), chlorophenylallyl [1,3-bis(2,6-diisopropylphenyl) imidazol-2-ylidene]palladium(II) (9 mg) as a palladium catalyst, potassium carbonate (1.6 g), tetrabutylammonium bromide (TBAB, 0.3 g), cyclopentyl methyl ether (CPME, 20 mL), and water (2 mL) were put in a flask and heated and stirred at a reflux temperature for four hours. After the reaction, the reaction solution was cooled. Water was added thereto, and the resulting mixture was stirred. Thereafter, the precipitate was filtered. The precipitate was dried, then heated and dissolved in chlorobenzene, and then filtered through a silica gel short pass column (eluent: toluene). The eluate was concentrated to obtain a solid. The solid was filtered and dried, and then subjected to sublimation purification to obtain compound (2-1080) (1.6 g)

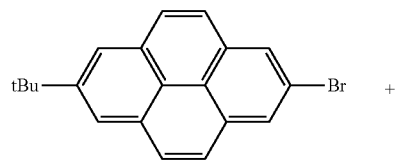

+

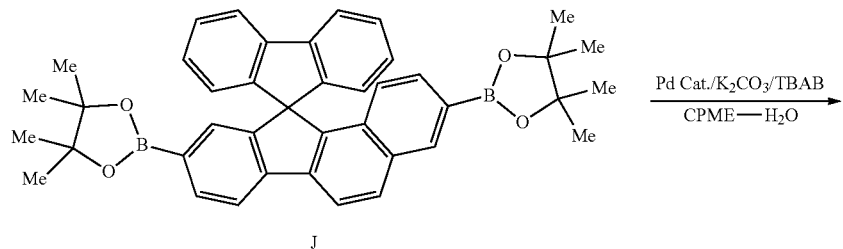

J

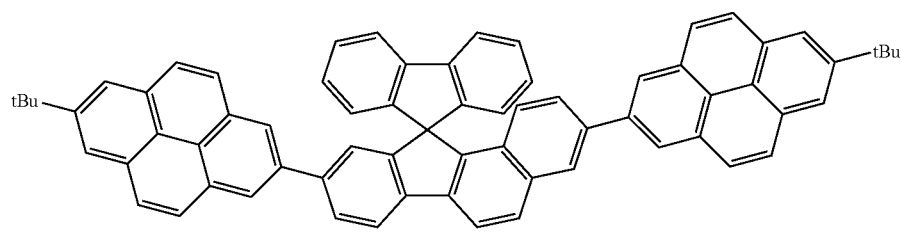

(2-1080)

The structure of compound (2-1080) thus obtained was identified by NMR measurement.

¹H-NMR (CDCl₃): 1.6 (s, 9H), 1.6 (s, 9H), 6.9 (d, 2H), 6.9 (d, 1H), 7.1 (dt, 2H), 7.2 (d, 1H), 7.5 (dt, 2H), 7.6 (dd, 1H), 7.9 (dd, 1H), 8.0 to 8.2 (m, 19H), 8.3 (s, 3H).

Synthesis Example (9): Synthesis of Compound (2-174)

2-(pyren-1-yl)naphtho[2,3-b]benzofuran

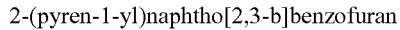

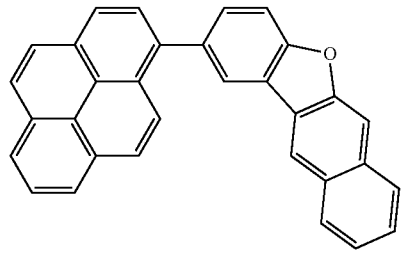
(2-174)

In a nitrogen atmosphere, 1-pyreneboronic acid (1.0 g), 2-bromobenzo[b]naphtho[2,3-d] furan (1.1 g) synthesized by a method described in WO 2014/141725 A, tetrakis (triphenylphosphine) palladium (0.09 g) as a palladium catalyst, potassium phosphate (1.7 g), xylene (15 mL), t-butyl alcohol (5 mL), and water (3 mL) were put in a flask and heated and stirred at a reflux temperature for two hours. After the reaction, the reaction solution was cooled. Water and ethyl acetate were added thereto, and the resulting mixture was stirred. Thereafter, the precipitate was filtered. The crude product was washed with water and methanol. The precipitate was dried, then heated and dissolved in chlorobenzene, and then filtered through a silica gel short pass column (eluent: toluene). The eluate was concentrated to obtain a solid. The solid was further subjected to reprecipitation with chlorobenzene for purification. The obtained solid was dried and then subjected to sublimation purification to obtain compound (2-174) (1.0 g).

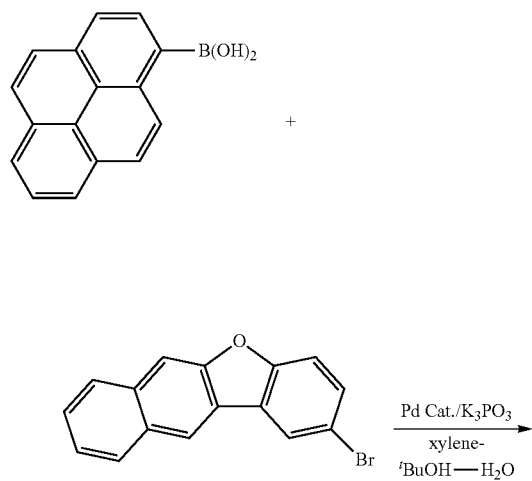

-continued

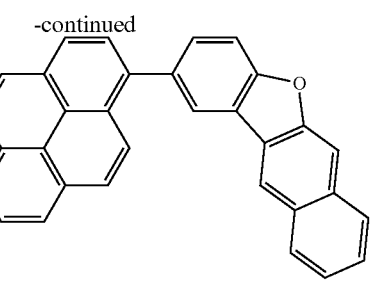
(2-174)

The structure of compound (2-174) thus obtained was identified by NMR measurement.

¹H-NMR (CDCl₃): 7.5 (m, 1H), 7.5 to 7.6 (m, 1H), 7.7 to 7.8 (m, 2H), 8.0 to 8.3 (m, 13H), 8.5 (s, 1H).

Synthesis Example (10): Synthesis of Compound (2-356)

2-(pyren-1-yl) dibenzo[g,p]chrysene

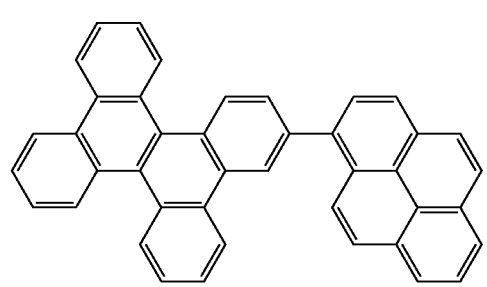
(2-356)

In a nitrogen atmosphere, 3-bromodibenzo[g,p]chrysene (14 g) synthesized by a method described in JP 2011-006397 A and tetrahydrofuran (THF, 200 mL) were put in a flask, and the resulting mixture was formed into a homogeneous solution. Thereafter, the solution was cooled to −78° C. in a dry ice-acetone bath, and a 1.6 M n-butyllithium/hexane solution (28 mL) was added dropwise thereto. The resulting solution was stirred at the same temperature for 0.5 hours, and then 2-isopropoxy-4,4,5,5-tetramethyl-1,3,2-dioxaborolane (12.8 g) was added thereto. The resulting solution was stirred at the same temperature for three hours. Thereafter, the temperature was raised, and diluted hydrochloric acid was added thereto to stop the reaction. Toluene was added thereto, and extraction was performed. Thereafter, the organic layer was concentrated, and the obtained crude product was purified with a silica gel column (eluent: toluene/heptane=7/3 (volume ratio)) to obtain intermediate K (11.5 g).

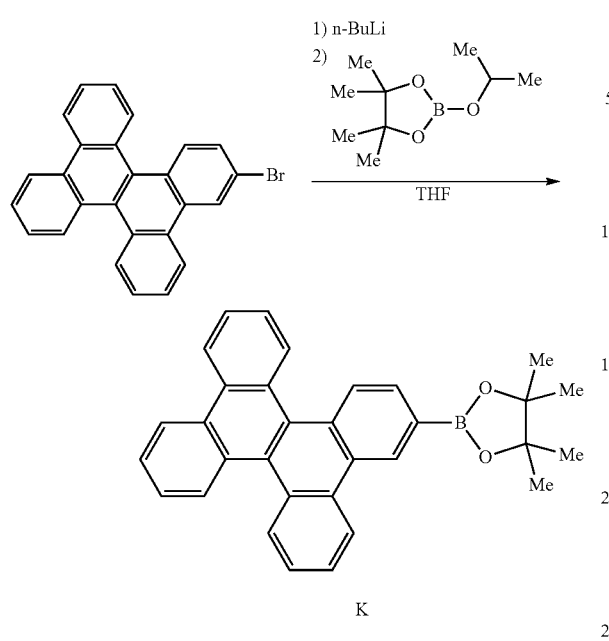

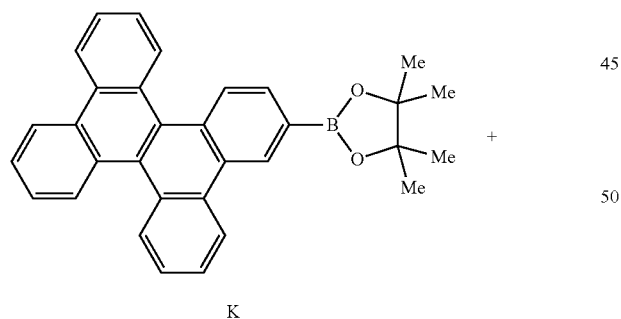

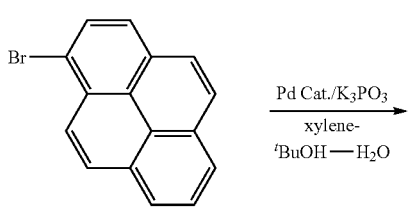

In a nitrogen atmosphere, intermediate K (1.0 g), 1-bromopyrene (0.59 g), bis(di t-butyl (4-dimethylaminophenyl) phosphine) dichloropalladium (16 mg) as a palladium catalyst, potassium phosphate (0.9 g), xylene (10 mL), t-butyl alcohol (3 mL), and water (2 mL) were put in a flask and stirred at reflux temperature for two hours. After the reaction, the reaction solution was cooled. Water and ethyl acetate were added thereto, and the resulting mixture was stirred. Thereafter, the precipitated precipitate was filtered. The obtained crude product was purified with a silica gel short pass column (eluent: toluene) and then subjected to reprecipitation with toluene/heptane for purification. The obtained solid was dried and then subjected to sublimation purification to obtain compound (2-356) (0.7 g).

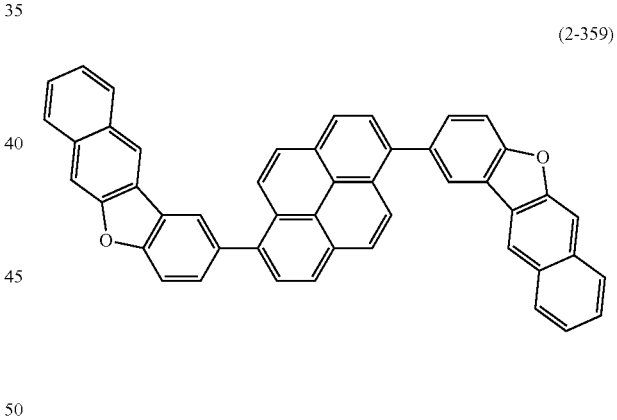

(2-356)

The structure of compound (2-356) thus obtained was identified by NMR measurement.

$^1$H-NMR (CDCl$_3$): 7.7 (m, 6H), 7.9 (dd, 1H) 8.0 to 8.1 (m, 2H), 8.1 to 8.3 (m, 5H), 8.3 (d, 1H), 8.4 (d, 1H), 8.7 to 8.8 (m, 5H), 8.9 (m, 1H), 8.9 (d, 1H), 9.0 (d, 1H).

Synthesis Example (11): Synthesis of Compound (2-359)

1,6-bis (naphtho[2,3-b]benzofuran-2-yl)-3a',5a'-dihydropyrene (2-359)

In a nitrogen atmosphere, 2-bromobenzo[b]naphtho[2,3-d]furan (10.8 g) synthesized by a method described in WO 2014/141725 A and tetrahydrofuran (THF, 200 mL) were put in a flask and cooled to −78° C. in a dry ice-acetone bath. A 1.6 M n-butyllithium/heptane solution (25 mL) was added dropwise thereto. The resulting solution was stirred at the same temperature for one hour, and then 2-isopropoxy-4,4, 5,5-tetramethyl-1,3,2-dioxaborolane (10 g) was added thereto. The resulting solution was stirred at the same temperature for two hours. Thereafter, the temperature was raised, and diluted hydrochloric acid was added thereto to stop the reaction. Toluene was added thereto, and extraction was performed. Thereafter, the organic layer was concentrated, and the obtained crude product was purified with a silica gel column (eluent: toluene/heptane=7/3 (volume ratio)) to obtain intermediate L (9.2 g).

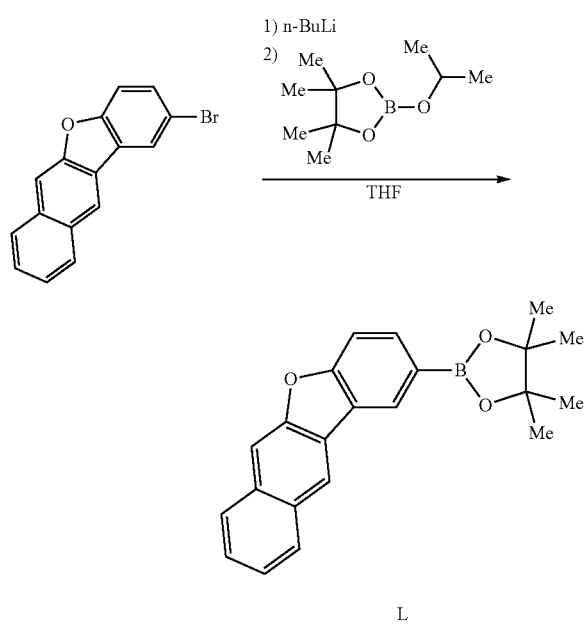

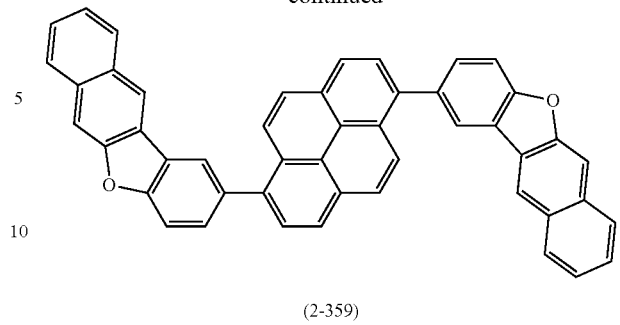

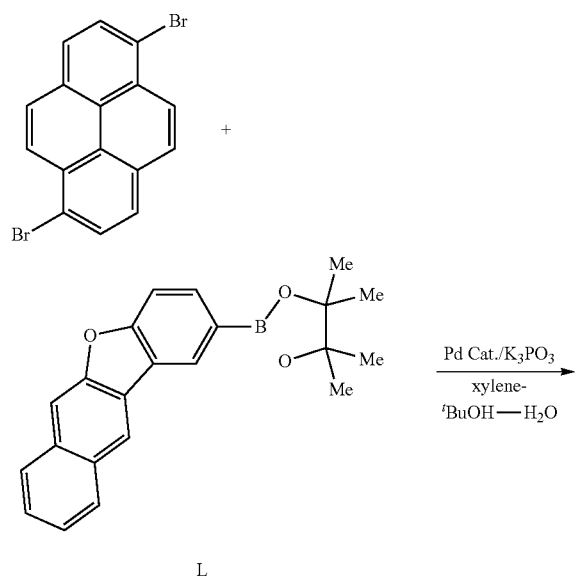

In a nitrogen atmosphere, 1,6-dibromopyrene (1.0 g), intermediate L (2.0 g), bis(di t-butyl (4-dimethylaminophenyl) phosphine) dichloropalladium (20 mg) as a palladium catalyst, potassium phosphate (2.4 g), xylene (15 mL), t-butyl alcohol (3 mL), and water (2 mL) were put in a flask and stirred at a reflux temperature for two hours. After the reaction, the reaction solution was cooled. Water and ethyl acetate were added thereto, and the resulting mixture was stirred. Thereafter, the precipitated precipitate was filtered. The obtained crude product was purified with a silica gel short pass column (eluent: toluene) and then washed with hot chlorobenzene for purification. The obtained solid was dried and then subjected to sublimation purification to obtain compound (2-359) (1.6 g)

(2-359)

Compound (2-359) thus obtained was identified by LC-MS measurement.

MS (ACPI) m/z=635 (M+H)

Other compounds used in the present invention can be synthesized by a method according to the Synthesis Examples described above by appropriately changing the compounds of raw materials.

Hereinafter, Examples of an organic EL element using the compounds according to an embodiment of the present invention will be described in order to describe the present invention in more detail, but the present invention is not limited thereto.

Organic EL elements according to Examples 1 to 12 and Comparative Example 1 were manufactured. For each of the organic EL elements, voltage (V), emission wavelength (nm), and external quantum efficiency (%) as characteristics at the time of light emission at 1000 cd/m² were measured.

A quantum efficiency of a luminescent element includes an internal quantum efficiency and an external quantum efficiency. The internal quantum efficiency indicates a ratio at which external energy injected as electrons (or holes) into a light emitting layer of the luminescent element is purely converted into photons. Meanwhile, the external quantum efficiency is calculated based on the amount of these photons emitted to an outside of the luminescent element. A part of the photons generated in the light emitting layer is absorbed or reflected continuously inside the luminescent element, and is not emitted to the outside of the luminescent element. Therefore, the external quantum efficiency is lower than the internal quantum efficiency.

A method for measuring the external quantum efficiency is as follows. Using a voltage/current generator R6144 manufactured by Advantest Corporation, a voltage at which luminance of an element was 1000 cd/m² was applied to cause the element to emit light. Using a spectral radiance meter SR-3AR manufactured by TOPCON Co., spectral radiance in a visible light region was measured from a direction perpendicular to a light emitting surface. Assuming that the light emitting surface is a perfectly diffusing surface, a numerical value obtained by dividing a spectral radiance value of each measured wavelength component by wavelength energy and multiplying the obtained value by n is the number of photons at each wavelength. Subsequently, the number of photons is integrated in the observed entire wavelength region, and this number is taken as the total number of photons emitted from the element. A numerical value obtained by dividing an applied current value by an elementary charge is taken as the number of carriers injected into the element. The external quantum efficiency is a numerical value obtained by dividing the total number of photons emitted from the element by the number of carriers injected into the element.

The following Table 1 indicates a material composition of each layer and EL characteristic data in organic EL elements manufactured according to Examples 1 to 12 and Comparative Example 1.

TABLE 1

| | Hole Injection layer 1 (40 nm) | Hole Injection layer 2 (5 nm) | Hole Transport layer 1 (15 nm) | Hole Transport layer 2 (10 nm) | Light emitting layer (25 nm) Host | Light emitting layer (25 nm) Dopant | Electron Transport layer 1 (5 nm) | Electron Transport layer 2 (25 nm) | Negative Electrode (1 nm/ 100 nm) | Wave length (nm) | Voltage (V) | External quantum efficiency |
|---|---|---|---|---|---|---|---|---|---|---|---|---|
| | | | | | Example | | | | | | | |
| 1 | HI | HAT-CN | HT-1 | HT-2 | 2-1 | 1-139 | ET-1 | ET-2 + Liq | Liq/MgAg | 462 | 4.1 | 6.7 |
| 2 | HI | HAT-CN | HT-1 | HT-2 | 2-1001 | 1-139 | ET-1 | ET-2 + Liq | Liq/MgAg | 465 | 3.8 | 6.5 |
| 3 | HI | HAT-CN | HT-1 | HT-2 | 2-1080 | 1-139 | ET-1 | ET-2 + Liq | Liq/MgAg | 463 | 3.7 | 6.3 |
| 4 | HI | HAT-CN | HT-1 | HT-2 | 2-46 | 1-139 | ET-1 | ET-2 + Liq | Liq/MgAg | 462 | 4.1 | 6.3 |
| 5 | HI | HAT-CN | HT-1 | HT-2 | 2-174 | 1-139 | ET-1 | ET-2 + Liq | Liq/MgAg | 463 | 4.0 | 6.1 |
| 6 | HI | HAT-CN | HT-1 | HT-2 | 2-350 | 1-139 | ET-1 | ET-2 + Liq | Liq/MgAg | 462 | 3.9 | 6.0 |
| 7 | HI | HAT-CN | HT-1 | HT-2 | 2-356 | 1-139 | ET-1 | ET-2 + Liq | Liq/MgAg | 462 | 3.9 | 6.0 |
| 8 | HI | HAT-CN | HT-1 | HT-3 | 2-1 | 1-139 | ET-1 | ET-2 + Liq | Liq/MgAg | 463 | 4.1 | 6.9 |
| 9 | HI | HAT-CN | HT-1 | HT-3 | 2-174 | 1-139 | ET-1 | ET-2 + Liq | Liq/MgAg | 461 | 4.0 | 6.4 |
| 10 | HI | HAT-CN | HT-1 | HT-3 | 2-359 | 1-139 | ET-1 | ET-2 + Liq | Liq/MgAg | 462 | 3.7 | 6.3 |
| 11 | HI | HAT-CN | HT-1 | HT-2 | 2-1 | 1-151 | ET-1 + Liq | | Liq/MgAg | 465 | 4.5 | 7.2 |
| 12 | HI | HAT-CN | HT-1 | HT-2 | 2-1 | 1-151 | ET-3 | ET-4 + Liq | Liq/MgAg | 466 | 4.0 | 7.0 |
| | | | | | Comparative Example | | | | | | | |
| 1 | HI | HAT-CN | HT-1 | HT-2 | A | 1-139 | ET-1 | ET-2 + Liq | Liq/MgAg | 462 | 5.0 | 5.2 |

In Table 1, "HI" represents $N^4,N^{4'}$-diphenyl-$N^4,N^{4'}$-bis(9-phenyl-9H-carbazol-3-yl)-[1,1'-biphenyl]-4,4'-diamine, "HAT-CN" represents 1,4,5,8,9,12-hexaazatriphenylene hexacarbonitrile, "HT-1" represents N-([1,1'-biphenyl]-4-yl)-9,9-dimethyl-N-(4-(9-phenyl-9H-carbazol-3-yl) phenyl)-9H-fluorene-2-amine[1,1'-biphenyl]-4-amine, "HT-2" represents N,N-bis(4-(dibenzo[b,d]furan-4-yl) phenyl)-[1, 1': 4',1"-terphenyl]-4-amine, "HT-3" represents N-([1,1'-biphenyl]-2-yl)-N-(9,9-dimethyl-9H-fluoren-2-yl)-9,9'-spirobi[fluorene]-4-amine, "ET-1" represents 4,6,8,10-tetraphenyl[1,4]benzoxaborinino[2,3,4-kl]phenoxaborinine, "ET-2" represents 3,3'-((2-phenylanthracene-9,10-diyl) bis (4,1-phenylene)) bis(4-methylpyridine), "ET-3" represents 9-(7-(dimesitylboryl)-9,9-dimethyl-9H-fluoren-2-yl)-3,6-dimethyl-9H-carbazole, "ET-4" represents 4-(3-(4-(10-phenylanthracen-9-yl) naphthalen-1-yl) phenyl) pyridine, and Comparative Example compound A represents 9-([$_1$,2'-binaphthalen]-7-yl)-10-phenylanthracene. Chemical structures thereof are indicated below together with "Liq".

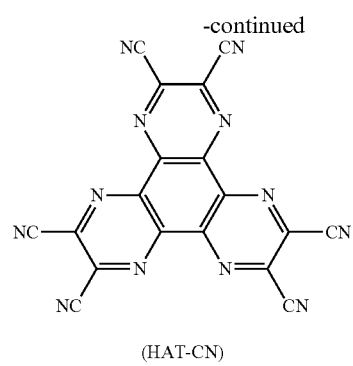

(HAT-CN)

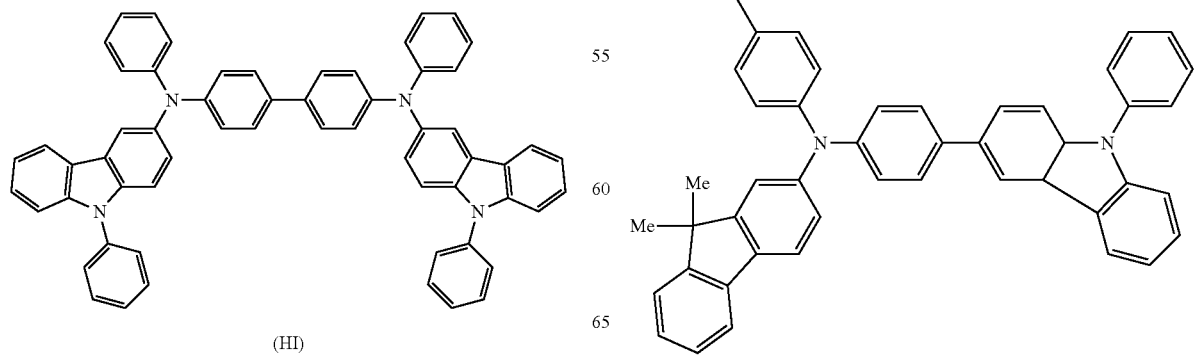

(HI)

(HT-1)

(HT-2)

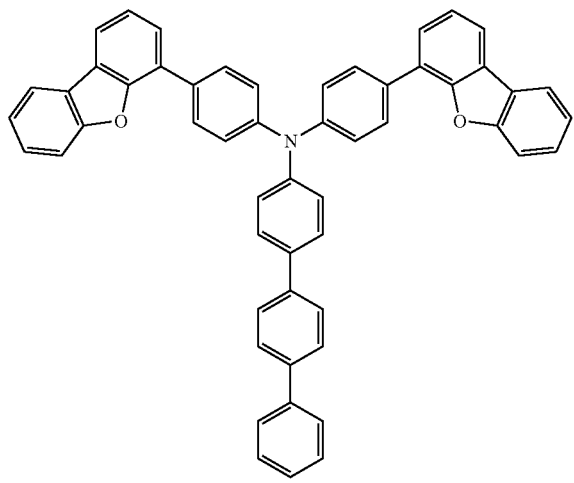

(HT-3)

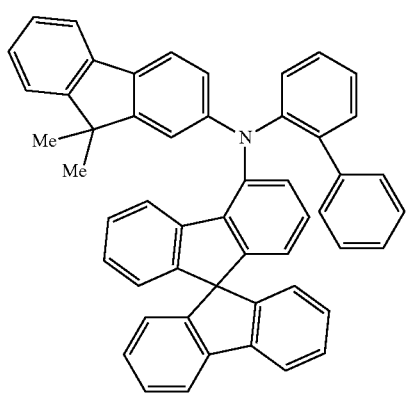

(ET-1)

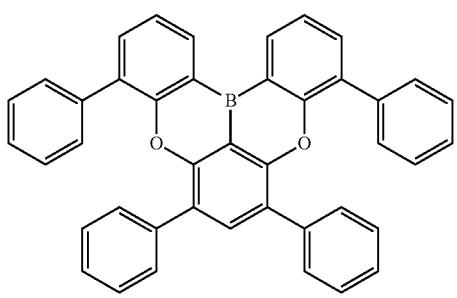

(ET-2)

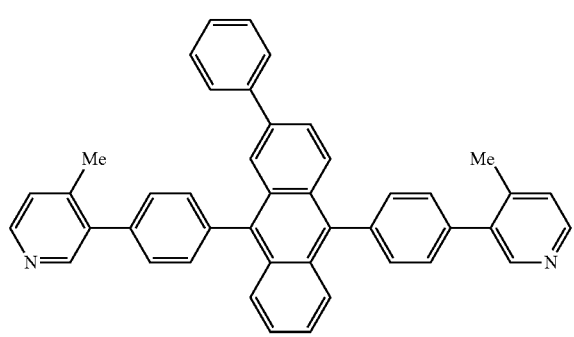

(ET-3)

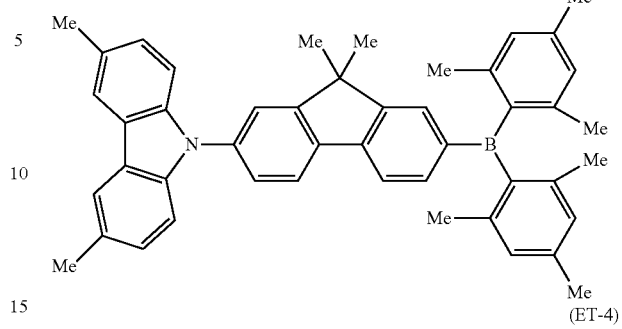

(ET-4)

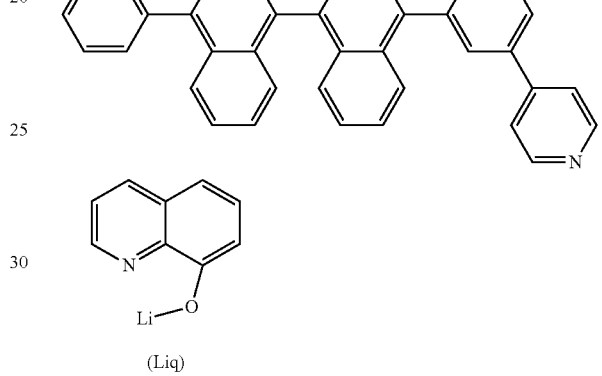

(Liq)

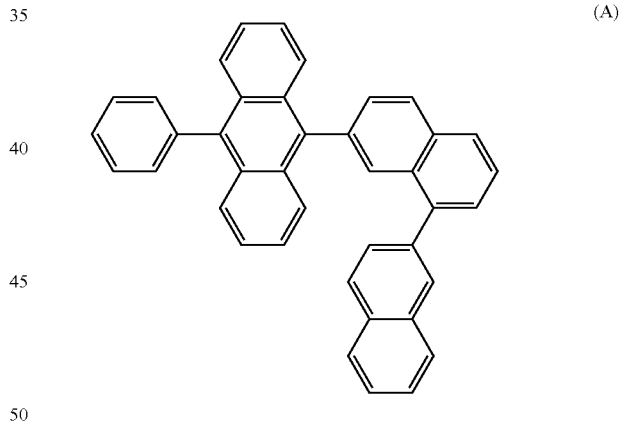

(A)

Example 1

Element Including Compound (2-1) as Host and Compound (1-139) as Dopant

A glass substrate (manufactured by Opto Science, Inc.) having a size of 26 mm×28 mm×0.7 mm, obtained by forming a film of ITO having a thickness of 180 nm by sputtering and polishing the ITO film to 150 nm, was used as a transparent supporting substrate. This transparent supporting substrate was fixed to a substrate holder of a commercially available vapor deposition apparatus (manufactured by Showa Shinku Co., Ltd.). Molybdenum vapor deposition boats containing HI, HAT-CN, HT-1, HT-2, compound (2-1), compound (1-139), ET-1, and ET-2, respectively, and aluminum nitride vapor deposition boats containing Liq, magnesium, and silver, respectively, were mounted thereon.

Layers as described below were formed sequentially on the ITO film of the transparent supporting substrate. A vacuum chamber was depressurized to $5 \times 10^{-4}$ Pa. First, HI was heated, and vapor deposition was performed so as to obtain a film thickness of 40 nm. Subsequently, HAT-CN was heated, and vapor deposition was performed so as to obtain a film thickness of 5 nm. Subsequently, HT-1 was heated, and vapor deposition was performed so as to obtain a film thickness of 15 nm. Subsequently, HT-2 was heated, and vapor deposition was performed so as to obtain a film thickness of 10 nm. Thus, hole injection/transport layers formed of four layers were formed. Subsequently, compounds (2-1) and (1-139) were simultaneously heated, and vapor deposition was performed so as to obtain a film thickness of 25 nm. Thus, a light emitting layer was formed. The vapor deposition rate was adjusted such that a weight ratio between compounds (2-1) and (1-139) was approximately 98:2. Subsequently, ET-1 was heated, and vapor deposition was performed so as to obtain a film thickness of 5 nm. Thus, an electron transport layer 1 was formed. Subsequently, ET-2 and Liq were simultaneously heated, and vapor deposition was performed so as to obtain a film thickness of 25 nm. Thus, an electron transport layer 2 was formed. The rate of deposition was regulated such that the weight ratio between ET-2 and Liq was approximately 50:50. The vapor deposition rate for each layer was 0.01 to 1 nm/sec. Thereafter, Liq was heated, and vapor deposition was performed at a vapor deposition rate of 0.01 to 0.1 nm/sec so as to obtain a film thickness of 1 nm. Subsequently, magnesium and silver were simultaneously heated, and vapor deposition was performed so as to obtain a film thickness of 100 nm. Thus, a negative electrode was formed to obtain an organic EL element. At this time, the vapor deposition rate was adjusted in a range between 0.1 nm to 10 nm/sec such that the ratio of the numbers of atoms between magnesium and silver was 10:1.

A direct current voltage was applied using an ITO electrode as a positive electrode and a magnesium/silver electrode as a negative electrode, and characteristics at the time of light emission at 1000 cd/m² were measured. As a result, blue light emission with a wavelength of 462 nm was obtained. The driving voltage was 4.1 V, and the external quantum efficiency was 6.7%.

Examples 2 to 12 and Comparative Example 1

Materials illustrated in Table 1 were selected as materials of the layers, and organic EL elements were obtained by a method according to Example 1. In Example 11, ET-1 and LIq were co-deposited so as to obtain a film thickness of 30 nm. Thus, an electron transport layer formed of one layer was formed. The organic EL characteristics were evaluated in a similar manner to Example 1 (Table 1). Note that blue light emission was obtained in all the elements.

Some of the compounds according to an embodiment of the present invention have been evaluated as a material for a light emitting layer of an organic EL element, and usefulness thereof has been described above. However, other compounds that have not been evaluated also have the same basic skeleton and have similar structures as a whole. A person skilled in the art can understand that the other compounds that have not been evaluated are similarly excellent materials for a light emitting layer.

According to a preferable embodiment of the present invention, it is possible to provide a polycyclic aromatic compound represented by formula (1) and a pyrene-based compound represented by formula (2), capable of obtaining optimum light emitting characteristics in combination with the polycyclic aromatic compound represented by formula (1) By manufacturing an organic EL element using a material for a light emitting layer obtained by combining these compounds, it is possible to provide an organic EL element particularly having excellent light emission efficiency and exhibiting well-balanced performance.

What is claimed is:

1. An organic electroluminescent element comprising a pair of electrodes composed of a positive electrode and a negative electrode and a light emitting layer disposed between the pair of electrodes, in which the light emitting layer comprises (A) at least one of a compound represented by the following general formula (1) and a multimer having a plurality of structures each represented by the following general formula (1), as a dopant material and (B) at least one pyrene-based compound represented by the following general formula (2) as a host material

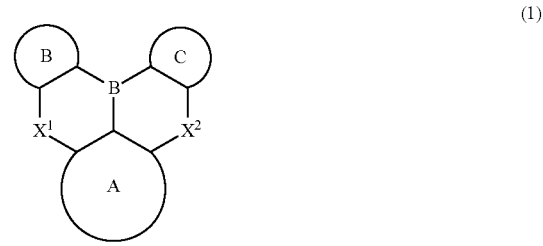

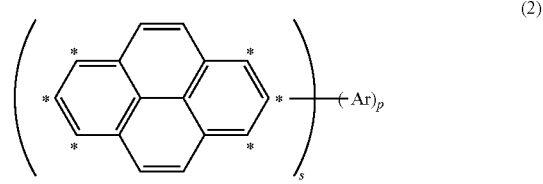

in the above formula (1), the ring A, ring B, and ring C each independently represent an aryl ring or a heteroaryl ring, and at least one hydrogen atom in these rings may be substituted, $X^1$ and $X^2$ each independently represent >O or >N—R, R in the >N—R represents an optionally substituted aryl, an optionally substituted heteroaryl, an optionally substituted alkyl, or an optionally substituted cycloalkyl, and R in the >N—R may be bonded to the ring A, ring B, and/or ring C with a linking group or a single bond, and at least one hydrogen atom in the compound or the structure represented by formula (1) may be each independently substituted by a halogen atom, cyano, or a deuterium atom, in the above formula (2), s pyrene moieties are bonded to p Ar moieties at any position of * in each of the pyrene moieties and any position in each of the Ar moieties, at least one hydrogen atom of the pyrene moieties may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, and at least one hydrogen atom in these substituents may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, s and p each independently represent an integer of 1 or 2, s and p do not simultaneously represent 2, when s represents 2, the two pyrene moieties including a substituent may be structurally the same or different, and when p represents 2, the two Ar moieties including a substituent may be structurally the same or different, and at least one hydrogen atom in the compound represented by formula (2) may be each independently substituted by a halogen atom, cyano, or a deuterium atom, and Ar's each independently represent a group represented by the following general formula (Ar-1) or (Ar-2)

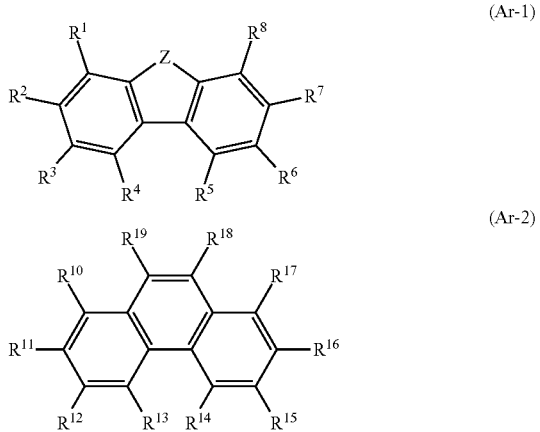

in each of the above formulas (Ar-1) and (Ar-2),

Z represents $>CR_2$, $>N-R$, $>O$, or $>S$,

R's in $>CR_2$ each independently represent an alkyl having 1 to 6 carbon atoms, a cycloalkyl having 3 to 14 carbon atoms, an aryl having 6 to 12 carbon atoms, or a heteroaryl having 2 to 12 carbon atoms, at least one hydrogen atom in the aryl and the heteroaryl may be substituted by an alkyl having 1 to 4 carbon atoms or a cycloalkyl having 5 to 10 carbon atoms, and R's may be bonded to each other to form a ring, R in $>N-R$ represents an alkyl having 1 to 4 carbon atoms, a cycloalkyl having 5 to 10 carbon atoms, an aryl having 6 to 12 carbon atoms, or a heteroaryl having 2 to 12 carbon atoms, and at least one hydrogen atom in the aryl and the heteroaryl may be substituted by an alkyl having 1 to 4 carbon atoms or a cycloalkyl having 5 to 10 carbon atoms, $R^1$ to $R^8$ and $R^{10}$ to $R^{19}$ each independently represent a hydrogen atom, an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, at least one hydrogen atom in these groups may be substituted by an alkyl having 1 to 6 carbon atoms or a cycloalkyl having 3 to 14 carbon atoms, adjacent groups among $R^1$ to $R^8$ or adjacent groups among $R^{10}$ to $R^{19}$ may be bonded to each other to form a fused ring, the fused rings thus formed may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 2 to 30 carbon atoms, an alkoxy having 1 to 30 carbon atoms, or an aryloxy having 6 to 30 carbon atoms, and at least one hydrogen atom in these substituents may be substituted by an alkyl having 1 to 6 carbon atoms or a cycloalkyl having 3 to 14 carbon atoms, at least one hydrogen atom in the group represented by the above formula (Ar-1) or (Ar-2) may be each independently substituted by a halogen atom, cyano, or a deuterium atom, and the pyrene moiety in formula (2) is bonded to any position in the group represented by the above formula (Ar-1) or (Ar-2).

2. The organic electroluminescent element according to claim 1, in which the compound represented by the above general formula (1) is a compound represented by the following general formula (1'),

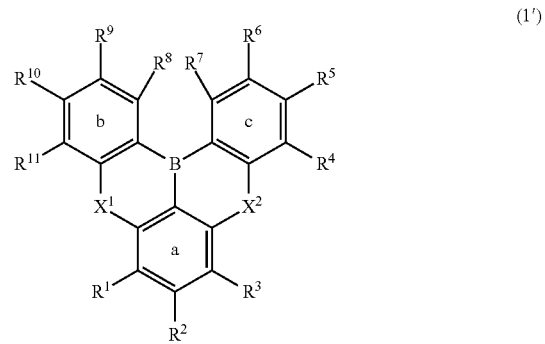

in the above formula (1'), $R^1$ to $R^{11}$ each independently represent a hydrogen atom, an aryl, a heteroaryl, a diarylamino, a diheteroarylamino, an arylheteroarylamino, an alkyl, a cycloalkyl, an alkoxy, or an aryloxy, at least one hydrogen atom in these groups may be each independently substituted by an aryl, a heteroaryl, an alkyl, or a cycloalkyl, adjacent groups among $R^1$ to $R^{11}$ may be bonded to each other to form an aryl ring or a heteroaryl ring together with ring a, ring b, or ring c, at least one hydrogen atom in the ring thus formed may be each independently substituted by an aryl, a heteroaryl, a diarylamino, a diheteroarylamino, an arylheteroarylamino, an alkyl, a cycloalkyl, an alkoxy, or an aryloxy, and at least one hydrogen atom in these substituents may be each independently substituted by an aryl, a heteroaryl, an alkyl, or a cycloalkyl, $X^1$ and $X^2$ each independently represent $>O$ or $>N-R$, R in the $>N-R$ represents an aryl having 6 to 12 carbon atoms, a heteroaryl having 2 to 15 carbon atoms, an alkyl having 1 to 6 carbon atoms, or a cycloalkyl having 3 to 14 carbon atoms, at least one hydrogen atom in the aryl or the heteroaryl may be substituted by an alkyl having 1 to 4 carbon atoms or a cycloalkyl having 5 to 10 carbon atoms, R in the $>N-R$ may be bonded to the ring a, ring b, and/or ring c via —O—, —S—, —C(—R)₂—, or a single bond, R in the —C(—R)₂— represents an alkyl having 1 to 6 carbon atoms or a cycloalkyl having 3 to 14 carbon atoms, and at least one hydrogen atom in the compound represented by formula (1') may be each independently substituted by a halogen atom, cyano, or a deuterium atom.

3. The organic electroluminescent element according to claim 1, in which the Ar's each independently represent a group represented by any one of the following general formulas (Ar-1-1) to (Ar-1-12) and (Ar-2-1) to (Ar-2-4),

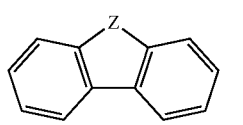 (Ar-1-1)

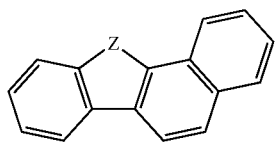 (Ar-1-2)

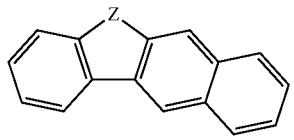 (Ar-1-3)

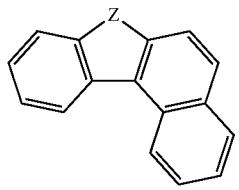 (Ar-1-4)

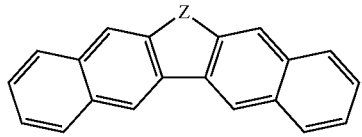 (Ar-1-5)

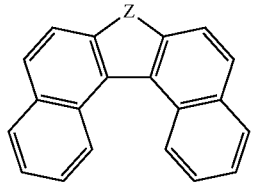 (Ar-1-6)

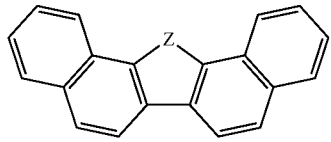 (Ar-1-7)

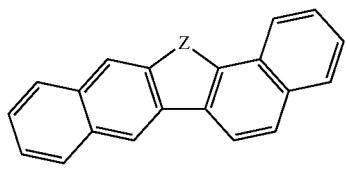 (Ar-1-8)

-continued

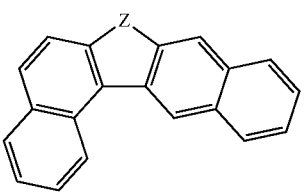 (Ar-1-9)

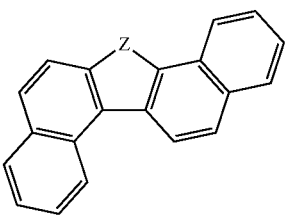 (Ar-1-10)

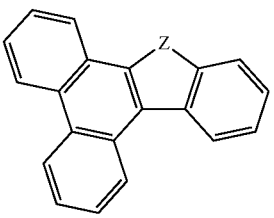 (Ar-1-11)

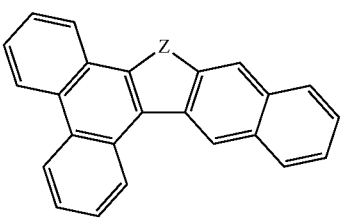 (Ar-1-12)

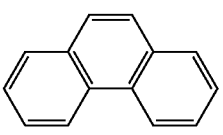 (Ar-2-1)

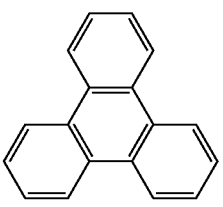 (Ar-2-2)

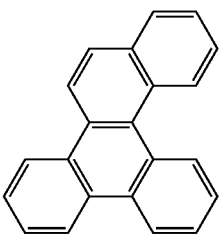 (Ar-2-3)

-continued (Ar-2-4)

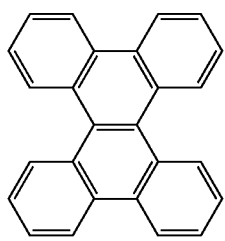

in each of the above formulas,

Z represents >CR$_2$, >N—R, >O, or >S,

R's in >CR$_2$ each independently represent an alkyl having 1 to 6 carbon atoms, a cycloalkyl having 3 to 14 carbon atoms, or an aryl having 6 to 12 carbon atoms, and R's may be bonded to each other to form a ring, R in >N—R represents an alkyl having 1 to 4 carbon atoms, a cycloalkyl having 5 to 10 carbon atoms, or an aryl having 6 to 12 carbon atoms, at least one hydrogen atom in each of groups represented by the above formulas may be each independently substituted by an aryl having 6 to 10 carbon atoms, a heteroaryl having 2 to 11 carbon atoms, an alkyl having 1 to 30 carbon atoms, or a cycloalkyl having 3 to 24 carbon atoms, at least one hydrogen atom in each of the groups represented by the above formulas may be each independently substituted by a halogen atom, cyano, or a deuterium atom, and the pyrene moiety in formula (2) is bonded to any position in a group represented by any one of the above formulas (Ar-1-1) to (Ar-1-12) and (Ar-2-1) to (Ar-2-4).

4. The organic electroluminescent element according to claim 1, in which the pyrene-based compound represented by the above general formula (2) is a compound represented by any one of the following structural formulas (2-1)

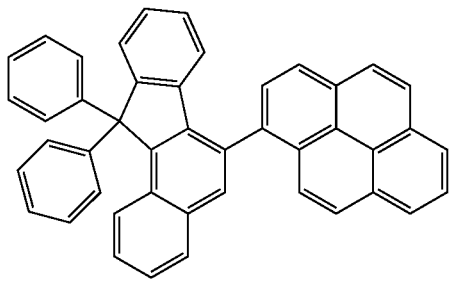

(2-46)

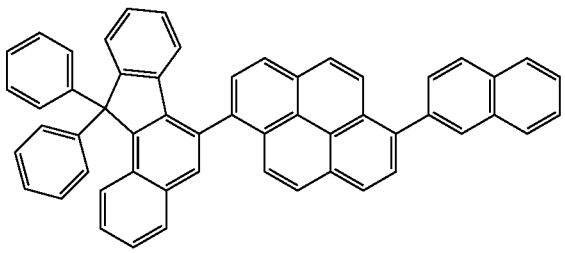

(2-174)

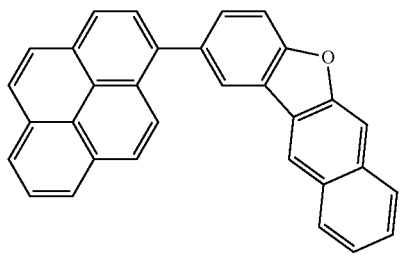

(2-350)

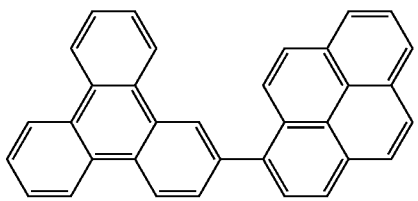

(2-356)

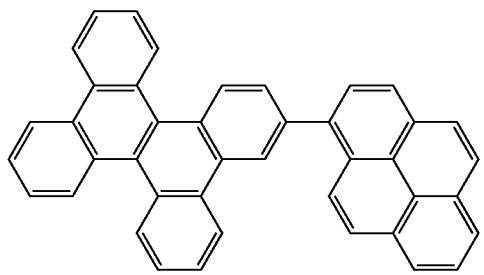

(2-359)

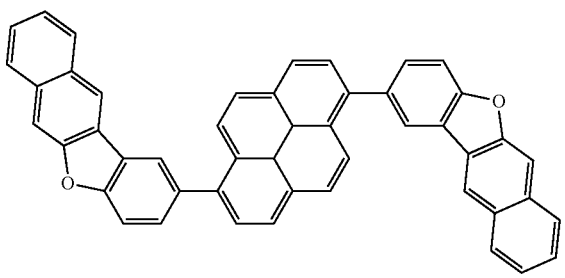

(2-1001)

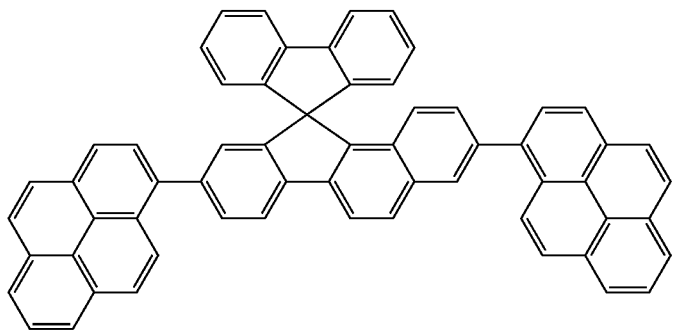

(2-1080)

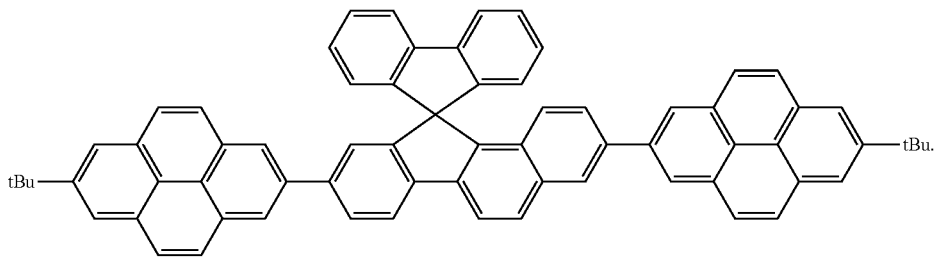

5. The organic electroluminescent element according to claim 1, further comprising an electron transport layer and/or an electron injection layer disposed between the negative electrode and the light emitting layer, in which at least one of the electron transport layer and the electron injection layer comprises at least one selected from the group consisting of a borane derivative, a pyridine derivative, a fluoranthene derivative, a BO-based derivative, an anthracene derivative, a benzofluorene derivative, a phosphine oxide derivative, a pyrimidine derivative, a carbazole derivative, a triazine derivative, a benzimidazole derivative, a phenanthroline derivative, and a quinolinol-based metal complex.

6. The organic electroluminescent element according to claim 5, in which the electron transport layer and/or the electron injection layer further comprise/comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

7. A display apparatus comprising the organic electroluminescent element according to claim 1.

8. A lighting apparatus comprising the organic electroluminescent element according to claim 1.

9. A pyrene-based compound represented by any one of the following structural formulas (2-1)

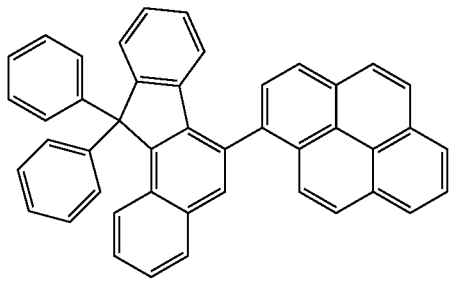

(2-46)

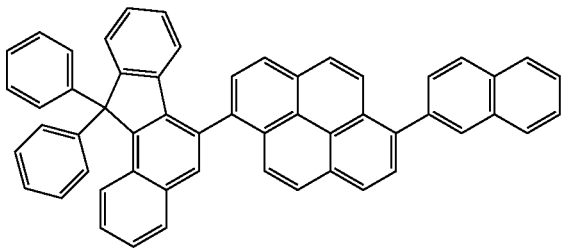

(2-356)

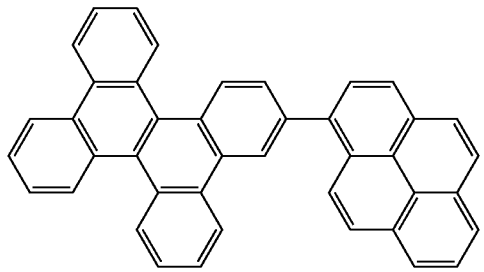

(2-1001)

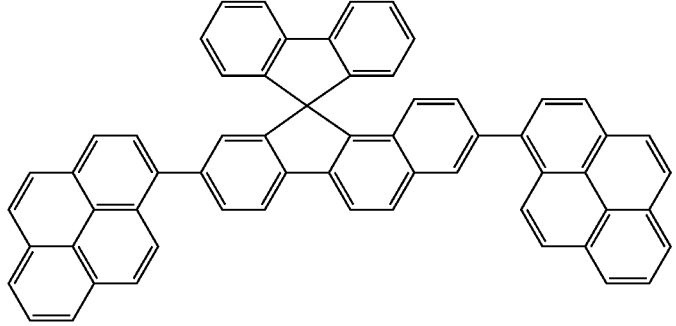

(2-1080)

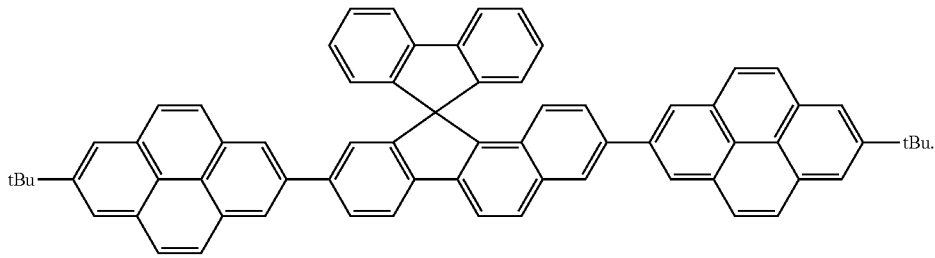

10. A pyrene-based compound represented by the following general formula (2)

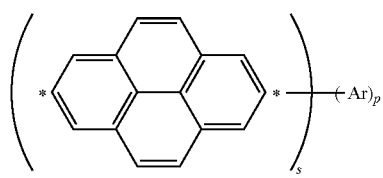
(2)

in the above formula (2),
s pyrene moieties are bonded to p Ar moieties at any position of * in each of the pyrene moieties and any position in each of the Ar moieties,
at least one hydrogen atom of the pyrene moieties may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 1 to 30 carbon atoms, an alkoxy having 1 to 30 carbon atoms, or an aryloxy having 1 to 30 carbon atoms, and at least one hydrogen atom in these substituents may be substituted by an alkyl having 1 to 6 carbon atoms or a cycloalkyl having 3 to 14 carbon atoms,
Ar represents a group represented by the following general formula (Ar-1) or (Ar-3),

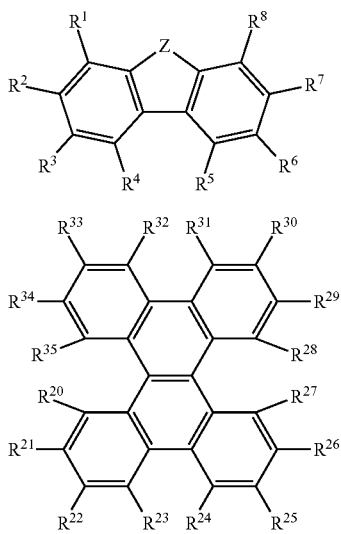

in each of the above formulas,
Z represents $>CR_2$,
R's in $>CR_2$ each independently represent an alkyl having 1 to 6 carbon atoms, a cycloalkyl having 3 to 14 carbon atoms, an aryl having 6 to 12 carbon atoms, or a heteroaryl having 2 to 12 carbon atoms, at least one hydrogen atom in the aryl and the heteroaryl may be substituted by an alkyl having 1 to 4 carbon atoms or a cycloalkyl having 5 to 10 carbon atoms, and R's may be bonded to each other to form a ring, $R^1$ to $R^8$ and $R^{20}$ to $R^{35}$ each independently represent a hydrogen atom, an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl having 1 to 30 carbon atoms, an alkoxy having 1 to 30 carbon atoms, or an aryloxy having 1 to 30 carbon atoms, at least one hydrogen atom in these groups may be substituted by an alkyl having 1 to 6 carbon atoms or a cycloalkyl having 3 to 14 carbon atoms, adjacent groups among $R^1$ to $R^8$ are bonded to each other to form a fused ring, adjacent groups among $R^{20}$ to $R^{35}$ may be bonded to each other to form a fused ring, the rings thus formed may be each independently substituted by an aryl having 6 to 10 carbon atoms, a heteroaryl having 2 to 11 carbon atoms, an alkyl having 1 to 30 carbon atoms, a cycloalkyl having 3 to 24 carbon atoms, an alkenyl group having 1 to 30 carbon atoms, an alkoxy having 1 to 30 carbon atoms, or an aryloxy having 1 to 30 carbon atoms, and at least one hydrogen atom in these substituents may be substituted by an alkyl having 1 to 6 carbon atoms or a cycloalkyl having 3 to 14 carbon atoms, s and p each independently represent an integer of 1 or 2, s and p do not simultaneously represent 2, when s represents 2, the two pyrene moieties including a substituent may be structurally the same or different, and when p represents 2, the two Ar moieties including a substituent may be structurally the same or different, and at least one hydrogen atom in the compound represented by formula (2) may be each independently substituted by a halogen atom, cyano, or a deuterium atom.

* * * * *